(12) United States Patent
Ullrich et al.

(10) Patent No.: US 9,169,241 B2
(45) Date of Patent: Oct. 27, 2015

(54) QUINOLINYLOXYPHENYLSULFONAMIDES

(71) Applicant: Max-Planck-Gesellschaft Zur Forderung der Wissenschaften E.V., München (DE)

(72) Inventors: Axel Ullrich, Munich (DE); Robert Torka, Kaufering (DE); Yixiang Zhang, Boston, MA (US); György Kéri, Budapest (HU); László Örfi, Budapest (HU); István Szabadkai, Budapest (HU)

(73) Assignee: Max-Planck-Gesellschaft Zur Forderung der Wissenschaften E.V., München (DE)

( * ) Notice: Subject to any disclaimer, the term of this patent is extended or adjusted under 35 U.S.C. 154(b) by 0 days.

(21) Appl. No.: 14/202,951

(22) Filed: Mar. 10, 2014

(65) Prior Publication Data
US 2014/0336191 A1    Nov. 13, 2014

Related U.S. Application Data

(63) Continuation of application No. 13/500,761, filed as application No. PCT/EP2010/006525 on Oct. 16, 2010, now Pat. No. 8,685,971.

(30) Foreign Application Priority Data

Oct. 16, 2009    (EP) ................... 09075468

(51) Int. Cl.
| | | |
|---|---|---|
| *C07D 417/12* | (2006.01) | |
| *C07D 215/20* | (2006.01) | |
| *C07D 413/12* | (2006.01) | |
| *C07D 401/14* | (2006.01) | |
| *C07D 409/14* | (2006.01) | |
| *C07D 405/12* | (2006.01) | |
| *C07D 401/12* | (2006.01) | |
| *C07D 409/12* | (2006.01) | |

(52) U.S. Cl.
CPC ............ *C07D 417/12* (2013.01); *C07D 215/20* (2013.01); *C07D 401/12* (2013.01); *C07D 401/14* (2013.01); *C07D 405/12* (2013.01); *C07D 409/12* (2013.01); *C07D 409/14* (2013.01); *C07D 413/12* (2013.01)

(58) Field of Classification Search
None
See application file for complete search history.

(56) References Cited

U.S. PATENT DOCUMENTS

2009/0131461 A1* 5/2009 Davidson et al. .......... 514/266.2
2011/0092503 A1* 4/2011 Ullrich et al. ............. 514/235.2

* cited by examiner

*Primary Examiner* — Timothy R Rozof
(74) *Attorney, Agent, or Firm* — Meyertons, Hood, Kivlin, Kowert & Goetzel, P.C.; Eric B. Meyertons

(57) ABSTRACT

The present invention relates to quinolinyloxyphenylsulfonamides and stereoisomeric forms, solvates, hydrates and/or pharmaceutically acceptable salts of these quinolinyloxyphenylsulfonamide compounds as well as pharmaceutical compositions containing at least one of these compounds together with at least one pharmaceutically acceptable carrier, excipient and/or diluent. Said quinolinyloxyphenylsulfonamides are useful for prophylaxsis, treatment and/or after-treatment of hyperproliferative disorders, such as cancer, tumors and particularly cancer metastases.

8 Claims, No Drawings

QUINOLINYLOXYPHENYLSULFONAMIDES

PRIORITY CLAIM

The present application is a continuation of U.S. patent application Ser. No. 13/500,761, filed Jul. 2, 2012, which claims priority to PCT/EP2010/06525 filed Oct. 16, 2010 which claims priority to EP 09075468.0 filed Oct. 16, 2009 which are incorporated herein by reference in their entirety.

BACKGROUND OF THE INVENTION

1. Field of the Invention

The present invention relates to quinolinyloxyphenylsulfonamides and stereoisomeric forms, solvates, hydrates and/or pharmaceutically acceptable salts of these quinolinyloxyphenylsulfonamide compounds as well as pharmaceutical compositions containing at least one of these compounds together with at least one pharmaceutically acceptable carrier, excipient and/or diluent. Said quinolinyloxyphenylsulfonamides are useful for prophylaxsis, treatment and/or after-treatment of hyperproliferative disorders, such as cancer, tumors and particularly cancer metastases.

2. Description of the Relevant Art

The international patent application PCT/EP2009/002798 refers to similar compounds which are inhibitors of receptor tyrosine kinases of the AXL receptor family. These compounds are suitable for the treatment or prevention of disorders associated with, accompanied by or caused by hyperfunction of a receptor of the AXL family. The compounds of PCT/EP2009/002798 are suitable for the treatment of hyperproliferative disorders, such as cancer and particularly cancer metastases.

SUMMARY OF THE INVENTION

It is object of the present invention to provide further compounds and pharmaceutically acceptable salts thereof which can be used as pharmaceutically active agents, especially for prophylaxis, treatment and after-treatment of cancer, tumors and particularly cancer metastases.

The object of the present invention is solved by the teaching of the independent claims. Further advantageous features, aspects and details of the invention are evident from the dependent claims, the description, and the examples of the present application.

In an embodiment, a method of treating a subject having or at risk of having AXL receptor tyrosine kinase induced cancer, tumors or cancer metastases includes administering to the subject who would benefit from such treatment a therapeutically effective amount a compound of the general formula (I) or a pharmaceutical composition containing at least one compound of the general formula (I)

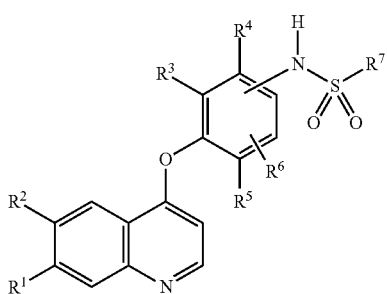

(I)

wherein
—$R^1$ or —$R^2$ represents —O—X—$R^8$;
if —$R^1$ represents —O—X—$R^8$ than —$R^2$ represents —H, —OH, —$OCH_3$, —$OCF_3$, —$OC_2H_5$, —$OC_3H_7$, —$OCH_2CH_2$—$OCH_3$, —$OCH_2CH_2$—$OC_2H_5$;

if —$R^2$ represents —O—X—$R^8$ than —$R^1$ represents —H, —OH, —$OCH_3$, —$OCF_3$, —$OC_2H_5$, —$OC_3H_7$, —$OCH_2CH_2$—$OCH_3$, —$OCH_2CH_2$—$OC_2H_5$;
—X— represents —$CR^{11}R^{12}$—$CR^{13}R^{14}$—, —$CR^{11}R^{12}$—$CR^{13}R^{14}$—$CR^{15}R^{16}$—, —$CR^{11}R^{12}$—$CR^{13}R^{14}$—$CR^{15}R^{16}$—$CR^{17}R^{18}$—, —$CR^{11}R^{12}$—$CR^{13}R^{14}$—$CR^{15}R^{16}$—$CR^{17}R^{18}$—$CR^{19}R^{20}$—, —$CR^{11}R^{12}$—$CR^{13}R^{14}$—$CR^{15}R^{16}$—$CR^{17}R^{18}$—$CR^{19}R^{20}$—$CR^{21}R^{22}$—, —$(CH_2)_n$—NH—, —CO—, —$(CH_2)_n$—CO—, —$(CH_2)_n$—NH—CO—NH—, —$(CH_2)_n$—NH—CO—, —$(CH_2)_n$—NH—CO—O—, —$(CH_2)_n$—CO—NH—, —$(CH_2)_n$—O—CO—NH—, —$(CH_2)_n$—O—CO—, —$(CH_2)_n$—O—, —$(CH_2)_n$—;
n is an integer selected from 1, 2, 3, 4, 5 and 6;
—$R^3$, —$R^4$, —$R^5$, —$R^6$ are independently of each other selected from hydrogen, halogen, nitro, $C_{1-6}$ alkyl, $C_3$-$C_{10}$-cycloalkyl, $C_{1-6}$ alkoxy, wherein the $C_{1-6}$ alkyl, $C_3$-$C_{10}$-cycloalkyl or $C_{1-6}$ alkoxy groups are optionally mono- or polysubstituted by hydroxyl, halogen, $C_{1-4}$ alkyl and/or $C_{1-4}$ alkoxy, wherein the $C_{1-4}$ alkyl and/or $C_{1-4}$ alkoxy groups are optionally mono- or polysubstituted by hydroxyl and/or halogen.
—$R^7$ represents
(i) a saturated or unsaturated three- to twelve-membered carbocyclic or heterocyclic ring system which is optionally mono- or polysubstituted by hydroxy, $C_{1-6}$ alkyl, $C_3$-$C_{10}$-cycloalkyl, $C_{2-6}$ alkenyl, $C_{2-6}$ alkynyl, $C_{1-6}$ alkoxy, a halogen atom, or a saturated or unsaturated three- to eight-membered carbocyclic or heterocyclic group, and the $C_{1-6}$ alkyl, $C_3$-$C_{10}$-cycloalkyl, $C_{2-6}$ alkenyl, $C_{2-6}$ alkynyl, and $C_{1-6}$ alkoxy groups are optionally substituted by a halogen atom or a saturated or unsaturated three- to eight-membered carbocyclic or heterocyclic group,
(ii) $C_{1-6}$ alkyl or $C_{1-6}$ alkoxy which is unsubstituted or substituted by a saturated or unsaturated three- to twelve-membered carbocyclic or heterocyclic ring system which is optionally mono- or polysubstituted by hydroxy, $C_{1-6}$ alkyl, $C_{2-6}$ alkenyl, $C_{2-6}$ alkynyl, $C_{1-6}$ alkoxy, a halogen atom, or a saturated or unsaturated three- to eight-membered carbocyclic or heterocyclic group, and the $C_{1-6}$ alkyl, $C_{2-6}$ alkenyl, $C_{2-6}$ alkynyl, and $C_{1-6}$ alkoxy groups are optionally substituted by a halogen atom or a saturated or unsaturated three- to eight-membered carbocyclic or heterocyclic group,
(iii) a nitrogen atom substituted with a saturated or unsaturated three- to twelve-membered or heterocyclic ring system which is optionally mono- or polysubstituted by hydroxy, $C_{1-6}$ alkyl, $C_{2-6}$ alkenyl, $C_{2-6}$ alkynyl, $C_{1-6}$ alkoxy, a halogen atom, or a saturated or unsaturated three- to eight-membered carbocyclic or heterocyclic group, and the $C_{1-6}$ alkyl, $C_{2-6}$ alkenyl, $C_{2-6}$ alkynyl, and $C_{1-6}$ alkoxy groups are optionally substituted by a halogen atom or a saturated or unsaturated three- to eight-membered carbocyclic or heterocyclic group,
—$R^8$ represents hydroxyl, halogen, $C_{1-6}$-alkoxy, $C_{1-6}$ alkylcarbonyl, carboxyl, $C_3$-$C_{10}$-cycloalkyl, $C_{1-6}$-alkoxycarbonyl, a heterocyclic group, a heterocycloalkyl group with one or two heteroatoms selected from O, N, S and 2 to 6 carbon atoms, $C_{1-6}$-alkyl, —NH—CO—$NR^9R^{10}$, —CO—$NR^9R^{10}$, —$NR^9R^{10}$;
—$R^9$ and —$R^{10}$ are independently of each other selected from hydrogen, $C_3$-$C_6$-cycloalkyl, $C_{1-6}$ alkyl optionally substituted by hydroxyl, halogen and/or $C_{1-4}$ alkoxy or
—$R^9$ and —$R^{10}$ may combine with the nitrogen atom attached thereto to form a saturated or unsaturated five- or six-membered heterocyclic group, wherein the heterocyclic group is optionally substituted by hydroxyl, amino, halogen, —COOH, $C_{1-6}$ alkyl, $C_{2-6}$ alkenyl, $C_{2-6}$ alkynyl, $C_{1-6}$ alkoxy, $C_{1-6}$ alkoxycarbonyl, $C_{1-6}$ alkylcarbonyl, $C_{1-6}$ acyloxy, a saturated or unsaturated three- to twelve-membered carbocyclic or heterocyclic ring system, wherein the $C_{1-6}$ alkyl, $C_{2-6}$ alkenyl, $C_{2-6}$ alkynyl, $C_{1-6}$ alkoxy, $C_{1-6}$ alkoxycarbonyl, $C_{1-6}$ alkylcarbonyl and/or $C_{1-6}$ acyloxy groups are optionally substituted by hydroxyl, $C_{1-6}$ alkoxy, or a saturated or unsaturated three- to twelve-membered carbocyclic or heterocyclic ring system;

wherein in the amino group one or both hydrogen atoms on said amino group are optionally substituted by $C_{1-6}$ alkyl or a saturated or unsaturated three- to twelve-membered carbocyclic or heterocyclic ring system, and the $C_{1-6}$ alkyl group is optionally substituted by hydroxyl, $C_{1-6}$ alkoxy, or a saturated or unsaturated three- to twelve-membered carbocyclic or heterocyclic ring system;

wherein the saturated or unsaturated three- to twelve-membered carbocyclic or heterocyclic ring system is optionally substituted by hydroxyl, $C_{1-6}$ alkyl, $C_{2-6}$ alkenyl, $C_{2-6}$ alkynyl, $C_{1-6}$ alkoxy, $C_{1-6}$ alkoxycarbonyl, or a saturated or unsaturated three- to twelve-membered carbocyclic or heterocyclic ring system, wherein the $C_{1-6}$ alkyl, $C_{2-6}$ alkenyl, and $C_{2-6}$ alkynyl groups are optionally substituted by hydroxyl, $C_{1-6}$ alkoxy, or a saturated or unsaturated three- to twelve-membered carbocyclic or heterocyclic ring system; when the carbocyclic or heterocyclic group is substituted by two $C_{1-6}$ alkyl groups, the two alkyl groups may combine together to form an alkylene chain; and the carbocyclic or heterocyclic group may be condensed with another saturated or unsaturated five- to seven-membered carbocyclic or heterocyclic group to form a bicyclic group;

$R^{11}$—$R^{22}$ represent independently of each other linear or branched, substituted or unsubstituted $C_1$-$C_{20}$-alkyl, —H, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OPh, —OCH$_2$-Ph, —OCPh$_3$, —SH, —SCH$_3$, —SC$_2$H$_5$, —SC$_3$H$_7$, —S-cyclo-C$_3$H$_5$, —SCH(CH$_3$)$_2$, —SC(CH$_3$)$_3$, —NO$_2$, —F, —Cl, —Br, —I, —N$_3$, —CN, —OCN, —NCO, —SCN, —NCS, —CHO, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, —COCN, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —OOC—CH$_3$, —OOC—C$_2$H$_5$, —OOC—C$_3$H$_7$, —OOC-cyclo-C$_3$H$_5$, —OOC—CH(CH$_3$)$_2$, —OOC—C(CH$_3$)$_3$, —CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON(cyclo-C$_3$H$_5$)$_2$, —CON[CH(CH$_3$)$_2$]$_2$, —CON[C(CH$_3$)$_3$]$_2$, —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —N[C(CH$_3$)$_3$]$_2$, —SOCH$_3$, —SOC$_2$H$_5$, —SOC$_3$H$_7$, —SO-cyclo-C$_3$H$_5$, —SOCH(CH$_3$)$_2$, —SOC(CH$_3$)$_3$, —SO$_2$CH$_3$, —SO$_2$C$_2$H$_5$, —SO$_2$C$_3$H$_7$, —SO$_2$-cyclo-C$_3$H$_5$, —SO$_2$CH(CH$_3$)$_2$, —SO$_2$C(CH$_3$)$_3$, —SO$_3$H, —SO$_3$CH$_3$, —SO$_3$C$_2$H$_5$, —SO$_3$C$_3$H$_7$, —SO$_3$-cyclo-C$_3$H$_5$, —SO$_3$CH(CH$_3$)$_2$, —SO$_3$C(CH$_3$)$_3$, —OCHF$_2$, —OCF$_3$, —OC$_2$F$_5$, —O—COOCH$_3$, —O—COOC$_2$H$_5$, —O—COOC$_3$H$_7$, —O—COO-cyclo-C$_3$H$_5$, —O—COOCH(CH$_3$)$_2$, —O—COOC(CH$_3$)$_3$, —NH—CO—NH$_2$, —NH—CO—NHCH$_3$, —NH—CO—NHC$_2$H$_5$, —NH—CO—NHC$_3$H$_7$, —NH—CO—NH-cyclo-C$_3$H$_5$, —NH—CO—NH[CH(CH$_3$)$_2$], —NH—CO—NH[C(CH$_3$)$_3$], —NH—CO—N(CH$_3$)$_2$, —NH—CO—N(C$_2$H$_5$)$_2$, —NH—CO—N(C$_3$H$_7$)$_2$, —NH—CO—N(cyclo-C$_3$H$_5$)$_2$, —NH—CO—N[CH(CH$_3$)$_2$]$_2$, —NH—CO—N[C(CH$_3$)$_3$]$_2$, —NH—CS—NH$_2$, —NH—CS—NH-cyclo-C$_3$H$_5$, —NH—CS—NHC$_3$H$_7$, —NH—CS—NH[CH(CH$_3$)$_2$], —NH—CS—NH[C(CH$_3$)$_3$], —NH—CS—N(CH$_3$)$_2$, —NH—CS—N(C$_2$H$_5$)$_2$, —NH—CS—N(C$_3$H$_7$)$_2$, —NH—CS—N(cyclo-C$_3$H$_5$)$_2$, —NH—CS—N[CH(CH$_3$)$_2$]$_2$, —NH—CS—N[C(CH$_3$)$_3$]$_2$, —NH—C(=NH)—NH$_2$, —NH—C(=NH)—NHCH$_3$, —NH—C(=NH)—NHC$_2$H$_5$, —NH—CS—NHC$_2$H$_5$, —NH—C(=NH)—NHC$_3$H$_7$, —NH—C(=NH)—NH-cyclo-C$_3$H$_5$, —NH—C(=NH)—NH[CH(CH$_3$)$_2$], —NH—C(=NH)—NH[C(CH$_3$)$_3$], —NH—CS—NHCH$_3$, —NH—C(=NH)—N(CH$_3$)$_2$, —NH—C(=NH)—N(C$_2$H$_5$)$_2$, —NH—C(=NH)—N(C$_3$H$_7$)$_2$, —NH—C(=NH)—N(cyclo-C$_3$H$_5$)$_2$, —Si(CH$_3$)$_3$, —NH—C(=NH)—N[CH(CH$_3$)$_2$]$_2$, —NH—C(=NH)—N[C(CH$_3$)$_3$]$_2$, —O—CO—NH$_2$, —O—CO—NHCH$_3$, —O—CO—NHC$_2$H$_5$, —O—CO—NHC$_3$H$_7$, —O—CO—NH-cyclo-C$_3$H$_5$, —O—CO—NH[CH(CH$_3$)$_2$], —O—CO—NH[C(CH$_3$)$_3$], —O—CO—N(CH$_3$)$_2$, —O—CO—N(C$_2$H$_5$)$_2$, —O—CO—N(C$_3$H$_7$)$_2$, —O—CO—N(cyclo-C$_3$H$_5$)$_2$, —O—CO—N[CH(CH$_3$)$_2$]$_2$, —O—CO—N[C(CH$_3$)$_3$]$_2$, —O—CO—OCH$_3$, —O—CO—OC$_2$H$_5$, —O—CO—OC$_3$H$_7$, —O—CO—O-cyclo-C$_3$H$_5$, —O—CO—OCH(CH$_3$)$_2$, —O—CO—OC(CH$_3$)$_3$, —CH$_2$F—CHF$_2$, —CF$_3$, —CH$_2$Cl, —CHCl$_2$, —CCl$_3$, —CH$_2$Br—CHBr$_2$, —CBr$_3$, —CH$_2$I—CHI$_2$, —CI$_3$, —CPh$_3$, —CH$_2$—CH$_2$F—CH$_2$—CHF$_2$, —CH$_2$—CF$_3$, —CH$_2$—CH$_2$Cl, —CH$_2$—CHCl$_2$, —CH$_2$—CCl$_3$, —CH$_2$—CH$_2$Br—CH$_2$—CHBr$_2$, —CH$_2$—CBr$_3$, —CH$_2$—CH$_2$I—CH$_2$—CHI$_2$, —CH$_2$—CI$_3$, —CH$_3$, —C$_2$H$_5$, —C$_3$H$_7$, -cyclo-C$_3$H$_5$, —CH(CH$_3$)$_2$, —C(CH$_3$)$_3$, —C$_4$H$_9$, —CH$_2$—CH(CH$_3$)$_2$, —CH$_2$—CH(CH$_3$)—C$_2$H$_5$, —C(CH$_3$)$_3$, -Ph, —CH$_2$-Ph, —CH=CH$_2$, —CH$_2$—CH=CH$_2$, —C(CH$_3$)=CH$_2$, —CH=CH—CH$_3$, —C$_2$H$_4$—CH=CH$_2$, —CH=C(CH$_3$)$_2$, —C≡CH, —C≡C—CH$_3$, —CH$_2$—C≡CH; and stereoisomeric forms, solvates, hydrates and/or pharmaceutically acceptable salts thereof.

Exemplary AXL receptor tyrosine kinase induced cancer, tumor or cancer metastase which may be treated using the compound of the general formula (I) include, but are not limited to, adenocarcinoma, choroidal melanoma, acute leukemia, acoustic neurinoma, ampullary carcinoma, anal carcinoma, astrocytoma, basal cell carcinoma, pancreatic cancer, desmoid tumor, bladder cancer, bronchial carcinoma, breast cancer, Burkitt's lymphoma, corpus cancer, CUP-syndrome (carcinoma of unknown primary), colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, glioblastomas, gynecologic tumors, ear, nose and throat tumors, hematologic neoplasias, hairy cell leukemia, urethral cancer, skin cancer, skin testis cancer, brain tumors (gliomas), brain metastases, testicle cancer, hypophysis tumor, carcinoids, Kaposi's sarcoma, laryngeal cancer, germ cell tumor, bone cancer, colorectal carcinoma, head and neck tumors (tumors of the ear, nose and throat area), colon carcinoma, craniopharyngiomas, oral cancer (cancer in the mouth area and on lips), cancer of the central nervous system, liver cancer, liver metastases, leukemia, eyelid tumor, lung cancer, lymph node cancer (Hodgkin's/Non-Hodgkin's), lymphomas, stomach cancer, malignant melanoma, malignant neoplasia, malignant tumors gastrointestinal tract, breast carcinoma, rectal cancer, medulloblastomas, melanoma, meningiomas, Hodgkin's disease, mycosis fungoides, nasal cancer, neurinoma, neuroblastoma, kidney cancer, renal cell carcinomas, non-Hodgkin's lymphomas, oligodendroglioma, esophageal carcinoma, osteolytic carcinomas and osteoplastic carcinomas, osteosarcomas, ovarial carcinoma, pancreatic carcinoma, penile cancer, plasmocytoma, prostate cancer, pharyngeal cancer, rectal carcinoma, retinoblastoma, vaginal cancer, thyroid carcinoma, Schneeberger disease, esophageal cancer, spinalioms, T-cell lymphoma (mycosis fungoides), thymoma, tube carcinoma, eye tumors, urethral cancer, urologic tumors, urothelial carcinoma, vulva cancer, wart appearance, soft tissue tumors, soft tissue sarcoma, Wilm's tumor, cervical carcinoma and tongue cancer.

DETAILED DESCRIPTION OF THE PREFERRED EMBODIMENTS

The novel quinolinyloxyphenylsulfonamides according to the present invention are represented by the following general formula (I)

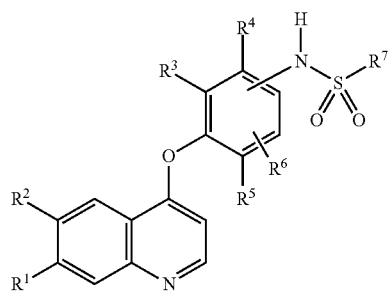

wherein
—$R^1$ or —$R^2$ represents —O—X—$R^8$;
if —$R^1$ represents —O—X—$R^8$ than —$R^2$ represents —H, —OH, —$OCH_3$, —$OCF_3$, —$OC_2H_5$, —$OC_3H_7$, —$OCH_2CH_2$—$OCH_3$, —$OCH_2CH_2$—$OC_2H_5$;
if —$R^2$ represents —O—X—$R^8$ than —$R^1$ represents —H, —OH, —$OCH_3$, —$OCF_3$, —$OC_2H_5$, —$OC_3H_7$, —$OCH_2CH_2$—$OCH_3$, —$OCH_2CH_2$—$OC_2H_5$;
—X— represents —$CR^{11}R^{12}$—, —$CR^{11}R^{12}$—$CR^{13}R^{14}$—, —$CR^{11}R^{12}$—$CR^{13}R^{14}$—$CR^{15}R^{16}$—, —$CR^{11}R^{12}$—$CR^{13}R^{14}$—$CR^{15}R^{16}$—$CR^{17}R^{18}$—, —$CR^{11}R^{12}$—$CR^{13}R^{14}$—$CR^{15}R^{16}$—$CR^{17}R^{18}$—$CR^{19}R^{20}$—, —$CR^{11}R^{12}$—$CR^{13}R^{14}$—$CR^{15}R^{16}$—$CR^{17}R^{18}$—$CR^{19}R^{20}$—$CR^{21}R^{22}$—, —$(CH_2)_n$—NH—, —CO—, —$(CH_2)_n$—CO—, —$(CH_2)_n$—NH—CO—NH—, —$(CH_2)_n$—NH—CO—, —$(CH_2)_n$—NH—CO—O—, —$(CH_2)_n$—CO—NH—, —$(CH_2)_n$—O—CO—NH—, —$(CH_2)_n$—O—CO—, —$(CH_2)_n$—O—, —$(CH_2)_n$—;
n is an integer selected from 1, 2, 3, 4, 5 and 6; —$R^3$, —$R^4$, —$R^5$, —$R^6$ are independently of each other selected from hydrogen, halogen, nitro, $C_{1-6}$ alkyl, $C_3$-$C_{10}$-cycloalkyl, $C_{1-6}$ alkoxy, wherein the $C_{1-6}$ alkyl, $C_3$-$C_{10}$-cycloalkyl or $C_{1-6}$ alkoxy groups are optionally mono- or polysubstituted by hydroxyl, halogen, $C_{1-4}$ alkyl and/or $C_{1-4}$ alkoxy, wherein the $C_{1-4}$ alkyl and/or $C_{1-4}$ alkoxy groups are optionally mono- or polysubstituted by hydroxyl and/or halogen.
—$R^7$ represents
(i) a saturated or unsaturated three- to twelve-membered carbocyclic or heterocyclic ring system which is optionally mono- or polysubstituted by hydroxy, $C_{1-6}$ alkyl, $C_3$-$C_{10}$-cycloalkyl, $C_{2-6}$ alkenyl, $C_{2-6}$ alkynyl, $C_{1-6}$ alkoxy, a halogen atom, or a saturated or unsaturated three- to eight-membered carbocyclic or heterocyclic group, and the $C_{1-6}$ alkyl, $C_3$-$C_{10}$-cycloalkyl, $C_{2-6}$ alkenyl, $C_{2-6}$ alkynyl, and $C_{1-6}$ alkoxy groups are optionally substituted by a halogen atom or a saturated or unsaturated three- to eight-membered carbocyclic or heterocyclic group, (ii) $C_{1-6}$ alkyl or $C_{1-6}$ alkoxy which is unsubstituted or substituted by a saturated or unsaturated three- to twelve-membered carbocyclic or heterocyclic ring system which is optionally mono- or polysubstituted by hydroxy, $C_{1-6}$ alkyl, $C_{2-6}$ alkenyl, $C_{2-6}$ alkynyl, $C_{1-6}$ alkoxy, a halogen atom, or a saturated or unsaturated three- to eight-membered carbocyclic or heterocyclic group, and the $C_{1-6}$ alkyl, $C_{2-6}$ alkenyl, $C_{2-6}$ alkynyl, and $C_{1-6}$ alkoxy groups are optionally substituted by a halogen atom or a saturated or unsaturated three- to eight-membered carbocyclic or heterocyclic group, (iii) a nitrogen atom substituted with a saturated or unsaturated three- to twelve-membered or heterocyclic ring system which is optionally mono- or polysubstituted by hydroxy, $C_{1-6}$ alkyl, $C_{2-6}$ alkenyl, $C_{2-6}$ alkynyl, $C_{1-6}$ alkoxy, a halogen atom, or a saturated or unsaturated three- to eight-membered carbocyclic or heterocyclic group, and the $C_{1-6}$ alkyl, $C_{2-6}$ alkenyl, $C_{2-6}$ alkynyl, and $C_{1-6}$ alkoxy groups are optionally substituted by a halogen atom or a saturated or unsaturated three- to eight-membered carbocyclic or heterocyclic group, —$R^8$ represents hydrogen, hydroxyl, halogen, $C_{1-6}$ alkoxy, $C_{1-6}$ alkylcarbonyl, carboxyl, $C_3$-$C_{10}$-cycloalkyl, $C_{1-6}$ alkoxycarbonyl, a heterocyclic group, a heterocycloalkyl group with one or two heteroatoms selected from O, N, S and 2 to 6 carbon atoms, $C_{1-6}$-alkyl, —NH—CO—$NR^9R^{10}$, —CO—$NR^9R^{10}$, —$NR^9R^{10}$;

—$R^9$ and —$R^{10}$ are independently of each other selected from hydrogen, $C_3$-$C_6$-cycloalkyl, $C_{1-6}$ alkyl optionally substituted by hydroxyl, halogen and/or $C_{1-4}$ alkoxy or —$R^9$ and —$R^{10}$ may combine with the nitrogen atom attached thereto to form a saturated or unsaturated five- or six-membered heterocyclic group, wherein the heterocyclic group is optionally substituted by hydroxyl, amino, halogen, —COOH, $C_{1-6}$ alkyl, $C_{2-6}$ alkenyl, $C_{2-6}$ alkynyl, $C_{1-6}$ alkoxy, $C_{1-6}$ alkoxycarbonyl, $C_{1-6}$ alkylcarbonyl, $C_{1-6}$ acyloxy, a saturated or unsaturated three- to twelve-membered carbocyclic or heterocyclic ring system, wherein the $C_{1-6}$ alkyl, $C_{2-6}$ alkenyl, $C_{2-6}$ alkynyl, $C_{1-6}$ alkoxy, $C_{1-6}$ alkoxycarbonyl, $C_{1-6}$ alkylcarbonyl and/or $C_{1-6}$ acyloxy groups are optionally substituted by hydroxyl, $C_{1-6}$ alkoxy, or a saturated or unsaturated three- to twelve-membered carbocyclic or heterocyclic ring system;

wherein in the amino group one or both hydrogen atoms on said amino group are optionally substituted by $C_{1-6}$ alkyl or a saturated or unsaturated three- to twelve-membered carbocyclic or heterocyclic ring system, and the $C_{1-6}$ alkyl group is optionally substituted by hydroxyl, $C_{1-6}$ alkoxy, or a saturated or unsaturated three- to twelve-membered carbocyclic or heterocyclic ring system;

wherein the saturated or unsaturated three- to twelve-membered carbocyclic or heterocyclic ring system is optionally substituted by hydroxyl, $C_{1-6}$ alkyl, $C_{2-6}$ alkenyl, $C_{2-6}$ alkynyl, $C_{1-6}$ alkoxy, $C_{1-6}$ alkoxycarbonyl, or a saturated or unsaturated three- to twelve-membered carbocyclic or heterocyclic ring system, wherein the $C_{1-6}$ alkyl, $C_{2-6}$ alkenyl, and $C_{2-6}$ alkynyl groups are optionally substituted by hydroxyl, $C_{1-6}$ alkoxy, or a saturated or unsaturated three- to twelve-membered carbocyclic or heterocyclic ring system; when the carbocyclic or heterocyclic group is substituted by two $C_{1-6}$ alkyl groups, the two alkyl groups may combine together to form an alkylene chain; and the carbocyclic or heterocyclic group may be condensed with another saturated or unsaturated five- to seven-membered carbocyclic or heterocyclic group to form a bicyclic group.

Preferably —$R^9$ is selected from hydrogen, $C_{1-6}$-alkyl which is optionally substituted by hydroxyl, halogen and/or $C_{1-4}$-alkoxy and —$R^{10}$ is selected from $C_{1-6}$-alkyl which is optionally substituted by hydroxyl, halogen and/or $C_{1-4}$-alkoxy.

$R^{11}$-$R^{22}$ represent independently of each other linear or branched, substituted or unsubstituted $C_1$-$C_{20}$-alkyl, —H, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OPh, —OCH$_2$-Ph, —OCPh$_3$, —SH, —SCH$_3$, —SC$_2$H$_5$, —SC$_3$H$_7$, —S-cyclo-C$_3$H$_5$, —SCH(CH$_3$)$_2$, —SC(CH$_3$)$_3$, —NO$_2$, —F, —Cl, —Br, —I, —N$_3$, —CN, —OCN, —NCO, —SON, —NCS, —CHO, —COCH$_3$, —COC$_2$H$_5$, —CO$_3$H$_7$, —CO-cyclo-C$_3$H$_5$, —COCH(H$_3$)$_2$, —CO(H$_3$)$_3$, —COOH, —COCN, —COOCH$_3$, —COOC$_2$H$_5$, —COOC$_3$H$_7$, —CO-cyclo-C$_3$H$_5$, —COOCH(H$_3$)$_2$, —COOC(H$_3$)$_3$, —OOC—CH$_3$, —OOC—C$_2$H$_5$, —OOC—C$_3$H$_7$, —OOC-cyclo-C$_3$H$_5$, —OOC—CH(CH$_3$)$_2$, —OOC—(CH$_3$)$_3$, —CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON(cyclo-C$_3$H$_5$)$_2$, —CON[CH(CH$_3$)$_2$]$_2$, —CON[C(CH$_3$)$_3$]$_2$, —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —N[C(CH$_3$)$_3$]$_2$, —SOCH$_3$, —SOC$_2$H$_5$, —SO$_3$H$_7$, —SO-cyclo-C$_3$H$_5$, —SOCH(CH$_3$)$_2$, —SOC(CH$_3$)$_3$, —SO$_2$CH$_3$, —SO$_2$C$_2$H$_5$, —SO$_2$C$_3$H$_7$, —SO$_2$-cyclo-C$_3$H$_5$, —SO$_2$CH(CH$_3$)$_2$, —SO$_2$(CH$_3$)$_3$, —SO$_3$H, —SO$_3$CH$_3$, —OCHF$_2$, —SO$_3$C$_2$H$_5$, —SO$_3$C$_3$H$_7$, —SO$_3$-cyclo-C$_3$H$_5$, —SO$_3$CH(CH$_3$)$_2$, —SO$_3$(CH$_3$)$_3$, —OCF$_3$, —OC$_2$F$_5$, —O—COOCH$_3$, —O—COOC$_2$H$_5$, —O—COOC$_3$H$_7$, —O—COO-cyclo-C$_3$H$_5$, —O—COOCH(CH$_3$)$_2$, —O—COOC(CH$_3$)$_3$, —NH—CO—NH$_2$, —NH—CO—NHCH$_3$, —NH—CO—NHC$_2$H$_5$, —NH—CO—NHC$_3$H$_7$, —NH—CO—NH-cyclo-C$_3$H$_5$, —NH—CO—NH[CH(CH$_3$)$_2$], —NH—CO—NH[C(CH$_3$)$_3$], —NH—CO—N(CH$_3$)$_2$, —NH—CO—N(C$_2$H$_5$)$_2$, —NH—CO—N(C$_3$H$_7$)$_2$, —NH—CO—N(cyclo-C$_3$H$_5$)$_2$, —NH—CO—N[CH(H$_3$)$_2$]$_2$, —NH—CO—N[C(CH$_3$)$_3$]$_2$, —NH—CS—NH$_2$, —NH—CS—NH-cyclo-C$_3$H$_5$, —NH—CS—NHC$_3$H$_7$, —NH—CS—NH[CH(CH$_3$)$_2$], —NH—CS—NH[C(CH$_3$)$_3$], —NH—CS—N(CH$_3$)$_2$, —NH—CS—N(C$_2$H$_5$)$_2$, —NH—CS—N(C$_3$H$_7$)$_2$, —NH—CS—N(cyclo-C$_3$H$_5$)$_2$, —NH—CS—N[CH(H$_3$)$_2$]$_2$, —NH—CS—N[C(CH$_3$)$_3$]$_2$, —NH—C(=NH)—NH$_2$, —NH—C(=NH)—NHCH$_3$, —NH—C(=NH)—NHC$_2$H$_5$, —NH—CS—NHC$_2$H$_5$, —NH—C(=NH)—NHC$_3$H$_7$, —NH—C(=NH)—NH-cyclo-C$_3$H$_5$, —NH—C(=NH)—NH[CH(CH$_3$)$_2$], —NH—C(=NH)—NH[C(CH$_3$)$_3$], —NH—CS—NHCH$_3$, —NH—C(=NH)—N(CH$_3$)$_2$, —NH—C(=NH)—N(C$_2$H$_5$)$_2$, —NH—C(=NH)—N(C$_3$H$_7$)$_2$, —NH—C(=NH)—N(cyclo-C$_3$H$_5$)$_2$, —NH—C(=NH)—N[CH(H$_3$)$_2$]$_2$, —NH—C(=NH)—N[C(CH$_3$)$_3$]$_2$, —O—CO—NH$_2$, —O—CO—NHCH$_3$, —O—CO—NHC$_2$H$_5$, —O—CO—NHC$_3$H$_7$, —O—CO—NH-cyclo-C$_3$H$_5$, —O—CO—NH[CH(CH$_3$)$_2$], —O—CO—NH[C(CH$_3$)$_3$], —O—CO—N(CH$_3$)$_2$, —O—CO—N(C$_2$H$_5$)$_2$, —O—CO—N(C$_3$H$_7$)$_2$, —O—CO—N(cyclo-C$_3$H$_5$)$_2$, —O—CO—N[CH(H$_3$)$_2$]$_2$, —O—CO—N[C(CH$_3$)$_3$]$_2$, —O—CO—OCH$_3$, —O—CO—OC$_2$H$_5$, —O—CO—OC$_3$H$_7$, —O—CO—O-cyclo-C$_3$H$_5$, —O—CO—OCH(CH$_3$)$_2$, —O—CO—O(CH$_3$)$_3$, —CH$_2$F—CHF$_2$, —CF$_3$, —CH$_2$Cl, —CHCl$_2$, —CCl$_3$, —CH$_2$Br—CHBr$_2$, —CBr$_3$, —CH$_2$I—CHI$_2$, —CI$_3$, —CH$_2$—CH$_2$F—CH$_2$—CHF$_2$, —CH$_2$—CF$_3$, —CH$_2$—CH$_2$Cl, —CH$_2$—CHCl$_2$, —CH$_2$—CCl$_3$, —CH$_2$—CH$_2$Br—CH$_2$—CHBr$_2$, —CH$_2$—CBr$_3$, —CH$_2$—CH$_2$I, —CH$_2$—CHI$_2$, —CH$_2$—Cl$_3$, —CH$_3$, —C$_2$H$_5$, —C$_3$H$_7$, -cyclo-C$_3$H$_5$, —CH(CH$_3$)$_2$, —C(CH$_3$)$_3$, —C$_4$H$_9$, —CH$_2$—CH(CH$_3$)$_2$, —CH(CH$_3$)—C$_2$H$_5$, —C(CH$_3$)$_3$, -Ph, —CH$_2$-Ph, —CPh$_3$, —CH=CH$_2$, —CH$_2$—CH=CH$_2$, —C(CH$_3$)=CH$_2$, —CH=CH—CH$_3$, —C$_2$H$_4$—CH=CH$_2$, —CH=C(CH$_3$)$_2$, —C≡CH, —C≡C—CH$_3$, —CH$_2$—C≡CH, —Si(CH$_3$)$_3$, and stereoisomeric forms, solvates, hydrates and/or pharmaceutically acceptable salts thereof.

As used herein, the term "$C_{1-6}$ alkyl" or "linear or branched $C_1$-$C_6$-alkyl" refers to —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —CH(CH$_3$)—C$_3$H$_7$, —CH$_2$—CH(CH$_3$)—C$_2$H$_5$, —CH(CH$_3$)—CH(CH$_3$)$_2$, —C$_5$H$_{11}$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, and —CH(CH$_3$)—C(CH$_3$)$_3$, wherein in the afore-mentioned groups one or more hydrogen atoms can be replaced by —OH, —OCH$_3$, —OC$_2$H$_5$, —SH, —SCH$_3$, —SC$_2$H$_5$, —NO$_2$, —F, —Cl, —Br, —I, —N$_3$, —COCH$_3$, —COC$_2$H$_5$, —COOCH$_3$, —COOC$_2$H$_5$, —OOC—CH$_3$, —OOC—C$_2$H$_5$, —COOH, —CONH$_2$, —CON(CH$_3$)$_2$, —CON(C$_2$H$_5$)$_2$, —NH$_2$, —NHCH$_3$, —NHC$_2$H$_5$, —N(CH$_3$)$_2$, —N(C$_2$H$_5$)$_2$, —SOCH$_3$, —SOC$_2$H$_5$, —SO$_3$H, —OCF$_3$, —CF$_3$, —C≡CH.

Preferred are —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, and —C$_5$H$_{11}$. Especially preferred are —CH$_3$, —C$_2$H$_5$, —C$_3$H$_7$.

As used herein, the term "$C_3$-$C_{10}$-cycloalkyl" or "carbocyclic group" refers to

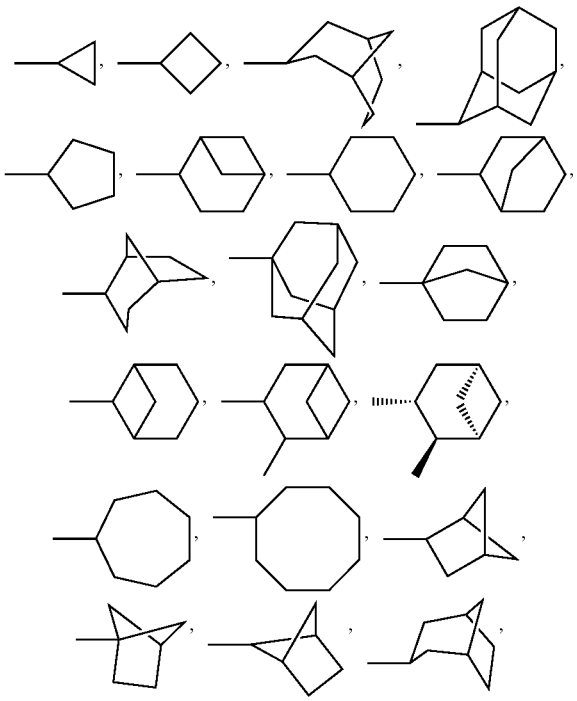

-continued

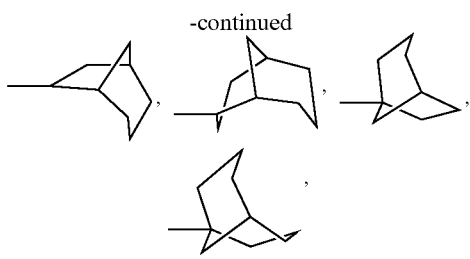

Preferred are the following cycloalkyls:

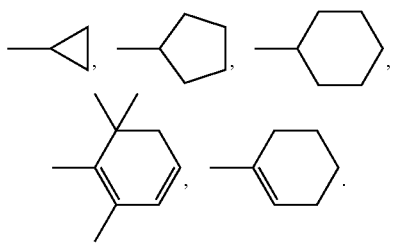

As used herein, the term "$C_{2-6}$ alkenyl" or "linear or branched $C_2$-$C_6$-alkenyl" refers to —CH=CH$_2$, —CH$_2$—CH=CH$_2$, —CH=CH—CH$_3$, —C$_2$H$_4$—CH=CH$_2$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH=CH$_2$, —C$_3$H$_6$—CH=CH$_2$, —C$_2$H$_4$—CH=CH—CH$_3$, —CH$_2$—CH=CH—C$_2$H$_5$, —CH=CH—C$_3$H$_7$, —CH$_2$—CH=CH—CH=CH$_2$, —CH=CH—CH=CH—CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —C$_2$H$_4$—C(CH$_3$)=CH$_2$, —CH$_2$—CH(CH$_3$)—CH=CH$_2$, —CH(CH$_3$)—CH$_2$—CH=CH$_2$, —CH$_2$—CH=C(CH$_3$)$_2$, —CH$_2$—C(CH$_3$)=CH—CH$_3$, —CH(CH$_3$)—CH=CH—CH$_3$, —CH=CH—CH(CH$_3$)$_2$, —CH=C(CH$_3$)—C$_2$H$_5$, —C(CH$_3$)=CH—C$_2$H$_5$, —C(CH$_3$)=C(CH$_3$)$_2$, —C(CH$_3$)$_2$—CH=CH$_2$, —CH(CH$_3$)—C(CH$_3$)=CH$_2$, —C(CH$_3$)=CH—CH=CH$_2$, —C(CH$_3$)—CH=CH$_2$, —CH=CH—C(CH$_3$)=CH$_2$, —C$_4$H$_8$—CH=CH$_2$, —C$_3$H$_6$—CH=CH—CH$_3$, —C$_2$H$_4$—CH=CH—C$_2$H$_5$, —CH$_2$—CH=CH—C$_3$H$_7$, —CH=CH—C$_4$H$_9$, —C$_3$H$_6$—C(CH$_3$)=CH$_2$, —C$_2$H$_4$—CH(CH$_3$)—CH=CH$_2$, —CH$_2$—CH(CH$_3$)—CH$_2$—CH=CH$_2$, —CH$_2$—CH=CH—CH$_3$, —CH(CH$_3$)—C$_2$H$_4$—CH=CH$_2$, —C$_2$H$_4$—CH=C(CH$_3$)$_2$, —C$_2$H$_4$—C(CH$_3$)=CH—CH$_3$, —CH$_2$—CH(CH$_3$)—CH=CH—CH$_3$, —CH(CH$_3$)—CH$_2$—CH=CH—CH$_3$, —C(CH$_3$)=CH$_2$, —CH$_2$—CH=CH—CH(CH$_3$)$_2$, —CH$_2$—CH=C(CH$_3$)—C$_2$H$_5$, —CH$_2$—C(CH$_3$)=CH—C$_2$H$_5$, —CH(CH$_3$)—CH=CH—C$_2$H$_5$, —CH=CH—CH$_2$—CH(CH$_3$)$_2$, —CH=CH—CH(CH$_3$)—C$_2$H$_5$, —CH=C(CH$_3$)—C$_3$H$_7$, —C(CH$_3$)=CH—C$_3$H$_7$, —CH$_2$—CH(CH$_3$)—C(CH$_3$)=CH$_2$, —CH(CH$_3$)—CH$_2$—C(CH$_3$)=CH$_2$, —CH(CH$_3$)—CH(CH$_3$)—CH=CH$_2$, —CH$_2$—C(CH$_3$)$_2$—CH=CH$_2$, —C(CH$_3$)$_2$—CH$_2$—CH=CH$_2$, —CH$_2$—C(CH$_3$)=C(CH$_3$)$_2$, —CH(CH$_3$)—CH=C(CH$_3$)$_2$, —C(CH$_3$)$_2$—CH=CH—CH$_3$, —CH(CH$_3$)—C(CH$_3$) =CH—CH$_3$, —CH=C(CH$_3$)—CH(CH$_3$)$_2$, —C(CH$_3$) =CH—CH(CH$_3$)$_2$, —C(CH$_3$)=C(CH$_3$)—C$_2$H$_5$, —C(CH$_3$)$_2$—C(CH$_3$)=CH$_2$, —CH(C$_2$H$_5$)—C(CH$_3$)=CH$_2$, —C(CH$_3$)(C$_2$H$_5$)—CH=CH$_2$, —CH(CH$_3$)—C(C$_2$H$_5$) =CH$_2$, —CH$_2$—C(C$_2$H$_5$)=CH—CH$_3$, —C[CH$_2$—CH (CH$_3$)$_2$]=CH$_2$, —C$_2$H$_4$—CH=CH—CH=CH$_2$, —CH$_2$—CH=CH—CH$_2$—CH=CH$_2$, —CH=CH—C$_2$H$_4$—CH=CH$_2$, —CH=CH—C(CH$_3$)$_3$, —CH$_2$—CH=CH—CH=CH—CH$_3$, —CH=CH—CH$_2$—CH=CH—CH$_3$, —C[CH(CH$_3$)(C$_2$H$_5$)]=CH$_2$, —CH=CH—CH=C$_2$H$_5$, —CH$_2$—CH=CH—C(CH$_3$)=CH$_2$, —C(C$_2$H$_5$)=CH—C$_2$H$_5$, —CH$_2$—CH=C(CH$_3$)—CH=CH$_2$, —CH$_2$—C(CH$_3$)=CH—CH=CH$_2$, —C(C$_2$H$_5$)=C(CH$_3$)$_2$, —CH(CH$_3$)—CH=CH—CH=CH$_2$, —CH=CH—CH$_2$—C(CH$_3$)=CH$_2$, —C(C$_4$H$_9$)=CH$_2$, —CH=CH—CH(CH$_3$)—CH=CH$_2$, —CH=C(CH$_3$)—CH$_2$—CH=CH$_2$, —C[C(CH$_3$)$_3$]=CH$_2$, —CH=C(CH$_3$)—CH=CH—CH$_3$, —C(CH$_3$)=CH—CH$_2$—CH=CH$_2$, —CH(C$_2$H$_5$)—CH=CH—CH$_3$, —CH=CH—C(CH$_3$) =CH—CH$_3$, —CH=CH—CH=C(CH$_3$)$_2$, —C(C$_3$H$_7$) =CH—CH$_3$, —C(CH$_3$)=CH—CH=CH—CH$_3$, —CH=C(CH$_3$)—C(CH$_3$)=CH$_2$, —CH$_2$—C(C$_3$H$_7$) =CH$_2$, —C(CH$_3$)=CH—C(CH$_3$)=CH$_2$, —C(CH$_3$)=C (CH$_3$)—CH=CH$_2$, and —CH=CH—CH=CH—CH=CH$_2$.

Preferred are —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$. Especially preferred are —CH=CH$_2$, —CH$_2$—CH=CH$_2$.

As used herein, the term "$C_{2-6}$ alkynyl" or "linear or branched $C_2$-$C_6$-alkynyl" refers to —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —C$_3$H$_6$—C≡CH, —C$_2$H$_4$—C≡C—CH$_3$, —CH$_2$—C≡C—C$_2$H$_5$, —C≡C—C$_3$H$_7$, —CH(CH$_3$)—C≡CH, —CH$_2$—CH(CH$_3$)—C≡CH, —CH(CH$_3$)—CH$_2$—C≡CH, —CH(CH$_3$)—C≡C—CH$_3$, —C$_4$H$_8$—C≡CH, —C$_3$H$_6$—C≡C—CH$_3$, —C$_2$H$_4$—C≡C—C$_2$H$_5$, —CH$_2$—C≡C—C$_3$H$_7$, —C$_2$H$_4$—CH (CH$_3$)—C≡CH, —CH$_2$—CH(CH$_3$)—CH$_2$—C≡CH, —CH(CH$_3$)—C$_2$H$_4$—C≡CH, —CH$_2$—CH(CH$_3$)—C≡C—CH$_3$, —CH(CH$_3$)—CH$_2$—C≡C—CH$_3$, —CH (CH$_3$)—C≡C—C$_2$H$_5$, —CH$_2$—C≡C—CH(CH$_3$)$_2$, —C≡C—CH(CH$_3$)—C$_2$H$_5$, —C≡C—CH$_2$—CH(CH$_3$)$_2$, —C≡C—C$_4$H$_9$, —C≡C—C(CH$_3$)$_3$, —CH(C$_2$H$_5$)—C≡C—CH$_3$, —C(CH$_3$)$_2$—C≡C—CH$_3$, —CH(C$_2$H$_5$)—CH$_2$—C≡CH, —CH$_2$—CH(C$_2$H$_5$)—C≡CH, —C(CH$_3$)$_2$—CH$_2$—C≡CH, —CH$_2$—C(CH$_3$)$_2$—C≡CH, —CH(CH$_3$)—CH(CH$_3$)—C≡CH, —CH(C$_3$H$_7$)—C≡CH, —C(CH$_3$)(C$_2$H$_5$)—C≡CH, —C≡C—C≡CH, —CH$_2$—C≡C—C≡CH, —C≡C—C≡C—CH$_3$, —CH(C≡CH)$_2$, —C$_2$H$_4$—C≡C—C≡CH, —CH$_2$—C≡C—C≡CH, —C≡C—C$_2$H$_4$—C≡CH, —CH$_2$—C≡C—C≡C—CH$_3$, —C≡C—CH$_2$—C≡C—CH$_3$, —C≡C—C≡C—C$_2$H$_5$, —C≡C—CH(CH$_3$)—C≡CH, —CH(CH$_3$)—C≡C—C≡CH, —CH(C≡CH)—CH$_2$—C≡CH, —C(C≡CH)$_2$—CH$_3$, —CH$_2$—CH(C≡CH)$_2$, —CH(C≡CH)—C≡C—CH$_3$. Preferred are —C≡CH and —C≡C—CH$_3$.

As used herein, the term "aryl" or "carbocyclic group" refers to phenyl, indenyl, indanyl, naphthyl, 1,2-dihydronaphthyl, 2,3-dihydronaphthyl, 1,2,3,4-tetrahydronaphthyl (tetralinyl), fluorenyl, anthryl (anthracenyl), 9,10-dihydroanthryl, 1,2,3,4-tetrahydro-anthryl, 1,2,3,4,5,6,7,8-octahydroanthryl, azulenyl, diphenylmethyl, benzyl, triphenylmethyl (trityl), styryl, naphthoquinonyl, acenaphthyl, anthraquinonyl, phenanthryl (phenanthrenyl) and especially to a mono- or bicyclic 6 to 10 membered ring system, preferably phenyl or napthyl.

As used herein, the term "heteroaryl" or "heterocyclic ring" or "heterocyclic group" refers to heteroaromatic groups which have from 5 to 10 ring atoms, from 1 to 4 of which are selected from O, N and/or S. Preferred groups have 1 or 2 heteroatoms in a 5- or 6-membered aromatic ring. Mono and bicyclic ring systems are included. Typical heteroaryl groups which are at least partially aromatic include pyridyl, furyl, thienyl, pyrrolyl, oxazolyl, thiazolyl, imidazolyl, isoxazolyl, isothiazolyl, oxadiazolyl, pyridazinyl, pyrimidyl, pyrazinyl, 1,3,5-triazinyl, 1,2,3-triazolyl, 1,3,4-thiadiazolyl, indolizinyl, indolyl, isoindolyl, benzo[b]furyl, thiophenyl, benzo[b]thienyl, indazolyl, benzimidazolyl, benzthiazolyl, thiazolyl, purinyl, quinolizinyl, quinolyl, isoquinolyl, quinazolinyl, quinoxalinyl, 1,8-naphthyridinyl, tetrahydroquinolyl, benzooxazolyl, chrom-2-onyl, indazolyl, indenyl. Said herteroaryl groups may further be substituted by one, two, three, four, five or more substituents selected from the group consisting of $R^{18}$-$R^{30}$, linear or branched $C_1$-$C_6$-alkyl, $C_3$-$C_6$-cycloalkyl, linear or branched $C_2$-$C_6$-alkenyl, linear or branched $C_2$-$C_6$-alkynyl and aryl.

Preferred heterocyclic groups from which also $R^7$ can be selected are:

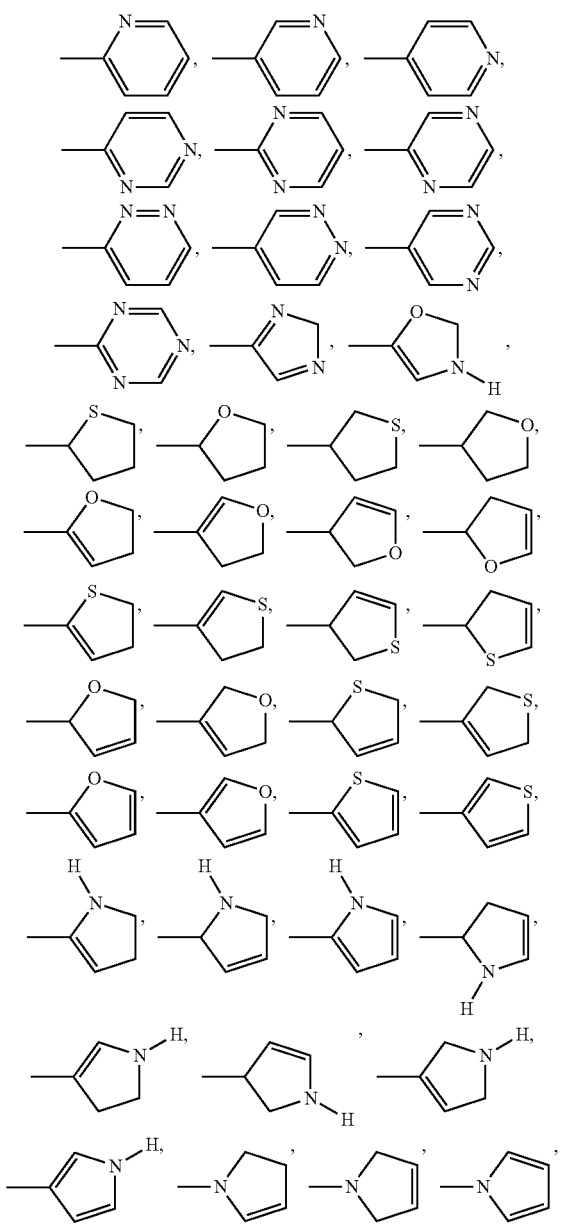
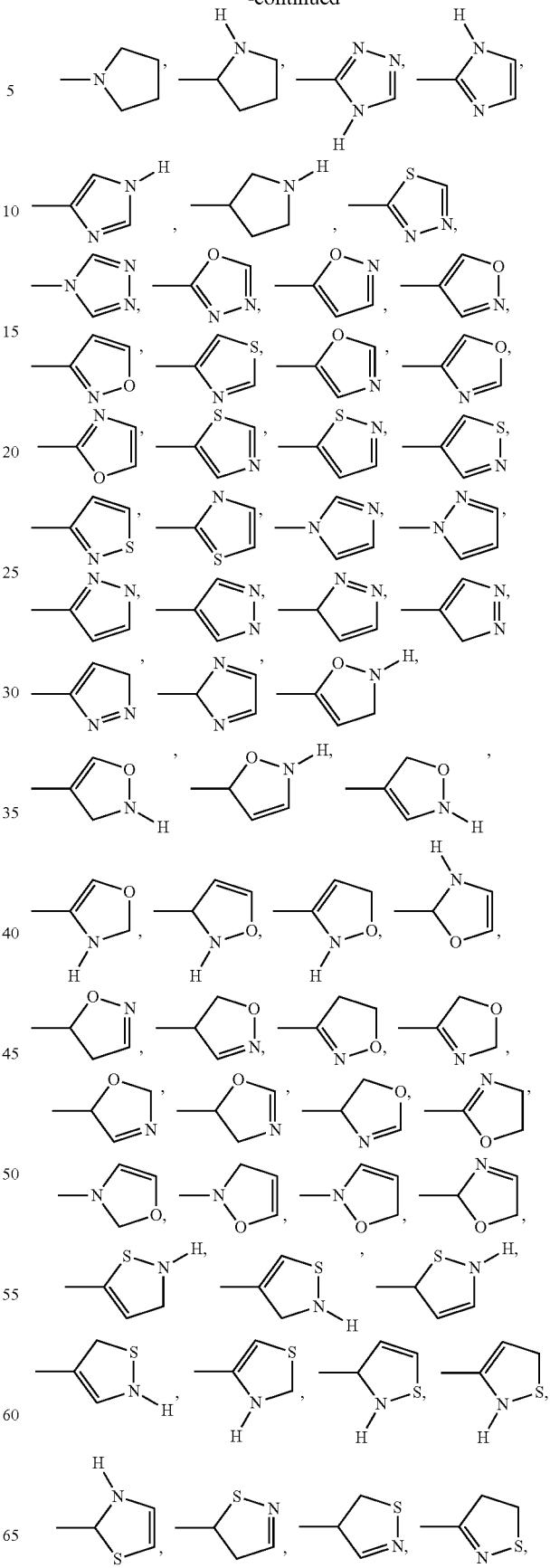

-continued
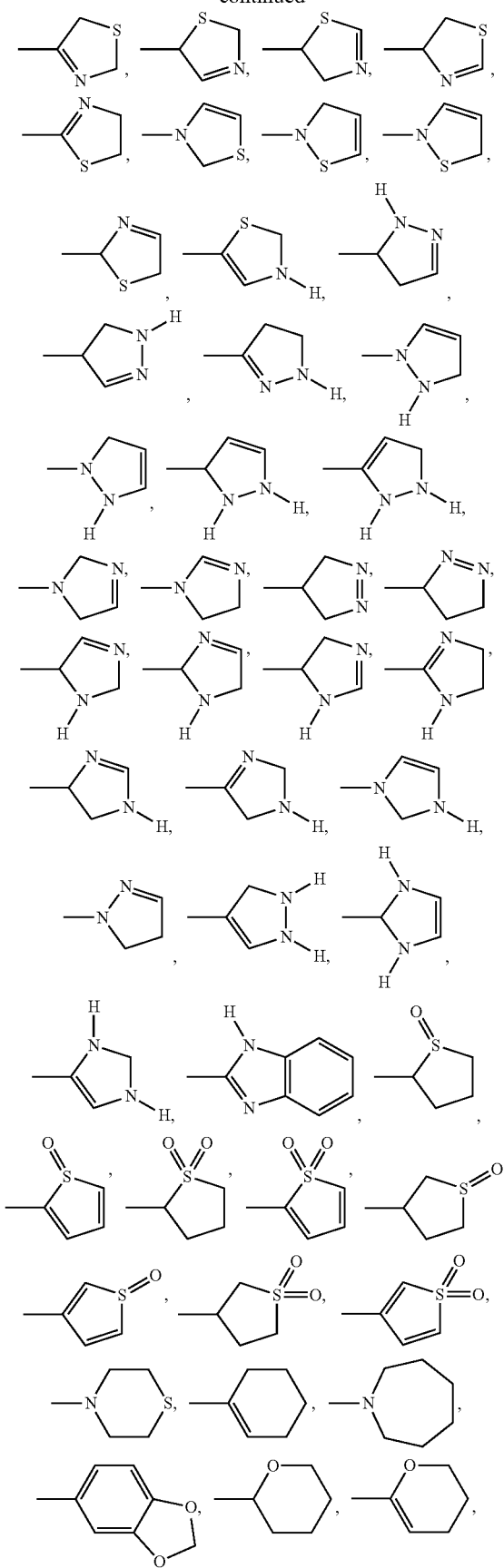
-continued
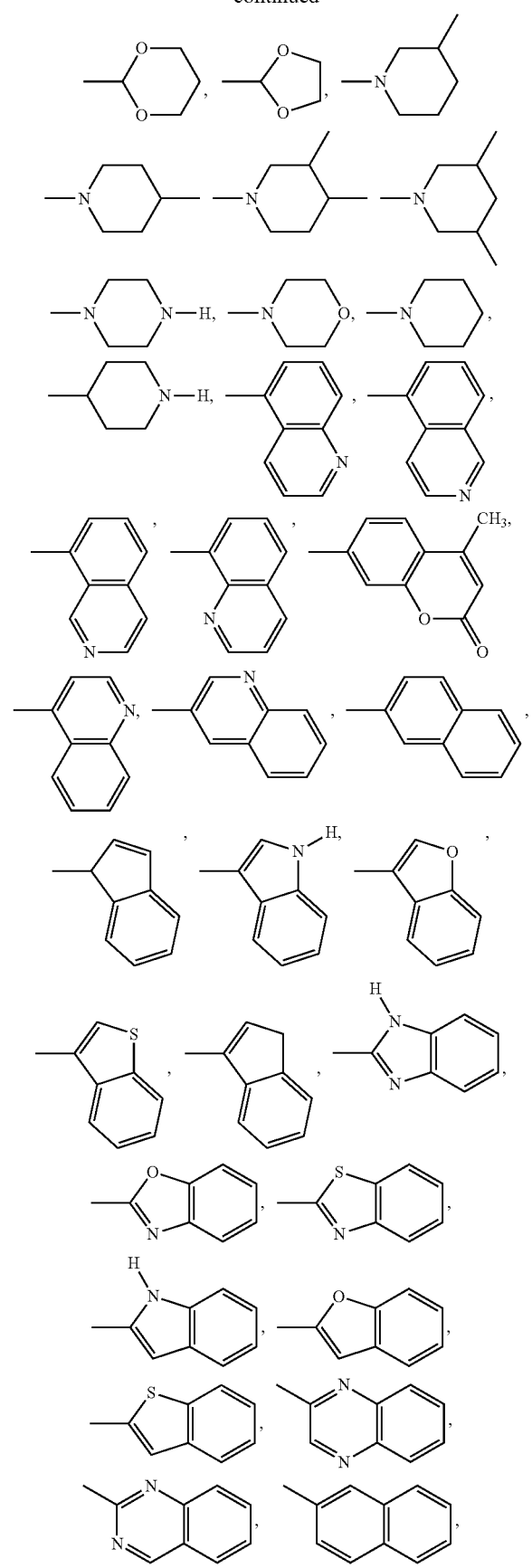

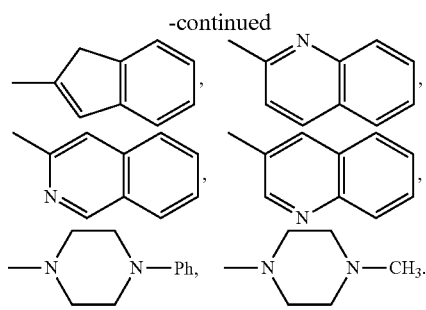

$R^7$ can also be selected from the above-mentioned heterocyclic groups. In addition $R^7$ can also stand for the following residue:

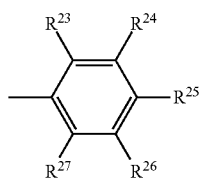

wherein $R^{23}$ to $R^{27}$ are independently of each other selected from the substituents mentioned below.

Preferred heterocyclic —$NR^9R^{10}$ groups are:

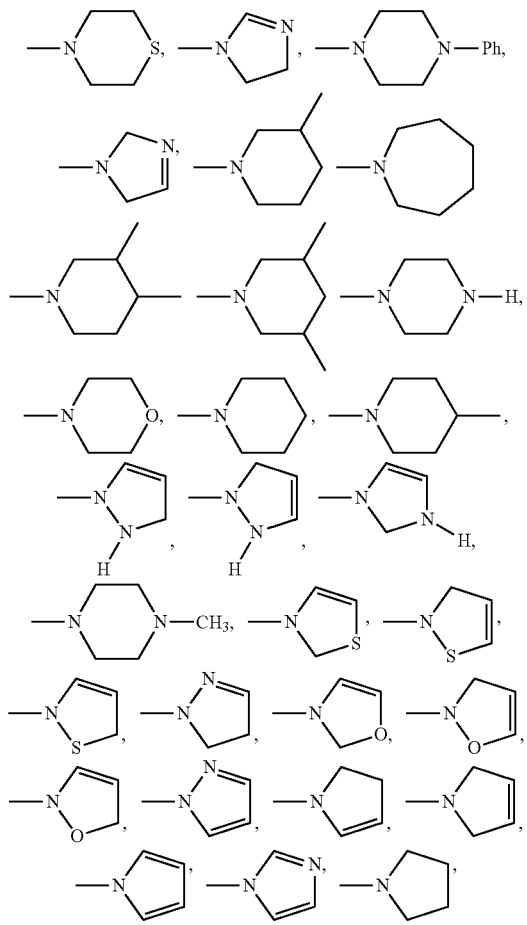

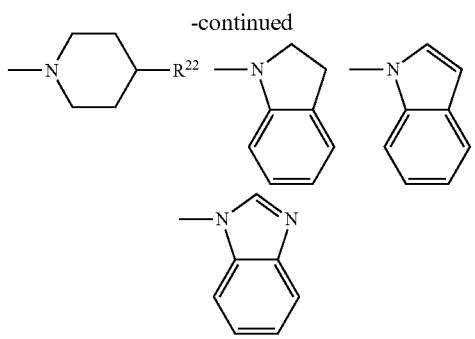

Said preferred herteroaryl groups and heterocyclic groups may further be substituted by one, two, three, four, five or more substituents selected from the group consisting of $R^{23}$-$R^{35}$, linear or branched $C_1$-$C_6$-alkyl, $C_3$-$C_{10}$-cycloalkyl, linear or branched $C_2$-$C_6$-alkenyl, linear or branched $C_2$-$C_6$-alkynyl and aryl.

As used herein, the term "heterocyclic group" or "heterocyclic ring" or "heterocyclic ring system" or "heterocyclyl" refers to carbocycles having at least one heteroatom in the ring such as oxygen, nitrogen, or sulfur. Such heterocycles may be saturated or partially unsaturated but not aromatic. Examples for heterocyclic residues are 1,3-dioxolane, benzo[1,3]dioxolyl, pyrazolinyl, pyranyl, thiomorpholinyl, pyrazolidinyl, piperidyl, piperazinyl, 1,4-dioxanyl, imidazolinyl, pyrrolinyl, imidazolidinyl, morpholinyl, 1,4-dithianyl, pyrrolidinyl, oxozolinyl, oxazolidinyl, isoxazolinyl, isoxazolidinyl, thiazolinyl, thiazolidinyl, isothiazolinyl, isothiazolidinyl, dihydropyranl, pyrrolidinyl, tetrahydrothiophenyl, tetrahydrofuranyl.

Aryl refers to phenyl, substituted phenyl and heteroaryl, wherein substituted phenyl and heteroaryl have the meanings as defined above.

As used herein, the term "$C_1$-$C_6$ alkyloxy" or "$C_1$-$C_6$ alkoxy" refers to the residue —O—$C_1$-$C_6$-alkyl, wherein $C_1$-$C_6$-alkyl has the meanings as defined above. The following $C_1$-$C_6$ alkoxy groups are preferred —O—$CH_3$, —O—$C_2H_5$, —O—$C_3H_7$, —O—$CH(CH_3)_2$, —O—$C_4H_9$, —O—$CH_2$—$CH(CH_3)_2$, —O—$CH(CH_3)$—$C_2H_5$, —O—$C(CH_3)_3$, and —O—$C_5H_{11}$. Most preferred are —O—$CH_3$, —O—$C_2H_5$ and —O—$C_3H$.

As used herein, the term "$C_1$-$C_6$ alkyloxycarbonyl" or "$C_1$-$C_6$ alkoxycarbonyl" refers to the residue —CO—O—$C_1$-$C_6$-alkyl, wherein $C_1$-$C_6$-alkyl has the meanings as defined above. Preferred $C_1$-$C_6$ alkoxycarbony groups are —CO—$OCH_3$, —CO—$OC_2H_5$, —CO—$OC_3H_7$, —CO—$OCH(CH_3)_2$, —CO—$OC_4H_9$, —CO—$OCH_2$—$CH(CH_3)_2$, —CO—$OCH(CH_3)$—$C_2H_5$, —CO—$OC(CH_3)_3$, and —CO—$OC_5H_{11}$. Most preferred are —CO—$OCH_3$, —CO—$OC_2H_5$, —CO—$OC_3H_7$.

As used herein, the term "$C_1$-$C_6$ alkylcarbonyl" or "$C_1$-$C_6$ alkanoyl" or "$C_1$-$C_6$ acyl" refers to the residue —CO—$C_1$-$C_6$-alkyl, wherein $C_1$-$C_6$-alkyl has the meanings as defined above. Preferred $C_1$-$C_6$ acyl groups are —CO—$CH_3$, —CO—$C_2H_5$, —CO—$C_3H_7$, —CO—$CH(CH_3)_2$, —CO—$C_4H_9$, —CO—$CH_2$—$CH(CH_3)_2$, —CO—$CH(CH_3)$—$C_2H_5$, —CO—$C(CH_3)_3$, and —CO—$C_5H_{11}$. Most preferred are —CO—$CH_3$, —CO—$C_2H_5$, —CO—$CO_3H_7$.

As used herein, the term "$C_1$-$C_6$ alkylcarbonyloxy" or "$C_1$-$C_6$ alkanoyloxy" or "$C_1$-$C_6$ acyloxy" refers to the residue —O—CO—$C_1$-$C_6$-alkyl, wherein $C_1$-$C_6$-alkyl has the meanings as defined above. Preferred $C_1$-$C_6$ acyloxy groups are —O—CO—$CH_3$, —O—CO—$C_2H_5$, —O—CO—$C_3H_7$, —O—CO—CH(CH₃)₂, —O—CO—C₄H₉, —O—CO—CH₂—CH(CH₃)₂, —O—CO—CH(CH₃)—C₂H₅, —O—CO—C(CH₃)₃, and —O—CO—C₅H₁₁. Most preferred are —O—CO—CH₃, —O—CO—C₂H₅, —O—CO—CO₃H₇.

The term "substituted" or "substituted alkyl", "substituted cycloalkyl", "substituted heterocyclyl", "substituted aryl", "substituted heteroaryl", "substituted heterocyclic group", "substituted carboicyclic group" respectively shall refer to the addressed residue such as "alkyl", "cycloalkyl", "heterocyclyl", "aryl", or "heteroaryl" bearing one, two, three, four, five or more, preferably one or two substituents $R^{23}$ to $R^{35}$ independently selected from the following group:

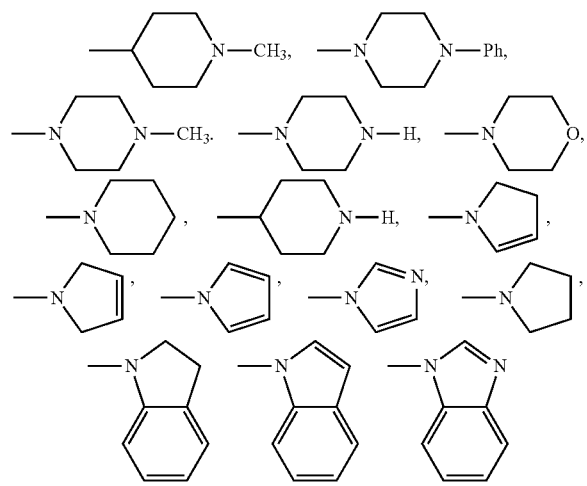

—OH, —OCH₃, —OC₂H₅, —OC₃H₇, —O-cyclo-C₃H₅, —OCH(CH₃)₂, —OC(CH₃)₃, —OC₄H₉, —OPh, —OCH₂-Ph, —OCPh₃, —SH, —SCH₃, —SC₂H₅, —SC₃H—S-cyclo-C₃H₅, —SCH(CH₃)₂, —SC(CH₃)₃, —NO₂, —F, —Cl, —Br, —I, —N₃, —CN, —OCN, —NCO, —SON, —NCS, —CHO, —COCH₃, —COC₂H₅, —CO₃H₇, —CO-cyclo-C₃H₅, —COCH(CH₃)₂, —COC(CH₃)₃, —COOH, —COCN, —COOCH₃, —COOC₂H₅, —COOC₃H₇, —COO-cyclo-C₃H₅, —COOCH(CH₃)₂, —COOC(CH₃)₃, —OOC—CH₃, —OOC—C₂H₅, —OOC—C₃H₇, —OOC-cyclo-C₃H₅, —OOC—CH(CH₃)₂, —OOC—(CH₃)₃, —OCHF₂, —CONH₂, —CONHCH₃, —CONHC₂H₅, —CONHC₃H₇, —CONH-cyclo-C₃H₅, —CONH[CH(CH₃)₂], —CONH[C(CH₃)₃], —CON(CH₃)₂, —CON(C₂H₅)₂, —CON(C₃H₇)₂, —CON(cyclo-C₃H₅)₂, —CON[CH(CH₃)₂]₂, —CON[C(CH₃)₃]₂, —NH₂, —NHCH₃, —NHC₂H₅, —NHC₃H₇, —NH-cyclo-C₃H₅, —NHCH(CH₃)₂, —NHC(CH₃)₃, —N(CH₃)₂, —N(C₂H₅)₂, —N(C₃H₇)₂, —N(cyclo-C₃H₅)₂, —N[CH(CH₃)₂]₂, —N[C(CH₃)₃]₂, —SOCH₃, —SOC₂H₅, —SO₃H₇, —SO-cyclo-C₃H₅, —SOCH(CH₃)₂, —SOC(CH₃)₃, —SO₂CH₃, —SO₂C₂H₅, —SO₂C₃H₇, —SO₂-cyclo-C₃H₅, —SO₂CH(CH₃)₂, —SO₂(CH₃)₃, —SO₃H, —SO₃CH₃, —SO₃C₂H₅, —SO₃C₃H₇, —SO₃-cyclo-C₃H₅, —SO₃CH(CH₃)₂, —SO₃(CH₃)₃, —OCF₃, —OC₂F₅, —O—COOCH₃, —O—COOC₂H₅, —O—COOC₃H₇, —O—COO-cyclo-C₃H₅, —O—COOCH(CH₃)₂, —O—COOC(CH₃)₃, —NH—CO—NH₂, —NH—CO—NHCH₃, —Si(CH₃)₃, —NH—CO—NHC₂H₅, —NH—CO—NHC₃H₇, —NH—CO—NH-cyclo-C₃H₅, —O—CO—NH₂, —O—CO—NHCH₃, —O—CO—NHC₂H₅, —O—CO—NHC₃H₇, —O—CO—NH-cyclo-C₃H₅, —O—CO—NH[CH(CH₃)₂], —O—CO—NH[C(CH₃)₃], —O—CO—N(H₃)₂, —O—CO—N(C₂H₅)₂, —O—CO—N(C₃H₇)₂, —O—CO—N(cyclo-C₃H₅)₂, —O—CO—N[CH(H₃)₂]₂, —O—CO—N[C(CH₃)₃]₂, —O—OCH₃, —O—CO—OC₂H₅, —O—CO₃H₇, —O—CO—O-cyclo-C₃H₅, —O—CO—OCH(CH₃)₂, —O—CO(CH₃)₃, —CH₂F—CHF₂, —CF₃, —CH₂Cl, —CHCl₂, —CCl₃, —CH₂Br—CHBr₂, —CBr₃, —CH₂I—CHI₂, —Cl₃, —CH₂—CH₂F—CH₂—CHF₂, —CH₂—CF₃, —CH₂—CH₂Cl, —CH₂—CHCl₂, —CH₂—CCl₃, —CH₂—CH₂Br—CH₂—CHBr₂, —CH₂—CBr₃, —CH₂—CH₂I, —CH₂—CH₂, —CH₂—Cl₃, -cyclo-C₃H₅, -Ph, —CH₂-Ph, —CPh₃, —CH═CH₂, —CH₂—CH═CH₂, —C(CH₃)═CH₂, —CH═CH—CH₃, —C₂H₄—CH═CH₂, —CH═C(CH₃)₂, —C≡CH, —C≡C—CH₃, —CH₂—C≡CH, —CH₃, —C₂H₅, —C₃H₇, —CH(CH₃)₂, —C₄H₉, —CH₂—CH(CH₃)₂, —CH(CH₃)—C₂H₅, —C(CH₃)₃, —CH(CH₃)—C₃H₇, —CH₂—CH(CH₃)—C₂H₅, —CH(CH₃)—CH(CH₃)₂, —C₅H₁₁, —C(CH₃)₂—C₂H₅, —CH₂—C(CH₃)₃, —CH(C₂H₅)₂, —C₂H₄—CH(CH₃)₂, —C₆H₁₃, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, and —CH(CH₃)—C(CH₃)₃.

Preferred residues $R^8$—X—O— are selected from:

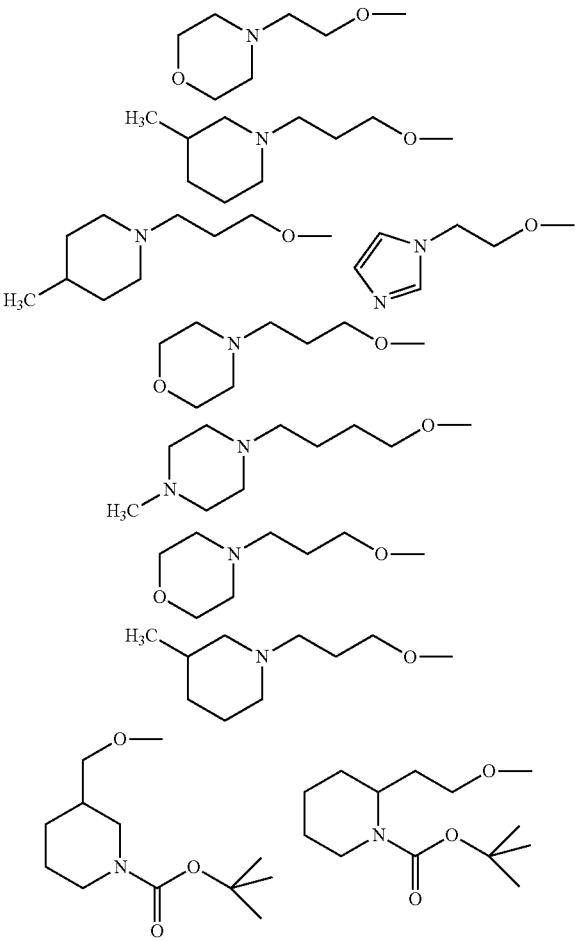

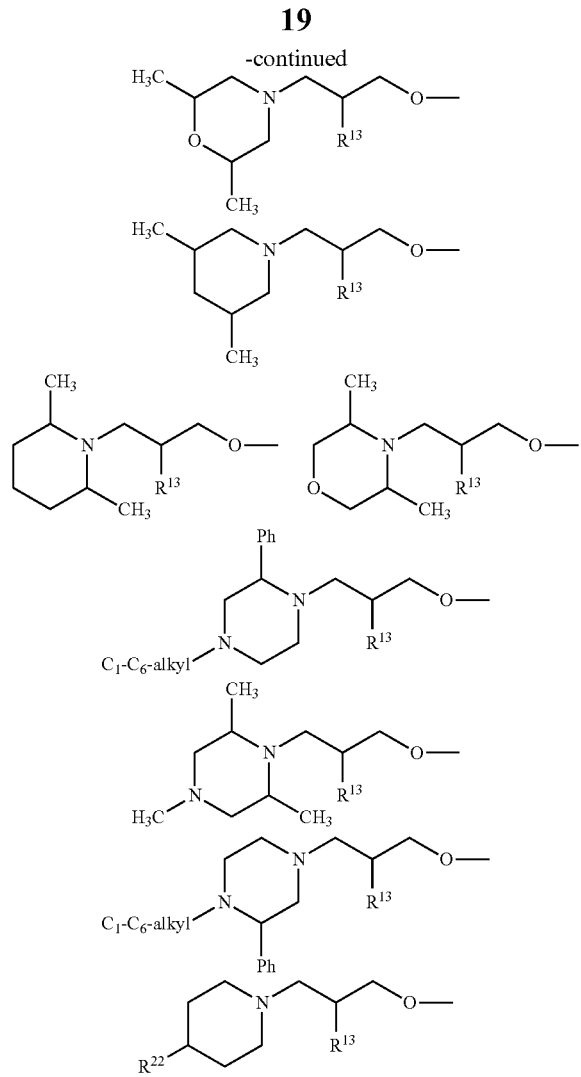

wherein
the substituent —R$^{13}$ has the meanings as defined herein;
the substituent —R$^{22}$ refers to the residues disclosed above and preferably to phenyl, benzyl, C$_1$-C$_6$-alkyl, pyrrolidin-1-yl, piperidin-1-yl, piperazin-1-yl, —OH, —CH$_2$—OH, —C$_2$H$_4$—OH, —OCH$_3$, —CH$_2$—OCH$_3$ or —C$_2$H$_4$—OCH$_3$.

Further preferred compounds of the present invention are such compounds wherein R$^8$—X—O— is selected from:

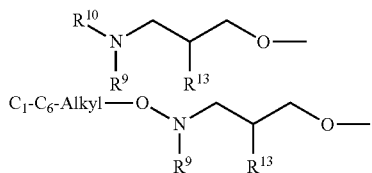

wherein
the substituents —R$^9$, —R$^{10}$, —R$^{13}$ and C$_1$-C$_6$-alkyl have the meanings as defined herein.

Another group of preferred compounds has residues R$^8$—X—O— selected from the following groups:

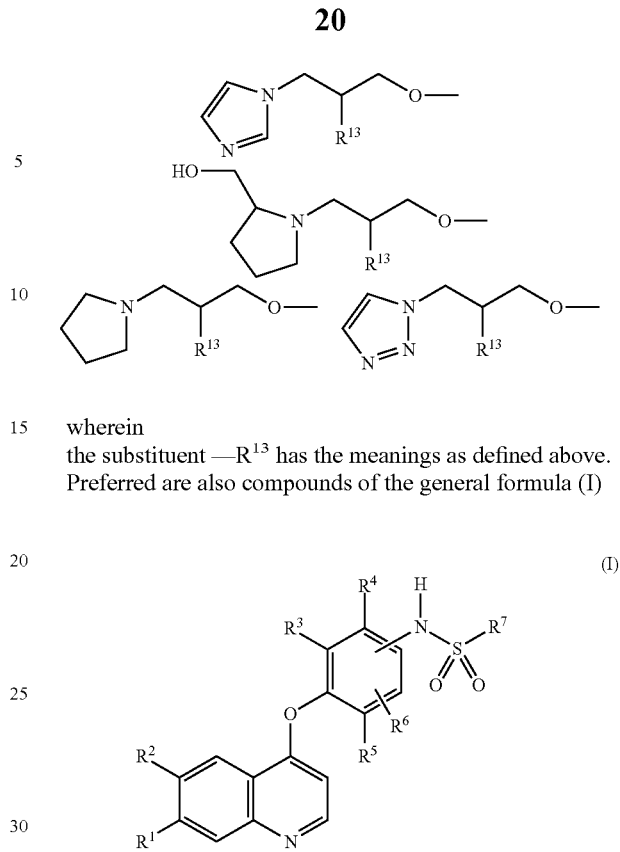

wherein
the substituent —R$^{13}$ has the meanings as defined above.
Preferred are also compounds of the general formula (I)

$$\text{(I)}$$

wherein
one of —R$^1$ and —R$^2$ represents —O—X—R$^8$;
and the other one of —R$^1$ and —R$^2$ represents —H, —OH, —OCH$_3$, —OCF$_3$, —OC$_2$H$_5$, —OC$_3$H$_7$, —OCH$_2$CH$_2$—OCH$_3$, —OCH$_2$CH$_2$—OC$_2$H$_5$;
—X— represents —CR$^{11}$R$^{12}$—, —CR$^{11}$R$^{12}$—CR$^{13}$R$^{14}$—, —CR$^{11}$R$^{12}$—CR$^{13}$R$^{14}$—CR$^{15}$R$^{16}$—, —CR$^{11}$R$^{12}$—CR$^{13}$R$^{14}$—CR$^{15}$R$^{16}$—CR$^{17}$R$^{18}$—, —CR$^{11}$R$^{12}$—CR$^{13}$R$^{14}$—CR$^{15}$R$^{16}$—CR$^{17}$R$^{18}$—CR$^{19}$R$^{20}$—, —(CH$_2$)$_n$—NH—, —CO—, —(CH$_2$)$_n$—CO—, —(CH$_2$)$_n$—NH—CO—NH—, —(CH$_2$)$_n$—NH—CO—, —(CH$_2$)$_n$—NH—CO—O—, —(CH$_2$)$_n$—CO—NR$^9$—, —(CH$_2$)$_n$—O—CO—NH—, —(CH$_2$)$_n$—O—CO—, —(CH$_2$)$_n$—O—, —(CH$_2$)$_n$—;
n is an integer selected from 1, 2, 3, 4, 5 and 6;
—R$^3$, —R$^4$, —R$^5$, —R$^6$ are independently of each other selected from —H, halogen, nitro, C$_{1-4}$-alkyl, C$_3$-C$_5$-cycloalkyl, C$_{1-6}$-alkoxy;
—R$^8$ represents —H, —OH, —F, —Cl, —Br, —I, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —CHO, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, -cyclo-C$_3$H$_5$, -cyclo-C$_4$H$_7$, -cyclo-C$_5$H$_9$, -cyclo-C$_6$H$_{11}$, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON(cyclo-C$_3$H$_5$)$_2$, —CON[CH(CH$_3$)$_2$]$_2$, —CON[C(CH$_3$)$_3$]$_2$, —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —N[C(CH$_3$)$_3$]$_2$, —OOC—CH$_3$, —OOC—C$_2$H$_5$, —OOC—C$_3$H$_7$, —OOC-cyclo-C$_3$H$_5$, —OOC—CH(CH$_3$)$_2$, —OOC—C (CH₃)₃, —NH—CO—NH₂, —NH—CO—NHCH₃, —NH—CO—NHC₂H₅, —NH—CO—NHC₃H₇, —NH—CO—NH-cyclo-C₃H₅, —NH—CO—NH[CH(CH₃)₂], —NH—CO—NH[C(CH₃)₃], —NH—CO—N(CH₃)₂, —NH—CO—N(C₂H₅)₂, —NH—CO—N(C₃H₇)₂, —NH—CO—N(cyclo-C₃H₅)₂, —NH—CO—N[CH(CH₃)₂]₂, —NH—CO—N[C(CH₃)₃]₂, —NH—COOCH₃, —NH—COOC₂H₅, —NH—COOC₃H₇, —NH—COO-cyclo-C₃H₅, —NH—COOCH(CH₃)₂, —NH—COOC(CH₃)₃, —O—CO—NH₂, —O—CO—NHCH₃, —O—CO—NHC₂H₅, —O—CO—NHC₃H₇, —O—CO—NH-cyclo-C₃H₅, —O—CO—NH[CH(CH₃)₂], —O—CO—NH[C(CH₃)₃], —O—CO—N(CH₃)₂, —O—CO—N(C₂H₅)₂, —O—CO—N(C₃H₇)₂, —O—CO—N(cyclo-C₃H₅)₂, —O—CO—N[CH(CH₃)₂]₂, —O—CO—N[C(CH₃)₃]₂, —NH—CO—NR⁹R¹⁰, —CO—NR⁹R¹⁰, —NR⁹R¹⁰, —CH₂F—CHF₂, —CF₃, —CH₂Cl, —CH₂Br, —CH₂—CH₂F, —CH₂—CH₂Cl, —CH₂—CH₂Br, —CH₃, —C₂H₅, —C₃H₇, —CH(CH₃)₂, —C(CH₃)₃, —C₄H₉, —C₅H₁₁, —CH₂—CH(CH₃)₂, —CH(CH₃)—C₂H₅, —C(CH₃)₃, -Ph, —CH₂-Ph, —CH=CH₂, —CH₂—CH=CH₂, —C≡CH,

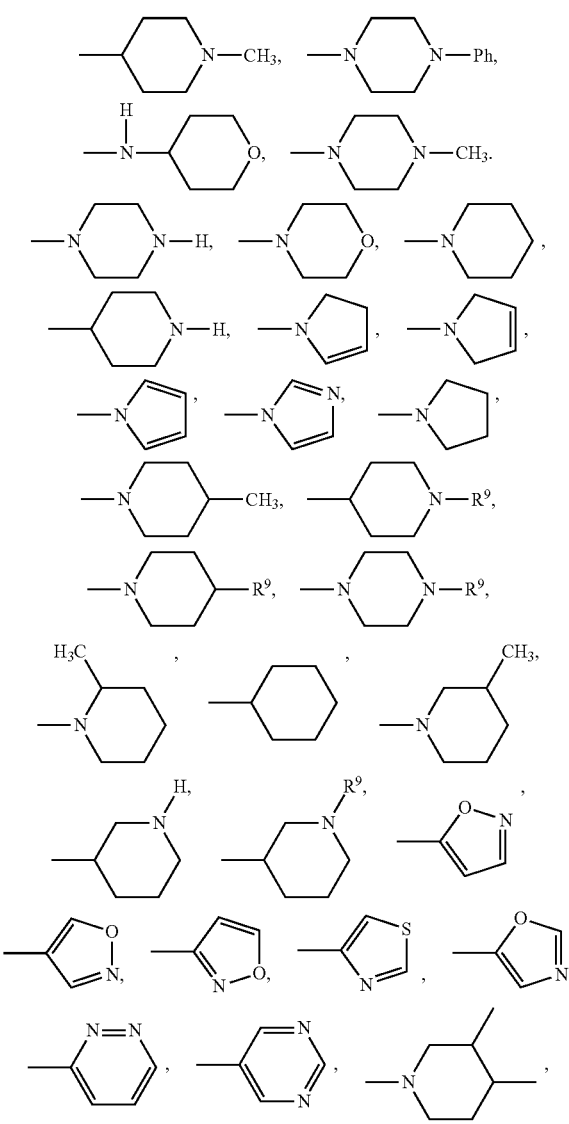

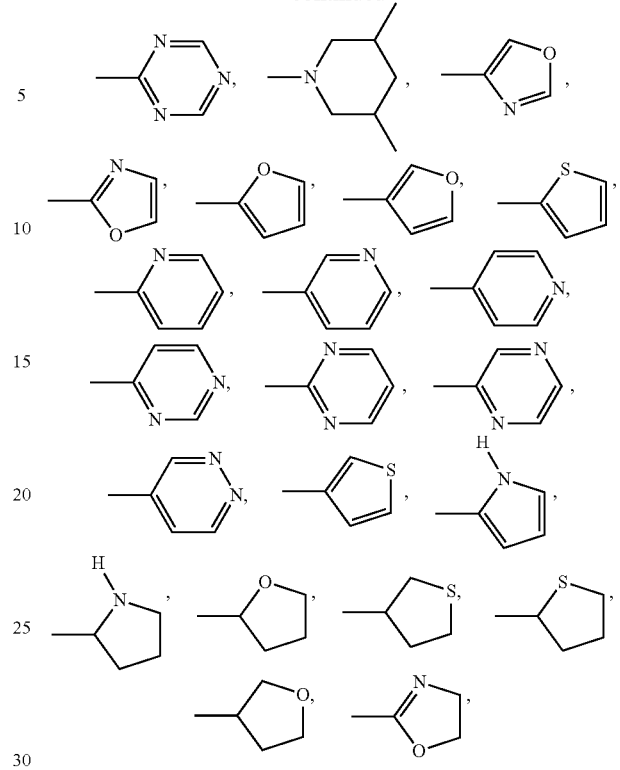

—R⁹ and —R¹⁰ are independently of each other selected from —H, —CH₂F—CHF₂, —CF₃, —CH₂Cl, —CH₂Br, —CH₂—CH₂F, —CH₂—CH₂Cl, —CH₂—CH₂Br, —CH₃, —C₂H₅, —C₃H₇, —CH(CH₃)₂, —C(CH₃)₃, —C₄H₉, —C₅H₁₁, —CH₂—CH(CH₃)₂, —CH(CH₃)—C₂H₅, —C(CH₃)₃, -cyclo-C₃H₅, -cyclo-C₄H₇, -cyclo-C₅H₉, 5-cyclo-C₆H₁₁;

—R⁷ represents one of the following groups —CH₃, —C₂H₅, —C₃H₇, —C₄H₉, —C₅H₁₁,

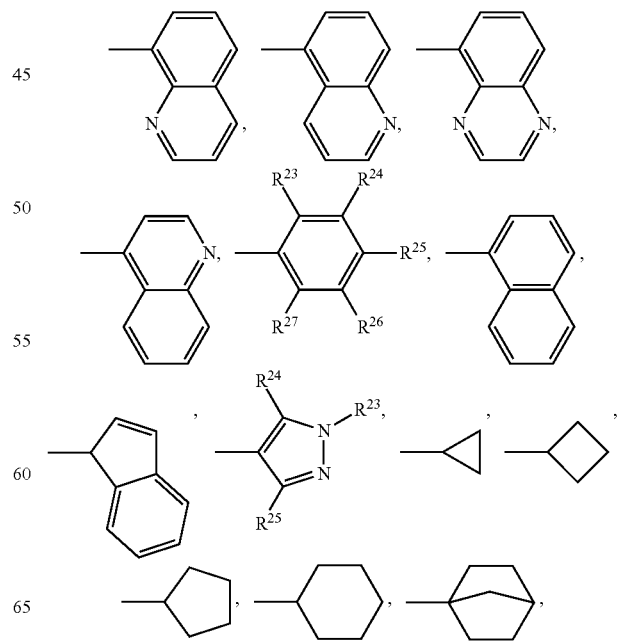

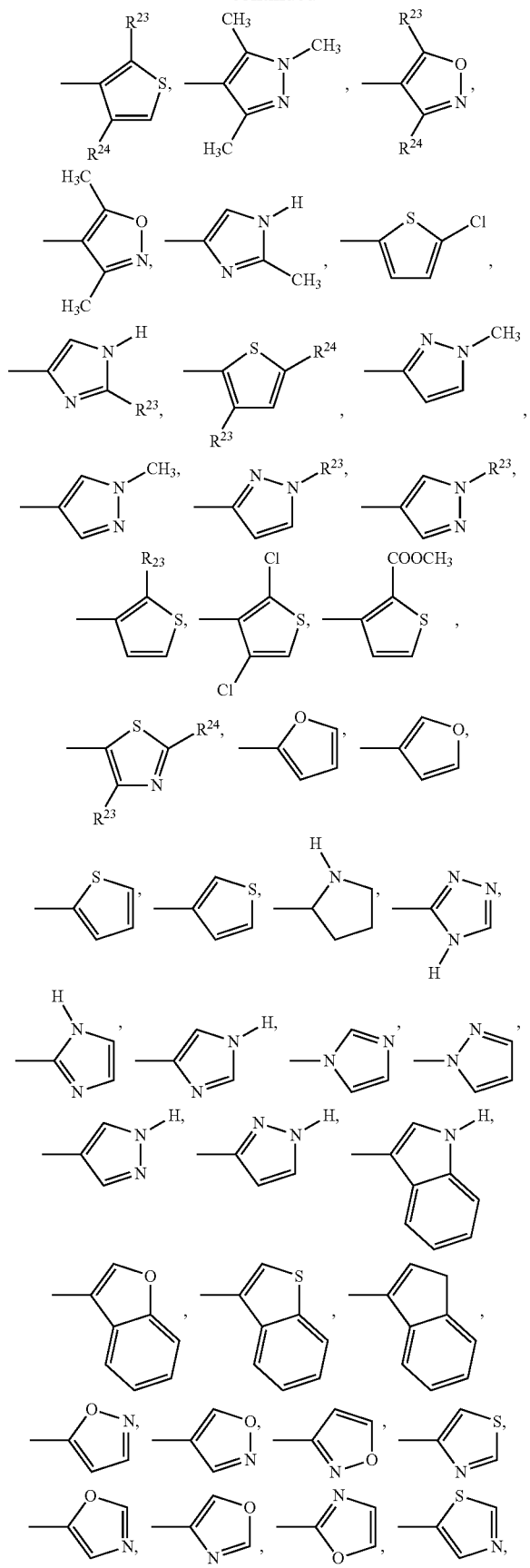
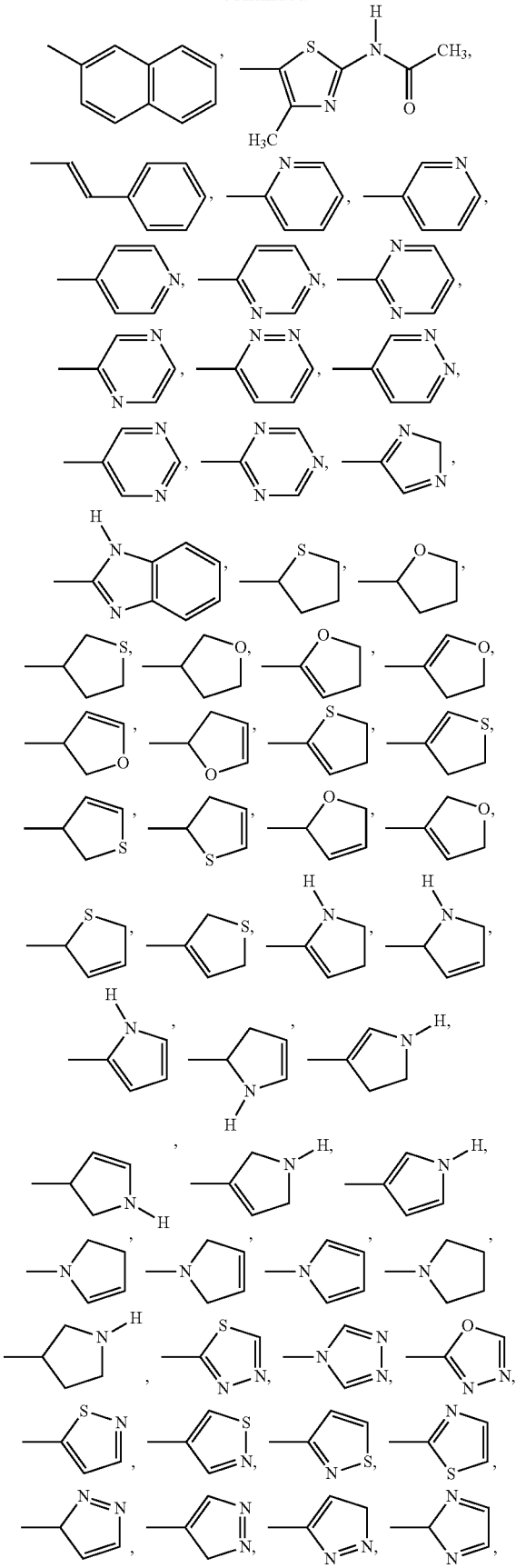

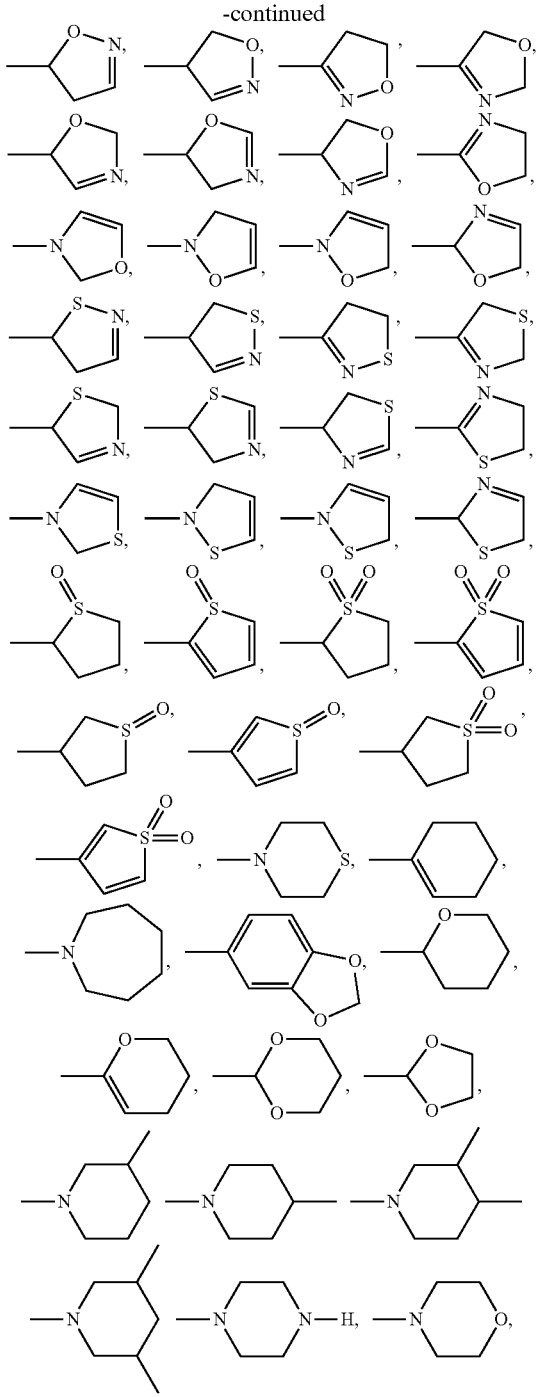

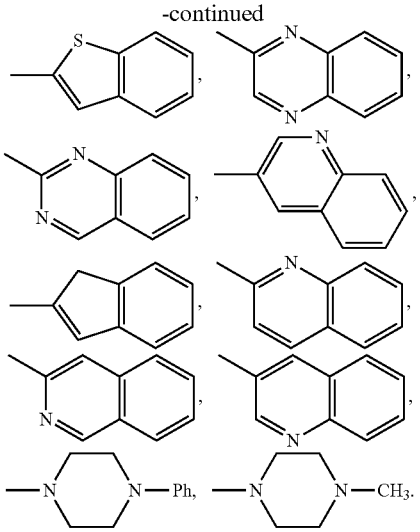

$R^{11}$-$R^{27}$ represent independently of each other —H, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OCH$_2$Ph, —OPh, —SH, —SCH$_3$, —SC$_2$H$_5$, —NO$_2$, —F, —CN, —Br, —I, —CN, —CHO, —COCH$_3$, —COC$_2$H$_5$, —COC$_3$H$_7$, —CO-cyclo-C$_3$H$_5$, —COCH(CH$_3$)$_2$, —COOH, —COOCH$_3$, —COOC$_2$H$_5$, —COOC$_3$H$_7$, —COO-cyclo-C$_3$H$_5$, —COOCH(CH$_3$)$_2$, —OOC—CH$_3$, —OOC—C$_2$H$_5$, —OOC—C$_3$H$_7$, —OOC-cyclo-C$_3$H$_5$, —OOC—CH(CH$_3$)$_2$, —CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CON(CH$_3$)$_2$, —CON(C$_2$H$_5$)$_2$, —CON(C$_3$H$_7$)$_2$, —CON(cyclo-C$_3$H$_5$)$_2$, —NH—OC—CH$_3$, —NH—OC—C$_2$H$_5$, —NH—OC—C$_3$H$_7$, —NH—OC-cyclo-C$_3$H$_5$, —NH—OC—CH(CH$_3$)$_2$, —NH—OC—C(CH$_3$)$_3$, —NH$_2$, —NHCH$_3$, —NHC$_2$H$_5$, —NHC$_3$H$_7$, —NH-cyclo-C$_3$H$_5$, —NHCH(CH$_3$)$_2$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —SOCH$_3$, —SOC$_2$H$_5$, —SO$_2$CH$_3$, —SO$_2$C$_2$H$_5$, —SO$_3$H, —SO$_3$CH$_3$, —SO$_3$C$_2$H$_5$, —SO$_3$C$_3$H$_7$, —OCF$_3$, —OC$_2$F$_5$, —OCH$_2$F—OCHF$_2$, —CH$_2$F—CHF$_2$, —CF$_3$, —CH$_2$Cl, —CH$_2$Br, —CH$_2$—CH$_2$F, —CH$_2$—CH$_2$Cl, —CH$_3$, —C$_2$H$_5$, —C$_3$H$_7$, -cyclo-C$_3$H$_5$, —CH(CH$_3$)$_2$, —C(CH$_3$)$_3$, —C$_4$H$_9$, —CH$_2$—CH(CH$_3$)$_2$, —CH(CH$_3$)—C$_2$H$_5$, —C(CH$_3$)$_3$, —CH=CH$_2$, —CH$_2$—CH=CH$_2$, —CH=CH—CH$_3$, —C≡CH, —C≡C—CH$_3$, —CH$_2$—C≡CH, -Ph, —CH$_2$-Ph, —CH=CH-Ph;

and stereoisomeric forms, solvates, hydrates and/or pharmaceutically acceptable salts thereof.

If —R$^1$ is —O—X—R$^8$, —R$^2$ is preferably —H, —OCH$_3$, —OCF$_3$, —OC$_2$H$_5$ and if —R$^2$ is —O—X—R$^8$, than —R$^1$ is preferably —H, —OCH$_3$, —OCF$_3$, —OC$_2$H$_5$.

Preferably —R$^3$, —R$^4$, —R$^5$, —R$^6$ are independently of each —OCH$_3$, —OC$_2$H$_5$, —OC$_3$H$_7$, —OCF$_3$, —F, —Cl, —Br, —I, —CH$_3$, —C$_2$H$_5$, —C$_3$H$_7$, -cyclo-C$_3$H$_5$, —CH(CH$_3$)$_2$, and more preferably —OCH$_3$, —OC$_2$H$_5$, —OCF$_3$, —F, —Cl, —Br, —CH$_3$, —C$_2$H$_5$. Moreover it is preferred if at least one of —R$^3$, —R$^4$ and —R$^5$ are selected from —F or —Cl. It is also preferred if at least one of —R$^3$ and —R$^4$ is —F and preferably —R$^3$ is —F.

Preferably —R$^7$ is one of the following groups —CH$_3$, —C$_2$H$_5$, —C$_3$H$_7$, —C$_4$H$_9$, —C$_5$H$_{11}$,

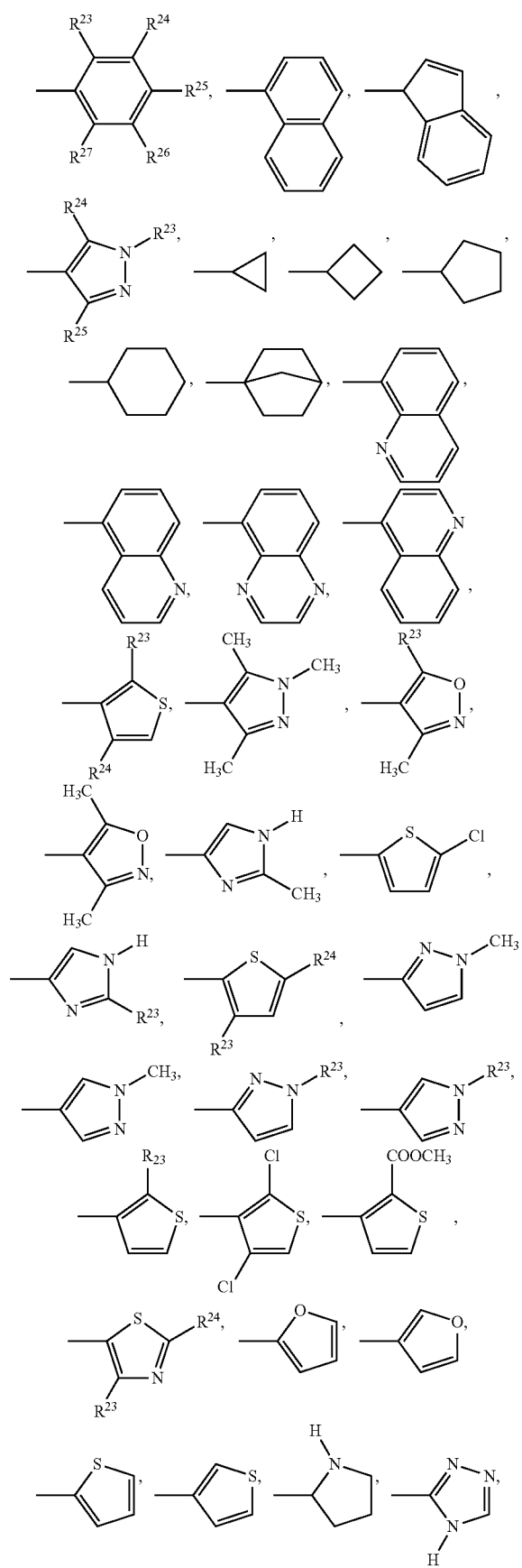
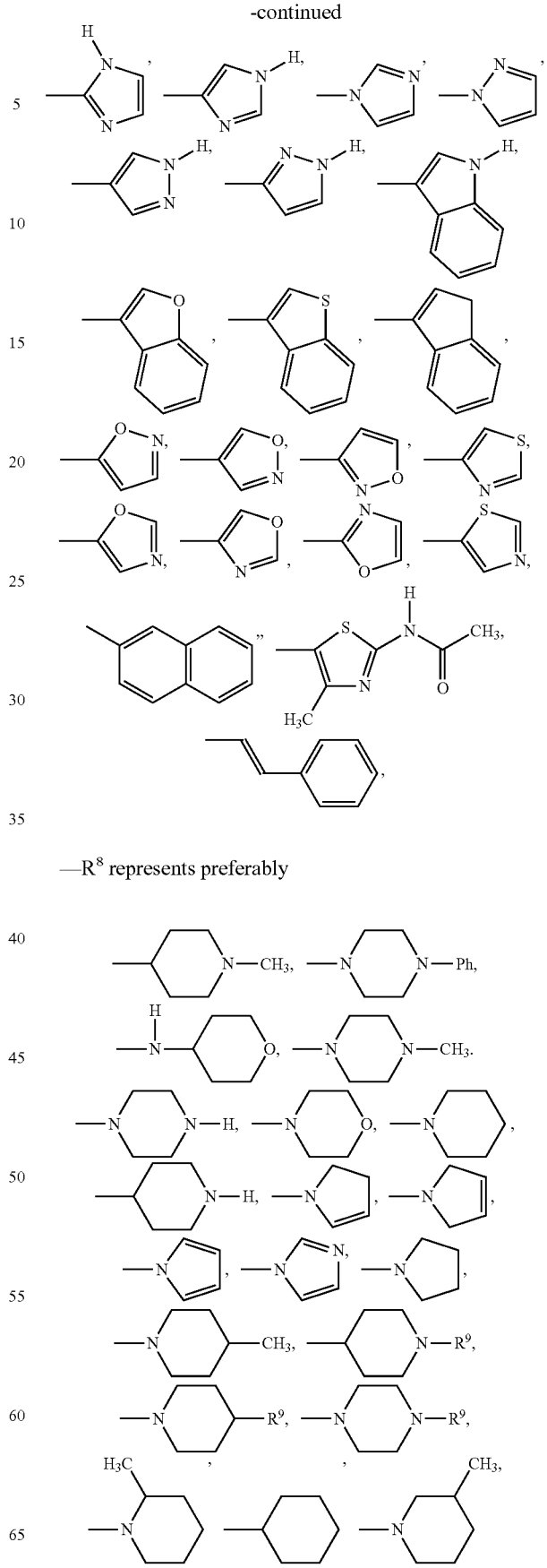
—$R^8$ represents preferably

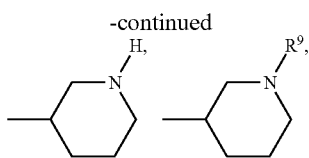

Compounds wherein $R^1$ and $R^2$ are a methoxy group are excluded from the present application. Such compounds having the substitution pattern of the compounds disclosed herein have shown moderate to low activity or no activity and are consequently not preferred. Also compounds of general formula (I), wherein both groups $R^1$ and $R^2$ are ethoxy groups are still not preferred and could also be excluded from the present invention. However compounds wherein both of $R^1$ and $R^2$ represent propoxy, butoxy, pentoxy etc. have shown activity and belong to the compounds of the present invention and are consequently not excluded from the scope of protection.

Excluded from this application and excluded from the patent claims and excluded from the general formula (I) are the following compounds which are excluded by the following disclaimer:

N'-(4-{[6,7-bis(methyloxy)quinolin-4-yl]oxy}-3-fluorophenyl)-N-methyl-N-(2-phenylethyl)sulfamide, N-(4-{[6,7-bis(methyloxy)quinolin-4-yl]oxy}-3-fluorophenyl)-1-phenylmethanesulfonamide, N-(4-{[6,7-bis(methyloxy)quinolin-4-yl]oxy}-3-fluorophenyl)-2-phenylethanesulfonamide, N-(4-{[6,7-bis(methyloxy)quinolin-4-yl]oxy}-3-fluorophenyl)-3-phenylpropane-1-sulfonamide.

The following specific compounds are also preferred which are selected from the group comprising or consisting of:

1) 2,5-Difluoro-N-{3-fluoro-4-[6-methoxy-7-(3-piperidin-1-yl-propoxy)-quinolin-4-yloxy]-phenyl}-benzenesulfonamide,
2) 2-Fluoro-N-{3-fluoro-4-[6-methoxy-7-(3-piperidin-1-yl-propoxy)-quinolin-4-yloxy]-phenyl}-benzenesulfonamide,
3) 4-Chloro-2-fluoro-N-{3-fluoro-4-[6-methoxy-7-(3-piperidin-1-yl-propoxy)-quinolin-4-yloxy]-phenyl}-benzenesulfonamide,
4) N-{3-Fluoro-4-[6-methoxy-7-(3-piperidin-1-yl-propoxy)-quinolin-4-yloxy]-phenyl}-2-trifluoromethyl-benzenesulfonamide,
5) N-{3-Fluoro-4-[6-methoxy-7-(3-piperidin-1-yl-propoxy)-quinolin-4-yloxy]-phenyl}-3-trifluoromethyl-benzenesulfonamide,
6) 2,6-Dichloro-N-{3-fluoro-4-[6-methoxy-7-(3-piperidin-1-yl-propoxy)-quinolin-4-yloxy]-phenyl}-benzenesulfonamide,
7) N-{3-Fluoro-4-[6-methoxy-7-(3-piperidin-1-yl-propoxy)-quinolin-4-yloxy]-phenyl}-2-nitro-benzenesulfonamide,
8) Biphenyl-3-sulfonic acid {3-fluoro-4-[6-methoxy-7-(3-piperidin-1-yl-propoxy)-quinolin-4-loxy]-phenyl}-amide,
9) 3-Difluoromethoxy-N-{3-fluoro-4-[6-methoxy-7-(3-piperidin-1-yl-propoxy)-quinolin-4-yloxy]-phenyl}-benzenesulfonamide,
10) N-{3-Fluoro-4-[6-methoxy-7-(3-piperidin-1-yl-propoxy)-quinolin-4-yloxy]-phenyl}-3-phenoxy-benzenesulfonamide,
11) 2,6-Difluoro-N-{3-fluoro-4-[6-methoxy-7-(3-piperidin-1-yl-propoxy)-quinolin-4-yloxy]-phenyl}-benzenesulfonamide,
12) 2,5-Difluoro-N-(3-fluoro-4-{6-methoxy-7-[3-(4-methyl-piperazin-1-yl)-propoxy]-quinolin-4-yloxy}-phenyl)-benzenesulfonamide,
13) Biphenyl-3-sulfonic acid (3-fluoro-4-{6-methoxy-7-[3-(4-methyl-piperazin-1-yl)-propoxy]-quinolin-4-yloxy}-phenyl)-amide,
14) N-(3-Fluoro-4-{6-methoxy-7-[3-(4-methyl-piperazin-1-yl)-propoxy]-quinolin-4-yloxy}-phenyl)-3-phenoxy-benzenesulfonamide,
15) 2-Cyano-N-(3-fluoro-4-{6-methoxy-7-[3-(4-methyl-piperazin-1-yl)-propoxy]-quinolin-4-yloxy}-phenyl)-benzenesulfonamide,
16) 2,4-Difluoro-N-(3-fluoro-4-{6-methoxy-7-[3-(4-methyl-piperazin-1-yl)-propoxy]-quinolin-4-yloxy}-phenyl)-benzenesulfonamide,
17) 2,3,4-Trifluoro-N-(3-fluoro-4-{6-methoxy-7-[3-(4-methyl-piperazin-1-yl)-propoxy]-quinolin-4-yloxy}-phenyl)-benzenesulfonamide,
18) 4-Fluoro-N-(3-fluoro-4-{6-methoxy-7-[3-(4-methyl-piperazin-1-yl)-propoxy]-quinolin-4-yloxy}-phenyl)-3-methoxy-benzenesulfonamide,
19) 2-Bromo-N-(3-fluoro-4-{6-methoxy-7-[3-(4-methyl-piperazin-1-yl)-propoxy]-quinolin-4-yloxy}-phenyl)-benzenesulfonamide,
20) 2,5-Dichloro-N-(3-fluoro-4-{6-methoxy-7-[3-(4-methyl-piperazin-1-yl)-propoxy]-quinolin-4-yloxy}-phenyl)-benzenesulfonamide,
21) N-(3-Fluoro-4-{6-methoxy-7-[3-(4-methyl-piperazin-1-yl)-propoxy]-quinolin-4-yloxy}-phenyl)-2-nitro-benzenesulfonamide,
22) 3-Fluoro-(3-fluoro-4-{6-methoxy-7-[3-(4-methyl-piperazin-1-yl)-propoxy]-quinolin-4-yloxy}-phenyl)-benzenesulfonamide,
23) 3-Chloro-4-fluoro-N-(3-fluoro-4-{6-methoxy-7-[3-(4-methyl-piperazin-1-yl)-propoxy]-quinolin-4-yloxy}-phenyl)-benzenesulfonamide,
24) N-(3-Fluoro-4-{6-methoxy-7-[3-(4-methyl-piperazin-1-yl)-propoxy]-quinolin-4-yloxy}-phenyl)-2-trifluoromethyl-benzenesulfonamide,
25) N-(3-Fluoro-4-{6-methoxy-7-[3-(4-methyl-piperazin-1-yl)-propoxy]-quinolin-4-yloxy}-phenyl)-2-trifluoromethoxy-benzenesulfonamide,
26) 2-Fluoro-N-(3-fluoro-4-{6-methoxy-7-[3-(4-methyl-piperazin-1-yl)-propoxy]-quinolin-4-yloxy}-phenyl)-benzenesulfonamide,
27) 4-Chloro-2-fluoro-N-(3-fluoro-4-{6-methoxy-7-[3-(4-methyl-piperazin-1-yl)-propoxy]-quinolin-4-yloxy}-phenyl)-benzenesulfonamide,
28) N-(3-Fluoro-4-{6-methoxy-7-[3-(4-methyl-piperazin-1-yl)-propoxy]-quinolin-4-yloxy}-phenyl)-2-methyl-benzenesulfonamide,
29) 2-Chloro-N-(3-fluoro-4-{6-methoxy-7-[3-(4-methyl-piperazin-1-yl)-propoxy]-quinolin-4-yloxy}-phenyl)-benzenesulfonamide,
30) 3-Difluoromethoxy-N-(3-fluoro-4-{6-methoxy-7-[3-(4-methyl-piperazin-1-yl)-propoxy]-quinolin-4-yloxy}-phenyl)-benzenesulfonamide,
31) Thiophene-2-sulfonic acid (3-fluoro-4-{6-methoxy-7-[3-(4-methyl-piperazin-1-yl)-propoxy]-quinolin-4-yloxy}-phenyl)-amide,
32) 2,6-Dichloro-N-(3-fluoro-4-{6-methoxy-7-[3-(4-methyl-piperazin-1-yl)-propoxy]-quinolin-4-yloxy}-phenyl)-benzenesulfonamide, 33) N-(3-Fluoro-4-{6-methoxy-7-[3-(4-methyl-piperazin-1-yl)-propoxy]-quinolin-4-yloxy}-phenyl)-2-methoxy-benzenesulfonamide, 34) 3,5-Dichloro-N-{3-fluoro-4-[6-methoxy-7-(3-piperidin-1-yl-propoxy)-quinolin-4-yloxy]-phenyl}-2-methoxy-benzenesulfonamide, 35) 3,5-Dichloro-N-(3-fluoro-4-{6-methoxy-7-[3-(4-methyl-piperazin-1-yl)-propoxy]-quinolin-4-yloxy}-phenyl)-2-methoxy-benzenesulfonamide.

36) N-(3-Fluoro-4-{6-methoxy-7-[3-(3-methyl-piperidin-1-yl)-propoxy]-quinolin-4-yloxy}-phenyl)-benzenesulfonamide, 37) 3-Fluoro-N-(3-fluoro-4-{6-methoxy-7-[3-(3-methyl-piperidin-1-yl)-propoxy]-quinolin-4-yloxy}-phenyl)-benzenesulfonamide, 38) 2-Chloro-N-(3-fluoro-4-{6-methoxy-7-[3-(3-methyl-piperidin-1-yl)-propoxy]-quinolin-4-yloxy}-phenyl)-benzenesulfonamide 39) 'N-(3-Fluoro-4-{6-methoxy-7-[3-(3-methyl-piperidin-1-yl)-propoxy]-quinolin-4-yloxy}-phenyl)-3-trifluoromethyl-benzenesulfonamide 40) N-(3-Fluoro-4-{6-methoxy-7-[3-(3-methyl-piperidin-1-yl)-propoxy]-quinolin-4-yloxy}-phenyl)-2-nitro-benzenesulfonamide 41) 3-Cyano-N-(3-fluoro-4-{6-methoxy-7-[3-(3-methyl-piperidin-1-yl)-propoxy]-quinolin-4-yloxy}-phenyl)-benzenesulfonamide, 42) N-(3-Fluoro-4-{6-methoxy-7-[3-(3-methyl-piperidin-1-yl)-propoxy]-quinolin-4-yloxy}-phenyl)-3-methoxy-benzenesulfonamide, 43) 3-Difluoromethoxy-N-(3-fluoro-4-{6-methoxy-7-[3-(3-methyl-piperidin-1-yl)-propoxy]-quinolin-4-yloxy}-phenyl)-benzenesulfonamide, 44) N-(3-Fluoro-4-{6-methoxy-7-[3-(3-methyl-piperidin-1-yl)-propoxy]-quinolin-4-yloxy}-phenyl)-2-methyl-benzenesulfonamide, 45) N-(3-Fluoro-4-{6-methoxy-7-[3-(3-methyl-piperidin-1-yl)-propoxy]-quinolin-4-yloxy}-phenyl)-2-trifluoromethoxy-benzenesulfonamide, 46) N-(3-Fluoro-4-{6-methoxy-7-[3-(3-methyl-piperidin-1-yl)-propoxy]-quinolin-4-yloxy}-phenyl)-3-trifluoromethoxy-benzenesulfonamide, 47) 2,4-Difluoro-N-(3-fluoro-4-{6-methoxy-7-[3-(3-methyl-piperidin-1-yl)-propoxy]-quinolin-4-yloxy}-phenyl)-benzenesulfonamide, 48) 3,4-Difluoro-N-(3-fluoro-4-{6-methoxy-7-[3-(3-methyl-piperidin-1-yl)-propoxy]-quinolin-4-yloxy}-phenyl)-benzenesulfonamide, 49) 2,3,4-Trifluoro-N-(3-fluoro-4-{6-methoxy-7-[3-(3-methyl-piperidin-1-yl)-propoxy]-quinolin-4-yloxy}-phenyl)-benzenesulfonamide, 50) 2,5-Dichloro-N-(3-fluoro-4-{6-methoxy-7-[3-(3-methyl-piperidin1-yl)-propoxy]-quinolin-4-yloxy}-phenyl)-benzenesulfonamide, 51) 2,6-Dichloro-N-(3-fluoro-4-{6-methoxy-7-[3-(3-methyl-piperidin-1-yl)-propoxy]-quinolin-4-yloxy}-phenyl)-benzenesulfonamide, 52) 3,4-Dichloro-N-(3-fluoro-4-{6-methoxy-7-[3-(3-methyl-piperidin-1-yl)-propoxy]-quinolin-4-yloxy}-phenyl)-benzenesulfonamide, 53) 3,5-Dichloro-N-(3-fluoro-4-{6-methoxy-7-[3-(3-methyl-piperidin-1-yl)-propoxy]-quinolin-4-yloxy}-phenyl)-benzenesulfonamide, 54) 3-Chloro-2-fluoro-N-(3-fluoro-4-{6-methoxy-7-[3-(3-methyl-piperidin-1-yl)-propoxy]-quinolin-4-yloxy}-phenyl)-benzenesulfonamide, 55) 2-Fluoro-N-(3-fluoro-4-{6-methoxy-7-[3-(3-methyl-piperidin-1-yl)-propoxy]-quinolin-4-yloxy}-phenyl)-5-methyl-benzenesulfonamide, 56) 3-Fluoro-N-(3-fluoro-4-{6-methoxy-7-[3-(3-methyl-piperidin-1-yl)-propoxy]-quinolin-4-yloxy}-phenyl)-4-methyl-benzenesulfonamide, 57) 3-Chloro-4-fluoro-N-(3-fluoro-4-{6-methoxy-7-[3-(3-methyl-piperidin-1-yl)-propoxy]-quinolin-4-yloxy}-phenyl)-benzenesulfonamide, 58) Naphthalene-1-sulfonic acid (3-fluoro-4-{6-methoxy-7-[3-(3-methyl-piperidin-1-yl)-propoxy]-quinolin-4-yloxy}-phenyl)-amide, 59) N-(3-Fluoro-4-{6-methoxy-7-[3-(3-methyl-piperidin-1-yl)-propoxy]-quinolin-4-yloxy}-phenyl)-3-phenoxy-benzenesulfonamide, 60) Cyclopropanesulfonic acid (3-fluoro-4-{6-methoxy-7-[3-(3-methyl-piperidin-1-yl)-propoxy]-quinolin-4-yloxy}-phenyl)-amide, 61) 1-Methyl-1H-pyrazole-3-sulfonic acid (3-fluoro-4-{6-methoxy-7-[3-(3-methyl-piperidin-1-yl)-propoxy]-quinolin-4-yloxy}-phenyl)-amide, 62) 5-Methyl-thiophene-2-sulfonic acid (3-fluoro-4-{6-methoxy-7-[3-(3-methyl-piperidin-1-yl)-propoxy]-quinolin-4-yloxy}-phenyl)-amide, 63) 5-Chloro-thiophene-2-sulfonic acid (3-fluoro-4-{6-methoxy-7-[3-(3-methyl-piperidin-1-yl)-propoxy]-quinolin-4-yloxy}-phenyl)-amide, 64) 2,4-Dichloro-thiophene-3-sulfonic acid (3-fluoro-4-{6-methoxy-7-[3-(3-methyl-piperidin-1-yl)-propoxy]-quinolin-4-yloxy}-phenyl)-amide, 65) Thiophene-3-sulfonic acid (3-fluoro-4-{6-methoxy-7-[3-(3-methyl-piperidin-1-yl)-propoxy]-quinolin-4-yloxy}-phenyl)-amide, 66) 3-(3-Fluoro-4-{6-methoxy-7-[3-(3-methyl-piperidin-1-yl)-propoxy]-quinolin-4-yloxy}-phenylsulfamoyl)-thiophene-2-carboxylic acid methyl ester, 67) Benzo[b]thiophene-3-sulfonic acid (3-fluoro-4-{6-methoxy-7-[3-(3-methyl-piperidin-1-yl)-propoxy]-quinolin-4-yloxy}-phenyl)-amide, 68) 1-Ethyl-1H-pyrazole-4-sulfonic acid (3-fluoro-4-{6-methoxy-7-[3-(3-methyl-piperidin-1-yl)-propoxy]-quinolin-4-yloxy}-phenyl)-amide, 69) 3-Chloro-N-(3-fluoro-4-{6-methoxy-7-[3-(3-methyl-piperidin-1-yl)-propoxy]-quinolin-4-yloxy}-phenyl)-benzenesulfonamide, 70) N-(3-Fluoro-4-{6-methoxy-7-[3-(3-methyl-piperidin-1-yl)-propoxy]-quinolin-4-yloxy}-phenyl)-3-methyl-benzenesulfonamide, 71) N-(3-Fluoro-4-{6-methoxy-7-[3-(3-methyl-piperidin-1-yl)-propoxy]-quinolin-4-yloxy}-phenyl)-2-methoxy-benzenesulfonamide, 72) 3-Cyano-4-fluoro-N-(3-fluoro-4-{6-methoxy-7-[3-(3-methyl-piperidin-1-yl)-propoxy]-quinolin-4-yloxy}-phenyl)-benzenesulfonamide, 73) 2-Phenyl-ethenesulfonic acid (3-fluoro-4-{6-methoxy-7-[3-(3-methyl-piperidin-1-yl)-propoxy]-quinolin-4-yloxy}-phenyl)-amide, 74) Quinoline-8-sulfonic acid (3-fluoro-4-{6-methoxy-7-[3-(3-methyl-piperidin-1-yl)-propoxy]-quinolin-4-yloxy}-phenyl)-amide, 75) 3,5-Dichloro-N-(3-fluoro-4-{6-methoxy-7-[3-(3-methyl-piperidin-1-yl)-propoxy]-quinolin-4-yloxy}-phenyl)-2-methoxy-benzenesulfonamide, 76) 3,5-Dichloro-N-{3-fluoro-4-[6-methoxy-7-(3-morpholin-4-yl-propoxy)-quinolin-4-yloxy]-phenyl}-2-methoxy-benzenesulfonamide, 77) 2,6-Difluoro-N-{3-fluoro-4-[6-methoxy-7-(3-morpholin-4-yl-propoxy)-quinolin-4-yloxy]-phenyl}-benzenesulfonamide,
78) N-{3-Fluoro-4-[6-methoxy-7-(3-piperidin-1-yl-propoxy)-quinolin-4-yloxy]-phenyl}-2-trifluoromethoxy-benzenesulfonamide,
79) Butane-1-sulfonic acid {3-fluoro-4-[6-methoxy-7-(3-morpholin-4-yl-propoxy)-quinolin-4-yloxy]-phenyl}-amide,
80) 2,5-Difluoro-N-{3-fluoro-4-[6-methoxy-7-(piperidin-3-ylmethoxy)-quinolin-4-yloxy]-phenyl}-benzenesulfonamide,
81) 2-Fluoro-N-{3-fluoro-4-[6-methoxy-7-(2-morpholin-4-yl-ethoxy)-quinolin-4-yloxy]-phenyl}-benzenesulfonamide,
82) 2,6-Difluoro-N-{3-fluoro-4-[6-methoxy-7-(2-morpholin-4-yl-ethoxy)-quinolin-4-yloxy]-phenyl}-benzenesulfonamide,
83) 2,5-Difluoro-N-{3-fluoro-4-[6-methoxy-7-(4-morpholin-4-yl-butoxy)-quinolin-4-yloxy]-phenyl}-benzenesulfonamide,
84) 2,5-Difluoro-N-{3-fluoro-4-[7-(4-morpholin-4-yl-butoxy)-quinolin-4-yloxy]-phenyl}-benzenesulfonamide,
85) N-(3-Fluoro-4-{6-[3-(4-methyl-piperazin-1-yl)-propoxy]-quinolin-4-yloxy}-phenyl)-2-trifluoromethyl-benzenesulfonamide,
86) N-(3-Fluoro-4-{7-methoxy-6-[3-(4-methyl-piperazin-1-yl)-propoxy]-quinolin-4-yloxy}-phenyl)-2-trifluoromethyl-benzenesulfonamide,
87) N-(3-Chloro-4-{6-methoxy-7-[3-(4-methyl-piperazin-1-yl)-propoxy]-quinolin-4-yloxy}-phenyl)-2-trifluoromethyl-benzenesulfonamide,
88) N-(3,5-Dichloro-4-{6-methoxy-7-[3-(4-methyl-piperazin-1-yl)-propoxy]-quinolin-4-yloxy}-phenyl)-2,6-difluoro-benzenesulfonamide,
89) N-(4-{6-Methoxy-7-[3-(4-methyl-piperidin-1-yl)-propoxy]-quinolin-4-yloxy}-3-methyl-phenyl)-2-trifluoromethyl-benzenesulfonamide,
90) 2,5-Difluoro-N-(3-methoxy-4-{6-methoxy-7-[3-(3-methyl-piperidin-1-yl)-propoxy]-quinolin-4-yloxy}-phenyl)-benzenesulfonamide,
91) N-{4-[6,7-Bis-(2-methoxy-ethoxy)-quinolin-4-yloxy]-3-fluoro-phenyl}-2,6-difluoro-benzenesulfonamide,
92) {4-[2-Fluoro-4-(2-fluoro-benzenesulfonylamino)-phenoxy]-6-methoxy-quinolin-7-yloxy}-acetic acid ethyl ester,
93) 2-{4-[2-Fluoro-4-(2-trifluoromethyl-benzenesulfonylamino)-phenoxy]-6-methoxy-quinolin-7-yloxy}-N,N-dimethyl-acetamide,
94) Cyclohexanecarboxylic acid 4-[4-(2,5-difluoro-benzenesulfonylamino)-2-fluoro-phenoxy]-6-methoxy-quinolin-7-yl ester,
95) N-(3-Fluoro-4-{6-methoxy-7-[3-(tetrahydro-pyran-4-ylamino)-propoxy]-quinolin-4-yloxy}-phenyl)-2-trifluoromethyl-benzenesulfonamide,
96) N-{4-[7-(3-Cyclopropylamino-propoxy)-6-methoxy-quinolin-4-yloxy]-3-fluoro-phenyl}-2-trifluoromethyl-benzenesulfonamide,
97) N-{4-[7-(3-Cyclobutylamino-propoxy)-6-methoxy-quinolin-4-yloxy]-3-fluoro-phenyl}-2-trifluoromethyl-benzenesulfonamide,
98) N-(4-{7-[3-(3-tert-Butyl-ureido)-propoxy]-6-methoxy-quinolin-4-yloxy}-3-fluoro-phenyl)-2-trifluoromethyl-benzenesulfonamide,
99) N-(3-Fluoro-4-{6-methoxy-7-[3-(2-methyl-piperidin-1-yl)-propoxy]-quinolin-4-yloxy}-phenyl)-2-trifluoromethyl-benzenesulfonamide,
100) N-{4-[7-(3-Dimethylamino-propoxy)-6-methoxy-quinolin-4-yloxy]-3-fluoro-phenyl}-2-trifluoromethyl-benzenesulfonamide,
101) N-{4-[7-(3-Diethylamino-propoxy)-6-methoxy-quinolin-4-yloxy]-3-fluoro-phenyl}-2-trifluoromethyl-benzenesulfonamide,
102) N-(3-{6-Methoxy-7-[3-(4-methyl-piperazin-1-yl)-propoxy]-quinolin-4-yloxy}-phenyl)-2-trifluoromethyl-benzenesulfonamide.
103) N-{3-Fluoro-4-[6-methoxy-7-(2-morpholin-4-yl-ethoxy)-quinolin-4-yloxy]-phenyl}-2-methoxy-benzenesulfonamide
104) 2,6-Dichloro-N-{3-fluoro-4-[6-methoxy-7-(2-morpholin-4-yl-ethoxy)-quinolin-4-yloxy]-phenyl}-benzenesulfonamide
105) Thiophene-2-sulfonic acid {3-fluoro-4-[6-methoxy-7-(2-morpholin-4-yl-ethoxy)-quinolin-4-yloxy]-phenyl}-amide
106) 2,5-Dichloro-N-{3-fluoro-4-[6-methoxy-7-(2-morpholin-4-yl-ethoxy)-quinolin-4-yloxy]-phenyl}-benzenesulfonamide
107) 1-Methyl-1H-pyrazole-3-sulfonic acid {3-fluoro-4-[6-methoxy-7-(2-morpholin-4-yl-ethoxy)-quinolin-4-yloxy]-amide
108) 2-Chloro-N-{3-fluoro-4-[6-methoxy-7-(2-morpholin-4-yl-ethoxy)-quinolin-4-yloxy]-phenyl}-benzenesulfonamide
109) N-{3-Fluoro-4-[6-methoxy-7-(2-morpholin-4-yl-ethoxy)-quinolin-4-yloxy]-phenyl}-2-nitro-benzenesulfonamide
110) 2,6-Difluoro-N-(3-fluoro-4-{6-methoxy-7-[3-(4-methyl-piperazin-1-yl)-propoxy]-quinolin-4-yloxy}-phenyl)-benzenesulfonamide
111) N-(3-Chloro-4-{6-methoxy-7-[3-(4-methyl-piperazin-1-yl)-propoxy]-quinolin-4-yl oxy}-phenyl)-2-fluoro-benzenesulfonamide
112) N-(3-Chloro-4-{6-methoxy-7-[3-(4-methyl-piperazin-1-yl)-propoxy]-quinolin-4-yloxy}-phenyl)-2,5-difluoro-benzenesulfonamide
113) Benzo[b]thiophene-3-sulfonic acid {3-fluoro-4-[6-methoxy-7-(3-piperidin-1-yl-propoxy)-quinolin-4-yloxy]-phenyl}-amide
114) Benzo[b]thiophene-3-sulfonic acid {3-fluoro-4-[6-methoxy-7-(3-morpholin-4-yl-propoxy)-quinolin-4-yloxy]-phenyl}-amide
115) Benzo[b]thiophene-3-sulfonic acid (3-fluoro-4-{6-methoxy-7-[3-(4-methyl-piperidin-1-yl)-propoxy]-quinolin-4-loxy}-phenyl)-amide
116) Benzo[b]thiophene-3-sulfonic acid (3-fluoro-4-{6-methoxy-7-[3-(4-methyl-piperazin-1-yl)-propoxy]-quinolin-4-yloxy}-phenyl)-amide
117) Benzo[b]thiophene-3-sulfonic acid (3-chloro-4-{6-methoxy-7-[3-(4-methyl-piperazin-1-yl)-propoxy]-quinolin-4-yloxy}-phenyl)-amide
118) N-(3-Chloro-4-{6-methoxy-7-[3-(4-methyl-piperazin-1-yl)-propoxy]-quinolin-4-yloxy}-phenyl)-2,6-difluoro-benzenesulfonamide
119) 2,6-Dichloro-N-(3-chloro-4-{6-methoxy-7-[3-(4-methyl-piperazin-1-yl)-propoxy]-quinolin-4-yloxy}-phenyl)-benzenesulfonamide
120) (3-{4-[2-Fluoro-4-(2-trifluoromethyl-benzenesulfonylamino)-phenoxy]-6-methoxy-quinolin-7-yloxy}-propyl)-carbamic acid tert-butyl ester
121) (3-{4-[4-(2,5-Difluoro-benzenesulfonylamino)-2-fluoro-phenoxy]-6-methoxy-quinolin-7-yloxy}-propyl)-carbamic acid tert-butyl ester 122) N-{4-[7-(3-Amino-propoxy)-6-methoxy-quinolin-4-yloxy]-3-fluoro-phenyl}-2,5-difluoro-benzenesulfonamide hydrochloride
123) 2,5-Difluoro-N-(3-{6-methoxy-7-[3-(4-methyl-piperazin-1-yl)-propoxy]-quinolin-4-yloxy}-phenyl)-benzenesulfonamide
124) 2,5-Dichloro-N-(3-chloro-4-{6-methoxy-7-[3-(4-methyl-piperazin-1-yl)-propoxy]-quinolin-4-yloxy}-phenyl)-benzenesulfonamide
125) 2,6-Difluoro-N-(3-{6-methoxy-7-[3-(4-methyl-piperazin-1-yl)-propoxy]-quinolin-4-yloxy}-phenyl)-benzenesulfonamide
126) N-(3-{6-Methoxy-7-[3-(4-methyl-piperazin-1-yl)-propoxy]-quinolin-4-yloxy}-phenyl)-2-trifluoromethoxy-benzenesulfonamide
127) 2,5-Dichloro-N-(3-{6-methoxy-7-[3-(4-methyl-piperazin-1-yl)-propoxy]-quinolin-4-yloxy}-phenyl)-benzenesulfonamide
128) 2,6-Dichloro-N-(3-{6-methoxy-7-[3-(4-methyl-piperazin-1-yl)-propoxy]-quinolin-4-yloxy}-phenyl)-benzenesulfonamide
129) Thiophene-2-sulfonic acid (3-{6-methoxy-7-[3-(4-methyl-piperazin-1-yl)-propoxy]-quinolin-4-yloxy}-phenyl)-amide
130) 5-Chloro-thiophene-2-sulfonic acid (3-{6-methoxy-7-[3-(4-methyl-piperazin-1-yl)-propoxy]-quinolin-4-yloxy}-phenyl)-amide
131) 5-Methyl-thiophene-2-sulfonic acid (3-{6-methoxy-7-[3-(4-methyl-piperazin-1-yl)-propoxy]-quinolin-4-yloxy}-phenyl)-amide
132) N-[5-(3-{6-Methoxy-7-[3-(4-methyl-piperazin-1-yl)-propoxy]-quinolin-4-yloxy}-phenylsulfamoyl)-4-methyl-thiazol-2-yl]-acetamide
133) Thiophene-3-sulfonic acid (3-{6-methoxy-7-[3-(4-methyl-piperazin-1-yl)-propoxy]-quinolin-4-yloxy}-phenyl)-amide
134) 2,5-Dichloro-thiophene-3-sulfonic acid (3-{6-methoxy-7-[3-(4-methyl-piperazin-1-yl)-propoxy]-quinolin-4-yloxy}-phenyl)-amide
135) 3-(3-{6-Methoxy-7-[3-(4-methyl-piperazin-1-yl)-propoxy]-quinolin-4-yloxy}-phenylsulfamoyl)-thiophene-2-carboxylic acid methyl ester
136) Benzo[b]thiophene-3-sulfonic acid (3-{6-methoxy-7-[3-(4-methyl-piperazin-1-yl)-propoxy]-quinolin-4-yloxy}-phenyl)-amide
137) Furan-2-sulfonic acid (3-{6-methoxy-7-[3-(4-methyl-piperazin-1-yl)-propoxy]-quinolin-4-yloxy}-phenyl)-amide
138) 3,5-Dimethyl-isoxazole-4-sulfonic acid (3-{6-methoxy-7-[3-(4-methyl-piperazin-1-yl)-propoxy]-quinolin-4-yloxy}-phenyl)-amide
139) 1-Methyl-1H-pyrazole-3-sulfonic acid (3-{6-methoxy-7-[3-(4-methyl-piperazin-1-yl)-propoxy]-quinolin-4-yloxy}-phenyl)-amide
140) 1-Ethyl-1H-pyrazole-4-sulfonic acid (3-{6-methoxy-7-[3-(4-methyl-piperazin-1-yl)-propoxy]-quinolin-4-yloxy}-phenyl)-amide
141) 2-Methyl-1H-imidazole-4-sulfonic acid (3-{6-methoxy-7-[3-(4-methyl-piperazin-1-yl)-propoxy]-quinolin-4-yloxy}-phenyl)-amide
142) Cyclopropanesulfonic acid (3-{6-methoxy-7-[3-(4-methyl-piperazin-1-yl)-propoxy]-quinolin-4-yloxy}-phenyl)-amide
143) 2-Phenyl-ethenesulfonic acid (3-{6-methoxy-7-[3-(4-methyl-piperazin-1-yl)-propoxy]-quinolin-4-yloxy}-phenyl)-amide
144) Thiophene-2-sulfonic acid (3-fluoro-4-{6-methoxy-7-[3-(2-methyl-piperidin-1-yl)-propoxy]-quinolin-4-yloxy}-phenyl)-amide
145) 5-Chloro-thiophene-2-sulfonic acid (3-fluoro-4-{6-methoxy-7-[3-(2-methyl-piperidin-1-yl)-propoxy]-quinolin-4-yloxy}-phenyl)-amide
146) 2,4-Dichloro-thiophene-3-sulfonic acid (3-fluoro-4-{6-methoxy-7-[3-(2-methyl-piperidin-1-yl)-propoxy]-quinolin-4-yloxy}-phenyl)-amide
147) Benzo[b]thiophene-3-sulfonic acid (3-fluoro-4-{6-methoxy-7-[3-(2-methyl-piperidin-1-yl)-propoxy]-quinolin-4-yloxy}-phenyl)-amide
148) Furan-2-sulfonic acid (3-fluoro-4-{6-methoxy-7-[3-(2-methyl-piperidin-1-yl)-propoxy]-quinolin-4-yloxy}-phenyl)-amide
149) 2-Methyl-1H-imidazole-4-sulfonic acid (3-fluoro-4-{6-methoxy-7-[3-(2-methyl-piperidin-1-yl)-propoxy]-quinolin-4-yloxy}-phenyl)-amide
150) 1-Methyl-1H-pyrazole-3-sulfonic acid (3-fluoro-4-{6-methoxy-7-[3-(2-methyl-piperidin-1-yl)-propoxy]-quinolin-4-yloxy}-phenyl)-amide
151) 2,5-Difluoro-N-(3-fluoro-4-{6-methoxy-7-[3-(2-methyl-piperidin-1-yl)-propoxy]-quinolin-4-yloxy}-phenyl)-benzenesulfonamide
152) 2,6-Difluoro-N-(3-fluoro-4-{6-methoxy-7-[3-(2-methyl-piperidin-1-yl)-propoxy]-quinolin-4-yloxy}-phenyl)-benzenesulfonamide
153) N-(3-Fluoro-4-{6-methoxy-7-[3-(2-methyl-piperidin-1-yl)-propoxy]-quinolin-4-yloxy}-phenyl)-2-trifluoromethoxy-benzenesulfonamide
154) 2,5-Dichloro-N-(3-fluoro-4-{6-methoxy-7-[3-(2-methyl-piperidin-1-yl)-propoxy]-quinolin-4-yloxy}-phenyl)-benzenesulfonamide
155) 3-{3-Fluoro-4-[6-methoxy-7-(3-piperidin-1-yl-propoxy)-quinolin-4-yloxy]-phenylsulfamoyl}-thiophene-2-carboxylic acid methyl ester
156) 3-(3-Fluoro-4-{6-methoxy-7-[3-(4-methyl-piperidin-1-yl)-propoxy]-quinolin-4-yloxy}-phenylsulfamoyl)-thiophene-2-carboxylic acid methyl ester
157) 3-{3-Fluoro-4-[6-methoxy-7-(3-morpholin-4-yl-propoxy)-quinolin-4-yloxy]-phenylsulfamoyl}-thiophene-2-carboxylic acid methyl ester
158) 3-(3-Fluoro-4-{6-methoxy-7-[3-(4-methyl-piperazin-1-yl)-propoxy]-quinolin-4-yloxy}-phenylsulfamoyl)-thiophene-2-carboxylic acid methyl ester
159) 1,3,5-Trimethyl-1H-pyrazole-4-sulfonic acid {3-fluoro-4-[6-methoxy-7-(3-piperidin-1-yl-propoxy)-quinolin-4-yloxy]-phenyl}-amide
160) 1,3,5-Trimethyl-1H-pyrazole-4-sulfonic acid (3-fluoro-4-{6-methoxy-7-[3-(4-methyl-piperidin-1-yl)-propoxy]-quinolin-4-yloxy}-phenyl)-amide
161) 1,3,5-Trimethyl-1H-pyrazole-4-sulfonic acid {3-fluoro-4-[6-methoxy-7-(3-morpholin-4-yl-propoxy)-quinolin-4-yloxy]-phenyl}-amide
162) 1,3,5-Trimethyl-1H-pyrazole-4-sulfonic acid (3-fluoro-4-{6-methoxy-7-[3-(4-methyl-piperazin-1-yl)-propoxy]-quinolin-4-yloxy}-phenyl)-amide
163) 1-Methyl-1H-pyrazole-3-sulfonic acid {3-fluoro-4-[6-methoxy-7-(3-piperidin-1-yl-propoxy)-quinolin-4-yloxy]-phenyl}-amide
164) 1-Methyl-1H-pyrazole-3-sulfonic acid (3-fluoro-4-{6-methoxy-7-[3-(4-methyl-piperidin-1-yl)-propoxy]-quinolin-4-yloxy}-phenyl)-amide
165) 1-Methyl-1H-pyrazole-3-sulfonic acid {3-fluoro-4-[6-methoxy-7-(3-morpholin-4-yl-propoxy)-quinolin-4-yloxy]-phenyl}-amide 166) 1-Methyl-1H-pyrazole-3-sulfonic acid (3-fluoro-4-{6-methoxy-7-[3-(4-methyl-piperazin-1-yl)-propoxy]-quinolin-4-yloxy}-phenyl)-amide
167) 2-Methyl-3H-imidazole-4-sulfonic acid {3-fluoro-4-[6-methoxy-7-(3-piperidin-1-yl-propoxy)-quinolin-4-yloxy]-phenyl}-amide
168) 2-Methyl-3H-imidazole-4-sulfonic acid (3-fluoro-4-{6-methoxy-7-[3-(4-methyl-piperidin-1-yl)-propoxy]-quinolin-4-yloxy}-phenyl)-amide
169) 2-Methyl-3H-imidazole-4-sulfonic acid {3-fluoro-4-[6-methoxy-7-(3-morpholin-4-yl-propoxy)-quinolin-4-yloxy]-phenyl}-amide
170) 2-Methyl-3H-imidazole-4-sulfonic acid (3-fluoro-4-{6-methoxy-7-[3-(4-methyl-piperazin-1-yl)-propoxy]-quinolin-4-yloxy}-phenyl)-amide
171) 2,5-Difluoro-N-(4-{6-methoxy-7-[3-(4-methyl-piperidin-1-yl)-propoxy]-quinolin-4-yloxy}-3-methyl-phenyl)-benzenesulfonamide
172) 2,6-Difluoro-N-(4-{6-methoxy-7-[3-(4-methyl-piperidin-1-yl)-propoxy]-quinolin-4-yloxy}-3-methyl-phenyl)-benzenesulfonamide
173) 2,6-Difluoro-N-(3-methoxy-4-{6-methoxy-7-[3-(4-methyl-piperidin-1-yl)-propoxy]-quinolin-4-yloxy}-phenyl)-benzenesulfonamide
174) N-(4-{6-Methoxy-7-[3-(4-methyl-piperidin-1-yl)-propoxy]-quinolin-4-yloxy}-3-methyl-phenyl)-2-trifluoromethoxy-benzenesulfonamide
175) 2,5-Dichloro-N-(4-{6-methoxy-7-[3-(4-methyl-piperidin-1-yl)-propoxy]-quinolin-4-yloxy}-3-methyl-phenyl)-benzenesulfonamide
176) 2,6-Dichloro-N-(4-{6-methoxy-7-[3-(4-methyl-piperidin-1-yl)-propoxy]-quinolin-4-yloxy}-3-methyl-phenyl)-benzenesulfonamide
177) N-{4-[7-(3-Dimethylamino-propoxy)-6-methoxy-quinolin-4-yloxy]-3-fluoro-phenyl}-2,5-difluoro-benzenesulfonamide
178) N-{4-[7-(3-Dimethylamino-propoxy)-6-methoxy-quinolin-4-yloxy]-3-fluoro-phenyl}-2,6-difluoro-benzenesulfonamide
179) N-{4-[7-(3-Dimethylamino-propoxy)-6-methoxy-quinolin-4-yloxy]-3-fluoro-phenyl}-2-trifluoromethoxy-benzenesulfonamide
180) 2,5-Dichloro-N-{4-[7-(3-dimethylamino-propoxy)-6-methoxy-quinolin-4-yloxy]-3-fluoro-phenyl}-benzenesulfonamide
181) 2,6-Dichloro-N-{4-[7-(3-dimethylamino-propoxy)-6-methoxy-quinolin-4-yloxy]-3-fluoro-phenyl}-benzenesulfonamide
182) 5-Chloro-thiophene-2-sulfonic acid {4-[7-(3-dimethylamino-propoxy)-6-methoxy-quinolin-4-yloxy]-3-fluoro-phenyl}-amide
183) N-(5-{4-[7-(3-Dimethylamino-propoxy)-6-methoxy-quinolin-4-yloxy]-3-fluoro-phenylsulfamoyl}-4-methyl-thiazol-2-yl)-acetamide
184) 3-{4-[7-(3-Dimethylamino-propoxy)-6-methoxy-quinolin-4-yloxy]-3-fluoro-phenylsulfamoyl}-thiophene-2-carboxylic acid methyl ester
185) Furan-2-sulfonic acid {4-[7-(3-dimethylamino-propoxy)-6-methoxy-quinolin-4-yloxy]-3-fluoro-phenyl}-amide
186) Thiophene-2-sulfonic acid {4-[7-(3-dimethylamino-propoxy)-6-methoxy-quinolin-4-yloxy]-3-fluoro-phenyl}-amide
187) 2,5-Difluoro-N-(4-fluoro-3-{6-methoxy-7-[3-(4-methyl-piperidin-1-yl)-propoxy]-quinolin-4-yloxy}-phenyl)-benzenesulfonamide
188) 2,6-Difluoro-N-(4-fluoro-3-{6-methoxy-7-[3-(4-methyl-piperidin-1-yl)-propoxy]-quinolin-4-yloxy}-phenyl)-benzenesulfonamide
189) N-(4-Fluoro-3-{6-methoxy-7-[3-(4-methyl-piperidin-1-yl)-propoxy]-quinolin-4-yloxy}-phenyl)-2-trifluoromethyl-benzenesulfonamide
190) N-(4-Fluoro-3-{6-methoxy-7-[3-(4-methyl-piperidin-1-yl)-propoxy]-quinolin-4-yloxy}-phenyl)-2-trifluoromethoxy-benzenesulfonamide
191) 2,5-Dichloro-N-(4-fluoro-3-{6-methoxy-7-[3-(4-methyl-piperidin-1-yl)-propoxy]-quinolin-4-yloxy}-phenyl)-benzenesulfonamide
192) 2,6-Dichloro-N-(4-fluoro-3-{6-methoxy-7-[3-(4-methyl-piperidin-1-yl)-propoxy]-quinolin-4-yloxy}-phenyl)-benzenesulfonamide
193) N-(2-Chloro-5-{6-methoxy-7-[3-(4-methyl-piperidin-1-yl)-propoxy]-quinolin-4-yloxy}-phenyl)-2,5-difluoro-benzenesulfonamide
194) N-(2-Chloro-5-{6-methoxy-7-[3-(4-methyl-piperidin-1-yl)-propoxy]-quinolin-4-yloxy}-phenyl)-2,6-difluoro-benzenesulfonamide
195) N-(2-Chloro-5-{6-methoxy-7-[3-(4-methyl-piperidin-1-yl)-propoxy]-quinolin-4-yloxy}-phenyl)-2-trifluoromethyl-benzenesulfonamide
196) N-(2-Chloro-5-{6-methoxy-7-[3-(4-methyl-piperidin-1-yl)-propoxy]-quinolin-4-yloxy}-phenyl)-2-trifluoromethoxy-benzenesulfonamide
197) 2,5-Dichloro-N-(2-chloro-5-{6-methoxy-7-[3-(4-methyl-piperidin-1-yl)-propoxy]-quinolin-4-yloxy}-phenyl)-benzenesulfonamide
198) 2,6-Dichloro-N-(2-chloro-5-{6-methoxy-7-[3-(4-methyl-piperidin-1-yl)-propoxy]-quinolin-4-yloxy}-phenyl)-benzenesulfonamide
199) 2,5-Difluoro-N-[3-fluoro-4-(6-methoxy-quinolin-4-yloxy)-phenyl]-benzenesulfonamide
200) 2,6-Difluoro-N-[3-fluoro-4-(6-methoxy-quinolin-4-yloxy)-phenyl]-benzenesulfonamide
201) N-[3-Fluoro-4-(6-methoxy-quinolin-4-yloxy)-phenyl]-2-trifluoromethyl-benzenesulfonamide
202) N-[3-Fluoro-4-(6-methoxy-quinolin-4-yloxy)-phenyl]-2-trifluoromethoxy-benzenesulfonamide
203) 2,5-Dichloro-N-[3-fluoro-4-(6-methoxy-quinolin-4-yloxy)-phenyl]-benzenesulfonamide
204) 2,6-Dichloro-N-[3-fluoro-4-(6-methoxy-quinolin-4-yloxy)-phenyl]-benzenesulfonamide
205) Naphthalene-2-sulfonic acid [3-fluoro-4-(6-methoxy-quinolin-4-yloxy)-phenyl]-amide
206) Cyclopropanesulfonic acid [3-fluoro-4-(6-methoxy-quinolin-4-yloxy)-phenyl]-amide
207) 2,5-Difluoro-N-(3-methoxy-4-{6-methoxy-7-[3-(4-methyl-piperidin-1-yl)-propoxy]-quinolin-4-yloxy}-phenyl)-benzenesulfonamide
208) N-(3-Methoxy-4-{6-methoxy-7-[3-(4-methyl-piperidin-1-yl)-propoxy]-quinolin-4-yloxy}-phenyl)-2-trifluoromethyl-benzenesulfonamide
209) N-(3,5-Dichloro-4-{6-methoxy-7-[3-(4-methyl-piperidin-1-yl)-propoxy]-quinolin-4-yloxy}-phenyl)-2,6-difluoro-benzenesulfonamide
210) N-(3,5-Dichloro-4-{6-methoxy-7-[3-(4-methyl-piperidin-1-yl)-propoxy]-quinolin-4-yloxy}-phenyl)-2-trifluoromethyl-benzenesulfonamide
211) Acetic acid 4-{4-[4-(2,5-difluoro-benzenesulfonylamino)-2-fluoro-phenoxy]-6-methoxy-quinolin-7-yloxy}-butyl ester
212) Acetic acid 4-{4-[2-fluoro-4-(2-trifluoromethyl-benzenesulfonylamino)-phenoxy]-6-methoxy-quinolin-7-yloxy}-butyl ester 213) N-{2-Fluoro-4-[6-methoxy-7-(3-pyrrolidin-1-yl-propoxy)-quinolin-4-yloxy]-phenyl}-2-trifluoromethyl-benzenesulfonamide
214) N-{3-Fluoro-4-[6-methoxy-7-(4-morpholin-4-yl-butoxy)-quinolin-4-yloxy]-phenyl}-2-trifluoromethyl-benzenesulfonamide
215) N-(2-Fluoro-4-{6-methoxy-7-[3-(3-methyl-piperidin-1-yl)-propoxy]-quinolin-4-yloxy}-phenyl)-2-trifluoromethyl-benzenesulfonamide The present invention also comprises pharmaceutically acceptable salts of the compounds according to the general formula (I), all stereoisomeric forms of the compounds according to the general formula (I) as well as solvates, especially hydrates or prodrugs thereof. A prodrug is commonly described as an inactive or protected derivative of an active ingredient or a drug, which is converted to the active ingredient or drug in the body.

In case, the inventive compounds bear basic and/or acidic substituents, they may form salts with organic or inorganic acids or bases. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o,m,p)-toluic acid, naphthylamine sulfonic acid, and other mineral or carboxylic acids well known to those skilled in the art. The salts are prepared by contacting the free base form with a sufficient amount of the desired acid to produce a salt in the conventional manner. Examples for suitable inorganic or organic bases are, for example, NaOH, KOH, $NH_4OH$, tetraalkylammonium hydroxide, lysine or arginine and the like. Salts may be prepared in a conventional manner using methods well known in the art, for example by treatment of a solution of the compound of the general formula (I) with a solution of an acid, selected out of the group mentioned above.

Some of the compounds of the present invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Certain compounds of the general formula (I) may exist in the form of optical isomers, e.g. diastereoisomers and mixtures of isomers in all ratios, e.g. racemic mixtures. The invention includes all such forms, in particular the pure isomeric forms. The different isomeric forms may be separated or resolved one from the other by conventional methods, or any given isomer may be obtained by conventional synthetic methods or by stereospecific or asymmetric syntheses. Where a compound according to the general formula (I) contains an alkene moiety, the alkene can be presented as a cis or trans isomer or a mixture thereof. When an isomeric form of a compound of the invention is provided substantially free of other isomers, it will preferably contain less than 5% w/w, more preferably less than 2% w/w and especially less than 1% w/w of the other isomers.

Another aspect of the present invention relates to the use of the inventive quinolinyloxyphenylsulfonamide derivatives as drugs, i.d. as pharmaceutically active agents applicable in medicine.

The inventive quinolinyloxyphenylsulfonamides are useful for the treatment and/or prevention of AXL receptor tyrosine kinase induced disorders, wherein the AXL receptor tyrosine kinase induced disorders are selected from the group comprising hyperproliferative disorders, breast, colon, prostate, lung, gastric, ovarian, endometrial, renal, hepatocellular, thyroid, uterine cancer, esophageal carcinoma, squamous cell carcinoma, leukemia, osteosarcoma, melanoma, glioblastoma, and neuroblastoma.

Moreover the inventive quinolinyloxyphenylsulfonamides are useful for the preparation of a pharmaceutical formulation for prophylaxis, treatment and after-treatment cancer, tumors and cancer metastases. Thus, the quinolinyloxyphenylsulfonamide compounds of the present invention can be used for prophylaxis and treatment of various cancer types and especially of cancer metastases.

Furthermore, the compounds of the present invention are useful for the treatment and after-treatment of various cancer types such as adenocarcinoma, choroidal melanoma, acute leukemia, acoustic neurinoma, ampullary carcinoma, anal carcinoma, astrocytoma, basal cell carcinoma, pancreatic cancer, desmoid tumor, bladder cancer, bronchial carcinoma, breast cancer, Burkitt's lymphoma, corpus cancer, CUP-syndrome (carcinoma of unknown primary), colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, cervix, glioblastomas, gynecologic tumors, ear, nose and throat tumors, hematologic neoplasias, hairy cell leukemia, urethral cancer, skin cancer, skin testis cancer, brain tumors (gliomas), brain metastases, testicle cancer, hypophysis tumor, carcinoids, Kaposi's sarcoma, laryngeal cancer, germ cell tumor, bone cancer, colorectal carcinoma, head and neck tumors (tumors of the ear, nose and throat area), colon carcinoma, craniopharyngiomas, oral cancer (cancer in the mouth area and on lips), cancer of the central nervous system, liver cancer, liver metastases, leukemia, eyelid tumor, lung cancer, lymph node cancer (Hodgkin's/Non-Hodgkin's), lymphomas, stomach cancer, malignant melanoma, malignant neoplasia, malignant tumors gastrointestinal tract, breast carcinoma, rectal cancer, medulloblastomas, melanoma, meningiomas, Hodgkin's disease, mycosis fungoides, nasal cancer, neurinoma, neuroblastoma, kidney cancer, renal cell carcinomas, non-Hodgkin's lymphomas, oligodendroglioma, esophageal carcinoma, osteolytic carcinomas and osteoplastic carcinomas, osteosarcomas, ovarial carcinoma, pancreatic carcinoma, penile cancer, plasmocytoma, prostate cancer, pharyngeal cancer, rectal carcinoma, retinoblastoma, vaginal cancer, thyroid carcinoma, Schneeberger disease, esophageal cancer, spinalioms, T-cell lymphoma (mycosis fungoides), thymoma, tube carcinoma, eye tumors, urethral cancer, urologic tumors, urothelial carcinoma, vulva cancer, wart appearance, soft tissue tumors, soft tissue sarcoma, Wilm's tumor, cervical carcinoma and tongue cancer.

Most active are the inventive compounds on lung cancer, lymph node cancer (Hodgkin's/Non-Hodgkin's), head and neck tumors (tumors of the ear, nose and throat area), breast cancer, ovarian cancer, gastric cancer, gastrointestinal tumors, intestinal tumors.

Another aspect of the present invention is directed to the use of at least one quinolinyloxyphenylsulfonamide compound and/or pharmaceutically acceptable salts thereof for the preparation of a pharmaceutical formulation for prophylaxis, treatment and/or after-treatment of cancer, tumors and especially cancer metastases.

Still another aspect of the present invention is directed to pharmaceutical compositions comprising at least one quinolinyloxyphenylsulfonamide compound of the present invention as active ingredient, together with at least one pharmaceutically acceptable carrier, excipient and/or diluents. The pharmaceutical compositions of the present invention can be prepared in a conventional solid or liquid carrier or diluent and a conventional pharmaceutically-made adjuvant at suitable dosage level in a known way. The preferred preparations are adapted for oral application. These administration forms include, for example, pills, tablets, film tablets, coated tablets, capsules, powders and deposits.

Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain at least one compound according to the present invention and/or a pharmaceutical acceptable salt thereof as active ingredient.

The pharmaceutical compositions according to the present invention containing at least one compound according to the present invention, and/or a pharmaceutical acceptable salt thereof as active ingredient will typically be administered together with suitable carrier materials selected with respect to the intended form of administration, i.e. for oral administration in the form of tablets, capsules (either solid filled, semi-solid filled or liquid filled), powders for constitution, extrudates, deposits, gels, elixirs, dispersable granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like. Moreover, suitable binders, lubricants, disintegrating agents and coloring agents may also be incorporated into the tablet or capsule.

Powders and tablets may contain about 5 to about 95 weight % of the quinolinyloxyphenylsulfonamide compound and/or the respective pharmaceutically active salt as active ingredient.

Suitable binders include starch, gelatin, natural sugars, corn sweeteners, natural and synthetic gums such as acacia, sodium alginate, carboxymethylcellulose, polyethylene glycol and waxes. Among suitable lubricants there may be mentioned boric acid, sodium benzoate, sodium acetate, sodium chloride, and the like. Suitable disintegrants include starch, methylcellulose, guar gum, and the like. Sweetening and flavoring agents as well as preservatives may also be included, where appropriate. The disintegrants, diluents, lubricants, binders etc. are discussed in more detail below.

Moreover, the pharmaceutical compositions of the present invention may be formulated in sustained release form to provide the rate controlled release of any one or more of the components or active ingredients to optimise the therapeutic effect(s), e.g. antihistaminic activity and the like. Suitable dosage forms for sustained release include tablets having layers of varying disintegration rates or controlled release polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration. Aerosol preparations suitable for inhalation may include solutions and solids in powder form, which may be present in combination with a pharmaceutically acceptable carrier such as an inert, compressed gas, e.g. nitrogen. For preparing suppositories, a low melting fat or wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations which are intended to be converted, shortly before use, to liquid form preparations for either oral or parenteral administration. Such liquid forms include solutions, suspensions, and emulsions.

The compounds according to the present invention may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methyl cellulose, polyvinyl alcohols, or denatured gelatins or starch for holding or containing compositions comprising the active ingredient(s). Capsules with hard shells are typically made of blended of relatively high gel strength gelatins from bones or pork skin. The capsule itself may contain small amounts of dyes, opaquing agents, plasticisers and/or preservatives. Under tablet a compressed or moulded solid dosage form is understood which comprises the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilised in a hydrophilic semi-solid matrix. Powders for constitution refers to powder blends containing the active ingredients and suitable diluents which can be suspended e.g. in water or in juice.

Suitable diluents are substances that usually make up the major portion of the composition or dosage form. Suitable diluents include sugars such as lactose, sucrose, mannitol, and sorbitol, starches derived from wheat, corn rice, and potato, and celluloses such as microcrystalline cellulose. The amount of diluent in the composition can range from about 5 to about 95% by weight of the total composition, preferably from about 25 to about 75 weight %, and more preferably from about 30 to about 60 weight %.

The term disintegrants refers to materials added to the composition to support break apart (disintegrate) and release the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscaramellose, alginates such as alginic acid and sodium alginate, clays such as bentonites, and effervescent mixtures. The amount of disintegrant in the composition may range from about 2 to about 20 weight % of the composition, more preferably from about 5 to about 10 weight %.

Binders are substances which bind or "glue" together powder particles and make them cohesive by forming granules, thus serving as the "adhesive" in the formulation. Binders add cohesive strength already available in the diluent or bulking agent. Suitable binders include sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20 weight % of the composition, preferably from about 3 to about 10 weight %, and more preferably from about 3 to about 6 weight %.

Lubricants refer to a class of substances which are added to the dosage form to enable the tablet granules etc. after being compressed to release from the mould or die by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules. The amount of lubricant in the composition may range from about 0.2 to about 5 weight % of the composition, preferably from about 0.5 to about 2 weight %, and more preferably from about 0.3 to about 1.5 weight % of the composition.

Glidents are materials that prevent caking of the components of the pharmaceutical composition and improve the flow characteristics of granulate so that flow is smooth and uniform. Suitable glidents include silicon dioxide and talc. The amount of glident in the composition may range from about 0.1 to about 5 weight % of the final composition, preferably from about 0.5 to about 2 weight %.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5 weight % of the composition, preferably from about 0.1 to about 1 weight %.

EXPERIMENTAL PART

Examples

1) Analytical Methods (HPLC, NMR, TLC and melting point)

Analytical HPLC/MS was performed on an Waters HPLC/MS system using reverse phase Method A: Waters XTerra MS C18 (5 cm×4.6 mm, 5 um), gradient 0-95% B (0.00 min 5% B, 0.50 min 5% B, 5.50 min 95% B, 6.00 min 95% B, 6.50 min 5% B, 7.00 min 5% B), Solvent A: Water/0.05% HCOOH, Solvent B: AcCN/0.05% HCOOH over 7.00 min, flow=2.0 ml/min. Separation module was Waters Alliance 2795.

Method B: Waters X Waters XBridge C18 (5 cm×4.6 mm, 3.5 um), gradient 0-95% B (0.00 min 5% B, 0.50 min 5% B, 5.50 min 95% B, 6.00 min 95% B, 6.50 min 5% B, 7.00 min 5% B), Solvent A: 5 mM $NH_4HCO_3$, Solvent B: AcCN over 7.00 min, flow=2.0 ml/min. Separation module was Waters Alliance 2795.

UV spectra were recorded using a Waters 996 DAD UV detector. Mass spectra were obtained using Waters SQD MS detector (Ionization: $ES^+/ES^-$, Source block temp: 110 C, Desolvation temp: 250° C., Desolvation Gas: 500 L/h, Cone Gas: 80 L/h, Capillary: 3000 V, Cone: 30 V, Extractor: 6 V, Rf Lens: 0.1 V, Scan: 80 to 1000 m/z in 1 sec., Inter-scan delay: 0.1 s).

$^1$H NMR spectra were recorded on a Bruker Avanve 300 MHz AV spectrometer in deuterated solvents (DMSO-$d_6$). Chemical shifts □ are in parts per million (ppm).

Thin-layer chromatography (TLC) analysis was performed with Kieselgel 60 F254 (Merck) plates and visualized using UV light.

Melting point measurement was Büchi melting Point B-54 instrument.

Synthesis of Compounds

First of all general methods will be presented for the synthesis of basic building blocks. In subsequent reactions these basic building blocks can be functionalized via common methods of organic syntheses to obtain the desired target compounds.

General Method 1: Starting from 4-Hydroxy-Acetophenone Derivatives

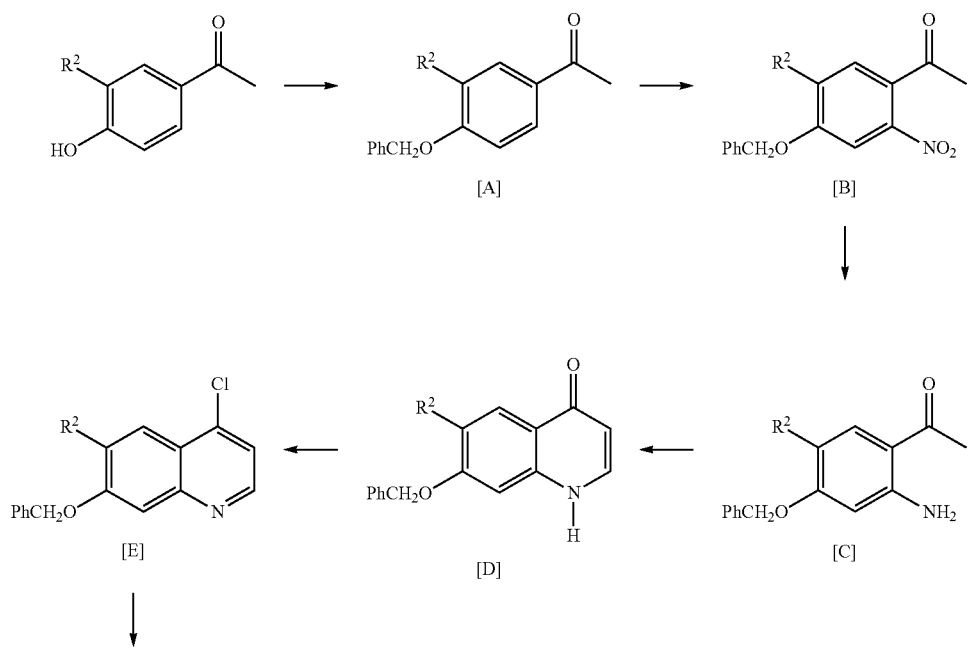

-continued

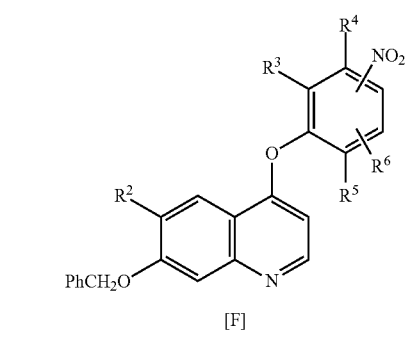
[F]

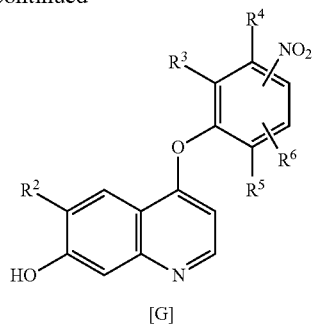
[G]

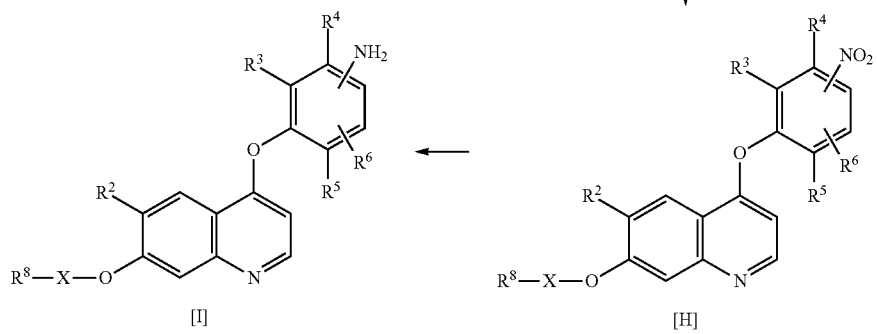
[I]                               [H]

R² has the meanings as disclosed herein and is, for instance, —OCH₃.

Synthesis of 1-(4-Benzyloxy-3-methoxy-phenyl)-ethanone [A]

The mixture of 31.62 g (190 mmol) 1-(4-hydroxy-3-methoxy-phenyl)-ethanone, 16.36 g (118 mmol) potassium carbonate, 0.5 g potassium iodide, 400 ml acetone and 33.15 g (190 mmol) ml benzyl bromide were refluxed for 2 days. The solvent was evaporated, the residue was taken up in 400 ml of water. The precipitate was filtered, washed with 100 ml of sodium carbonate saturated aqueous solution and 2×100 ml of water, then dried on air to give 47.8 g of product [A]. Yield 98%.

Synthesis of 1-(4-Benzyloxy-5-methoxy-2-nitro-phenyl)-ethanone [B]

1-(4-Benzyloxy-3-methoxy-phenyl)-ethanone (24.61 g, 96 mmol) was dissolved in acetic acid (100 ml) and the mixture was cooled to 10° C. Nitric acid fuming (Fluka ID 84392, 100%, 10 ml, 240 mmol) was added dropwise to the cooled solution over 2 hours. The reaction mixture was allowed to come to room temperature and stirred for 16 hours. The reaction mixture was poured into water (400 ml). The precipitate was filtered, washed with water, then taken up in sodium hydrogencarbonate saturated aqueous solution (300 ml) and stirred for 2 hours. The precipitate was filtered, washed with water and dried. The raw product was recrystallized fromethyl alcohol (1000 ml) to give 18.25 g of product [B]. Yield 65%.

Synthesis of 1-(2-amino-4-benzyloxy-5-methoxy-phenyl)-ethanone [C]

A mixture of 1-(4-Benzyloxy-5-methoxy-2-nitro-phenyl)-ethanone (11.94 g 39.6 mmol), ammonium chloride (13.48 g, 250 mmol), zinc powder (65.39 g, 1000 mmol), ethyl alcohol (720 ml) and water (70 ml) was refluxed until completion (5 hours). The mixture was filtered through celite and washed with hot ethyl alcohol. The filtrate was evaporated in vacuum. The residue was taken up in the mixture of chloroform (200 ml), water (200 ml) and the pH of this mixture was set to 8 by adding sodium hydroxide solution. The two layers were separated, the aqueous layer was extracted with chloroform (2×50 ml). The organic layers were combined, washed with water and over Na₂SO₄, and concentrated to give 9.25 product [C]. Yield 86%.

Synthesis of 7-benzyloxy-6-methoxy-1H-quinolin-4-one [D]

A mixture of sodium methylate (270 mmol, 14.75 g, favorable prepared from sodium metal and methanol before use), 1,2-dimeythoxyethane (122 ml) and 1-(2-amino-4-benzyloxy-5-methoxy-phenyl)-ethanone (6.68 g 24 mmol) was stirred at 0° C. for 1 hour. Ethyl formate (10.7 ml, 9.81 g, 132 mmol) was added to the reaction mixture, that was allowed to come to room temperature and stirred for further 4 hours. The mixture was diluted with water (50 ml) and acidified to pH 1 by adding hydrochloric acid (1N, 185 ml). The precipitate was filtered, washed with water and dried to give 6.51 g of product [D]. Yield: 94%.

Synthesis of 7-benzyloxy-4-chloro-6-methoxy-quinoline [E]

A mixture of 7-benzyloxy-6-methoxy-4-quinolone (9.72 g 34.5 mmol) and phosphorus oxychloride (130 ml) was stirred at 110° C. for 3 hours. The stirred mixture was concentrated at atmospheric pressure. The residue was dissolved in chloroform (150 ml), then ice and water was added to the solution. The mixture was rendered weakly alkaline by the addition of saturated sodium carbonate solution. The two phases were separated, the aqueous layer was extracted with chloroform. The extract was washed with water, dried over sodium sulfate, and the solvent was removed by evaporation under the reduced pressure. The residue was solidified under diisopropyl ether to give 9.82 g of product [E]. Yield: 94%.

Synthesis of 7-benzyloxy-4-(2-fluoro-4-nitro-phenoxy)-6-methoxy-quinoline [F]

A mixture of 7-benzyloxy-4-chloro-6-methoxy-quinoline (2.04 g, 6.8 mmol), 2-fluoro-4-nitrophenol (2.34 g 14.9 mmol) and chlorobenzene (40 ml) was stirred at reflux temperature for 2 days. The reaction mixture was cooled, diluted with saturated sodium carbonate solution (30 ml) and stirred for 3 hours. The precipitate was filtered and the filtrate was separated. The aqueous layer was extracted with chloroform (3×30 ml). The organic layers were combined, washed with water and dried over sodium sulfate. The solvent was removed by evaporation under the reduced pressure. The residue was purified by column chromatography. The pure product was solidified under diisopropyl ether to give 1.11 g of product [F]. Yield: 39%.

Synthesis of 4-(2-fluoro-4-nitro-phenoxy)-6-methoxy-quinolin-7-ol [G]

7-Benzyloxy-4-(2-fluoro-4-nitro-phenoxy)-6-methoxy-quinoline (2.75 g, 6.54 mmol) was added slowly in portion into hydrobromic acid solution (33% in acetic acid, 45 ml). The mixture was stirred at room temperature for 2 hours, then poured into diethyl ether (300 ml). The precipitate was filtered and washed with diethyl ether. The solid hydrobromide salt was stirred in the mixture of sodium acetate aqueous solution (10%, 60 ml) and ethyl acetate (15 ml) for 1 day. The precipitate was filtered, washed with water and dried to give 1.82 g of product [G]. Yield: 86% The free hydroxy group of compound [G] was substituted with the residue R$^8$—X— by an etherification reaction or a nucleophilic substitution to result in compound [H]. For the coupling, for reagent could be used chloroalkyl-(Cl—X—R$^8$), bromoalkyl (Br—X—R$^8$) or mesylate (MeSO$_2$—X—R$^8$) derivatives as well.

Alternatively, the preparation of compound H can be prepared with an another method. Some potential intermediate—H-1, H-2, H-3—are described in the literature that can be used for preparing the corresponding H compound, see J. Med. Chem. 2008, 51 (18), 5766-5779 (Noel D. Angelo et. al.).

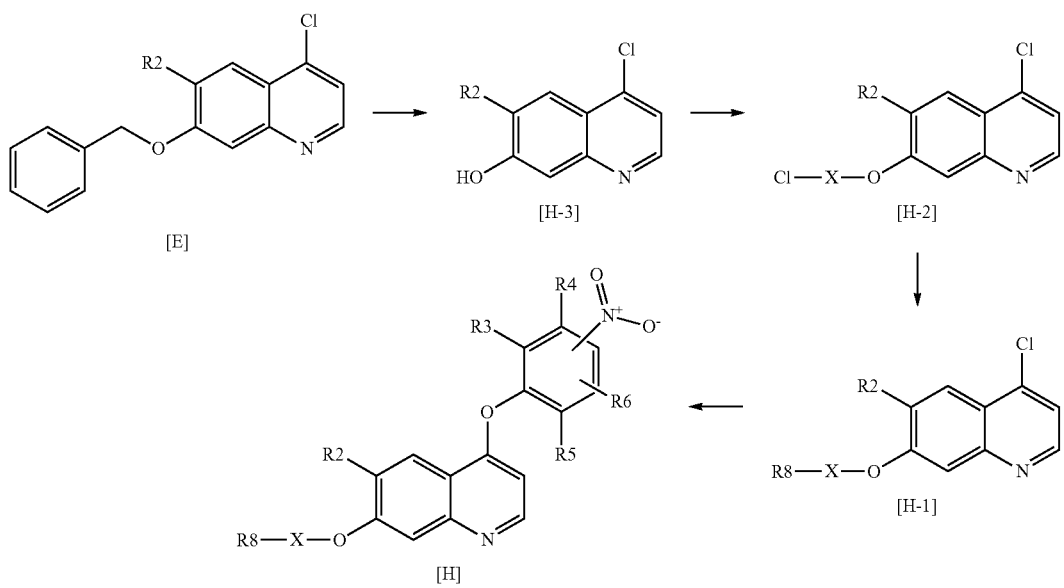

The nitro group of compound [H] was reduced to the amino group as described above for compound [C]. The preparation of the sulfonamide group is described below.

General Method Starting from 3-Hydroxy-Acetophenone Derivatives $R^1$ has the meanings as disclosed herein and is, for instance, —$OCH_3$.

The D' compound can be prepared in the similar manner as described in the patent US 2005/0029264, Example 13 (Atsushi Miwa et al.).

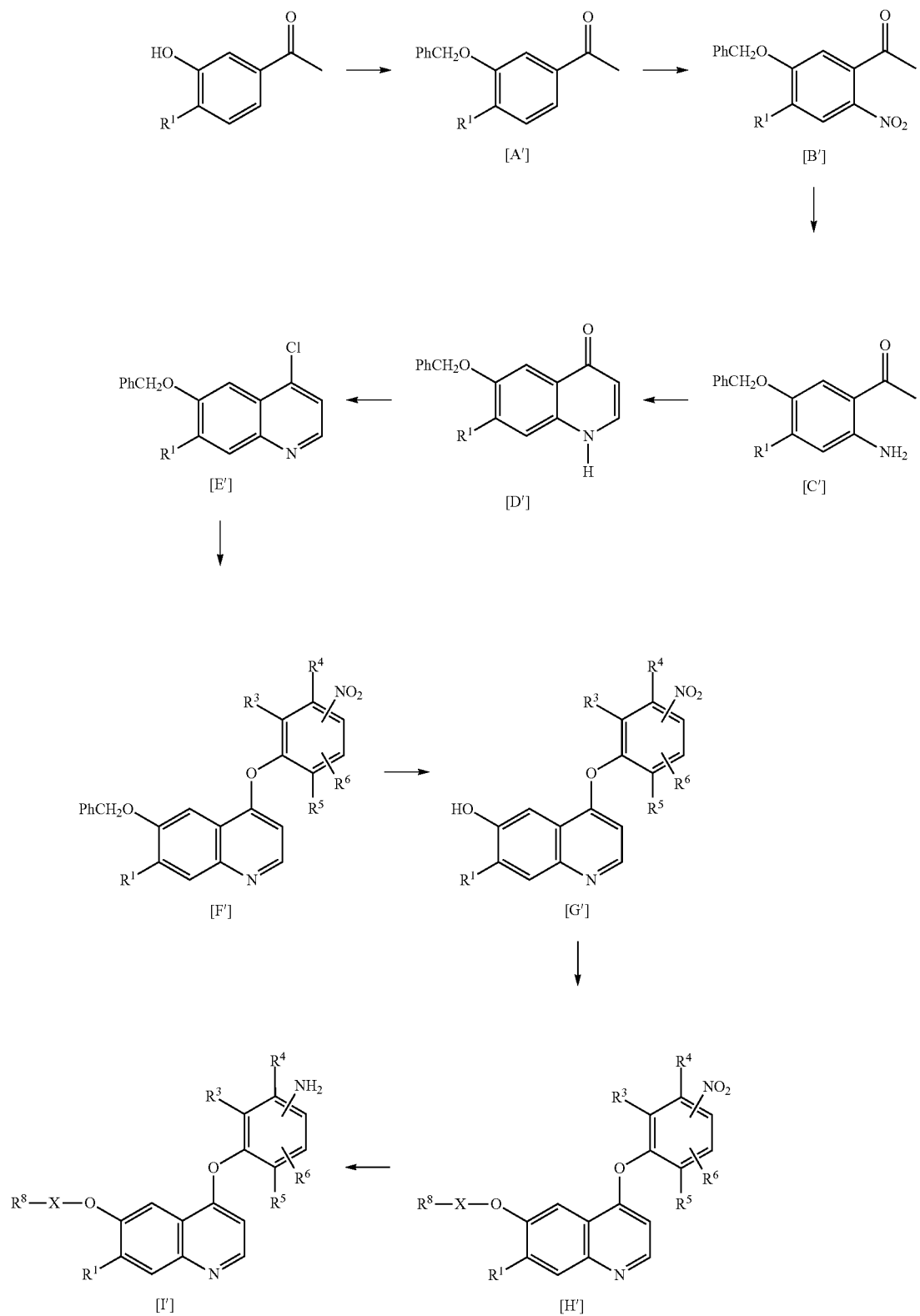

General Method 2: Starting from Aniline Derivatives

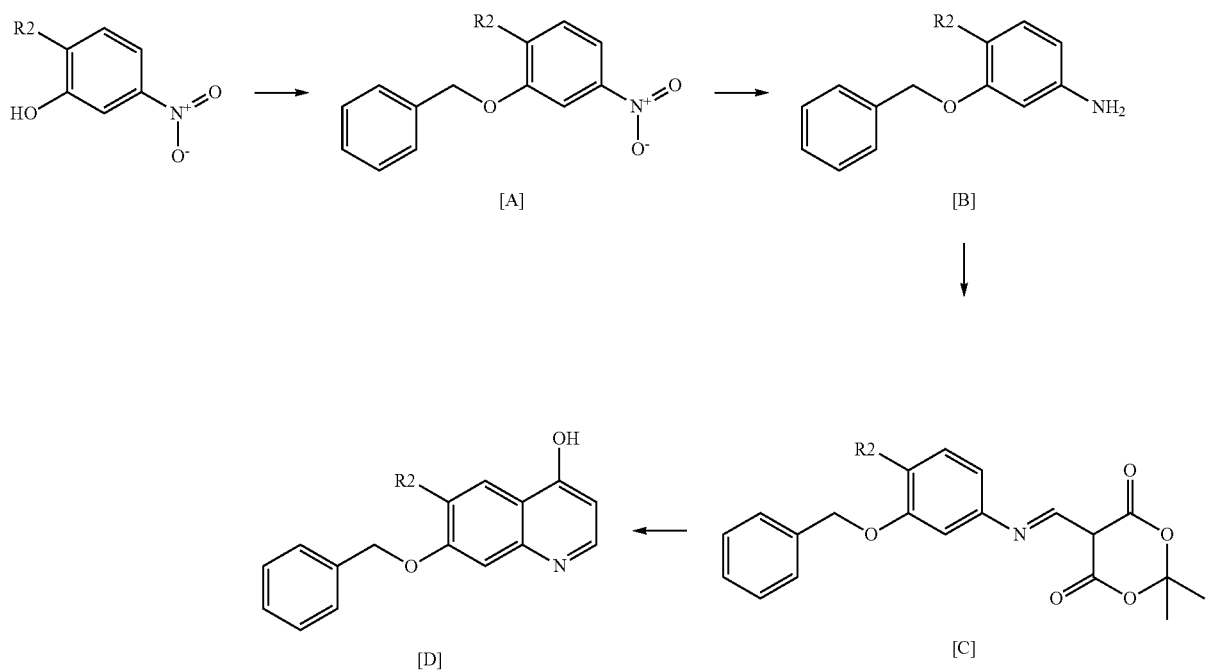

$R^2$ has the meanings as disclosed herein and is, for instance, —$OCH_3$.

For some embodiments, compounds, showed in Reaction Scheme can be prepared according to the described literature. For example the preparation of compound D (where $R^2$ is a hydrogen atom) is described in the patent WO 2005/032484, Example 1 (Lindstrom Kyle et al.).

In certain embodiments, benzyloxy group is at the position 6 in the quinoline ring and can be prepared in the similar manner [WO 2005/032484, Example 2 (Lindstrom Kyle et al.)]:

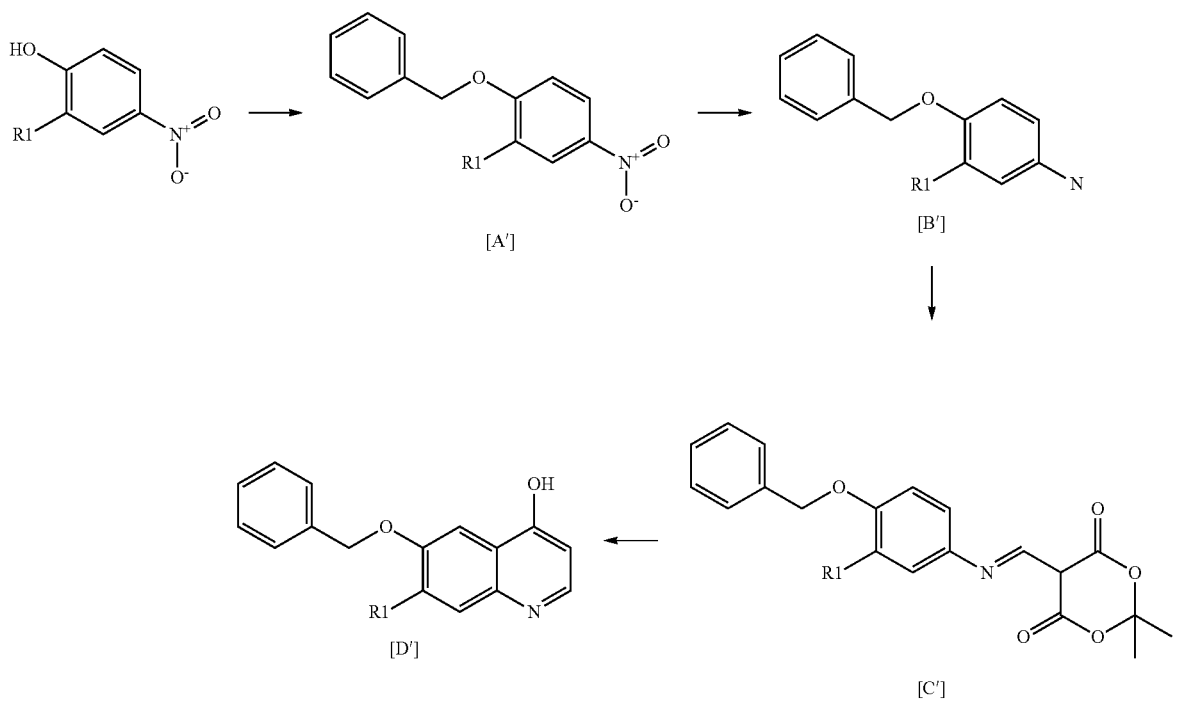

General Procedure for Sulfonamide Compounds

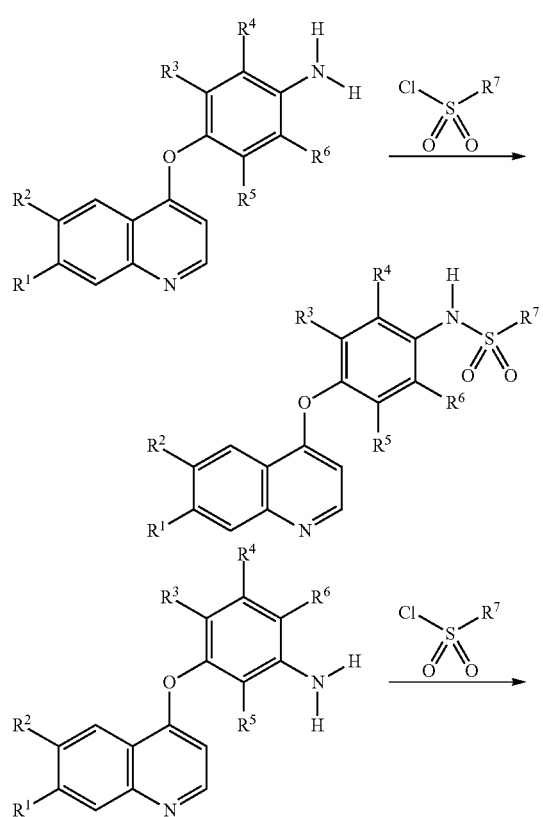

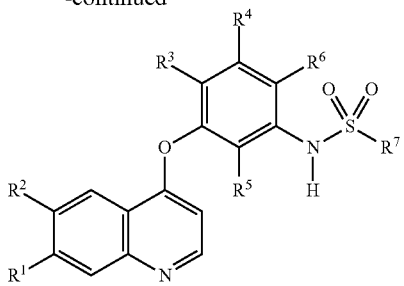

0.31 mmol appropriately substituted sulfonylchloride and 0.3 mmol appropriate substituted 4-(4-amino-phenoxy) quinoline derivative was dissolved 3 ml abs. pyridine and stirred while the starting amine disappears according to the TLC (at room temperature 1-21 days or at 60° C. for 24 hours). The reaction mixture was poured into 50 ml of water and extracted with 3×30 ml of chloroform. The organic phase was washed with water, dried over anhydrous sodium sulfate, filtrated and evaporated. The residue was purified on TLC plate (saturated with vapour of $NH_4OH$, eluent chloroform-methanol 9:1). The pure product was solidified under diisopropyl ether.

General Procedure for Modification of Sulfonamide Compounds

There are some other possibilities to modify the sulfonamide derivatives. For example using a protected aminoalkyl reagent we could prepare the protected derivative [G+3]. After removing the protective group the free amine [G+4] can be prepared, which is convenient material for produce further derivatives, e.g. react with isocyanate or with aldehyde or ketone (reductive alkylation).

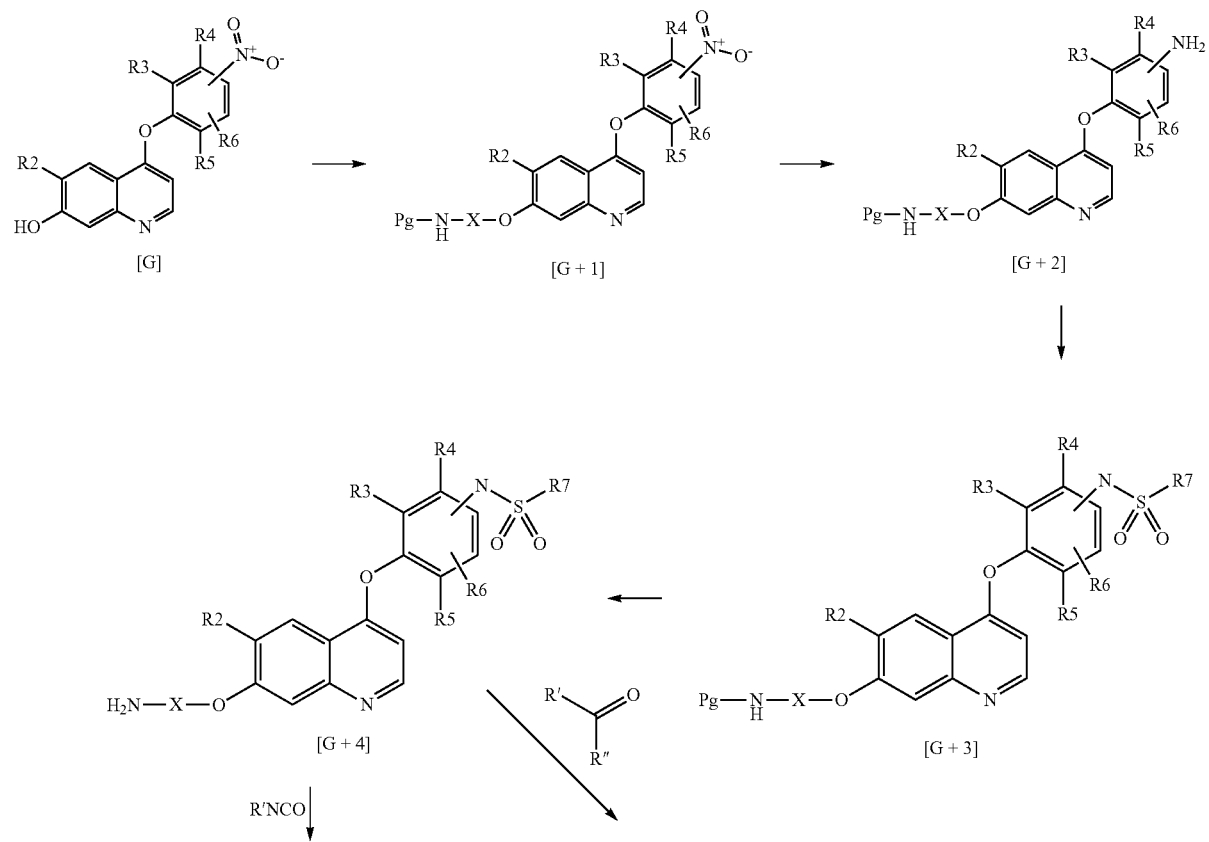

-continued

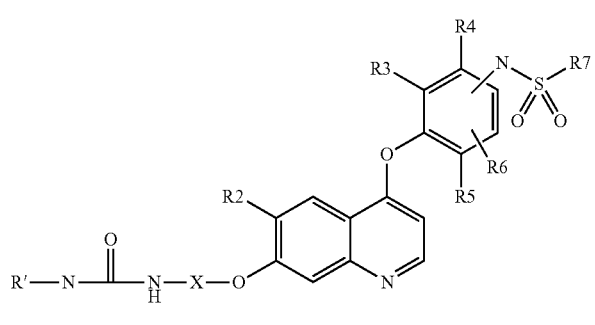

[G + 5']

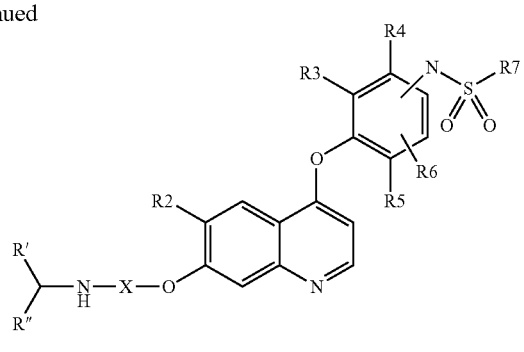

[G + 5']

The synthesis is equivalent to the above reaction scheme for these inventive compounds wherein $R^2$ represents $R^8$—X—. The general reaction scheme is shown below. The single reaction protocols are the same as disclosed above.

Example 1

2,5-Difluoro-N-{3-fluoro-4-[6-methoxy-7-(3-piperidin-1-yl-propoxy)-quinolin-4-yloxy]-phenyl}-benzenesulfonamide

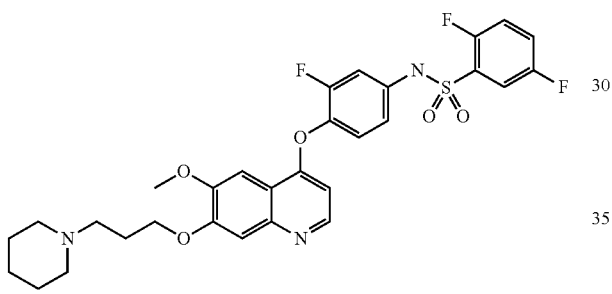

$C_{30}H_{30}F_3N_3O_5S$ Mw. 601.65
LC/MS purity: 99%, m/z 600 [M–H]⁻, 602 [M+H]⁺ Rt. 3.12 min. (Method B)
¹H NMR (300 MHz, DMSO-d6): 9.0 (bs, 1H), 8.41 (d, 1H), 7.61-7.03 (m, 8H), 6.30 (d, 1H), 4.26 (t, 2H), 3.97 (s, 3H), 3.40 (bs, 2H), 3.33 (bs, 2H), 2.45 (bs, 2H), 2.11 (bs, 6H), 1.63 (bs, 2H).
Melting point: 206-208° C.
Yield: 46%

Example 2

2-Fluoro-N-{3-fluoro-4-[6-methoxy-7-(3-piperidin-1-yl-propoxy)-quinolin-4-yloxy]-phenyl}-benzenesulfonamide

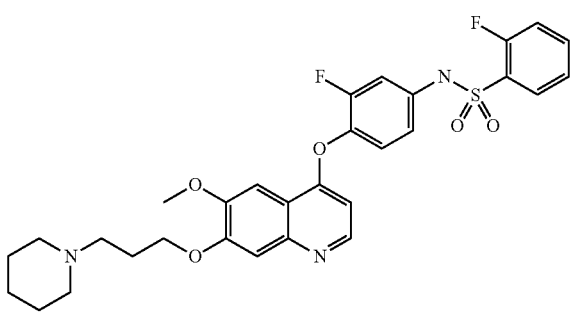 [SMILES: COc1cc2c(Oc3ccc(NS(=O)(=O)c4ccccc4F)cc3F)ccnc2cc1OCCCN1CCCCC1]

$C_{30}H_{31}F_2N_3O_5S$ Mw. 583.66
LC/MS purity: 99%, m/z 582 [M–H]⁻, 584 [M+H]⁺ Rt. 3.18 min. (Method B)
¹H NMR (300 MHz, DMSO-d6): 9.2 (bs, 1H), 8.43 (d, 1H), 7.84 (t, 1H), 7.60 (d, 1H), 7.47 (s, 1H), 7.32 (m, 3H), 7.18 (t, 1H), 6.99 (d, 1H), 6.87 (d, 1H), 6.33 (d, 1H), 4.18 (t, 2H), 3.92 (s, 3H), 2.43 (bs, 6H), 1.96 (t, 2H), 1.52 (bs, 4H), 1.40 (bs, 2H).
Melting point: 214-216° C.
Yield: 38%

Example 3

4-Chloro-2-fluoro-N-{3-fluoro-4-[6-methoxy-7-(3-piperidin-1-yl-propoxy)-quinolin-4-yloxy]-phenyl}-benzenesulfonamide

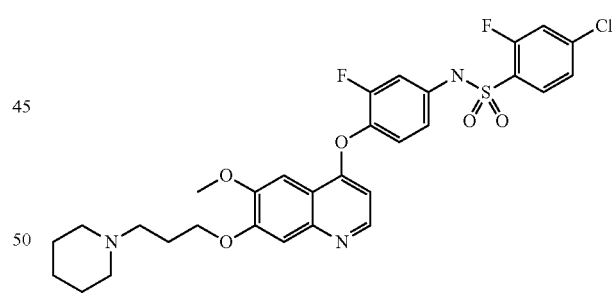

$C_{30}H_{30}ClF_2N_3O_5S$ Mw. 618.10
LC/MS purity: 100%, m/z 616 [M–H]⁻, 618 [M+H]⁺ Rt. 3.32 min. (Method B)
¹H NMR (300 MHz, DMSO-d6): 9.8 (bs, 1H), 8.43 (d, 1H), 7.82 (t, 1H), 7.56 (dd, 1H), 7.49 (s, 1H), 7.39 (m, 2H), 7.15 (t, 1H), 6.96 (dd, 1H), 6.82 (d, 1H), 6.35 (d, 1H), 4.19 (t, 2H), 3.92 (s, 3H), 2.58 (m, 6H), 2.02 (m, 2H), 1.56 (m, 4H), 1.43 (m, 2H).
Melting point: 122-124° C.
Yield: 36%

Example 4

N-{3-Fluoro-4-[6-methoxy-7-(3-piperidin-1-yl-propoxy)-quinolin-4-yloxy]-phenyl}-2-trifluoromethyl-benzenesulfonamide

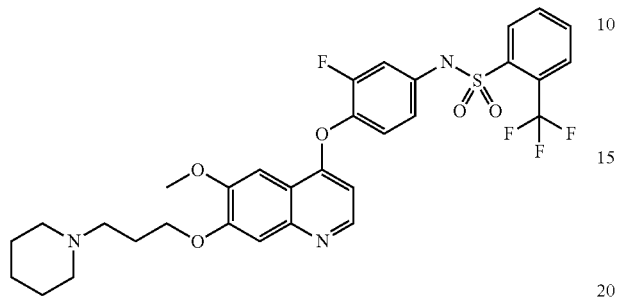

$C_{31}H_{31}F_4N_3O_5S$ Mw. 633.67

LC/MS purity: 100%, m/z 632 [M−H]⁻, 634 [M+H]⁺ Rt. 3.36 min. (Method B)

¹H NMR (300 MHz, DMSO-d6): 10.0 (bs, 1H), 8.45 (d, 1H), 8.14 (d, 1H), 7.93 (d, 1H), 7.78 (m, 2H), 7.48 (s, 1H), 7.38 (s, 1H), 7.21 (t, 1H), 7.00 (dd, 1H), 6.88 (d, 1H), 6.36 (d, 1H), 4.19 (t, 2H), 3.64 (s, 3H), 2.62 (m, 6H), 2.03 (m, 2H), 1.59 (m, 4H), 1.44 (m, 2H).

Melting point: 173-175° C.

Yield: 48%

Example 5

N-{3-Fluoro-4-[6-methoxy-7-(3-piperidin-1-yl-propoxy)-quinolin-4-yloxy]-phenyl}-3-trifluoromethyl-benzenesulfonamide

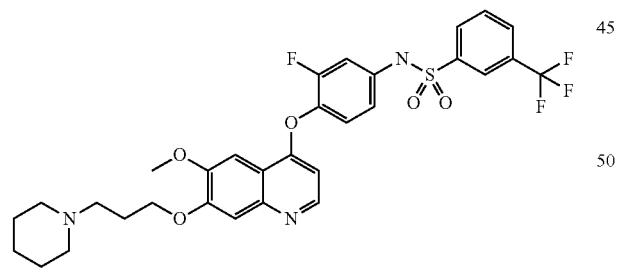

$C_{31}H_{31}F_4N_3O_5S$ Mw. 633.67

LC/MS purity: 100%, m/z 632 [M−H]⁻, 634 [M+H]⁺ Rt. 3.34 min. (Method B)

¹H NMR (300 MHz, DMSO-d6): 9.8 (bs, 1H), 8.43 (d, 1H), 8.00 (m, 3H), 7.78 (t, 2H), 7.48 (s, 1H), 7.38 (s, 1H), 7.22 (t, 1H), 7.04 (dd, 1H), 6.89 (d, 1H), 6.32 (d, 1H), 4.19 (t, 1H), 3.92 (s, 3H), 2.64 (m, 6H), 2.02 (m, 2H), 1.56 (m, 4H), 1.44 (m, 2H).

Melting point: 123-126° C.

Yield: 61%

Example 6

2,6-Dichloro-N-{3-fluoro-4-[6-methoxy-7-(3-piperidin-1-yl-propoxy)-quinolin-4-yloxy]-phenyl}-benzenesulfonamide

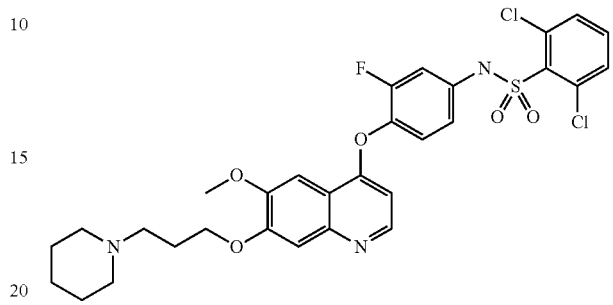

$C_{30}H_{30}Cl_2FN_3O_5S$ Mw. 634.56

LC/MS purity: 99%, m/z 632 [M−H]⁻, 634 [M+H]⁺ Rt. 3.31 min. (Method B)

¹H NMR (300 MHz, DMSO-d6): 9.8 (bs, 1H), 8.42 (d, 1H), 7.48 (m, 3H), 7.37 (m, 2H), 7.08 (t, 1H), 6.90 (d, 1H), 6.73 (d, 1H), 6.33 (d, 1H), 4.18 (t, 2H), 3.92 (s, 3H), 2.52 (m, 6H), 1.99 (m, 2H), 1.53 (m, 4H), 1.41 (m, 2H).

Melting point: 206-208° C.

Yield: 35%

Example 7

N-{3-Fluoro-4-[6-methoxy-7-(3-piperidin-1-yl-propoxy)-quinolin-4-yloxy]-phenyl}-2-nitro-benzenesulfonamide

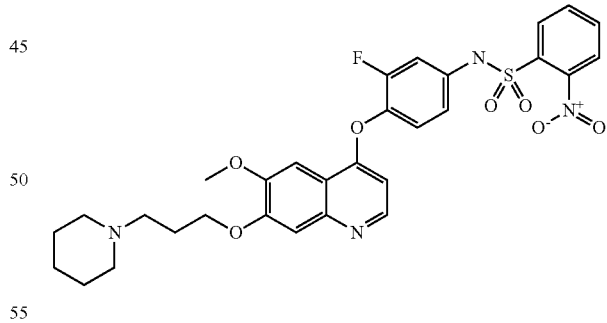

$C_{30}H_{31}FN_4O_7S$ Mw. 610.67

LC/MS purity: 100%, m/z 609 [M−H]⁻, 611 [M+H]⁺ Rt. 2.99 min. (Method B)

¹H NMR (300 MHz, DMSO-d6): 11 (bs, 1H), 8.43 (d, 1H), 7.93 (t, 1H), 7.65 (m, 3H), 7.49 (s, 1H), 7.38 (s, 1H), 7.06 (t, 1H), 6.84 (dd, 1H), 6.72 (d, 1H), 6.35 (d, 1H), 4.20 (t, 2H), 3.93 (s, 3H), 2.71 (bs, 6H), 2.07 (m, 2H), 1.60 (bs, 4H), 1.46 (bs, 2H).

Melting point: 113-116° C.

Yield: 41%

Example 8

Biphenyl-3-sulfonic acid {3-fluoro-4-[6-methoxy-7-(3-piperidin-1-yl-propoxy)-quinolin-4-loxy]-phenyl}-amide

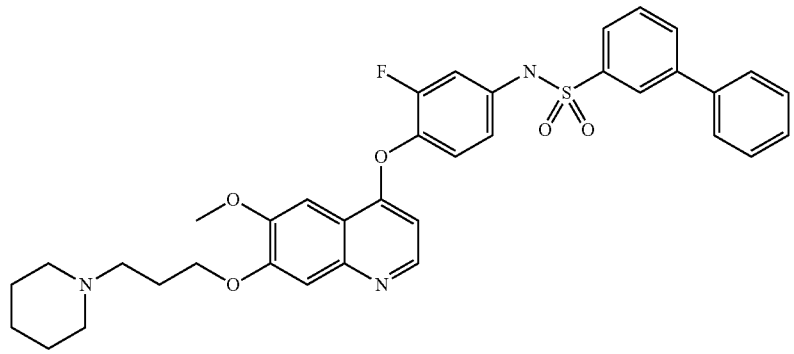 [SMILES: COc1cc2c(Oc3ccc(NS(=O)(=O)c4cccc(-c5ccccc5)c4)cc3F)ccnc2cc1OCCCN1CCCCC1]

$C_{36}H_{36}FN_3O_5S$ Mw. 641.77

LC/MS purity: 100%, m/z 640 [M−H]⁻, 642 [M+H]⁺ Rt. 3.95 min. (Method B)

$^1$H NMR (300 MHz, DMSO-d6): 10.6 (bs, 1H), 8.37 (d, 1H), 8.03 (s, 1H), 7.95 (d, 1H), 7.79 (d, 1H), 7.68 (m, 3H), 7.49 (m, 4H), 7.37 (s, 1H), 7.32 (t, 1H), 7.16 (dd, 1H), 7.00 (d, 1H), 6.28 (d, 1H), 4.17 (t, 2H), 3.90 (s, 3H), 2.44 (bs, 6H), 1.97 (m, 2H), 1.53 (bs, 4H), 1.39 (m, 2H).

Melting point: 113-115° C.

Yield: 47%

Example 9

3-Difluoromethoxy-N-{3-fluoro-4-[6-methoxy-7-(3-piperidin-1-yl-propoxy)-quinolin-4-yloxy]-phenyl}-benzenesulfonamide

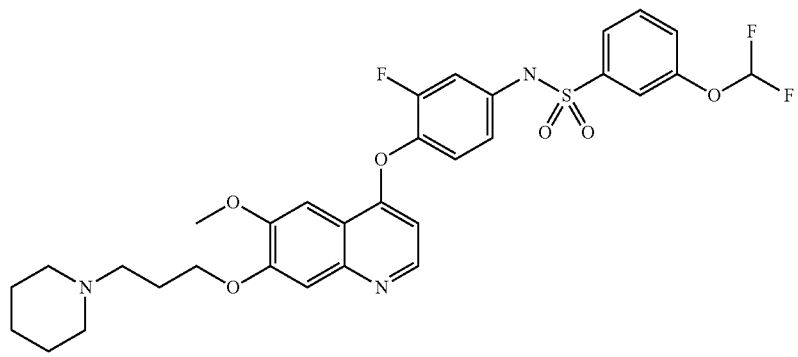 [SMILES: COc1cc2c(Oc3ccc(NS(=O)(=O)c4cccc(OC(F)F)c4)cc3F)ccnc2cc1OCCCN1CCCCC1]

$C_{31}H_{32}F_3N_3O_6S$ Mw. 631.68

LC/MS purity: 100%, m/z 630 [M−H]⁻, 632 [M+H]⁺ Rt. 3.44 min. (Method B)

$^1$H NMR (300 MHz, DMSO-d6): 10.2 (bs, 1H), 8.43 (d, 1H), 8.66-7.21 (m, 7H), 7.05 (d, 1H), 6.91 (d, 1H), 6.33 (d, 1H), 4.18 (t, 2H), 3.92 (s, 3H), 3.59 (m, 1H), 2.52 (bs, 6H), 1.99 (m, 2H), 1.52 (bs, 4H), 1.41 (m, 2H).

Melting point: 105-106° C.

Yield: 77%

Example 10

N-{3-Fluoro-4-[6-methoxy-7-(3-piperidin-1-yl-propoxy)-quinolin-4-yloxy]-phenyl}-3-phenoxy-benzenesulfonamide

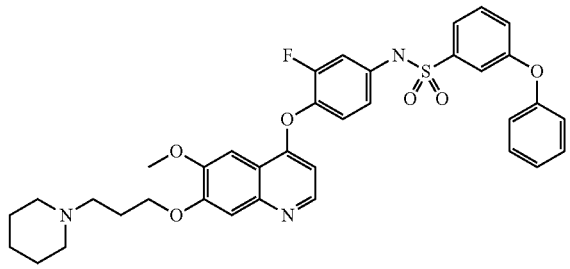 [SMILES: COc1cc2c(Oc3ccc(NS(=O)(=O)c4cccc(Oc5ccccc5)c4)cc3F)ccnc2cc1OCCCN1CCCCC1]

$C_{36}H_{36}FN_3O_6S$ Mw. 657.77

LC/MS purity: 97%, m/z 656 [M−H]⁻, 658 [M+H]⁺ Rt. 3.93 min. (Method B)

¹H NMR (300 MHz, DMSO-d6): 10.4 (bs, 1H), 8.43 (d, 1H), 7.58-7.24 (m, 10H), 7.07-6.90 (m, 4H), 6.35 (d, 1H), 4.18 (t, 2H), 3.93 (s, 3H), 2.49 (bs, 6H), 1.99 (bs, 2H), 1.53 (bs, 4H), 1.41 (bs, 2H).

Melting point: 146-147° C.

Yield: 38%

Example 11

2,6-Difluoro-N-{3-fluoro-4-[6-methoxy-7-(3-piperidin-1-yl-propoxy)-quinolin-4-yloxy]-phenyl}-benzenesulfonamide

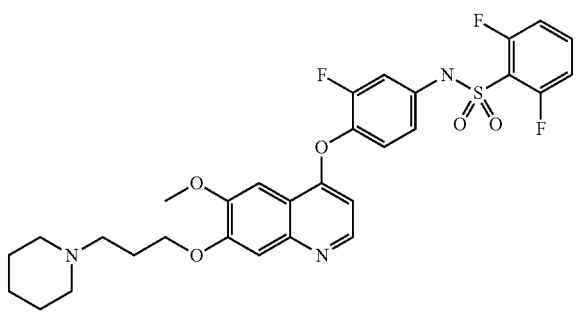 [SMILES: COc1cc2c(Oc3ccc(NS(=O)(=O)c4c(F)cccc4F)cc3F)ccnc2cc1OCCCN1CCCCC1]

$C_{30}H_{30}F_3N_3O_5S$ Mw. 601.65

LC/MS purity: 98%, m/z 600 [M−H]⁻, 602 [M+H]⁺ Rt. 2.99 min. (Method B)

¹H NMR (300 MHz, DMSO-d6): 10.2 (bs, 1H), 8.44 (d, 1H), 7.59 (t, 1H), 7.49 (s, 1H), 7.39 (s, 1H), 7.20 (m, 3H), 7.04 (d, 1H), 6.89 (d, 1H), 6.35 (d, 1H), 4.20 (t, 2H), 3.92 (s, 3H), 2.70 (bs, 6H), 2.06 (bs, 2H), 1.45 (bs, 4H), 1.24 (bs, 2H).

Melting point: 242-244° C.

Yield: 27%

Example 12

2,5-Difluoro-N-(3-fluoro-4-{6-methoxy-7-[3-(4-methyl-piperazin-1-yl)-propoxy]-quinolin-4-yloxy}-phenyl)-benzenesulfonamide

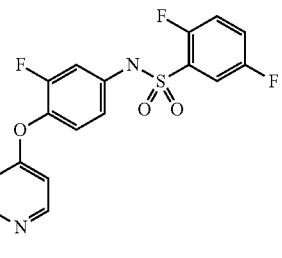

$O_{30}H_{31}F_3N_4O_5S$ Mw. 616.66

LC/MS purity: 99%, m/z 615 [M−H]⁻, 617 [M+H]⁺ Rt. 2.91 min. (Method B)

¹H NMR (300 MHz, DMSO-d6): 10.3 (bs, 1H), 8.43 (d, 1H), 7.60 (m, 1H), 7.42 (m, 4H), 7.19 (t, 1H), 7.02 (dd, 1H), 6.88 (d, 1H), 6.35 (d, 1H), 4.18 (t, 2H), 4.01 (bs, 4H), 3.92 (s, 3H), 3.35 (bs, 6H), 2.26 (s, 3H), 1.95 (m, 2H).

Melting point: 124-126° C.

Yield: 24%

Example 13

Biphenyl-3-sulfonic acid (3-fluoro-4-{6-methoxy-7-[3-(4-methyl-piperazin-1-yl)-propoxy]-quinolin-4-yloxy}-phenyl)-amide

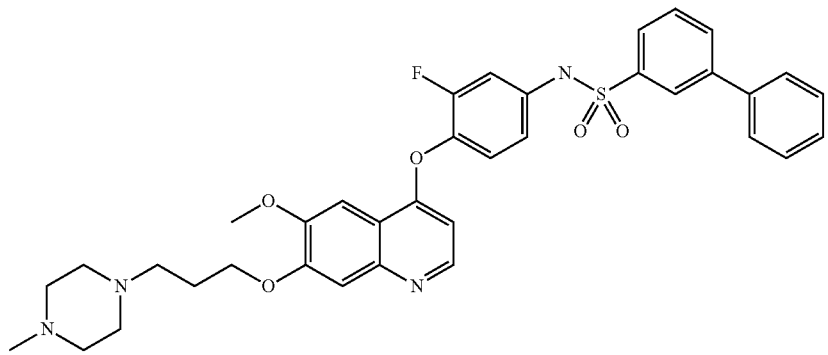 [SMILES: COc1cc2c(Oc3ccc(NS(=O)(=O)c4cccc(-c5ccccc5)c4)cc3F)ccnc2cc1OCCCN1CCN(C)CC1]

C₃₆H₃₇FN₄O₅S Mw. 656.78
LC/MS purity: 97%, m/z 655 [M−H]⁻, 657 [M+H]⁺ Rt. 3.71 min. (Method B)
¹H NMR (300 MHz, DMSO-d6): 10.5 (bs, 1H), 8.36 (d, 1H), 8.03 (d, 1H), 7.96 (t, 1H), 7.79 (d, 1H), 7.67 (m, 3H), 7.52-7.12 (m, 6H), 7.04 (dd, 1H), 6.90 (d, 1H), 6.28 (d, 1H), 4.17 (t, 2H), 3.93 (s, 3H), 2.40 (bs, 10H), 2.19 (s, 3H), 1.96 (t, 2H).
Melting point: 190-191° C.
Yield: 40%

Example 14

N-(3-Fluoro-4-{6-methoxy-7-[3-(4-methyl-piperazin-1-yl)-propoxy]-quinolin-4-yloxy}-phenyl)-3-phenoxy-benzenesulfonamide

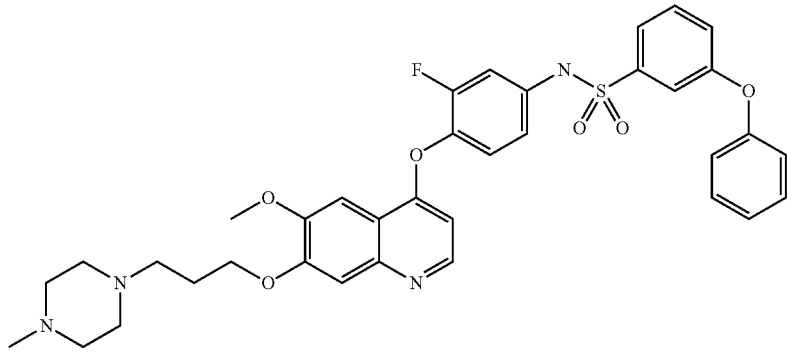 [SMILES: COc1cc2c(Oc3ccc(NS(=O)(=O)c4cccc(Oc5ccccc5)c4)cc3F)ccnc2cc1OCCCN1CCN(C)CC1]

C₃₆H₃₇FN₄O₆S Mw. 672.78
LC/MS purity: 97%, m/z 671 [M−H]⁻, 673 [M+H]⁺ Rt. 3.68 min. (Method B)
¹H NMR (300 MHz, DMSO-d6): 11 (bs, 1H), 8.43 (s, 1H), 7.62-7.23 (m, 10H), 7.10-6.92 (m, 4H), 6.35 (d, 1H), 4.18 (t, 2H), 3.93 (s, 3H), 2.47 (m, 4H), 2.40 (m, 6H), 2.19 (s, 3H), 1.96 (t, 2H).
Melting point: 140-141° C.
Yield: 24%

Example 15

2-Cyano-N-(3-fluoro-4-{6-methoxy-7-[3-(4-methyl-piperazin-1-yl)-propoxy]-quinolin-4-yloxy}-phenyl)-benzenesulfonamide

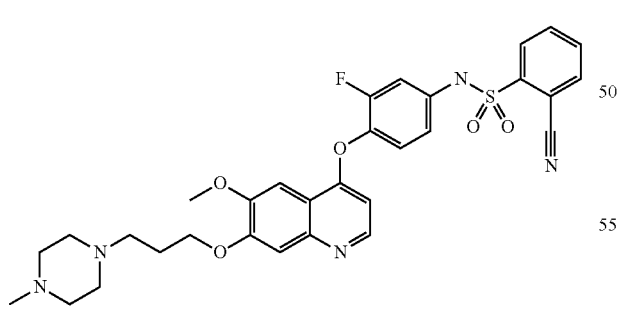

C₃₁H₃₂FN₅O₅S Mw. 605.69
LC/MS purity: 99%, m/z 604 [M−H]⁻, 606 [M+H]⁺ Rt. 2.73 min. (Method B)
¹H NMR (300 MHz, DMSO-d6): 10.6 (bs, 1H), 8.44 (d, 1H), 7.50 (m, 3H), 7.37 (m, 3H), 7.28 (t, 1H), 7.10 (d, 1H), 6.96 (d, 1H), 6.34 (d, 1H), 4.17 (t, 2H), 3.92 (s, 3H), 2.44 (m, 4H), 2.36 (m, 6H), 2.16 (s, 3H), 1.94 (m, 2H).
Melting point: 109-111° C.
Yield: 22%

Example 16

2,4-Difluoro-N-(3-fluoro-4-{6-methoxy-7-[3-(4-methyl-piperazin-1-yl)-propoxy]-quinolin-4-yloxy}-phenyl)-benzenesulfonamide

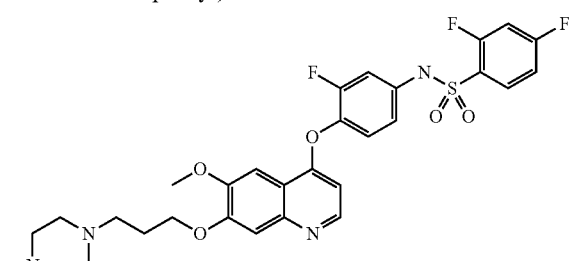
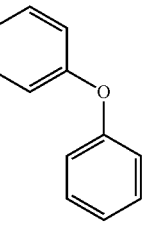

C₃₀H₃₁F₃N₄O₅S Mw. 616.66
LC/MS purity: 99%, m/z 615 [M−H]⁻, 617 [M+H]⁺ Rt. 2.93 min. (Method B)
¹H NMR (300 MHz, DMSO-d6): 10 (bs, 1H), 8.43 (d, 1H), 7.93 (t, 1H), 7.47 (m, 2H), 7.36 (s, 1H), 7.22 (m, 2H), 7.08 (dd, 1H), 6.92 (dd, 1H), 6.34 (d, 1H), 4.18 (t, 2H), 3.92 (s, 3H), 2.44 (m, 4H), 2.36 (m, 6H), 2.18 (s, 3H), 1.96 (t, 2H).
Melting point: 99-102° C.
Yield: 42%

Example 17

2,3,4-Trifluoro-N-(3-fluoro-4-{6-methoxy-7-[3-(4-methyl-piperazin-1-yl)-propoxy]-quinolin-4-yloxy}-phenyl)-benzenesulfonamide

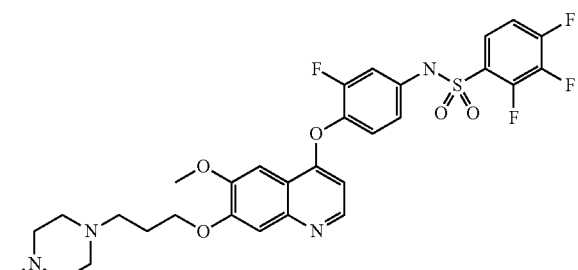

C₃₀H₃₀F₄N₄O₅S Mw. 634.65
LC/MS purity: 98%, m/z 633 [M−H]⁻, 635 [M+H]⁺ Rt. 2.98 min. (Method B)
¹H NMR (300 MHz, DMSO-d6): 10.2 (bs, 1H), 8.44 (d, 1H), 7.92 (d, 1H), 7.80 (d, 1H), 7.77 (t, 1H), 7.48 (s, 1H), 7.38 (s, 1H), 7.26 (t, 1H), 7.02 (d, 1H), 6.36 (d, 1H), 4.21 (t, 2H), 3.98 (s, 3H), 2.45 (m, 4H), 2.36 (m, 6H), 2.18 (s, 3H), 1.95 (t, 2H).
Melting point: 88-90° C.
Yield: 45%

Example 18

4-Fluoro-N-(3-fluoro-4-{6-methoxy-7-[3-(4-methyl-piperazin-1-yl)-propoxy]-quinolin-4-yloxy}-phenyl)-3-methoxy-benzenesulfonamide

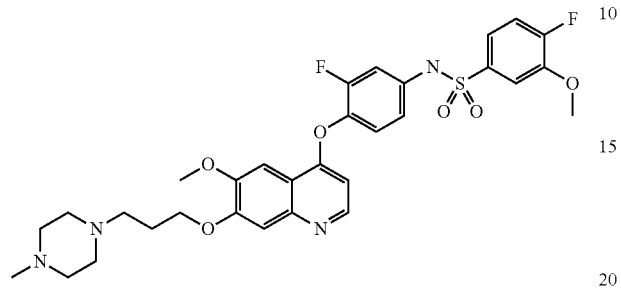

$C_{31}H_{34}F_2N_4O_6S$ Mw. 628.70

LC/MS purity: 99%, m/z 627 [M–H]⁻, 629 [M+H]⁺ Rt. 3.19 min. (Method B)

¹H NMR (300 MHz, DMSO-d6): 10.9 (bs, 1H), 8.44 (d, 1H), 7.52-7.28 (m, 6H), 7.10 (d, 1H), 6.94 (dd, 1H), 6.34 (d, 1H), 4.17 (t, 2H), 3.92 (s, 3H), 3.88 (s, 3H), 2.44 (m, 4H), 2.37 (m, 6H), 2.19 (s, 3H), 1.94 (t, 2H).

Melting point: 167-169° C.

Yield: 60%

Example 19

2-Bromo-N-(3-fluoro-4-{6-methoxy-7-[3-(4-methyl-piperazin-1-yl)-propoxy]-quinolin-4-yloxy}-phenyl)-benzenesulfonamide

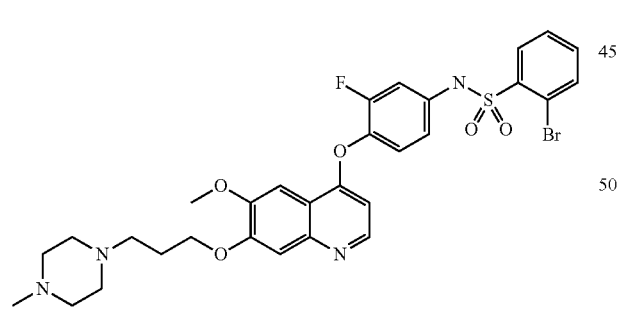

$C_{30}H_{32}BrFN_4O_5S$ Mw. 659.58

LC/MS purity: 98%, m/z 657 [M–H]⁻, 659 [M+H]⁺ Rt. 3.17 min. (Method B)

¹H NMR (300 MHz, DMSO-d6): 10.5 (bs, 1H), 8.43 (d, 1H), 8.11 (d, 1H), 7.81 (d, 1H), 7.57-7.46 (m, 3H), 7.36 (s, 1H), 7.26 (t, 1H), 7.05 (d, 1H), 6.94 (d, 1H), 6.34 (d, 1H), 4.17 (t, 2H), 3.91 (s, 3H), 2.45 (bs, 10H), 2.20 (s, 3H), 1.95 (t, 2H).

Melting point: 98-101° C.

Yield: 40%

Example 20

2,5-Dichloro-N-(3-fluoro-4-{6-methoxy-7-[3-(4-methyl-piperazin-1-yl)-propoxy]-quinolin-4-yloxy}-phenyl)-benzenesulfonamide

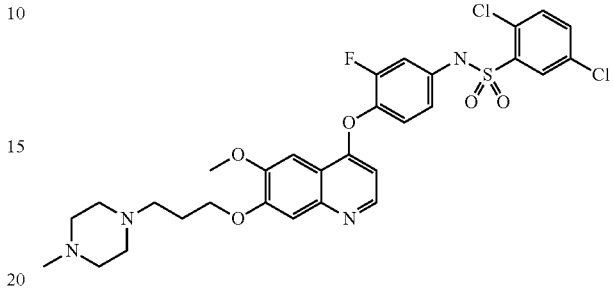

$C_{30}H_{31}Cl_2FN_4O_5S$ Mw. 649.57

LC/MS purity: 98%, m/z 647 [M–H]⁻, 649 [M+H]⁺ Rt. 3.20 min. (Method B)

¹H NMR (300 MHz, DMSO-d6): 11 (bs, 1H), 8.42 (d, 1H), 7.98 (bs, 1H), 7.60 (bs, 2H), 7.48 (bs, 1H), 7.38 (bs, 1H), 7.18 (t, 1H), 6.98 (d, 1H), 6.85 (d, 1H), 6.34 (d, 1H), 4.18 (t, 2H), 3.92 (s, 3H), 2.50 (bs, 10H), 2.28 (s, 3H), 1.78 (m, 2H).

Melting point: 134-136° C.

Yield: 38%

Example 21

N-(3-Fluoro-4-{6-methoxy-7-[3-(4-methyl-piperazin-1-yl)-propoxy]-quinolin-4-yloxy}-phenyl)-2-nitro-benzenesulfonamide

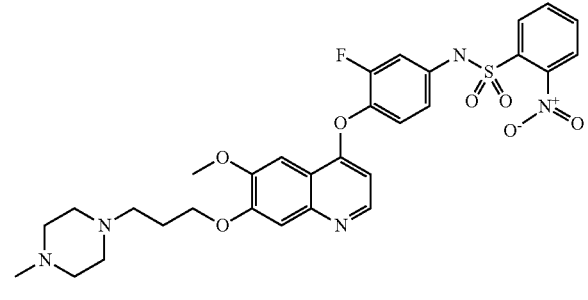 [SMILES: COc1cc2c(Oc3ccc(NS(=O)(=O)c4ccccc4[N+](=O)[O-])cc3F)ccnc2cc1OCCCN1CCN(C)CC1]

$C_{30}H_{32}FN_5O_7S$ Mw. 625.68

LC/MS purity: 99%, m/z 624 [M–H]⁻, 626 [M+H]⁺ Rt. 2.81 min. (Method B)

¹H NMR (300 MHz, DMSO-d6): 10.4 (bs, 1H), 8.43 (d, 1H), 7.96 (m, 1H), 7.77 (m, 1H), 7.70 (m, 2H), 7.48 (s, 1H), 7.37 (s, 1H), 7.15 (t, 1H), 6.94 (d, 1H), 6.79 (d, 1H), 6.35 (d, 1H), 4.18 (t, 2H), 3.92 (s, 3H), 2.73 (m, 4H), 2.54 (m, 6H), 2.35 (s, 3H), 1.98 (m, 2H).

Melting point: 125-128° C.

Yield: 29%

Example 22

3-Fluoro-(3-fluoro-4-{6-methoxy-7-[3-(4-methyl-piperazin-1-yl)-propoxy]-quinolin-4-yloxy}-phenyl)-benzenesulfonamide

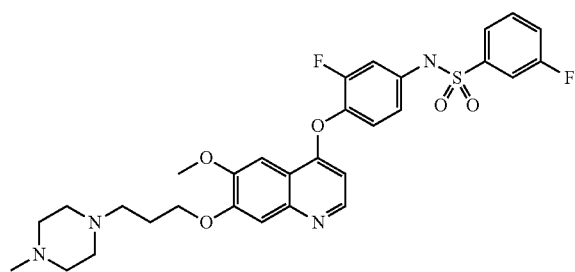 [SMILES: COc1cc2c(Oc3ccc(NS(=O)(=O)c4cccc(F)c4)cc3F)ccnc2cc1OCCCN1CCN(C)CC1]

$C_{30}H_{32}F_2N_4O_5S$ Mw. 598.67

LC/MS purity: 99%, m/z 597 [M−H]⁻, 599 [M+H]⁺ Rt. 3.07 min. (Method B)

¹H NMR (300 MHz, DMSO-d6): 10.9 (bs, 1H), 8.44 (d, 1H), 7.63-7.47 (m, 5H), 7.37 (s, 1H), 7.29 (t, 1H), 7.00 (dd, 1H), 6.94 (d, 1H), 6.35 (d, 1H), 4.17 (t, 2H), 3.92 (s, 3H), 2.45 (m, 10H), 2.20 (s, 3H), 1.96 (m, 2H).

Melting point: 82-84° C.

Yield: 48%

Example 23

3-Chloro-4-fluoro-N-(3-fluoro-4-{6-methoxy-7-[3-(4-methyl-piperazin-1-yl)-propoxy]-quinolin-4-yloxy}-phenyl)-benzenesulfonamide

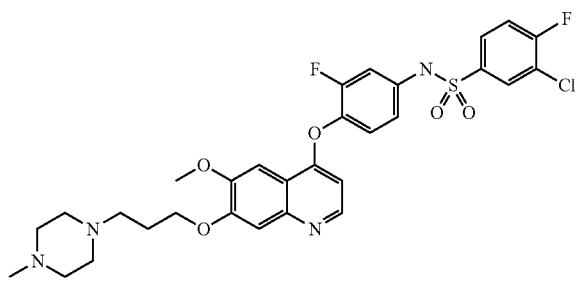 [SMILES: COc1cc2c(Oc3ccc(NS(=O)(=O)c4ccc(F)c(Cl)c4)cc3F)ccnc2cc1OCCCN1CCN(C)CC1]

$C_{30}H_{31}ClF_2N_4O_5S$ Mw. 633.12

LC/MS purity: 98%, m/z 631 [M−H]⁻, 633 [M+H]⁺ Rt. 3.24 min. (Method B)

¹H NMR (300 MHz, DMSO-d6): 10.5 (bs, 1H), 8.44 (d, 1H), 7.91 (dd, 1H), 7.77 (m, 1H), 7.59 (t, 1H), 7.48 (s, 1H), 7.37 (s, 1H), 7.25 (t, 1H), 7.06 (d, 1H), 6.90 (d, 1H), 6.36 (d, 1H), 4.18 (t, 2H), 3.92 (s, 3H), 2.46 (bs, 10H), 2.22 (s, 3H), 1.96 (m, 2H).

Melting point: 108-110° C.

Yield: 57%

Example 24

N-(3-Fluoro-4-{6-methoxy-7-[3-(4-methyl-piperazin-1-yl)-propoxy]-quinolin-4-yloxy}-phenyl)-2-trifluoromethyl-benzenesulfonamide

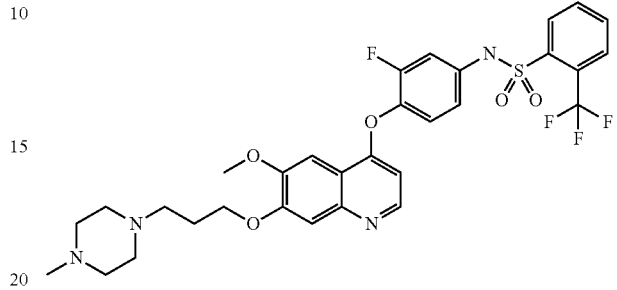

$C_{31}H_{32}F_4N_4O_5S$ Mw. 648.68

LC/MS purity: 99%, m/z 647 [M−H]⁻, 649 [M+H]⁺ Rt. 3.11 min. (Method B)

¹H NMR (300 MHz, DMSO-d6): 11 (bs, 1H), 8.44 (d, 1H), 8.14 (d, 1H), 7.95 (d, 1H), 7.80 (m, 2H), 7.47 (s, 1H), 7.36 (s, 1H), 7.24 (t, 1H), 7.02 (dd, 1H), 6.90 (d, 1H), 6.35 (d, 1H), 4.17 (t, 2H), 3.91 (s, 3H), 2.45 (bs, 10H), 2.23 (s, 3H), 1.96 (m, 2H).

Melting point: 102-106° C.

Yield: 26%

Example 25

N-(3-Fluoro-4-{6-methoxy-7-[3-(4-methyl-piperazin-1-yl)-propoxy]-quinolin-4-yloxy}-phenyl)-2-trifluoromethoxy-benzenesulfonamide

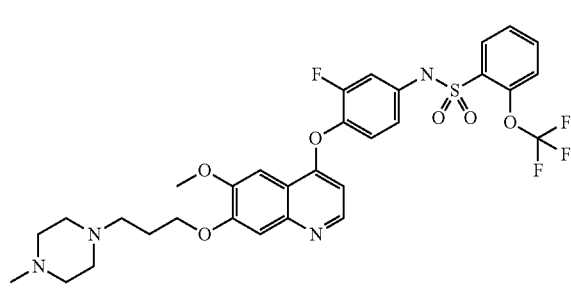 [SMILES: COc1cc2c(Oc3ccc(NS(=O)(=O)c4ccccc4OC(F)(F)F)cc3F)ccnc2cc1OCCCN1CCN(C)CC1]

$C_{31}H_{32}F_4N_4O_6S$ Mw. 664.68

LC/MS purity: 100%, m/z 663 [M−H]⁻, 665 [M+H]⁺ Rt. 3.26 min. (Method B)

¹H NMR (300 MHz, DMSO-d6): 9.8 (bs, 1H), 8.44 (d, 1H), 8.01 (d, 1H), 7.73 (t, 1H), 7.52 (m, 2H), 7.47 (s, 1H), 7.36 (s, 1H), 7.26 (t, 1H), 7.07 (d, 1H), 6.91 (d, 1H), 6.33 (d, 1H), 4.18 (t, 2H), 3.91 (s, 3H), 2.44 (bs, 10H), 2.23 (s, 3H), 1.96 (m, 2H).

Melting point: 86-90° C.

Yield: 23%

Example 26

2-Fluoro-N-(3-fluoro-4-{6-methoxy-7-[3-(4-methyl-piperazin-1-yl)-propoxy]-quinolin-4-yloxy}-phenyl)-benzenesulfonamide

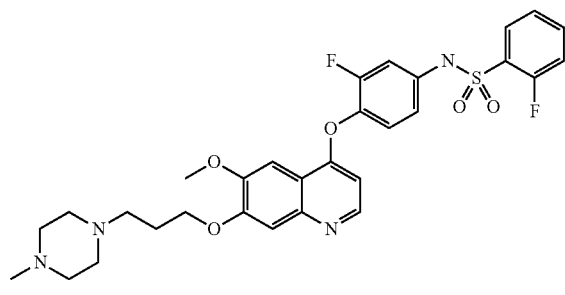 [SMILES: COc1cc2c(Oc3ccc(NS(=O)(=O)c4ccccc4F)cc3F)ccnc2cc1OCCCN1CCN(C)CC1]

$C_{30}H_{32}F_2N_4O_5S$ Mw. 598.67

LC/MS purity: 100%, m/z 597 [M−H]⁻, 599 [M+H]⁺ Rt. 2.85 min. (Method B)

¹H NMR (300 MHz, DMSO-d6): 11.5 (bs, 1H), 8.43 (d, 1H), 7.88 (t, 1H), 7.68 (d, 1H), 7.47-7.28 (m, 5H), 7.09 (d, 1H), 6.96 (d, 1H), 6.33 (d, 1H), 4.17 (t, 2H), 3.91 (s, 3H), 2.43 (bs, 10H), 2.20 (s, 3H), 1.96 (m, 2H).

Melting point: 185-186° C.

Yield: 28%

Example 27

4-Chloro-2-fluoro-N-(3-fluoro-4-{6-methoxy-7-[3-(4-methyl-piperazin-1-yl)-propoxy]-quinolin-4-yloxy}-phenyl)-benzenesulfonamide

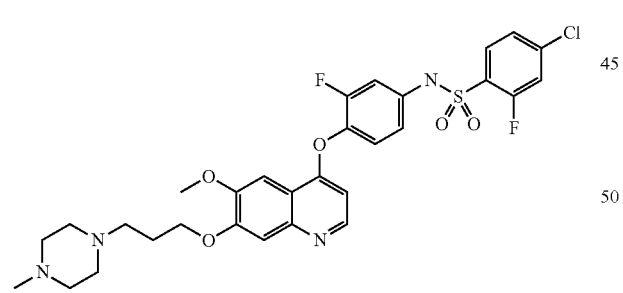

$C_{30}H_{31}ClF_2N_4O_5S$ Mw. 633.12

LC/MS purity: 100%, m/z 631 [M−H]⁻, 633 [M+H]⁺ Rt. 3.05 min. (Method B)

¹H NMR (300 MHz, DMSO-d6): 10 (bs, 1H), 8.44 (d, 1H), 7.85 (t, 1H), 7.63 (d, 1H), 7.48 (s, 1H), 7.43 (d, 1H), 7.37 (s, 1H), 7.22 (t, 1H), 7.04 (d, 1H), 6.89 (d, 1H), 6.35 (d, 1H), 4.18 (t, 2H), 3.92 (s, 3H), 2.50 (bs, 10H), 2.25 (s, 3H), 1.98 (m, 2H).

Melting point: 106-110° C.

Yield: 26%

Example 28

N-(3-Fluoro-4-{6-methoxy-7-[3-(4-methyl-piperazin-1-yl)-propoxy]-quinolin-4-yloxy}-phenyl)-2-methyl-benzenesulfonamide

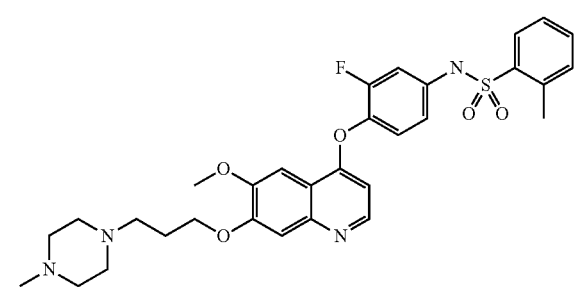 [SMILES: COc1cc2c(Oc3ccc(NS(=O)(=O)c4ccccc4C)cc3F)ccnc2cc1OCCCN1CCN(C)CC1]

$C_{31}H_{35}FN_4O_5S$ Mw. 594.71

LC/MS purity: 99%, m/z 593 [M−H]⁻, 595 [M+H]⁺ Rt. 3.28 min. (Method B)

¹H NMR (300 MHz, DMSO-d6): 11 (bs, 1H), 8.43 (d, 1H), 7.91 (t, 1H), 7.53-7.24 (m, 6H), 7.05 (d, 1H), 6.94 (d, 1H), 6.32 (d, 1H), 4.17 (t, 2H), 3.91 (s, 3H), 2.62 (s, 3H), 2.40 (m, 10H), 2.16 (s, 3H), 1.95 (m, 2H).

Melting point: 73-75° C.

Yield: 35%

Example 29

2-Chloro-N-(3-fluoro-4-{6-methoxy-7-[3-(4-methyl-piperazin-1-yl)-propoxy]-quinolin-4-yloxy}-phenyl)-benzenesulfonamide

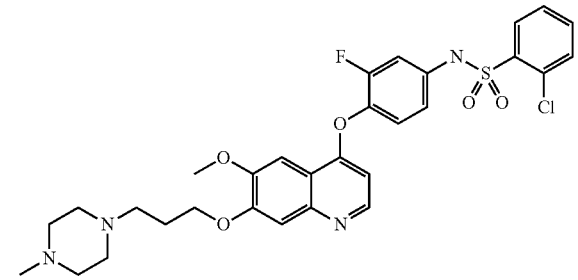

$C_{30}H_{32}ClFN_4O_5S$ Mw. 615.13

LC/MS purity: 99%, m/z 613 [M−H]⁻, 615 [M+H]⁺ Rt. 3.09 min. (Method B)

¹H NMR (300 MHz, DMSO-d6): 11.2 (bs, 1H), 8.43 (d, 1H), 8.08 (d, 1H), 7.62 (m, 2H), 7.52 (m, 1H), 7.46 (s, 1H), 7.36 (s, 1H), 7.26 (t, 1H), 7.06 (dd, 1H), 6.94 (d, 1H), 6.32 (d, 1H), 4.17 (t, 2H), 3.91 (s, 3H), 2.43 (m, 10H), 2.19 (s, 3H), 1.96 (m, 2H).
Melting point: 96-98° C.
Yield: 36%

Example 30

3-Difluoromethoxy-N-(3-fluoro-4-{6-methoxy-7-[3-(4-methyl-piperazin-1-yl)-propoxy]-quinolin-4-yloxy}-phenyl)-benzenesulfonamide

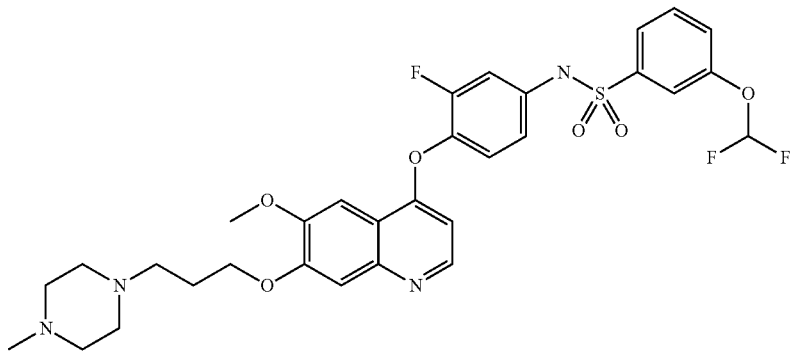 [SMILES: COc1cc2c(Oc3ccc(NS(=O)(=O)c4cccc(OC(F)F)c4)cc3F)ccnc2cc1OCCCN1CCN(C)CC1]

$C_{31}H_{33}F_3N_4O_6S$ Mw. 646.69
LC/MS purity: 100%, m/z 645 [M−H]⁻, 647 [M+H]⁺ Rt. 3.15 min. (Method B)
¹H NMR (300 MHz, DMSO-d6): 10.4 (bs, 1H), 7.65-7.26 (m, 8H), 7.09 (d, 1H), 6.95 (d, 1H), 6.33 (d, 1H), 4.17 (t, 2H), 3.92 (s, 3H), 3.51 (m, 1H), 2.43 (m, 10H), 2.20 (s, 3H), 1.96 (m, 2H).
Melting point: 95-97° C.
Yield: 41%

Example 31

Thiophene-2-sulfonic acid (3-fluoro-4-{6-methoxy-7-[3-(4-methyl-piperazin-1-yl)-propoxy]-quinolin-4-yloxy}-phenyl)-amide

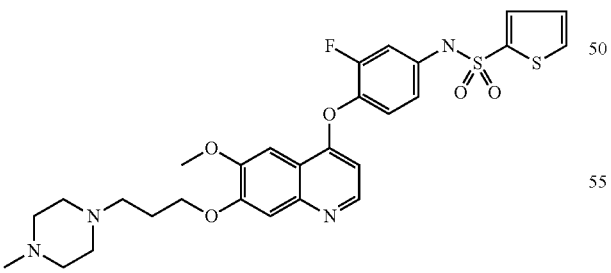

$C_{28}H_{31}FN_4O_5S_2$ Mw. 586.71
LC/MS purity: 99%, m/z 585 [M−H]⁻, 587 [M+H]⁺ Rt. 2.81 min. (Method B)
¹H NMR (300 MHz, DMSO-d6): 10.1 (bs, 1H), 8.45 (d, 1H), 7.88 (d, 1H), 7.56 (d, 1H), 7.49 (s, 1H), 7.38 (s, 1H), 7.32 (t, 1H), 7.13 (m, 2H), 7.00 (d, 1H), 6.36 (d, 1H), 4.18 (t, 2H), 3.93 (s, 3H), 2.43 (m, 10H), 2.21 (s, 3H), 1.96 (m, 2H).
Melting point: 201-202° C.
Yield: 46%

Example 32

2,6-Dichloro-N-(3-fluoro-4-{6-methoxy-7-[3-(4-methyl-piperazin-1-yl)-propoxy]-quinolin-4-yloxy}-phenyl)-benzenesulfonamide

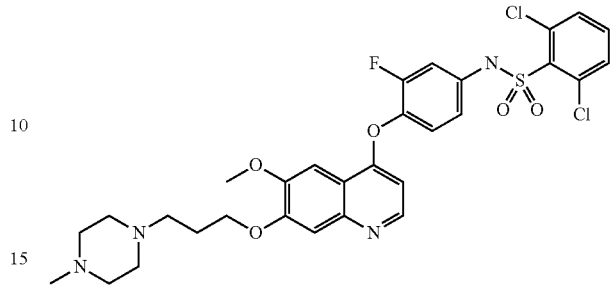

$C_{30}H_{31}Cl_2FN_4O_5S$ Mw. 649.57
LC/MS purity: 99%, m/z 647 [M−H]⁻, 649 [M+H]⁺ Rt. 3.03 min. (Method B)
¹H NMR (300 MHz, DMSO-d6): 10.4 (bs, 1H), 8.43 (d, 1H), 7.59 (m, 2H), 7.48 (m, 2H), 7.36 (s, 1H), 7.25 (t, 1H), 7.05 (d, 1H), 6.90 (d, 1H), 6.33 (d, 1H), 4.18 (t, 2H), 3.91 (s, 3H), 2.50 (bs, 10H), 2.20 (s, 3H), 1.97 (m, 2H).
Melting point: 113-116° C.
Yield: 38%

Example 33

N-(3-Fluoro-4-{6-methoxy-7-[3-(4-methyl-piperazin-1-yl)-propoxy]-quinolin-4-yloxy}-phenyl)-2-methoxy-benzenesulfonamide

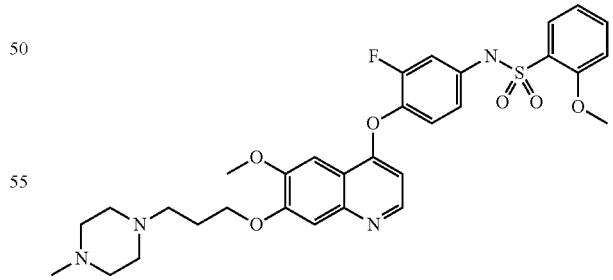

$C_{31}H_{35}FN_4O_6S$ Mw. 610.71
LC/MS purity: 97%, m/z 609 [M−H]⁻, 611 [M+H]⁺ Rt. 3.33 min. (Method B)
¹H NMR (300 MHz, DMSO-d6): 10.3 (bs, 1H), 8.42 (d, 1H), 7.82 (d, 1H), 7.62 (t, 1H), 7.45 (s, 1H), 7.36 (s, 1H), 7.31 (s, 1H), 7.21 (d, 1H), 7.14-6.99 (m, 3H), 6.28 (d, 1H), 4.17 (t, 2H), 3.90 (s, 6H), 2.39 (m, 10H), 2.15 (s, 3H), 1.94 (m, 2H).
Melting point: 168-170° C.
Yield: 36%

Example 34

3,5-Dichloro-N-{3-fluoro-4-[6-methoxy-7-(3-piperidin-1-yl-propoxy)-quinolin-4-yloxy]-phenyl}-2-methoxy-benzenesulfonamide

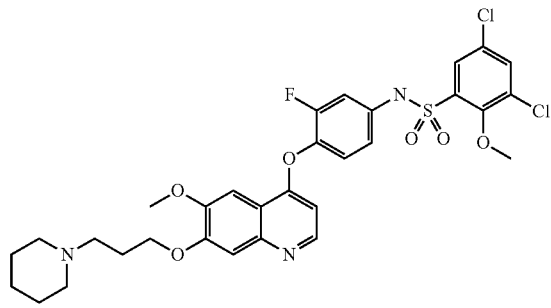 [SMILES: COc1cc2c(Oc3ccc(NS(=O)(=O)c4cc(Cl)cc(Cl)c4OC)cc3F)ccnc2cc1OCCCN1CCCCC1]

$C_{31}H_{32}Cl_2FN_3O_6S$ Mw. 664.59

LC/MS purity: 97%, m/z 662 [M−H]⁻, 664 [M+H]⁺ Rt. 3.91 min. (Method B)

¹H NMR (300 MHz, DMSO-d6): 10.5 (bs, 1H), 8.44 (d, 1H), 7.88 (bs, 1H), 7.76 (bs, 1H), 7.49 (s, 1H), 7.38 (s, 1H), 7.20 (t, 1H), 7.02 (d, 1H), 6.87 (d, 1H), 6.36 (d, 1H), 4.19 (t, 2H), 3.92 (s, 6H), 2.61 (bs, 6H), 2.03 (bs, 2H), 1.90 (bs, 4H), 1.80 (bs, 2H).

Melting point: 173-175° C.

Yield: 27%

Example 35

3,5-Dichloro-N-(3-fluoro-4-{6-methoxy-7-[3-(4-methyl-piperazin-1-yl)-propoxy]-quinolin-4-yloxy}-phenyl)-2-methoxy-benzenesulfonamide

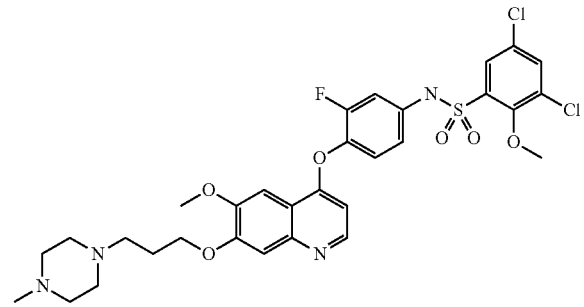 [SMILES: COc1cc2c(Oc3ccc(NS(=O)(=O)c4cc(Cl)cc(Cl)c4OC)cc3F)ccnc2cc1OCCCN1CCN(C)CC1]

$C_{31}H_{33}Cl_2FN_4O_6S$ Mw. 679.60

LC/MS purity: 98%, m/z 677 [M−H]⁻, 679 [M+H]⁺ Rt. 3.79 min. (Method B)

¹H NMR (300 MHz, DMSO-d6): 10.4 (bs, 1H), 8.44 (d, 1H), 7.93 (d, 1H), 7.76 (d, 1H), 7.48 (s, 1H), 7.37 (s, 1H), 7.25 (t, 1H), 7.05 (dd, 1H), 6.91 (d, 1H), 6.36 (d, 1H), 4.18 (t, 2H), 3.92 (s, 6H), 2.50 (bs, 10H), 2.25 (s, 3H), 1.97 (m, 2H).

Melting point: 183-185° C.

Yield: 36%

Example 36

N-(3-Fluoro-4-{6-methoxy-7-[3-(3-methyl-piperidin-1-yl)-propoxy]-quinolin-4-yloxy}-phenyl)-benzenesulfonamide

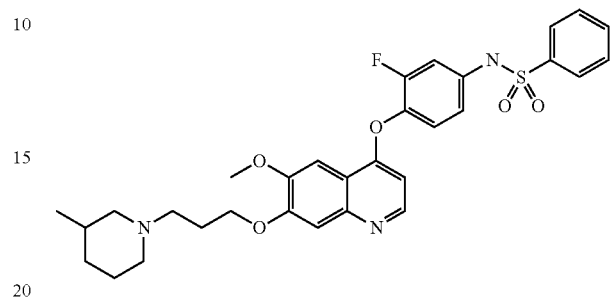

$C_{31}H_{34}FN_3O_5S$ Mw. 579.70

LC/MS purity: 99%, m/z 578 [M−H]⁻, 580 [M+H]⁺ Rt. 3.70 min. (Method B)

¹H NMR (300 MHz, DMSO-d6): 10.6 (bs, 1H), 8.44 (d, 1H), 7.80 (d, 2H), 7.58 (m, 3H), 7.47 (s, 1H), 7.37 (s, 1H), 7.28 (t, 1H), 7.09 (d, 1H), 6.95 (d, 1H), 6.33 (d, 1H), 4.17 (t, 2H), 3.91 (s, 3H), 2.80 (m, 2H), 2.45 (m, 2H), 1.96 (m, 2H), 1.90 (m, 1H), 1.58 (m, 4H), 1.38 (m, 1H), 0.86 (m, 1H), 0.84 (d, 3H)

Melting point: 160-161° C.

Yield: 32%

Example 37

3-Fluoro-N-(3-fluoro-4-{6-methoxy-7-[3-(3-methyl-piperidin-1-yl)-propoxy]-quinolin-4-yloxy}-phenyl)-benzenesulfonamide

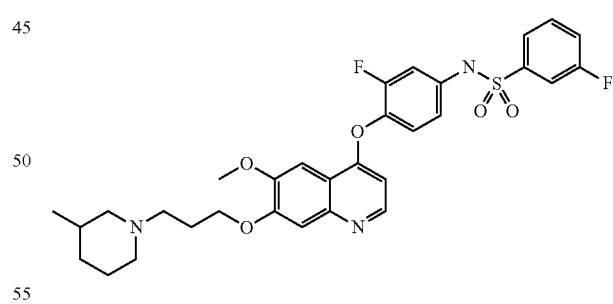

$C_{31}H_{33}F_2N_3O_5S$ Mw. 597.69

LC/MS purity: 99%, m/z 596 [M−H]⁻, 598 [M+H]⁺ Rt. 3.55 min. (Method B)

¹H NMR (300 MHz, DMSO-d6): 10.6 (bs, 1H), 8.44 (d, 1H), 7.62 (bs, 2H), 7.57 (t, 1H), 7.45 (m, 2H), 7.37 (s, 1H), 7.25 (t, 1H), 7.07 (dd, 1H), 6.92 (d, 1H), 6.35 (d, 1H), 4.18 (t, 2H), 3.92 (s, 3H), 2.86 (m, 2H), 2.53 (m, 2H), 1.98 (m, 3H), 1.65 (m, 4H), 1.50 (m, 1H), 0.88 (m, 1H), 0.84 (d, 3H)

Melting point: 113-115° C.

Yield: 26%

Example 38

2-Chloro-N-(3-fluoro-4-{6-methoxy-7-[3-(3-methyl-piperidin-1-yl)-propoxy]-quinolin-4-yloxy}-phenyl)-benzenesulfonamide

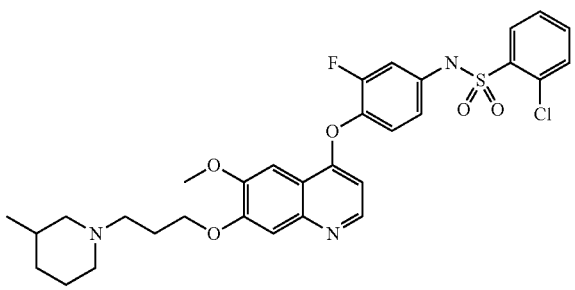

$C_{31}H_{33}ClFN_3O_5S$ Mw. 614.14

LC/MS purity: 98%, m/z 612 [M−H]⁻, 614 [M+H]⁺ Rt. 3.67 min. (Method B)

¹H NMR (300 MHz, DMSO-d6): 10.8 (bs, 1H), 8.43 (d, 1H), 8.08 (d, 1H), 7.62 (bs, 2H), 7.52 (m, 1H), 7.46 (s, 1H), 7.37 (s, 1H), 7.26 (t, 1H), 7.06 (d, 1H), 6.97 (d, 1H), 6.33 (d, 1H), 4.18 (t, 2H), 3.91 (s, 3H), 2.87 (m, 2H), 2.55 (m, 2H), 1.98 (m, 3H), 1.69 (m, 4H), 1.49 (m, 1H), 0.89 (m, 1H), 0.84 (d, 3H)

Melting point: 115-118° C.

Yield: 22%

Example 39

'N-(3-Fluoro-4-{6-methoxy-7-[3-(3-methyl-piperidin-1-yl)-propoxy]-quinolin-4-yloxy}-phenyl)-3-trifluoromethyl-benzenesulfonamide

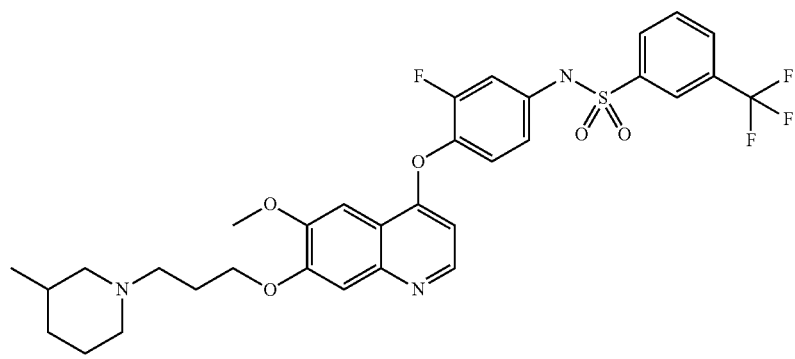 [SMILES: COc1cc2c(Oc3ccc(NS(=O)(=O)c4cccc(C(F)(F)F)c4)cc3F)ccnc2cc1OCCCN1CCCC(C)C1]

$C_{32}H_{33}F_4N_3O_5S$ Mw. 647.69

LC/MS purity: 99%, m/z 646 [M−H]⁻, 648 [M+H]⁺ Rt. 3.01 min. (Method A)

¹H NMR (300 MHz, DMSO-d6): 10 (bs, 1H), 8.43 (d, 1H), 8.02 (m, 3H), 7.80 (t, 1H), 7.48 (s, 1H), 7.38 (s, 1H), 7.25 (t, 1H), 7.07 (dd, 1H), 6.91 (d, 1H), 6.32 (d, 1H), 4.19 (t, 2H), 3.92 (s, 3H), 2.96 (m, 2H), 2.63 (m, 2H), 2.55 (m, 3H), 1.82 (m, 1H), 1.66 (m, 3H), 1.52 (m, 1H), 0.92 (m, 1H), 0.84 (d, 3H)

Melting point: 128-130° C.

Yield: 41%

Example 40

N-(3-Fluoro-4-{6-methoxy-7-[3-(3-methyl-piperidin-1-yl)-propoxy]-quinolin-4-yloxy}-phenyl)-2-nitro-benzenesulfonamide

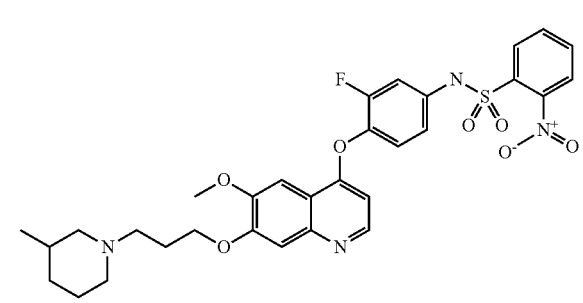 [SMILES: COc1cc2c(Oc3ccc(NS(=O)(=O)c4ccccc4[N+](=O)[O-])cc3F)ccnc2cc1OCCCN1CCCC(C)C1]

$C_{31}H_{33}FN_4O_7S$ Mw. 624.69

LC/MS purity: 100%, m/z 623 [M−H]⁻, 625 [M+H]⁺ Rt. 3.26 min. (Method B)

¹H NMR (300 MHz, DMSO-d6): 10.5 (bs, 1H), 8.43 (d, 1H), 7.94 (m, 1H), 7.73 (m, 1H), 7.50 (s, 1H), 7.39 (s, 1H), 7.10 (t, 1H), 6.89 (dd, 1H), 6.76 (d, 1H), 6.36 (d, 1H), 4.21 (t, 2H), 3.93 (s, 3H), 3.09 (m, 2H), 2.80 (m, 2H), 2.22 (m, 1H), 2.09 (m, 3H), 1.68 (m, 3H), 1.56 (m, 1H), 0.96 (m, 1H), 0.87 (d, 3H)

Melting point: 136-138° C.

Yield: 19%

Example 41

3-Cyano-N-(3-fluoro-4-{6-methoxy-7-[3-(3-methyl-piperidin-1-yl)-propoxy]-quinolin-4-yloxy}-phenyl)-benzenesulfonamide

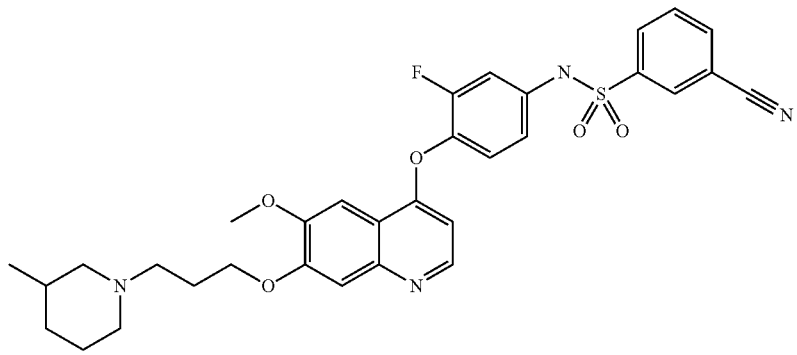 [SMILES: COc1cc2c(Oc3ccc(NS(=O)(=O)c4cccc(C#N)c4)cc3F)ccnc2cc1OCCCN1CCCC(C)C1]

C$_{32}$H$_{33}$FN$_4$O$_5$S Mw. 604.71
LC/MS purity: 99%, m/z 603 [M−H]$^−$, 605 [M+H]$^+$ Rt. 3.29 min. (Method B)
$^1$H NMR (300 MHz, DMSO-d6): 10.5 (bs, 1H), 8.44 (d, 1H), 8.14 (s, 1H), 8.05 (t, 2H), 7.75 (t, 1H), 7.49 (s, 1H), 7.38 (s, 1H), 7.22 (t, 1H), 7.04 (dd, 1H), 6.32 (d, 1H), 6.35 (d, 1H), 4.20 (t, 2H), 3.92 (s, 3H), 2.96 (m, 2H), 2.64 (m, 2H), 2.05 (m, 3H), 1.85 (m, 1H), 1.66 (m, 3H), 1.56 (m, 1H), 0.92 (m, 1H), 0.86 (d, 3H)

Melting point: 125-127° C.
Yield: 26%

Example 42

N-(3-Fluoro-4-{6-methoxy-7-[3-(3-methyl-piperidin-1-yl)-propoxy]-quinolin-4-yloxy}-phenyl)-3-methoxy-benzenesulfonamide

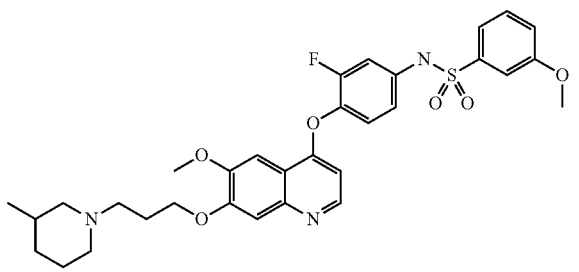

C$_{32}$H$_{36}$FN$_3$O$_6$S Mw. 609.72

LC/MS purity: 98%, m/z 608 [M−H]$^−$, 610 [M+H]$^+$ Rt. 3.75 min. (Method B)

$^1$H NMR (300 MHz, DMSO-d6): 10.6 (bs, 1H), 8.44 (d, 1H), 7.49 (m, 2H), 7.36 (m, 2H), 7.30 (m, 2H), 7.20 (d, 1H), 7.14 (d, 1H), 6.99 (d, 1H), 6.35 (d, 1H), 4.18 (t, 2H), 3.91 (s, 3H), 3.80 (s, 3H), 2.82 (m, 2H), 2.48 (m, 2H), 1.97 (m, 2H), 1.90 (m, 1H), 1.62 (m, 4H), 1.49 (m, 1H), 0.92 (m, 1H), 0.84 (d, 3H)

Melting point: 172-174° C.

Yield: 35%

Example 43

3-Difluoromethoxy-N-(3-fluoro-4-{6-methoxy-7-[3-(3-methyl-piperidin-1-yl)-propoxy]-quinolin-4-yloxy}-phenyl)-benzenesulfonamide

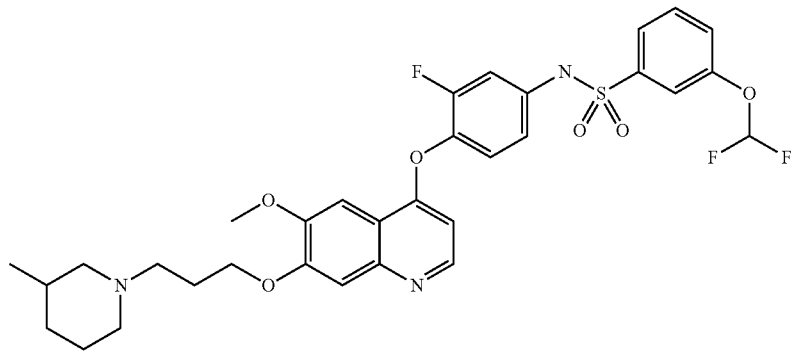 [SMILES: COc1cc2c(Oc3ccc(NS(=O)(=O)c4cccc(OC(F)F)c4)cc3F)ccnc2cc1OCCCN1CCCC(C)C1]

$C_{32}H_{34}F_3N_3O_6S$ Mw. 645.70

LC/MS purity: 99%, m/z 644 [M−H]⁻, 646 [M+H]⁺ Rt. 3.70 min. (Method B)

¹H NMR (300 MHz, DMSO-d6): 10.5 (bs, 1H), 8.44 (bs, 1H), 7.65-7.32 (m, 7H), 7.09 (d, 1H), 6.96 (d, 1H), 6.34 (bs, 1H), 4.18 (bs, 2H), 3.92 (s, 3H), 3.57 (m, 1H), 2.89 (bs, 2H), 2.55 (bs, 2H), 2.00 (bs, 3H), 1.63 (bs, 4H), 1.51 (m, 1H), 0.88 (m, 1H), 0.86 (d, 3H)

Melting point: 99-100° C.

Yield: 25%

Example 44

N-(3-Fluoro-4-{6-methoxy-7-[3-(3-methyl-piperidin-1-yl)-propoxy]-quinolin-4-yloxy}-phenyl)-2-methyl-benzenesulfonamide

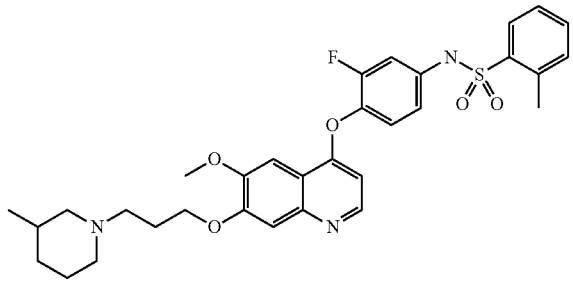 [SMILES: COc1cc2c(Oc3ccc(NS(=O)(=O)c4ccccc4C)cc3F)ccnc2cc1OCCCN1CCCC(C)C1]

$C_{32}H_{36}FN_3O_5S$ Mw. 593.72

LC/MS purity: 99%, m/z 592 [M−H]⁻, 594 [M+H]⁺ Rt. 3.89 min. (Method B)

¹H NMR (300 MHz, DMSO-d6): 10.7 (bs, 1H), 8.43 (d, 1H), 7.92 (d, 1H), 7.51-7.25 (m, 6H), 7.05 (d, 1H), 6.94 (d, 1H), 6.32 (d, 1H), 4.17 (t, 2H), 3.91 (s, 3H), 2.80 (m, 2H), 2.62 (s, 3H), 2.52 (m, 2H), 1.96 (m, 2H), 1.88 (m, 1H), 1.61 (m, 4H), 1.48 (m, 1H), 0.90 (m, 1H), 0.84 (d, 3H)

Melting point: 99-100° C.

Yield: 26%

Example 45

N-(3-Fluoro-4-{6-methoxy-7-[3-(3-methyl-piperidin-1-yl)-propoxy]-quinolin-4-yloxy}-phenyl)-2-trifluoromethoxy-benzenesulfonamide

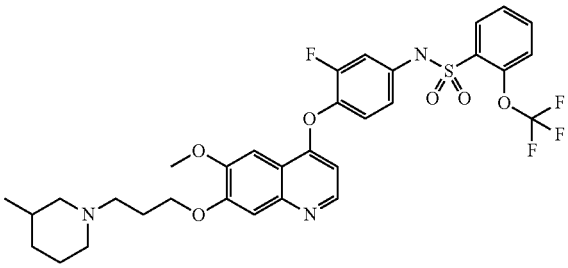 [SMILES: COc1cc2c(Oc3ccc(NS(=O)(=O)c4ccccc4OC(F)(F)F)cc3F)ccnc2cc1OCCCN1CCCC(C)C1]

$C_{32}H_{33}F_4N_3O_6S$ Mw. 663.69

LC/MS purity: %, m/z 642 [M−H]⁻, 644 [M+H]⁺ Rt. 3.84 min. (Method B)

¹H NMR (300 MHz, DMSO-d6): 10.4 (bs, 1H), 8.43 (d, 1H), 7.98 (d, 1H), 7.67 (t, 1H), 7.48 (bs, 3H), 7.37 (s, 1H), 7.18 (t, 1H), 7.00 (d, 1H), 6.84 (d, 1H), 6.33 (d, 1H), 4.18 (t, 2H), 3.92 (s, 3H), 2.83 (m, 2H), 2.56 (m, 2H), 1.99 (m, 3H), 1.63 (m, 4H), 1.51 (m, 1H), 0.89 (m, 1H), 0.84 (d, 3H)

Melting point: 128-130° C.

Yield: 21%

Example 46

N-(3-Fluoro-4-{6-methoxy-7-[3-(3-methyl-piperidin-1-yl)-propoxy]-quinolin-4-yloxy}-phenyl)-3-trifluoromethoxy-benzenesulfonamide

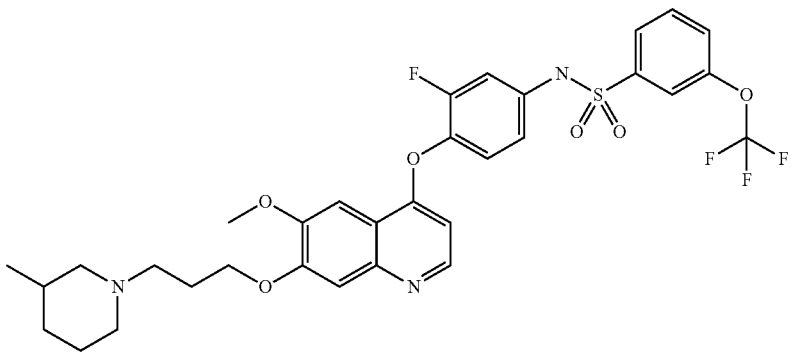 [SMILES: COc1cc2c(Oc3ccc(NS(=O)(=O)c4cccc(OC(F)(F)F)c4)cc3F)ccnc2cc1OCCCN1CCCC(C)C1]

$C_{32}H_{33}F_4N_3O_6S$ Mw. 663.69
LC/MS purity: 99%, m/z 662 [M−H]⁻, 664 [M+H]⁺ Rt. 3.87 min. (Method B)
¹H NMR (300 MHz, DMSO-d6): 10 (bs, 1H), 8.42 (d, 1H), 7.79 (d, 1H), 7.66 (m, 2H), 7.56 (d, 1H), 7.48 (s, 1H), 7.37 (s, 1H), 7.19 (t, 1H), 7.01 (dd, 1H), 6.86 (d, 1H), 6.32 (d, 1H), 4.18 (t, 2H), 3.92 (s, 3H), 2.87 (m, 2H), 2.54 (m, 2H), 1.98 (m, 3H), 1.65 (m, 4H), 1.51 (m, 1H), 0.88 (m, 1H), 0.84 (d, 3H)
Melting point: 102-104° C.
Yield: 21%

Example 47

2,4-Difluoro-N-(3-fluoro-4-{6-methoxy-7-[3-(3-methyl-piperidin-1-yl)-propoxy]-quinolin-4-yloxy}-phenyl)-benzenesulfonamide

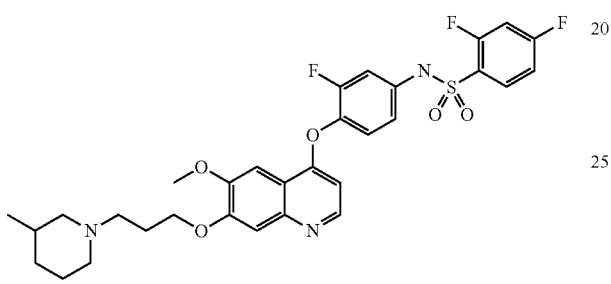

$C_{31}H_{32}F_3N_3O_5S$ Mw. 615.68
LC/MS purity: 99%, m/z 614 [M−H]⁻, 616 [M+H]⁺ Rt. 3.48 min. (Method B)
¹H NMR (300 MHz, DMSO-d6): 10.5 (bs, 1H), 8.44 (d, 1H), 7.92 (m, 1H), 7.48 (s, 2H), 7.44 (d, 1H), 7.38 (s, 1H), 7.25 (m, 2H), 7.05 (dd, 1H), 6.91 (d, 1H), 6.35 (d, 1H), 4.19 (t, 2H), 3.92 (s, 3H), 2.92 (m, 2H), 2.60 (m, 2H), 2.03 (m, 3H), 1.78 (m, 1H), 1.65 (m, 3H), 1.54 (m, 1H), 0.92 (m, 1H), 0.85 (d, 3H)
Melting point: 118-120° C.
Yield: 18%

Example 48

3,4-Difluoro-N-(3-fluoro-4-{6-methoxy-7-[3-(3-methyl-piperidin-1-yl)-propoxy]-quinolin-4-yloxy}-phenyl)-benzenesulfonamide $C_{31}H_{32}F_3N_3O_5S$ Mw. 615.68
LC/MS purity: 99%, m/z 614 [M−H]⁻, 616 [M+H]⁺ Rt. 3.59 min. (Method B)
¹H NMR (300 MHz, DMSO-d6): 10.5 (bs, 1H), 8.43 (d, 1H), 7.78 (t, 1H), 7.59 (m, 2H), 7.48 (s, 1H), 7.37 (s, 1H), 7.21 (t, 2H), 7.04 (d, 1H), 6.88 (d, 1H), 6.36 (d, 1H), 4.18 (t, 2H), 3.92 (s, 3H), 2.98 (m, 2H), 2.55 (m, 2H), 2.00 (m, 3H), 1.70 (m, 3H), 1.51 (m, 1H), 0.90 (m, 1H), 0.84 (d, 3H)
Melting point: 120-122° C.
Yield: 34%

Example 49

2,3,4-Trifluoro-N-(3-fluoro-4-{6-methoxy-7-[3-(3-methyl-piperidin-1-yl)-propoxy]-quinolin-4-yloxy}-phenyl)-benzenesulfonamide

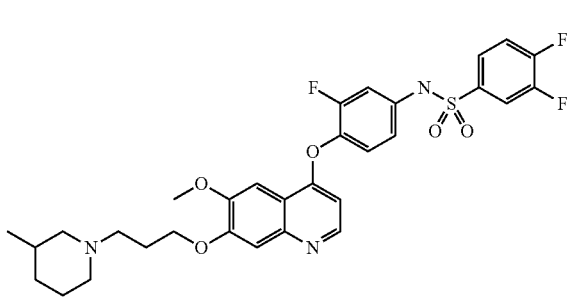 [SMILES: COc1cc2c(Oc3ccc(NS(=O)(=O)c4ccc(F)c(F)c4)cc3F)ccnc2cc1OCCCN1CCCC(C)C1]

$C_{31}H_{31}F_4N_3O_5S$ Mw. 633.67
LC/MS purity: 100%, m/z 632 [M−H]⁻, 634 [M+H]⁺ Rt. 3.46 min. (Method B)
¹H NMR (300 MHz, DMSO-d6): 10.2 (bs, 1H), 8.44 (d, 1H), 7.64 (m, 1H), 7.50 (s, 1H), 7.39 (m, 2H), 7.16 (t, 1H), 6.98 (dd, 1H), 6.84 (d, 1H), 6.37 (d, 1H), 4.21 (t, 2H), 3.93 (s, 3H), 3.11 (m, 2H), 2.81 (m, 2H), 2.16 (m, 4H), 1.69 (m, 3H), 1.58 (m, 1H), 0.96 (m, 1H), 0.88 (d, 3H)
Melting point: 134-136° C.
Yield: 28%

Example 50

2,5-Dichloro-N-(3-fluoro-4-{6-methoxy-7-[3-(3-methyl-piperidin1-yl)-propoxy]-quinolin-4-yloxy}-phenyl)-benzenesulfonamide $C_{31}H_{32}Cl_2FN_3O_5S$ Mw. 648.59
LC/MS purity: 99%, m/z 646 [M−H]⁻, 648 [M+H]⁺ Rt. 3.03 min. (Method A)
¹H NMR (300 MHz, DMSO-d6): 10.4 (bs, 1H), 8.44 (d, 1H), 7.98 (s, 1H), 7.60 (bs, 2H), 7.48 (s, 1H), 7.39 (s, 1H), 7.18 (t, 1H), 6.98 (d, 1H), 6.86 (d, 1H), 6.35 (d, 1H), 4.18 (t, 2H), 3.92 (s, 3H), 3.04 (m, 2H), 2.74 (m, 2H), 2.23 (m, 1H), 2.07 (m, 2H), 1.95 (m, 1H), 1.68 (m, 3H), 1.56 (m, 1H), 0.95 (m, 1H), 0.87 (d, 3H)
Melting point: 127-129° C.
Yield: 29%

Example 51

2,6-Dichloro-N-(3-fluoro-4-{6-methoxy-7-[3-(3-methyl-piperidin-1-yl)-propoxy]-quinolin-4-yloxy}-phenyl)-benzenesulfonamide

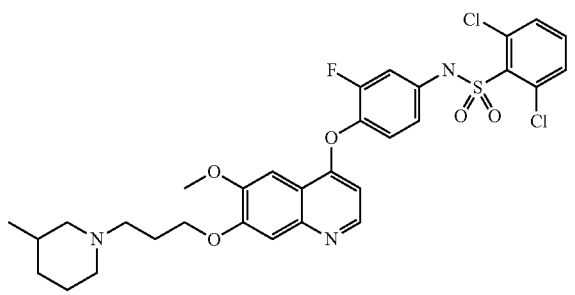 [SMILES: COc1cc2c(Oc3ccc(NS(=O)(=O)c4c(Cl)cccc4Cl)cc3F)ccnc2cc1OCCCN1CCCC(C)C1]

$C_{31}H_{32}Cl_2FN_3O_5S$ Mw. 648.59

LC/MS purity: 99%, m/z 646 [M−H]⁻, 648 [M+H]⁺ Rt. 3.59 min. (Method B)

¹H NMR (300 MHz, DMSO-d6): 10.6 (bs, 1H), 8.43 (d, 1H), 7.58 (d, 1H), 7.57 (s, 1H), 7.48 (m, 2H), 7.38 (s, 1H), 7.22 (t, 1H), 7.02 (dd, 1H), 6.88 (d, 1H), 6.34 (d, 1H), 4.20 (t, 2H), 3.92 (s, 3H), 3.01 (m, 2H), 2.70 (m, 2H), 2.16 (m, 1H), 2.05 (m, 2H), 1.91 (m, 1H), 1.68 (m, 3H), 1.55 (m, 1H), 0.98 (m, 1H), 0.86 (d, 3H)

Melting point: 119-121° C.

Yield: 16%

Example 52

3,4-Dichloro-N-(3-fluoro-4-{6-methoxy-7-[3-(3-methyl-piperidin-1-yl)-propoxy]-quinolin-4-yloxy}-phenyl)-benzenesulfonamide

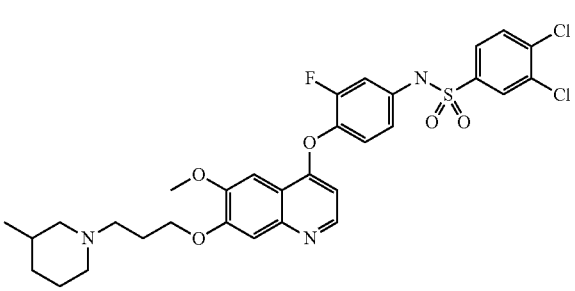

$C_{31}H_{32}Cl_2FN_3O_5S$ Mw. 648.59

LC/MS purity: 99%, m/z 646 [M−H]⁻, 648 [M+H]⁺ Rt. 3.11 min. (Method A)

¹H NMR (300 MHz, DMSO-d6): 10.4 (bs, 1H), 8.44 (d, 1H), 7.92 (d, 1H), 7.80 (d, 1H), 7.71 (dd, 1H), 7.49 (s, 1H), 7.39 (s, 1H), 7.23 (t, 1H), 7.05 (dd, 1H), 6.89 (d, 1H), 6.36 (d, 1H), 4.20 (t, 2H), 3.93 (s, 3H), 2.98 (m, 2H), 2.67 (m, 2H), 2.13 (m, 1H), 2.03 (m, 2H), 1.86 (m, 1H), 1.67 (m, 3H), 1.57 (m, 1H), 0.92 (m, 1H), 0.86 (d, 3H)

Melting point: 123-124° C.

Yield: 15%

Example 53

3,5-Dichloro-N-(3-fluoro-4-{6-methoxy-7-[3-(3-methyl-piperidin-1-yl)-propoxy]-quinolin-4-yloxy}-phenyl)-benzenesulfonamide

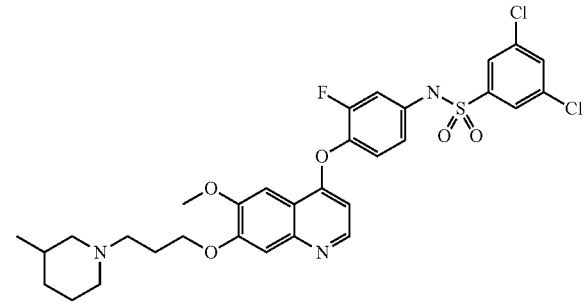 [SMILES: COc1cc2c(Oc3ccc(NS(=O)(=O)c4cc(Cl)cc(Cl)c4)cc3F)ccnc2cc1OCCCN1CCCC(C)C1]

$C_{31}H_{32}Cl_2FN_3O_5S$ Mw. 648.59

LC/MS purity: 98%, m/z 646 [M−H]⁻, 648 [M+H]⁺ Rt. 3.13 min. (Method A)

¹H NMR (300 MHz, DMSO-d6): 10.3 (bs, 1H), 8.44 (d, 1H), 7.81 (d, 1H), 7.69 (s, 1H), 7.68 (s, 1H), 7.50 (s, 1H), 7.39 (s, 1H), 7.20 (t, 1H), 7.01 (dd, 1H), 6.86 (d, 1H), 6.36 (d, 1H), 4.21 (t, 2H), 3.93 (s, 3H), 3.06 (m, 2H), 2.76 (m, 2H), 2.23 (m, 1H), 2.06 (m, 2H), 1.97 (m, 1H), 1.69 (m, 3H), 1.57 (m, 1H), 0.92 (m, 1H), 0.87 (d, 3H)

Melting point: 126-128° C.

Yield: 19%

Example 54

3-Chloro-2-fluoro-N-(3-fluoro-4-{6-methoxy-7-[3-(3-methyl-piperidin-1-yl)-propoxy]-quinolin-4-yloxy}-phenyl)-benzenesulfonamide

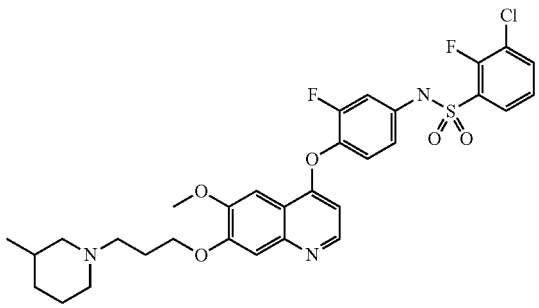 [SMILES: COc1cc2c(Oc3ccc(NS(=O)(=O)c4cccc(Cl)c4F)cc3F)ccnc2cc1OCCCN1CCCC(C)C1]

$C_{31}H_{32}ClF_2N_3O_5S$ Mw. 632.13

LC/MS purity: 98%, m/z 630 [M−H]⁻, 632 [M+H]⁺ Rt. 3.50 min. (Method B)

¹H NMR (300 MHz, DMSO-d6): 10.3 (bs, 1H), 8.43 (d, 1H), 7.81 (d, 1H), 7.76 (d, 1H), 7.49 (s, 1H), 7.39 (s, 1H), 7.33 (t, 1H), 7.19 (t, 1H), 7.02 (dd, 1H), 6.87 (d, 1H), 6.36 (d, 1H), 4.20 (t, 2H), 3.93 (s, 3H), 3.03 (m, 2H), 2.73 (m, 2H), 2.20 (m, 1H), 2.06 (m, 2H), 1.94 (m, 1H), 1.68 (m, 3H), 1.56 (m, 1H), 0.93 (m, 1H), 0.86 (d, 3H)

Melting point: 125-127° C.

Yield: 18%

Example 55

2-Fluoro-N-(3-fluoro-4-{6-methoxy-7-[3-(3-methyl-piperidin-1-yl)-propoxy]-quinolin-4-yloxy}-phenyl-5-methyl-benzenesulfonamide

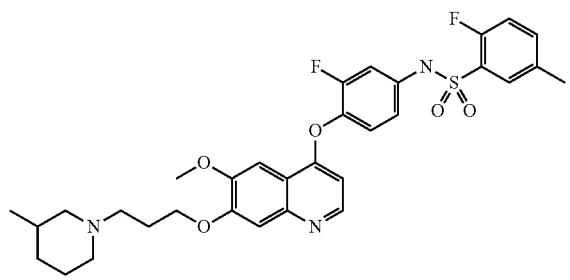

$C_{32}H_{35}F_2N_3O_5S$ Mw. 611.71

LC/MS purity: 99%, m/z 610 [M−H]⁻, 612 [M+H]⁺ Rt. 3.73 min. (Method B)

¹H NMR (300 MHz, DMSO-d6): 10.2 (bs, 1H), 8.44 (d, 1H), 7.69 (d, 1H), 7.49 (d, 1H), 7.47 (s, 1H), 7.38 (s, 1H), 7.30 (td, 2H), 7.12 (dd, 1H), 6.99 (d, 1H), 6.34 (d, 1H), 4.19 (t, 2H), 3.92 (s, 3H), 2.90 (m, 2H), 2.57 (s, 2H), 2.34 (s, 3H), 2.01 (m, 3H), 1.74 (m, 1H), 1.61 (m, 3H), 1.52 (m, 1H), 0.90 (m, 1H), 0.85 (d, 3H)

Melting point: 149-151° C.

Yield: 23%

Example 56

3-Fluoro-N-(3-fluoro-4-{6-methoxy-7-[3-(3-methyl-piperidin-1-yl)-propoxy]-quinolin-4-yloxy}-phenyl)-4-methyl-benzenesulfonamide

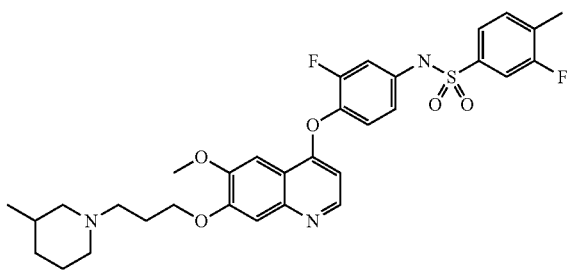

$C_{32}H_{35}F_2N_3O_5S$ Mw. 611.71

LC/MS purity: 99%, m/z 610 [M−H]⁻, 612 [M+H]⁺ Rt. 3.85 min. (Method B)

¹H NMR (300 MHz, DMSO-d6): 10.5 (bs, 1H), 8.44 (d, 1H), 7.52 (m, 4H), 7.38 (s, 1H), 7.31 (t, 1H), 7.13 (dd, 1H), 6.98 (d, 1H), 6.36 (d, 1H), 4.19 (t, 2H), 3.92 (s, 3H), 2.88 (m, 2H), 2.54 (m, 2H), 2.29 (m, 3H), 1.99 (m, 3H), 1.63 (m, 4H), 1.54 (m, 1H), 0.89 (m, 1H), 0.84 (d, 3H)

Melting point: 174-176° C.

Yield: 19%

Example 57

3-Chloro-4-fluoro-N-(3-fluoro-4-{6-methoxy-7-[3-(3-methyl-piperidin-1-yl)-propoxy]-quinolin-4-yloxy}-phenyl)-benzenesulfonamide

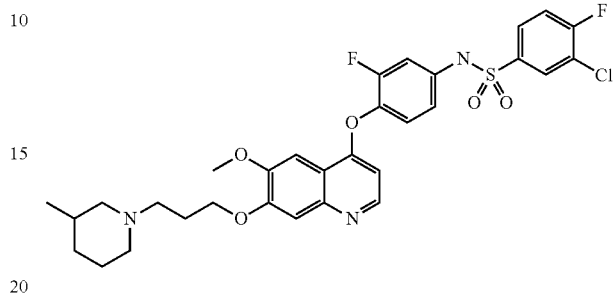

$C_{31}H_{32}ClF_2N_3O_5S$ Mw. 632.13

LC/MS purity: 96%, m/z 630 [M−H]⁻, 632 [M+H]⁺ Rt. 2.97 min. (Method A)

¹H NMR (300 MHz, DMSO-d6): 10.6 (bs, 1H), 8.44 (d, 1H), 7.91 (dd, 1H), 7.77 (m, 1H), 7.58 (t, 1H), 7.48 (s, 1H), 7.38 (s, 1H), 7.24 (t, 1H), 7.06 (dd, 1H), 6.89 (d, 1H), 6.36 (d, 1H), 4.19 (t, 2H), 3.92 (s, 3H), 2.83 (m, 2H), 2.61 (s, 2H), 2.03 (m, 3H), 1.78 (m, 1H), 1.63 (m, 3H), 1.52 (m, 1H), 0.91 (m, 1H), 0.85 (d, 3H)

Melting point: 124-126° C.

Yield: 30%

Example 58

Naphthalene-1-sulfonic acid (3-fluoro-4-{6-methoxy-7-[3-(3-methyl-piperidin-1-yl)-propoxy]-quinolin-4-yloxy}-phenyl)-amide

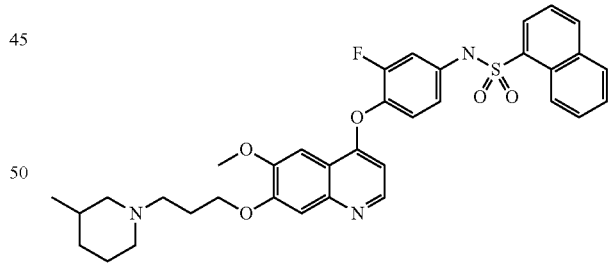

$C_{35}H_{36}FN_3O_5S$ Mw. 629.76

LC/MS purity: 99%, m/z 628 [M−H]⁻, 630 [M+H]⁺ Rt. 2.95 min. (Method A)

¹H NMR (300 MHz, DMSO-d6): 10.4 (bs, 1H), 8.82 (d, 1H), 8.39 (d, 1H), 8.20 (m, 2H), 8.06 (d, 1H), 7.65 (m, 3H), 7.42 (s, 1H), 7.35 (s, 1H), 7.16 (t, 1H), 6.99 (d, 1H), 6.85 (d, 1H), 6.26 (d, 1H), 4.16 (t, 2H), 3.89 (s, 3H), 2.83 (m, 2H), 2.48 (m, 2H), 1.96 (m, 3H), 1.62 (m, 4H), 1.49 (m, 1H), 0.89 (m, 1H), 0.84 (d, 3H)

Melting point: 131-133° C.

Yield: 21%

Example 59

N-(3-Fluoro-4-{6-methoxy-7-[3-(3-methyl-piperidin-1-yl)-propoxy]-quinolin-4-yloxy}-phenyl)-3-phenoxy-benzenesulfonamide

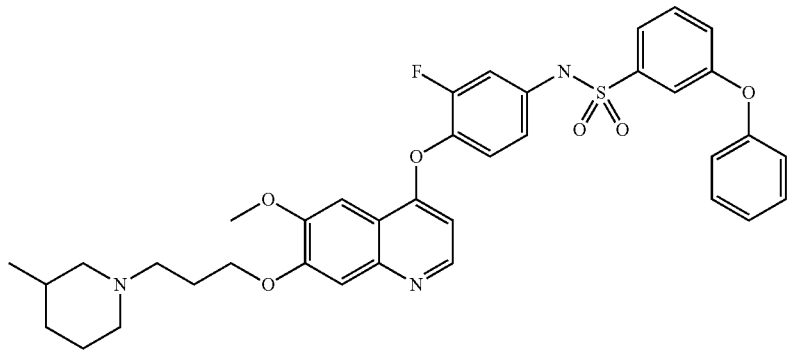 [SMILES: COc1cc2c(Oc3ccc(NS(=O)(=O)c4cccc(Oc5ccccc5)c4)cc3F)ccnc2cc1OCCCN1CCCC(C)C1]

C$_{37}$H$_{38}$FN$_3$O$_6$S Mw. 671.79
LC/MS purity: 98%, m/z 670 [M−H]$^-$, 672 [M+H]$^+$ Rt. 3.18 min. (Method A)
$^1$H NMR (300 MHz, DMSO-d6): 10.4 (bs, 1H), 8.44 (d, 1H), 7.62-7.22 (m, 10H), 7.04 (m, 3H), 6.93 (d, 1H), 6.35 (d, 1H), 4.19 (t, 2H), 3.93 (s, 3H), 2.86 (m, 2H), 2.48 (m, 2H), 1.99 (m, 3H), 1.65 (m, 4H), 1.51 (m, 1H), 0.88 (m, 1H), 0.84 (d, 3H)
Melting point: 146-147° C.
Yield: 24%

Example 60

Cyclopropanesulfonic acid (3-fluoro-4-{6-methoxy-7-[3-(3-methyl-piperidin-1-yl)-propoxy]-quinolin-4-yloxy}-phenyl)-amide

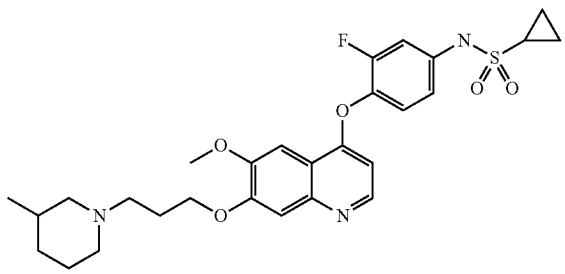 [SMILES: COc1cc2c(Oc3ccc(NS(=O)(=O)C4CC4)cc3F)ccnc2cc1OCCCN1CCCC(C)C1]

C$_{28}$H$_{34}$FN$_3$O$_5$S Mw. 543.66
LC/MS purity: 96%, m/z 542 [M−H]$^-$, 544 [M+H]$^+$ Rt. 3.65 min. (Method B)
$^1$H NMR (300 MHz, DMSO-d6): 10.3 (bs, 1H), 8.47 (d, 1H), 7.52 (s, 1H), 7.45 (d, 1H), 7.39 (s, 1H), 7.28 (d, 1H), 7.17 (d, 1H), 6.45 (d, 1H), 4.19 (t, 2H), 3.94 (s, 3H), 3.17 (m, 1H), 2.77 (m, 3H), 2.44 (m, 2H), 1.96 (m, 2H), 1.84 (m, 1H), 1.61 (m, 3H), 1.48 (m, 1H), 0.99 (m, 2H), 0.97 (m, 2H), 0.88 (m, 1H), 0.84 (d, 3H)
Melting point: 158-160° C.
Yield: 11%

Example 61

1-Methyl-1H-pyrazole-3-sulfonic acid (3-fluoro-4-{6-methoxy-7-[3-(3-methyl-piperidin-1-yl)-propoxy]-quinolin-4-yloxy}-phenyl)-amide

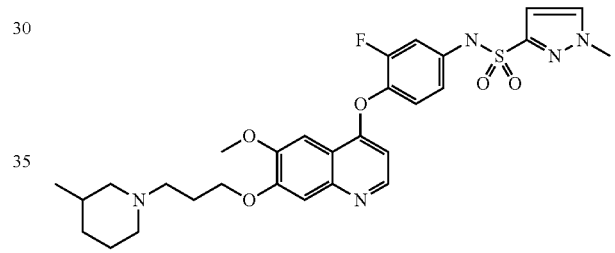

C$_{29}$H$_{34}$FN$_5$O$_5$S Mw. 583.69
LC/MS purity: 97%, m/z 582 [M−H]$^-$, 584 [M+H]$^+$ Rt. 3.09 min. (Method B)
$^1$H NMR (300 MHz, DMSO-d6): 10.2 (bs, 1H), 8.45 (d, 1H), 7.84 (d, 1H), 7.49 (s, 1H), 7.37 (s, 1H), 7.30 (t, 1H), 7.15 (dd, 1H), 7.00 (d, 1H), 6.63 (d, 1H), 6.38 (d, 1H), 4.18 (t, 2H), 3.93 (s, 3H), 3.90 (s, 3H), 2.78 (m, 2H), 2.44 (m, 2H), 1.96 (m, 2H), 1.85 (m, 1H), 1.58 (m, 4H), 1.46 (m, 1H), 0.85 (m, 1H), 0.83 (d, 3H)
Melting point: 164-166° C.
Yield: 31%

Example 62

5-Methyl-thiophene-2-sulfonic acid (3-fluoro-4-{6-methoxy-7-[3-(3-methyl-piperidin-1-yl)-propoxy]-quinolin-4-yloxy}-phenyl)-amide

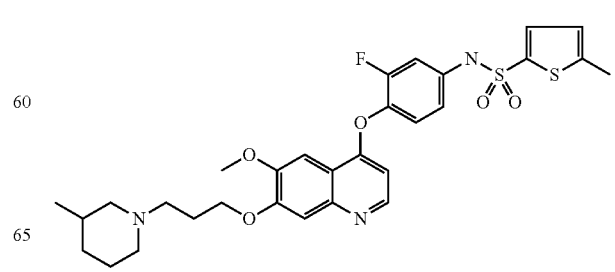

C₃₀H₃₄FN₃O₅S₂ Mw. 599.75
LC/MS purity: 99%, m/z 598 [M−H]⁻, 600 [M+H]⁺ Rt. 3.62 min. (Method B)
¹H NMR (300 MHz, DMSO-d6): 10.5 (bs, 1H), 8.45 (d, 1H), 7.49 (s, 1H), 7.38 (s, 1H), 7.36 (s, 1H), 7.30 (t, 1H), 7.12 (dd, 1H), 6.98 (d, 1H), 6.83 (d, 1H), 6.38 (d, 1H), 4.18 (t, 2H), 3.93 (s, 3H), 2.85 (m, 2H), 2.54 (m, 2H), 2.46 (s, 3H), 1.97 (m, 3H), 1.63 (m, 4H), 1.50 (m, 1H), 0.88 (m, 1H), 0.84 (d, 3H)
Melting point: 99-101° C.
Yield: 29%

Example 63

5-Chloro-thiophene-2-sulfonic acid (3-fluoro-4-{6-methoxy-7-[3-(3-methyl-piperidin-1-yl)-propoxy]-quinolin-4-yloxy}-phenyl)-amide

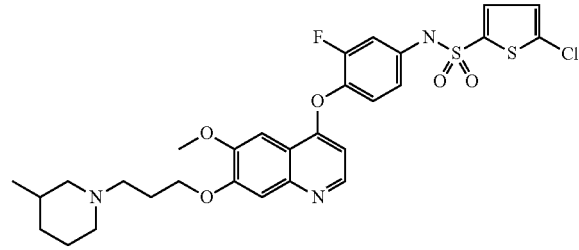 [SMILES: COc1cc2c(Oc3ccc(NS(=O)(=O)c4ccc(Cl)s4)cc3F)ccnc2cc1OCCCN1CCCC(C)C1]

C₂₉H₃₁ClFN₃O₅S₂ Mw. 620.17
LC/MS purity: 99%, m/z 618 [M−H]⁻, 620 [M+H]⁺ Rt. 3.50 min. (Method B)
¹H NMR (300 MHz, DMSO-d6): 10.8 (bs, 1H), 8.46 (d, 1H), 7.51 (s, 1H), 7.40 (s, 1H), 7.33 (s, 1H), 7.23 (t, 1H), 7.12 (d, 1H), 7.04 (d, 1H), 6.91 (d, 1H), 6.39 (d, 1H), 4.21 (t, 2H), 3.93 (s, 3H), 3.16 (m, 2H), 2.79 (m, 2H), 2.28 (s, 1H), 2.09 (m, 3H), 1.68 (m, 3H), 1.58 (m, 1H), 0.96 (m, 1H), 0.88 (d, 3H)
Melting point: 100-103° C.
Yield: 19%

Example 64

2,4-Dichloro-thiophene-3-sulfonic acid (3-fluoro-4-{6-methoxy-7-[3-(3-methyl-piperidin-1-yl)-propoxy]-quinolin-4-yloxy}-phenyl)-amide

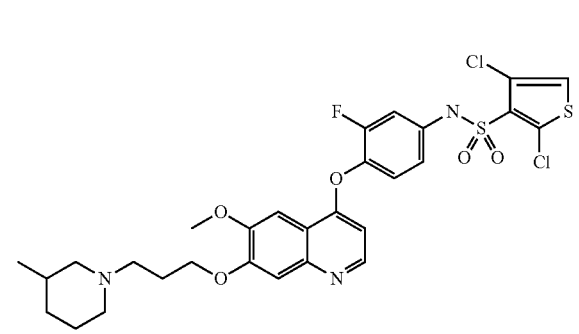 [SMILES: COc1cc2c(Oc3ccc(NS(=O)(=O)c4c(Cl)csc4Cl)cc3F)ccnc2cc1OCCCN1CCCC(C)C1]

C₂₉H₃₀Cl₂FN₃O₅S₂ Mw. 654.61
LC/MS purity: 98%, m/z 652 [M−H]⁻, 654 [M+H]⁺ Rt. 3.03 min. (Method A)
¹H NMR (300 MHz, DMSO-d6): 10.5 (bs, 1H), 8.45 (d, 1H), 7.51 (s, 1H), 7.38 (s, 1H), 7.18 (s, 1H), 7.16 (t, 1H), 6.97 (d, 1H), 6.82 (d, 1H), 6.39 (d, 1H), 4.20 (t, 2H), 3.93 (s, 3H), 3.17 (m, 2H), 2.68 (m, 2H), 2.18 (m, 1H), 2.06 (m, 2H), 1.88 (m, 1H), 1.67 (m, 3H), 1.53 (m, 1H), 0.93 (m, 1H), 0.86 (d, 3H)
Melting point: 119-121° C.
Yield: 39%

Example 65

Thiophene-3-sulfonic acid (3-fluoro-4-{6-methoxy-7-[3-(3-methyl-piperidin-1-yl)-propoxy]-quinolin-4-yloxy}-phenyl)-amide

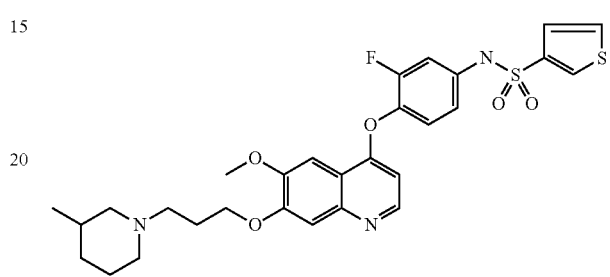

C₂₉H₃₂FN₃O₅S₂ Mw. 585.72
LC/MS purity: 99%, m/z 584 [M−H]⁻, 586 [M+H]⁺ Rt. 3.49 min. (Method B)
¹H NMR (300 MHz, DMSO-d6): 10.4 (bs, 1H), 8.44 (d, 1H), 8.19 (d, 1H), 7.71 (m, 1H), 7.48 (s, 1H), 7.37 (s, 1H), 7.30 (m, 2H), 7.13 (dd, 1H), 6.99 (d, 1H), 6.36 (d, 1H), 4.18 (t, 2H), 3.92 (s, 3H), 2.80 (m, 2H), 2.46 (m, 2H), 1.95 (m, 2H), 1.87 (m, 1H), 1.66 (m, 1H), 1.60 (m, 3H), 1.48 (m, 1H), 0.92 (m, 1H), 0.84 (d, 3H)
Melting point: 174-176° C.
Yield: 28%

Example 66

3-(3-Fluoro-4-{6-methoxy-7-[3-(3-methyl-piperidin-1-yl)-propoxy]-quinolin-4-yloxy}-phenylsulfamoyl)-thiophene-2-carboxylic acid methyl ester

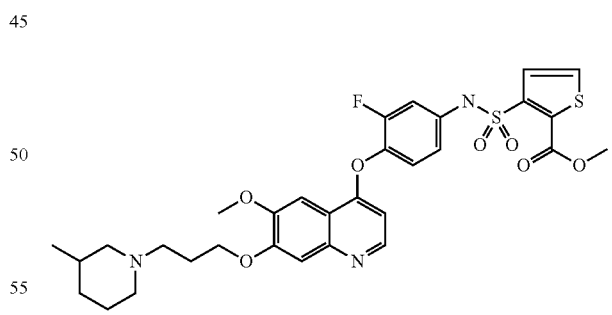

C₃₁H₃₄FN₃O₇S₂ Mw. 643.76
LC/MS purity: 98%, m/z 642 [M−H]⁻, 644 [M+H]⁺ Rt. 3.78 min. (Method B)
¹H NMR (300 MHz, DMSO-d6): 10.4 (bs, 1H), 8.45 (d, 1H), 7.94 (d, 1H), 7.48 (s, 1H), 7.47 (s, 1H), 7.37 (s, 1H), 7.30 (t, 1H), 7.13 (dd, 1H), 6.98 (d, 1H), 6.36 (d, 1H), 4.18 (t, 2H), 3.92 (s, 3H), 3.88 (m, 3H), 2.85 (m, 2H), 2.54 (s, 2H), 1.96 (m, 3H), 1.65 (m, 4H), 1.47 (m, 1H), 0.92 (d, 1H), 0.92 (d, 3H)
Melting point: 132-134° C.
Yield: 9%

Example 67

Benzo[b]thiophene-3-sulfonic acid (3-fluoro-4-{6-methoxy-7-[3-(3-methyl-piperidin-1-yl)-propoxy]-quinolin-4-yloxy}-phenyl)-amide

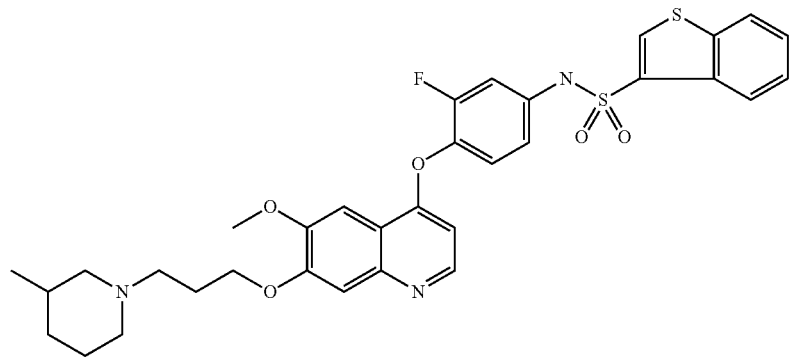 [SMILES: COc1cc2c(Oc3ccc(NS(=O)(=O)c4csc5ccccc45)cc3F)ccnc2cc1OCCCN1CCCC(C)C1]

$C_{33}H_{34}FN_3O_5S_2$ Mw. 635.78
LC/MS purity: 99%, m/z 634 [M−H]$^−$, 636 [M+H]$^+$ Rt. 3.86 min. (Method B)
$^1$H NMR (300 MHz, DMSO-d6): 10.4 (bs, 1H), 8.57 (s, 1H), 8.41 (d, 1H), 8.25 (d, 1H), 8.09 (d, 1H), 7.54 (m, 2H), 7.45 (s, 1H), 7.36 (s, 1H), 7.22 (t, 1H), 7.09 (d, 1H), 6.93 (d, 1H), 6.29 (d, 1H), 4.16 (t, 2H), 3.90 (s, 3H), 2.85 (m, 2H), 2.51 (m, 2H), 1.96 (m, 3H), 1.65 (m, 4H), 1.49 (m, 1H), 0.92 (m, 1H), 0.84 (d, 3H)
Melting point: 126-128° C.
Yield: 26%

Example 68

1-Ethyl-1H-pyrazole-4-sulfonic acid (3-fluoro-4-{6-methoxy-7-[3-(3-methyl-piperidin-1-yl)-propoxy]-quinolin-4-yloxy}-phenyl)-amide

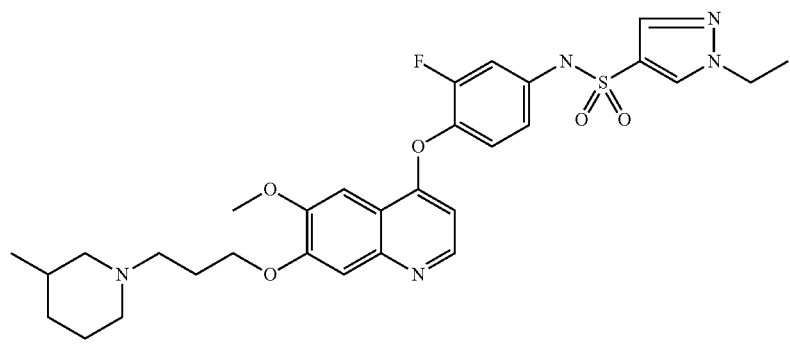 [SMILES: CCn1cc(S(=O)(=O)Nc2ccc(Oc3ccnc4cc(OCCCN5CCCC(C)C5)c(OC)cc34)c(F)c2)cn1]

$C_{30}H_{36}FN_5O_5S$ Mw. 597.71
LC/MS purity: 99%, m/z 596 [M−H]$^−$, 598 [M+H]$^+$ Rt. 3.35 min. (Method B)
$^1$H NMR (300 MHz, DMSO-d6): 10.4 (bs, 1H), 8.45 (d, 1H), 8.33 (s, 1H), 7.75 (s, 1H), 7.49 (s, 1H), 7.38 (s, 1H), 7.36 (t, 1H), 7.16 (d, 1H), 7.03 (d, 1H), 6.38 (d, 1H), 4.16 (m, 4H), 3.93 (s, 3H), 2.80 (m, 2H), 2.45 (m, 2H), 1.96 (m, 2H), 1.85 (m, 1H), 1.65 (m, 1H), 1.59 (m, 3H), 1.48 (m, 1H), 1.34 (t, 3H), 0.91 (m, 1H), 0.83 (d, 3H)
Melting point: 152-154° C.
Yield: 43%

Example 69

3-Chloro-N-(3-fluoro-4-{6-methoxy-7-[3-(3-methyl-piperidin-1-yl)-propoxy]-quinolin-4-yloxy}-phenyl)-benzenesulfonamide

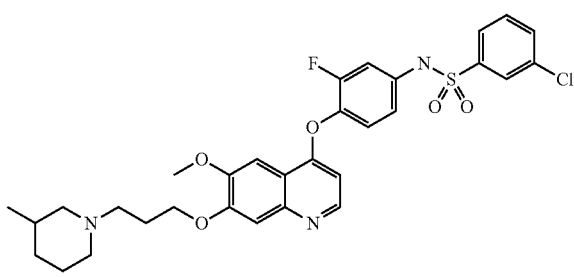 [SMILES: COc1cc2c(Oc3ccc(NS(=O)(=O)c4cccc(Cl)c4)cc3F)ccnc2cc1OCCCN1CCCC(C)C1]

$C_{31}H_{33}ClFN_3O_5S$ Mw. 614.14
LC/MS purity: 98%, m/z 612 [M−H]⁻, 614 [M+H]⁺ Rt. 2.90 min. (Method A)
¹H NMR (300 MHz, DMSO-d6): 10.2 (bs, 1H), 8.44 (d, 1H), 7.75 (s, 1H), 7.74 (d, 1H), 7.67 (d, 1H), 7.58 (t, 1H), 7.48 (s, 1H), 7.38 (s, 1H), 7.25 (t, 1H), 7.06 (d, 1H), 6.91 (d, 1H), 6.35 (d, 1H), 4.19 (t, 2H), 3.92 (s, 3H), 2.89 (m, 2H), 2.55 (m, 2H), 1.99 (m, 3H), 1.69 (m, 4H), 1.51 (m, 1H), 0.92 (m, 1H), 0.85 (d, 3H)
Melting point: 110-112° C.
Yield: 43%

Example 70

N-(3-Fluoro-4-{6-methoxy-7-[3-(3-methyl-piperidin-1-yl)-propoxy]-quinolin-4-yloxy}-phenyl)-3-methyl-benzenesulfonamide

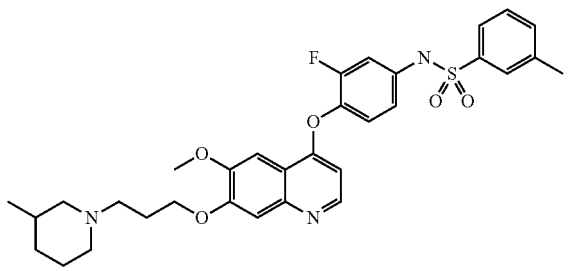

$C_{32}H_{36}FN_3O_5S$ Mw. 593.72
LC/MS purity: 98%, m/z 592 [M−H]⁻, 594 [M+H]⁺ Rt. 2.85 min. (Method A)
¹H NMR (300 MHz, DMSO-d6): 10.2 (bs, 1H), 8.44 (d, 1H), 7.63 (s, 1H), 7.60 (d, 1H), 7.47 (m, 3H), 7.38 (s, 1H), 7.31 (s, 1H), 7.12 (d, 1H), 6.95 (d, 1H), 6.34 (d, 1H), 4.18 (t, 2H), 3.91 (s, 3H), 2.80 (m, 2H), 2.46 (m, 2H), 2.37 (s, 3H), 1.96 (m, 2H), 1.85 (m, 1H), 1.60 (m, 4H), 1.46 (m, 1H), 0.93 (m, 1H), 0.84 (d, 3H)
Melting point: 168-170° C.
Yield: 37%

Example 71

N-(3-Fluoro-4-{6-methoxy-7-[3-(3-methyl-piperidin-1-yl)-propoxy]-quinolin-4-yloxy}-phenyl)-2-methoxy-benzenesulfonamide

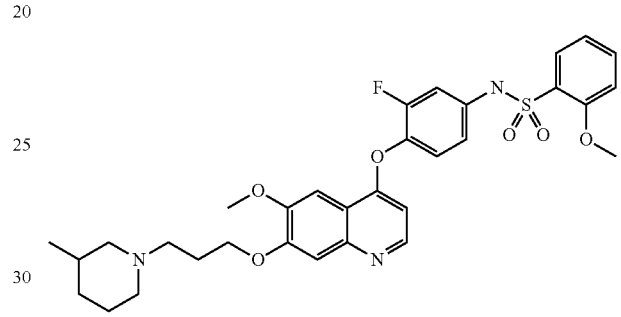

$C_{32}H_{36}FN_3O_6S$ Mw. 609.72
LC/MS purity: 100%, m/z 608 [M−H]⁻, 610 [M+H]⁺ Rt. 2.71 min. (Method A)
¹H NMR (300 MHz, DMSO-d6): 10.3 (bs, 1H), 8.43 (d, 1H), 7.83 (d, 1H), 7.61 (t, 1H), 7.45 (s, 1H), 7.36 (s, 1H), 7.29 (t, 1H), 7.20 (d, 1H), 7.08 (m, 2H), 6.98 (d, 1H), 6.29 (d, 1H), 4.17 (t, 2H), 3.89 (s, 6H), 2.77 (m, 2H), 2.42 (m, 2H), 1.95 (m, 2H), 1.82 (m, 1H), 1.61 (m, 4H), 1.51 (m, 1H), 0.93 (m, 1H), 0.83 (d, 3H)
Melting point: 175-176° C.
Yield: 35%

Example 72

3-Cyano-4-fluoro-N-(3-fluoro-4-{6-methoxy-7-[3-(3-methyl-piperidin-1-yl)-propoxy]-quinolin-4-yloxy}-phenyl)-benzenesulfonamide

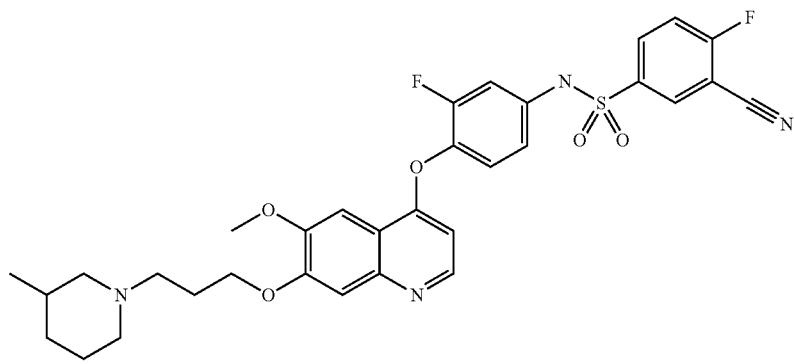 [SMILES: COc1cc2c(Oc3ccc(NS(=O)(=O)c4ccc(F)c(C#N)c4)cc3F)ccnc2cc1OCCCN1CCCC(C)C1]

$C_{32}H_{32}F_2N_4O_5S$ Mw. 622.70

LC/MS purity: 99%, m/z 621 [M−H]⁻, 623 [M+H]⁺ Rt. 2.82 min. (Method A)

¹H NMR (300 MHz, DMSO-d6): 10.2 (bs, 1H), 8.44 (d, 1H), 8.22 (d, 1H), 8.11 (m, 1H), 7.64 (t, 1H), 7.49 (s, 1H), 7.38 (s, 1H), 7.16 (t, 1H), 6.99 (d, 1H), 6.84 (d, 1H), 6.37 (d, 1H), 4.20 (t, 2H), 3.93 (s, 3H), 2.99 (m, 2H), 2.67 (m, 2H), 2.14 (m, 1H), 2.06 (m, 2H), 1.87 (m, 1H), 1.67 (m, 3H), 1.54 (m, 1H), 0.93 (m, 1H), 0.83 (d, 3H)

Melting point: 125-127° C.

Yield: 8%

Example 73

2-Phenyl-ethenesulfonic acid (3-fluoro-4-{6-methoxy-7-[3-(3-methyl-piperidin-1-yl)-propoxy]-quinolin-4-yloxy}-phenyl)-amide

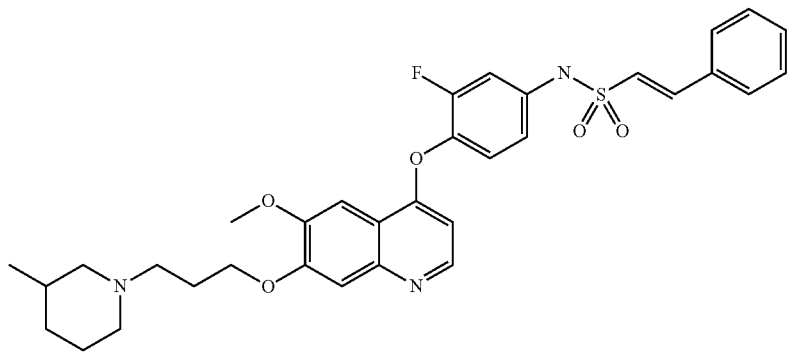 [SMILES: COc1cc2c(Oc3ccc(NS(=O)(=O)/C=C/c4ccccc4)cc3F)ccnc2cc1OCCCN1CCCC(C)C1]

$C_{33}H_{36}FN_3O_5S$ Mw. 605.73

LC/MS purity: 98%, m/z 604 [M−H]⁻, 606 [M+H]⁺ Rt. 2.91 min. (Method A)

¹H NMR (300 MHz, DMSO-d6): 10.5 (bs, 1H), 8.41 (d, 1H), 7.70 (bs, 2H), 7.48 (s, 1H), 7.42-7.24 (m, 7H), 7.17 (d, 1H), 7.03 (d, 1H), 6.37 (d, 1H), 4.17 (bs, 2H), 3.93 (s, 3H), 2.77 (m, 2H), 2.43 (m, 2H), 1.96 (m, 2H), 1.84 (m, 1H), 1.59 (m, 4H), 1.48 (m, 1H), 0.92 (m, 1H), 0.83 (d, 3H)

Melting point: 104-106° C.

Yield: 27%

Example 74

Quinoline-8-sulfonic acid (3-fluoro-4-{6-methoxy-7-[3-(3-methyl-piperidin-1-yl)-propoxy]-quinolin-4-yloxy}-phenyl)-amide

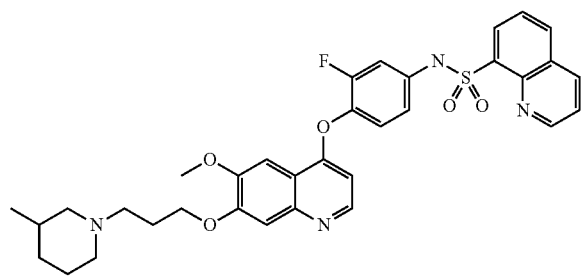 [SMILES: COc1cc2c(Oc3ccc(NS(=O)(=O)c4cccc5cccnc45)cc3F)ccnc2cc1OCCCN1CCCC(C)C1]

$C_{34}H_{35}FN_4O_5S$ Mw. 630.74

LC/MS purity: 98%, m/z 629 [M−H]⁻, 631 [M+H]⁺ Rt. 2.62 min. (Method A)

¹H NMR (300 MHz, DMSO-d6): 10.5 (bs, 1H), 9.15 (d, 1H), 8.55 (d, 1H), 8.45 (d, 1H), 8.39 (d, 1H), 8.33 (d, 1H), 7.74 (m, 2H), 7.40 (s, 1H), 7.34 (s, 1H), 7.17 (t, 1H), 7.14 (d, 1H), 6.97 (d, 1H), 6.21 (d, 1H), 4.15 (t, 2H), 3.87 (s, 3H), 2.78 (m, 2H), 2.43 (m, 2H), 1.94 (m, 2H), 1.82 (m, 1H), 1.58 (m, 5H), 0.89 (m, 1H), 0.82 (d, 3H)

Melting point: 190-191° C.

Yield: 25%

Example 75

3,5-Dichloro-N-(3-fluoro-4-{6-methoxy-7-[3-(3-methyl-piperidin-1-yl)-propoxy]-quinolin-4-yloxy}-phenyl)-2-methoxy-benzenesulfonamide

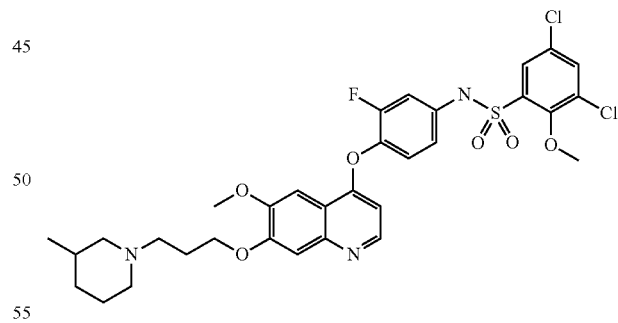

$C_{32}H_{34}Cl_2FN_3O_6S$ Mw. 678.61

LC/MS purity: 97%, m/z 676 [M−H]⁻, 678 [M+H]⁺ Rt. 3.19 min. (Method A)

¹H NMR (300 MHz, DMSO-d6): 10.5 (bs, 1H), 8.44 (d, 1H), 7.90 (d, 1H), 7.76 (d, 1H), 7.49 (s, 1H), 7.38 (s, 1H), 7.22 (t, 1H), 7.04 (dd, 1H), 6.89 (d, 1H), 6.36 (d, 1H), 4.19 (t, 2H), 3.92 (s, 3H), 3.91 (s, 3H), 2.96 (m, 2H), 2.64 (m, 2H), 2.03 (m, 3H), 1.82 (m, 1H), 1.66 (m, 3H), 1.51 (m, 1H), 0.92 (m, 1H), 0.86 (d, 3H)

Melting point: 145-146° C.

Yield: 17%

Example 76

3,5-Dichloro-N-{3-fluoro-4-[6-methoxy-7-(3-morpholin-4-yl-propoxy)-quinolin-4-yloxy]-phenyl}-2-methoxy-benzenesulfonamide

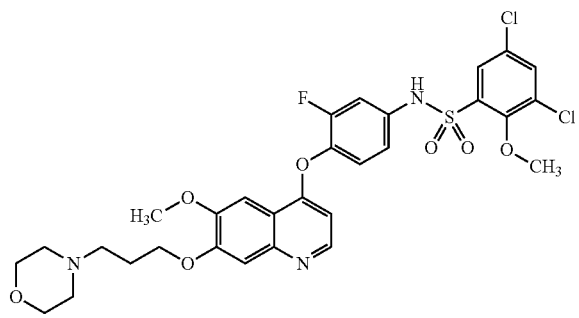 [SMILES: COc1cc2c(Oc3ccc(NS(=O)(=O)c4cc(Cl)cc(Cl)c4OC)cc3F)ccnc2cc1OCCCN1CCOCC1]

$C_{30}H_{30}Cl_2FN_3O_7S$ Mw. 666.56

LC/MS purity: 98%, m/z 664 [M−H]⁻, 666 [M+H]⁺ Rt. 3.00 min. (Method A)

¹H NMR (300 MHz, DMSO-d6): 10.8 (bs, 1H), 8.44 (d, 1H), 8.00 (d, 1H), 7.79 (d, 1H), 7.48 (s, 1H), 7.38 (s, 1H), 7.32 (t, 1H), 7.12 (dd, 1H), 6.98 (d, 1H), 6.36 (d, 1H), 4.19 (t, 2H), 3.94 (s, 3H), 3.92 (s, 3H), 3.59 (m, 4H), 2.49 (m, 2H), 2.42 (m, 4H), 1.97 (m, 2H)

Melting point: 189-191° C.

Yield: 24%

Example 77

2,6-Difluoro-N-{3-fluoro-4-[6-methoxy-7-(3-morpholin-4-yl-propoxy)-quinolin-4-yloxy]-phenyl}-benzenesulfonamide

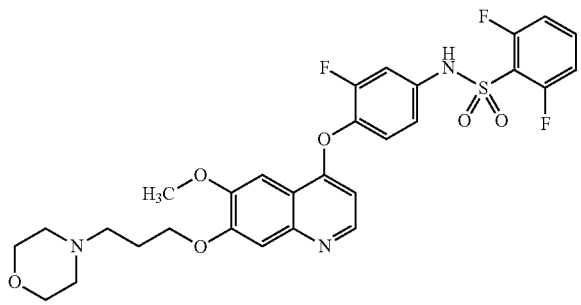 [SMILES: COc1cc2c(Oc3ccc(NS(=O)(=O)c4c(F)cccc4F)cc3F)ccnc2cc1OCCCN1CCOCC1]

$C_{29}H_{28}F_3N_3O_6S$ Mw. 603.62

LC/MS purity: 98%, m/z 602 [M−H]⁻, 604 [M+H]⁺ Rt. 2.95 min. (Method B)

¹H NMR (300 MHz, DMSO-d6): 11 (bs, 1H), 8.44 (d, 1H), 7.68 (m, 1H), 7.48 (s, 1H), 7.38 (s, 1H), 7.36-7.24 (m, 3H), 7.14 (dd, 1H), 7.00 (d, 1H), 6.34 (d, 1H), 4.19 (t, 2H), 3.92 (s, 3H), 3.59 (m, 4H), 2.49 (m, 2H), 2.41 (m, 4H), 1.96 (m, 2H)

Melting point: 190-192° C.

Yield: 23%

Example 78

N-{3-Fluoro-4-[6-methoxy-7-(3-piperidin-1-yl-propoxy)-quinolin-4-yloxy]-phenyl}-2-trifluoromethoxy-benzenesulfonamide

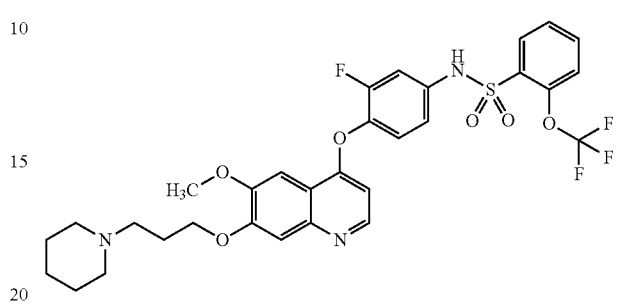

$C_{31}H_{31}F_4N_3O_6S$ Mw. 649.67

LC/MS purity: 98%, m/z 648 [M−H]⁻, 650 [M+H]⁺ Rt. 2.90 min. (Method A)

¹H NMR (300 MHz, DMSO-d6): 10.5 (bs, 1H), 8.44 (d, 1H), 8.00 (d, 1H), 7.70 (t, 1H), 7.52 (m, 2H), 7.48 (s, 1H), 7.38 (s, 1H), 7.22 (t, 1H), 7.05 (dd, 1H), 6.89 (d, 1H), 6.33 (d, 1H), 4.19 (t, 2H), 3.93 (s, 3H), 2.62 (m, 2H), 2.56 (m, 4H), 2.03 (m, 2H), 1.55 (m, 4H), 1.43 (m, 2H)

Melting point: 156-158° C.

Yield: 26%

Example 79

Butane-1-sulfonic acid {3-fluoro-4-[6-methoxy-7-(3-morpholin-4-yl-propoxy)-quinolin-4-yloxy]-phenyl}-amide

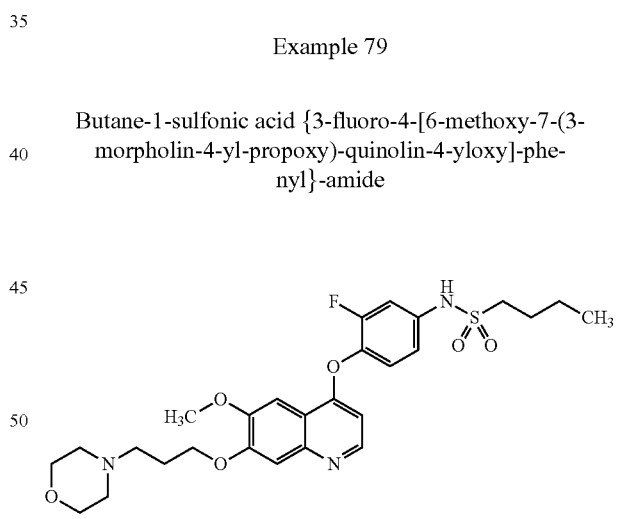

$C_{27}H_{34}FN_3O_6S$ Mw. 547.65

LC/MS purity: 98%, m/z 546 [M−H]⁻, 548 [M+H]⁺ Rt. 3.59 min.

¹H NMR (300 MHz, DMSO-d6): 10.14 (s, 1H), 8.47 (d, 1H), 7.51 (s, 1H), 7.44 (t, 1H), 7.40 (s, 1H), 7.27 (dd, 1H), 7.14 (d, 1H), 6.46 (d, 1H), 4.20 (t, 2H), 3.94 (s, 3H), 3.59 (m, 4H), 3.20 (m, 2H), 2.47 (m, 2H), 2.39 (m, 4H), 1.98 (m, 2H), 1.68 (m, 2H), 1.39 (m, 2H), 0.87 (t, 3H)

Melting point: 98-100° C.

Yield: 18%

Example 80

2,5-Difluoro-N-{3-fluoro-4-[6-methoxy-7-(piperidin-3-ylmethoxy)-quinolin-4-yloxy]-phenyl}-benzenesulfonamide

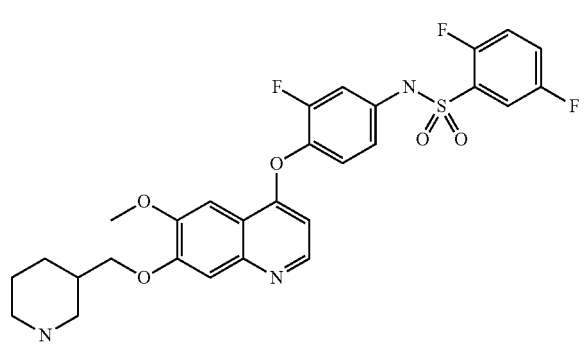 [SMILES: COc1cc2c(Oc3ccc(NS(=O)(=O)c4cc(F)ccc4F)cc3F)ccnc2cc1OCC1CCCNC1]

$C_{28}H_{26}F_3N_3O_5S$ Mw. 573.60

LC/MS purity: %, m/z [M−H]⁻, [M+H]⁺ Rt. min. (Method B)

Yield: 34%

Example 81

2-Fluoro-N-{3-fluoro-4-[6-methoxy-7-(2-morpholin-4-yl-ethoxy)-quinolin-4-yloxy]-phenyl}-benzenesulfonamide

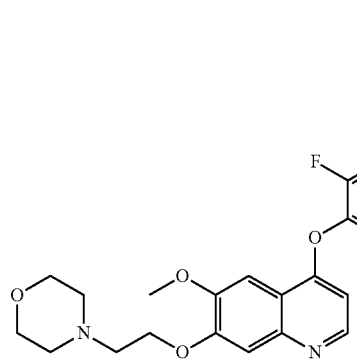

$C_{28}H_{27}F_2N_3O_6S$ Mw. 571.60

LC/MS purity: 98%, m/z 570 [M−H]⁻, 572 [M+H]⁺, Rt. 3.06 min. (Method B)

¹H NMR (300 MHz, DMSO-d6): 11 (bs, 1H), 8.44 (s, 1H), 7.90 (s, 1H), 7.73 (s, 1H), 7.38 (m, 5H), 7.15 (d, 1H), 7.03 (d, 1H), 6.33 (s, 1H), 4.27 (bs, 2H), 3.90 (s, 3H), 3.59 (s, 4H), 2.79 (bs, 2H), 2.52 (s, 4H)

Melting point: 168-169° C.

Yield: 67%

Example 82

2,6-Difluoro-N-{3-fluoro-4-[6-methoxy-7-(2-morpholin-4-yl-ethoxy)-quinolin-4-yloxy]-phenyl}-benzenesulfonamide

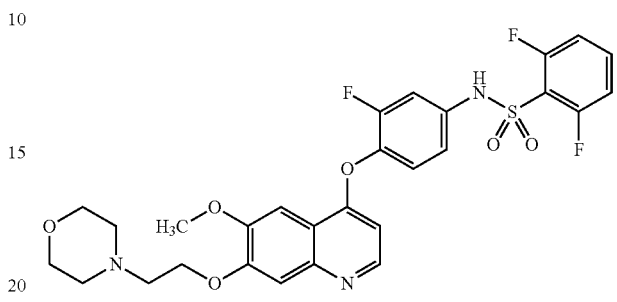

$C_{28}H_{26}F_3N_3O_6S$ Mw. 589.60

LC/MS purity: 97%, m/z 588 [M−H]⁻, 590 [M+H]⁺ Rt. 2.88 min. (Method B)

¹H NMR (300 MHz, DMSO-d6): 11 (bs, 1H), 8.45 (s, 1H), 7.71 (s, 1H), 7.47 (s, 1H), 7.42 (s, 1H), 7.36-7.26 (m, 5H), 7.16 (d, 1H), 7.03 (d, 1H), 6.35 (s, 1H), 4.27 (bs, 2H), 3.91 (s, 3H), 3.60 (s, 4H), 2.80 (bs, 2H), 2.57 (s, 4H)

Melting point: 182-183° C.

Yield: 32%

Example 83

2,5-Difluoro-N-{3-fluoro-4-[6-methoxy-7-(4-morpholin-4-yl-butoxy)-quinolin-4-yloxy]-phenyl}-benzenesulfonamide

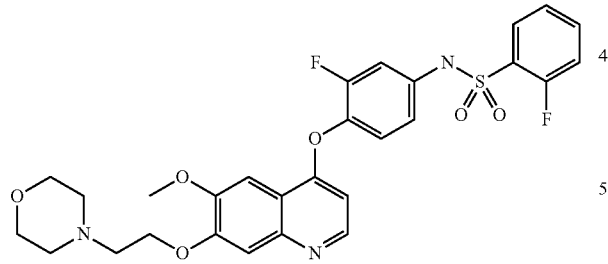

$C_{30}H_{30}F_3N_3O_6S$ Mw. 617.65

LC/MS purity: 97%, m/z 616 [M−H]⁻, 618 [M+H]⁺ Rt. 3.22 min. (Method B)

¹H NMR (300 MHz, DMSO-d6): 11.1 (bs, 1H), 8.44 (d, 1H), 7.67-7.53 (m, 3H), 7.47 (s, 1H), 7.38 (s, 1H), 7.30 (t, 1H), 7.12 (d, 1H), 6.98 (d, 1H), 6.35 (d, 1H), 4.17 (t, 2H), 3.92 (s, 3H), 3.58 (m, 4H), 2.39 (m, 6H), 1.82 (m, 2H), 1.64 (m, 2H)

Melting point: 156-158° C.

Yield: 29%

Example 84

2,5-Difluoro-N-{3-fluoro-4-[7-(4-morpholin-4-yl-butoxy)-quinolin-4-yloxy]-phenyl}-benzenesulfonamide

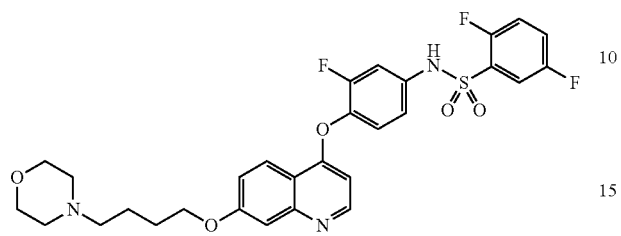

$C_{29}H_{28}F_3N_3O_5S$ Mw. 587.62
LC/MS purity: %, m/z [M–H]⁻, [M+H]⁺ Rt. min. (Method B)
Yield: 30%

Example 85

N-(3-Fluoro-4-{6-[3-(4-methyl-piperazin-1-yl)-propoxy]-quinolin-4-yloxy}-phenyl)-2-trifluoromethyl-benzenesulfonamide

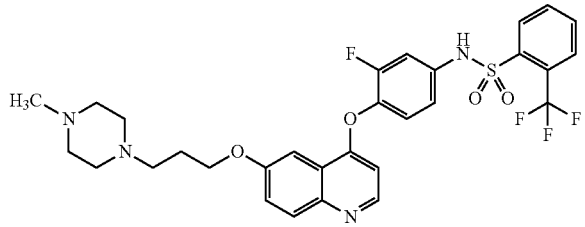 [SMILES: CN1CCN(CCCOc2ccc3nccc(Oc4ccc(NS(=O)(=O)c5ccccc5C(F)(F)F)cc4F)c3c2)CC1]

$C_{30}H_{30}F_4N_4O_4S$ Mw. 618.66
LC/MS purity: 97%, m/z 617 [M–H]⁻, 619 [M+H]⁺ Rt. 3.18 min. (Method B)
¹H NMR (300 MHz, DMSO-d6): 10 (bs, 1H), 8.50 (d, 1H), 8.15 (d, 1H), 7.97-7.78 (m, 4H), 7.52 (m, 1H), 7.43 (dd, 1H), 7.27 (t, 1H), 7.05 (d, 1H), 6.93 (d, 1H), 6.49 (d, 1H), 4.16 (t, 2H), 2.44 (m, 10H), 2.19 (s, 3H), 1.95 (m, 2H)
Melting point: 101-103° C.
Yield: 27%

Example 86

N-(3-Fluoro-4-{7-methoxy-6-[3-(4-methyl-piperazin-1-yl)-propoxy]-quinolin-4-yloxy}-phenyl)-2-trifluoromethyl-benzenesulfonamide

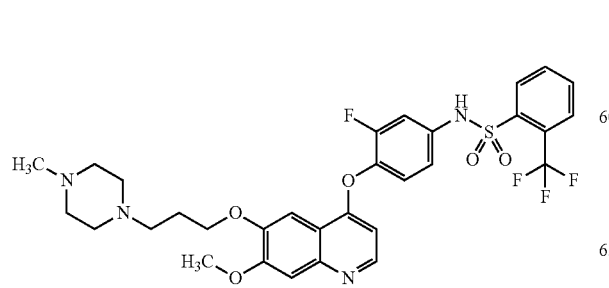

$C_{31}H_{32}F_4N_4O_5S$ Mw. 648.68
LC/MS purity: 97%, m/z 647 [M–H]⁻, 649 [M+H]⁺ Rt. 3.07 min. (Method B)
¹H NMR (300 MHz, DMSO-d6): 10 (bs, 1H), 8.43 (d, 1H), 8.13 (d, 1H), 7.95 (d, 1H), 7.80 (m, 2H), 7.47 (s, 1H), 7.38 (s, 1H), 7.25 (t, 1H), 7.05 (d, 1H), 6.91 (d, 1H), 6.35 (d, 1H), 4.15 (t, 2H), 3.93 (s, 3H), 2.44 (m, 10H), 2.17 (s, 3H), 1.96 (m, 2H)
Melting point: 113-115° C.
Yield: 23%

Example 87

N-(3-Chloro-4-{6-methoxy-7-[3-(4-methyl-piperazin-1-yl)-propoxy]-quinolin-4-yloxy}-phenyl)-2-trifluoromethyl-benzenesulfonamide

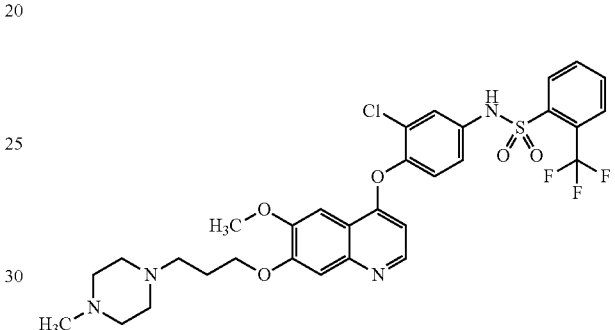

$C_{31}H_{32}ClF_3N_4O_5S$ Mw. 665.14
LC/MS purity: 99%, m/z 663 [M–H]⁻, 665 [M+H]⁺ Rt. 3.17 min. (Method B)
¹H NMR (300 MHz, DMSO-d6): 11 (bs, 1H), 8.43 (d, 1H), 8.13 (d, 1H), 7.93 (d, 1H), 7.80 (m, 2H), 7.47 (s, 1H), 7.37 (s, 1H), 7.22 (m, 2H), 7.04 (d, 1H), 6.26 (s, 1H), 4.18 (bs, 2H), 3.91 (s, 3H), 2.48 (s, 10H), 2.24 (s, 3H), 1.96 (m, 2H).
Melting point: 103-105° C.
Yield: 26%

Example 88

N-(3,5-Dichloro-4-{6-methoxy-7-[3-(4-methyl-piperazin-1-yl)-propoxy]-quinolin-4-yloxy}-phenyl)-2,6-difluoro-benzenesulfonamide

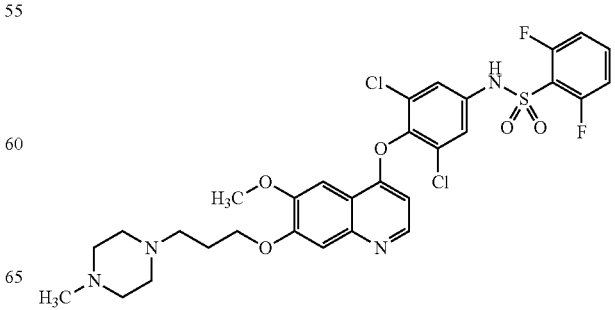

C₃₀H₃₀₀C₂F₂N₄O₅S Mw. 667.56
LC/MS purity: %, m/z [M−H]⁻, [M+H]⁺ Rt. min. (Method B)
Yield: 20%

Example 89

N-(4-{6-Methoxy-7-[3-(4-methyl-piperidin-1-yl)-propoxy]-quinolin-4-yloxy}-3-methyl-phenyl)-2-trifluoromethyl-benzenesulfonamide

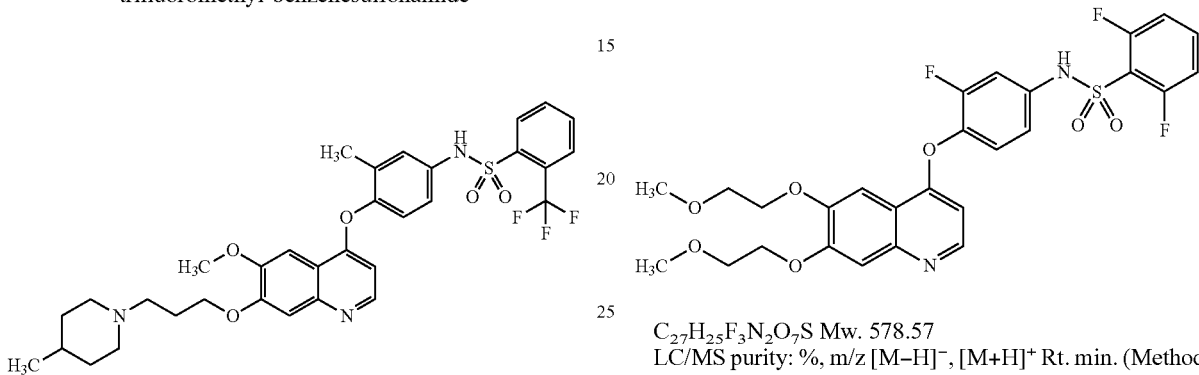

C₃₃H₃₆F₃N₃O₅S Mw. 643.73
LC/MS purity: 99%, m/z 642 [M−H]⁻, 644 [M+H]⁺ Rt. 4.03 min. (Method B)
¹H NMR (300 MHz, DMSO-d6): 10.6 (bs, 1H), 8.40 (d, 1H), 8.12 (d, 1H), 7.89 (d, 1H), 7.85 (m, 2H), 7.50 (s, 1H), 7.36 (s, 1H), 7.09 (s, 1H), 7.02 (m, 2H), 6.17 (d, 1H), 4.17 (t, 2H), 3.91 (s, 3H), 2.87 (m, 2H), 2.47 (m, 2H), 2.01 (m, 3H), 1.93 (m, 4H), 1.58 (m, 2H), 1.33 (m, 1H), 1.18 (m, 2H), 0.88 (d, 3H)
Melting point: 165-167° C.
Yield: 25%

Example 90

2,5-Difluoro-N-(3-methoxy-4-{6-methoxy-7-[3-(3-methyl-piperidin-1-yl)-propoxy]-quinolin-4-yloxy}-phenyl)-benzenesulfonamide

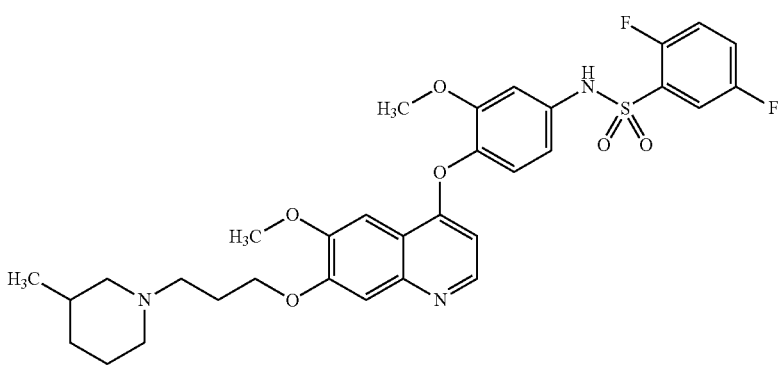 [SMILES: COc1cc2c(Oc3ccc(NS(=O)(=O)c4cc(F)ccc4F)cc3OC)ccnc2cc1OCCCN1CCCC(C)C1]

C₃₂H₃₅F₂N₃O₆S Mw. 627.71
LC/MS purity: %, m/z [M−H]⁻, [M+H]⁺ Rt. min. (Method B)
Yield: 28%

Example 91

N-{4-[6,7-Bis-(2-methoxy-ethoxy)-quinolin-4-yloxy]-3-fluoro-phenyl}-2,6-difluoro-benzenesulfonamide

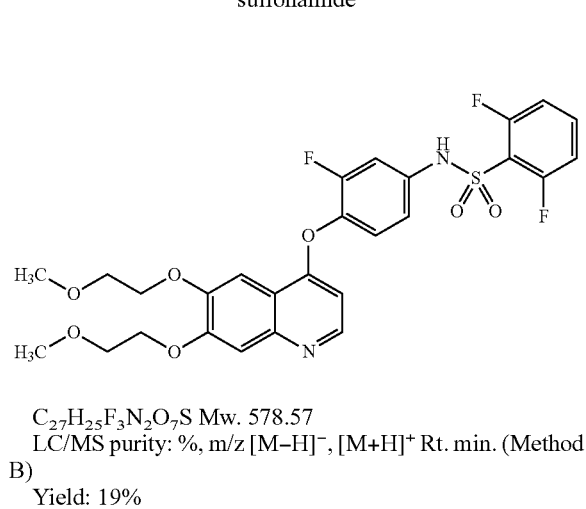

C₂₇H₂₅F₃N₂O₇S Mw. 578.57
LC/MS purity: %, m/z [M−H]⁻, [M+H]⁺ Rt. min. (Method B)
Yield: 19%

Example 92

{4-[2-Fluoro-4-(2-fluoro-benzenesulfonylamino)-phenoxy]-6-methoxy-quinolin-7-yloxy}-acetic acid ethyl ester

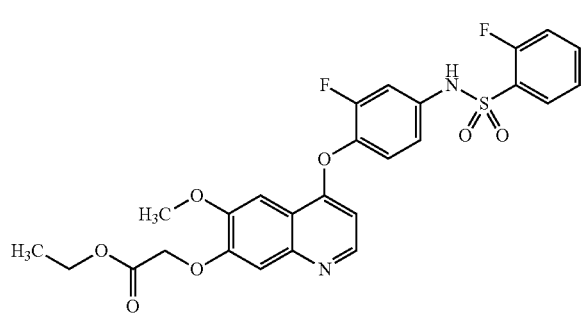 [SMILES: CCOC(=O)COc1cc2nccc(Oc3ccc(NS(=O)(=O)c4ccccc4F)cc3F)c2cc1OC]

$C_{26}H_{22}F_2N_2O_7S$ Mw. 544.54

LC/MS purity: 97%, m/z 543 [M−H]⁻, 545 [M+H]⁺ Rt. 3.50 min. (Method B)

¹H NMR (300 MHz, DMSO-d6): 10.99 (s, 1H), 8.45 (d, 1H), 7.91 (t, 1H), 7.75 (m, 1H), 7.50 (s, 1H), 7.40 (m, 3H), 7.30 (s, 1H), 7.17 (dd, 1H), 7.05 (d, 1H), 6.35 (d, 1H), 5.00 (s, 2H), 4.20 (q, 2H), 3.94 (s, 3H), 1.28 (t, 3H)

Melting point: 87-89° C.

Yield: 23%

Example 93

2-{4-[2-Fluoro-4-(2-trifluoromethyl-benzenesulfonylamino)-phenoxy]-6-methoxy-quinolin-7-yloxy}-N,N-dimethyl-acetamide

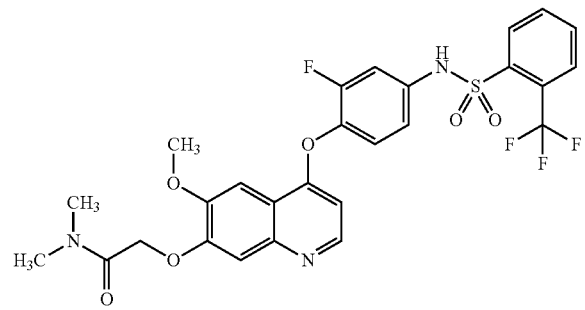 [SMILES: COc1cc2c(Oc3ccc(NS(=O)(=O)c4ccccc4C(F)(F)F)cc3F)ccnc2cc1OCC(=O)N(C)C]

$C_{27}H_{23}F_4N_3O_6S$ Mw. 593.56

LC/MS purity: 97%, m/z 592 [M−H]⁻, 594 [M+H]⁺ Rt. 3.24 min. (Method B)

¹H NMR (300 MHz, DMSO-d6): 11.2 (bs, 1H), 8.43 (d, 1H), 8.15 (d, 1H), 8.01 (d, 1H), 7.88 (m, 2H), 7.47 (s, 1H), 7.36 (t, 1H), 7.29 (s, 1H), 7.14 (d, 1H), 7.02 (d, 1H), 6.36 (d, 1H), 5.03 (s, 2H), 3.92 (s, 3H), 2.86 (s, 3H), 3.11 (s, 3H)

Melting point: 134-135° C.

Yield: 33%

Example 94

Cyclohexanecarboxylic acid 4-[4-(2,5-difluoro-benzenesulfonylamino)-2-fluoro-phenoxy]-6-methoxy-quinolin-7-yl ester

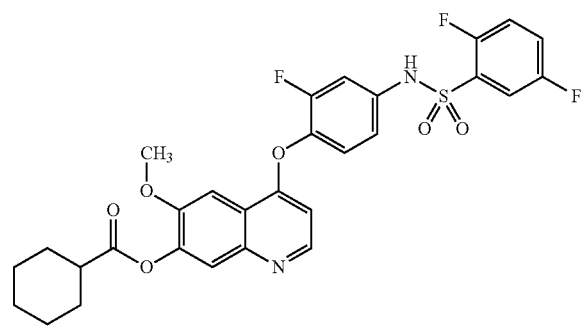 [SMILES: COc1cc2c(Oc3ccc(NS(=O)(=O)c4cc(F)ccc4F)cc3F)ccnc2cc1OC(=O)C1CCCCC1]

$C_{29}H_{25}F_3N_2O_6S$ Mw. 586.59

LC/MS purity: 82%, m/z 585 [M−H]⁻, 587 [M+H]⁺ Rt. 4.54 min. (Method A)

Yield: 22%

Example 95

N-(3-Fluoro-4-{6-methoxy-7-[3-(tetrahydro-pyran-4-ylamino)-propoxy]-quinolin-4-yloxy}-phenyl)-2-trifluoromethyl-benzenesulfonamide

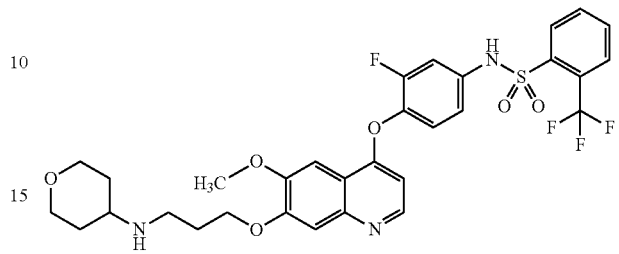

$C_{31}H_{31}F_4N_3O_6S$ Mw. 649.67

LC/MS purity: %, m/z [M−H]⁻, [M+H]⁺ Rt. min. (Method B)

Yield: 17%

Example 96

N-{4-[7-(3-Cyclopropylamino-propoxy)-6-methoxy-quinolin-4-yloxy]-3-fluoro-phenyl}-2-trifluoromethyl-benzenesulfonamide

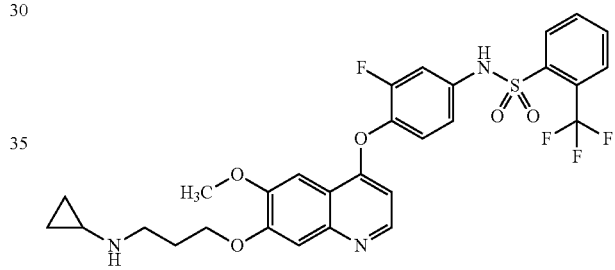

$C_{29}H_{27}F_4N_3O_5S$ Mw. 605.61

LC/MS purity: %, m/z [M−H]⁻, [M+H]⁺ Rt. min. (Method B)

Yield: 21%

Example 97

N-{4-[7-(3-Cyclobutylamino-propoxy)-6-methoxy-quinolin-4-yloxy]-3-fluoro-phenyl}-2-trifluoromethyl-benzenesulfonamide

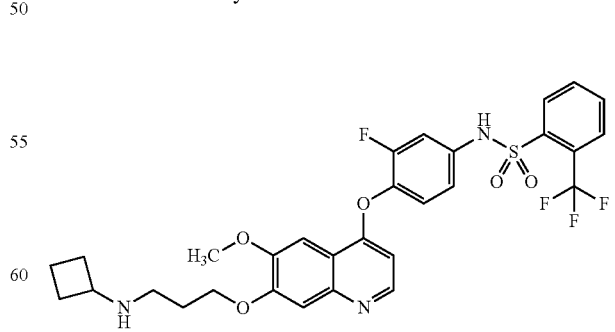

$C_{30}H_{29}F_4N_3O_5S$ Mw. 619.64

LC/MS purity: %, m/z [M−H]⁻, [M+H]⁺ Rt. min. (Method B)

Yield: 16%

Example 98

N-(4-{7-[3-(3-tert-Butyl-ureido)-propoxy]-6-methoxy-quinolin-4-yloxy}-3-fluoro-phenyl)-2-trifluoromethyl-benzenesulfonamide

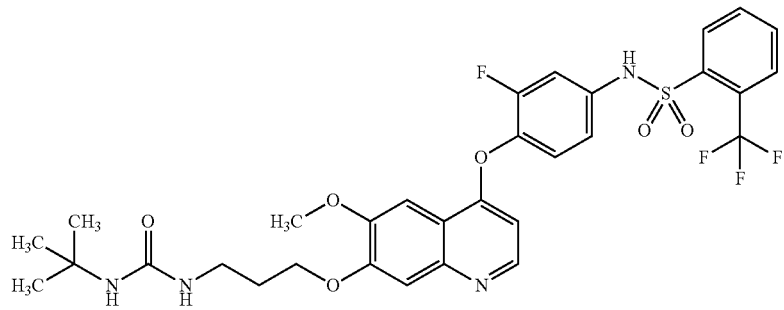 [SMILES: COc1cc2c(Oc3ccc(NS(=O)(=O)c4ccccc4C(F)(F)F)cc3F)ccnc2cc1OCCCNC(=O)NC(C)(C)C]

C₃₁H₃₂F₄N₄O₆S Mw. 664.68
LC/MS purity: 96%, m/z 663 [M−H]⁻, 665 [M+H]⁺ Rt. 3.53 min. (Method B)
¹H NMR (300 MHz, DMSO-d6): 11.04 (bs, 1H), 10 (bs, 1H), 8.46 (d, 1H), 8.15 (d, 1H), 7.91 (s, 2H), 7.48 (s, 1H), 7.38 (s, 2H), 7.18 (d, 1H), 7.04 (d, 1H), 6.38 (d, 1H), 5.76 (bs, 1H), 5.56 (bs, 1H), 4.15 (bs, 2H), 3.92 (s, 3H), 3.15 (bs, 2H), 1.89 (bs, 2H), 1.21 (s, 9H)

Melting point: 106-108° C.
Yield: 15%

Example 99

N-(3-Fluoro-4-{6-methoxy-7-[3-(2-methyl-piperidin-1-yl)-propoxy]-quinolin-4-yloxy}-phenyl)-2-trifluoromethyl-benzenesulfonamide

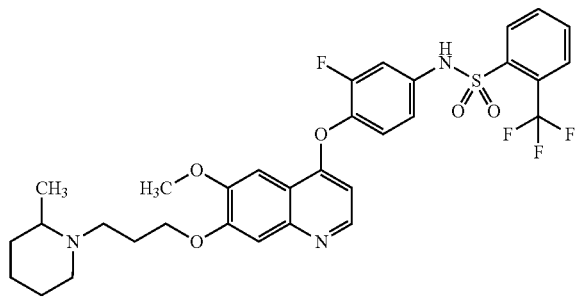 [SMILES: COc1cc2c(Oc3ccc(NS(=O)(=O)c4ccccc4C(F)(F)F)cc3F)ccnc2cc1OCCCN1CCCCC1C]

C₃₂H₃₃F₄N₃O₅S Mw. 647.69
LC/MS purity: 98%, m/z 646 [M−H]⁻, 648 [M+H]⁺ Rt. 3.36 min. (Method B)
¹H NMR (300 MHz, DMSO-d6): 10 (bs, 1H), 8.44 (d, 1H), 8.13 (d, 1H), 7.90 (d, 1H), 7.75 (m, 2H), 7.48 (s, 1H), 7.38 (s, 1H), 7.18 (t, 1H), 6.97 (dd, 1H), 6.84 (d, 1H), 6.35 (d, 1H), 4.19 (t, 2H), 3.92 (s, 3H), 2.99 (m, 2H), 2.63 (m, 2H), 2.40 (m, 1H), 2.00 (m, 2H), 1.56 (m, 4H), 1.30 (m, 2H), 1.09 (d, 3H).

Melting point: 115-116° C.
Yield: 20%

Example 100

N-{4-[7-(3-Dimethylamino-propoxy)-6-methoxy-quinolin-4-yloxy]-3-fluoro-phenyl}-2-trifluoromethyl-benzenesulfonamide

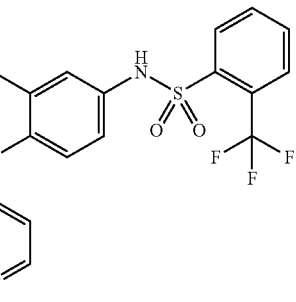

C₂₈H₂₇F₄N₃O₅S Mw. 593.60
LC/MS purity: 100%, m/z 592 [M−H]⁻, 594 [M+H]⁺ Rt. 0.90 min. (Method B)
¹H NMR (300 MHz, DMSO-d6): 10.4 (bs, 1H), 8.43 (s, 1H), 8.12 (d, 1H), 7.90 (d, 1H), 7.75 (m, 2H), 7.48 (s, 1H), 7.37 (s, 1H), 7.17 (t, 1H), 6.96 (d, 1H), 6.84 (d, 1H), 6.35 (d, 1H), 4.18 (t, 2H), 3.92 (s, 3H), 2.58 (t, 2H), 2.50 (s, 6H), 1.99 (m, 2H)

Melting point: 89-91° C.
Yield: 35%

Example 101

N-{4-[7-(3-Diethylamino-propoxy)-6-methoxy-quinolin-4-yloxy]-3-fluoro-phenyl}-2-trifluoromethyl-benzenesulfonamide

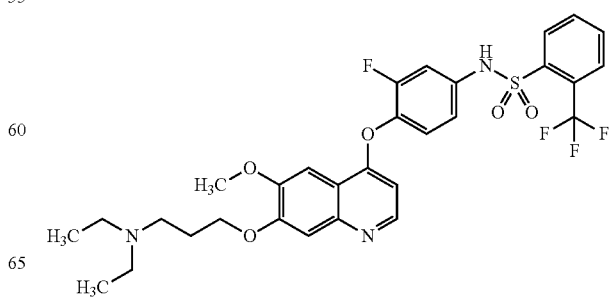

$C_{30}H_{31}F_4N_3O_5S$ Mw. 621.66

LC/MS purity: %, m/z [M–H]⁻, [M+H]⁺ Rt. min. (Method B)

Yield: 30%

Example 102

N-(3-{6-Methoxy-7-[3-(4-methyl-piperazin-1-yl)-propoxy]-quinolin-4-yloxy}-phenyl)-2-trifluorom-ethyl-benzenesulfonamide

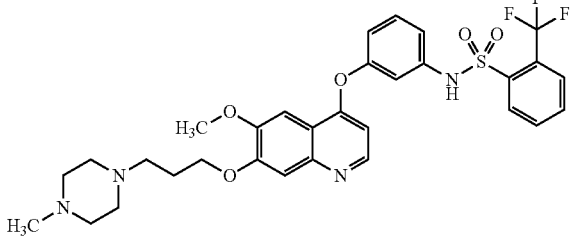

$C_{31}H_{33}F_3N_4O_5S$ Mw. 630.69

LC/MS purity: 98%, m/z 629 [M–H]⁻, 631 [M+H]⁺ Rt. 3.41 min. (Method B)

¹H NMR (300 MHz, DMSO-d6): 10 (bs, 1H), 8.41 (d, 1H), 8.03 (d, 1H), 7.88 (d, 1H) 7.74 (bs, 2H), 7.36 (bs, 2H), 7.26 (t, 1H), 6.91 (d, 1H), 6.78 (s, 1H), 6.72 (d, 1H), 6.30 (d, 1H), 4.18 (bs, 2H), 3.87 (s, 3H), 2.36 (m, 10H), 2.17 (s, 3H), 1.96 (m, 2H).

Melting point: 155-156° C.

Yield: 27%

Example 103

N-{3-Fluoro-4-[6-methoxy-7-(2-morpholin-4-yl-ethoxy)-quinolin-4-yloxy]-phenyl}-2-methoxy-ben-zenesulfonamide

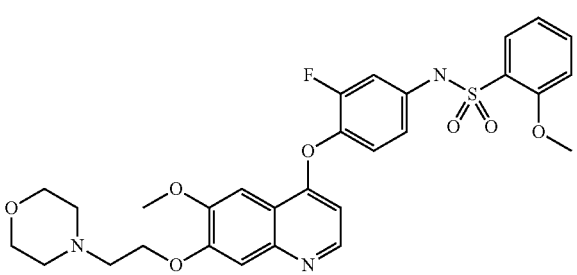 [SMILES: COc1cc2c(Oc3ccc(NS(=O)(=O)c4ccccc4OC)cc3F)ccnc2cc1OCCN1CCOCC1]

$C_{29}H_{30}FN_3O_7S$ Mw. 583.64

LC/MS purity: 98%, m/z 582 [M–H]⁻, 584 [M+H]⁺ Rt. 3.46 min. (Method B)

¹H NMR (300 MHz, DMSO-d6): 10.40 (s, 1H), 8.43 (d, 1H), 7.83 (d, 1H), 7.62 (t, 1H), 7.46 (s, 1H), 7.41 (s, 1H), 7.30 (t, 1H), 7.21 (d, 1H), 7.13-6.90 (m, 3H), 6.29 (d, 1H), 4.26 (t, 2H), 3.90 (s, 6H), 3.60 (t, 4H), 2.78 (t, 2H), 2.52 (t, 4H)

Melting point: 182-183° C.

Yield: 41%

Example 104

2,6-Dichloro-N-{3-fluoro-4-[6-methoxy-7-(2-mor-pholin-4-yl-ethoxy)-quinolin-4-yloxy]-phenyl}-ben-zenesulfonamide

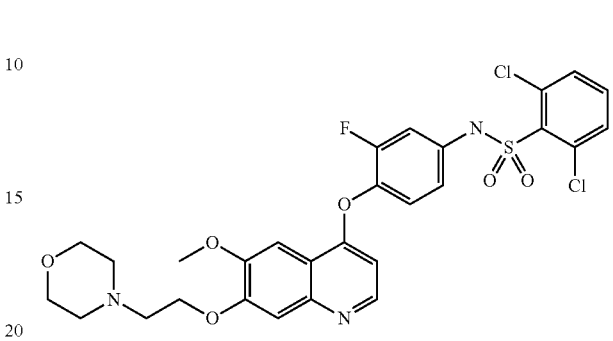

$C_{28}H_{26}Cl_2FN_3O_6S$ Mw. 622.50

LC/MS purity: 98%, m/z 622 [M–H]⁻, 624 [M+H]⁺ Rt. 3.12 min. (Method B)

¹H NMR (300 MHz, DMSO-d6): 11.21 (bs, 1H), 8.44 (s, 1H), 7.66 (m, 2H), 7.59 (d, 1H), 7.47 (s, 1H), 7.42 (s, 1H), 7.34 (d, 1H), 7.15 (d, 1H), 7.00 (d, 1H), 6.33 (s, 1H), 4.27 (bs, 2H), 3.91 (s, 3H), 3.59 (s, 4H), 2.80 (bs, 2H), 2.52 (s, 4H).

Melting point: 210-211° C.

Yield: 54%

Example 105

Thiophene-2-sulfonic acid {3-fluoro-4-[6-methoxy-7-(2-morpholin-4-yl-ethoxy)-quinolin-4-yloxy]-phe-nyl}-amide

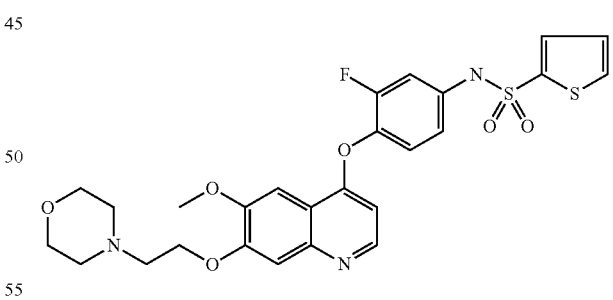

$C_{26}H_{26}FN_3O_6S_2$ Mw. 559.64

LC/MS purity: 98%, m/z 558 [M–H]⁻, 560 [M+H]⁺ Rt. 2.85 min. (Method B)

¹H NMR (300 MHz, DMSO-d6): 10.5 (bs, 1H), 8.47 (d, 1H), 8.04 (s, 1H), 7.70 (s, 2H), 7.48 (s, 1H), 7.43 (s, 1H), 7.30 (t, 1H), 7.13 (d, 1H), 6.97 (d, 1H), 6.36 (d, 1H), 4.26 (t, 2H), 3.93 (s, 3H), 3.59 (s, 4H), 2.81 (m, 2H), 2.56 (bs, 4H).

Melting point: 146-147° C.

Yield: 55%

Example 106

2,5-Dichloro-N-{3-fluoro-4-[6-methoxy-7-(2-morpholin-4-yl-ethoxy)-quinolin-4-yloxy]-phenyl}-benzenesulfonamide

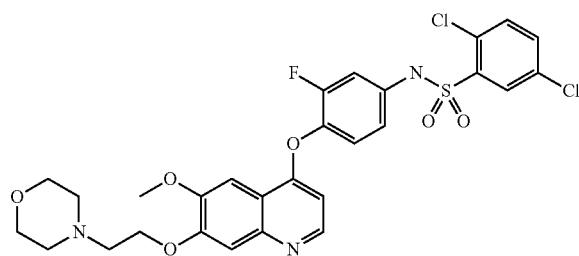 [SMILES: COc1cc2c(Oc3ccc(NS(=O)(=O)c4cc(Cl)ccc4Cl)cc3F)ccnc2cc1OCCN1CCOCC1]

$C_{28}H_{26}Cl_2FN_3O_6S$ Mw. 622.50

LC/MS purity: 97%, m/z 622 [M−H]⁻, 624 [M+H]⁺ Rt. 3.28 min. (Method B)

¹H NMR (300 MHz, DMSO-d6): 11.1 (bs, 1H), 8.44 (s, 1H), 8.03 (s, 1H), 7.71 (s, 2H), 7.47 (s, 1H), 7.42 (s, 1H), 7.33 (t, 1H), 7.12 (d, 1H), 6.99 (d, 1H), 6.34 (s, 1H), 4.27 (bs, 2H), 3.91 (s, 3H), 3.59 (s, 4H), 2.80 (bs, 2H), 2.53 (s, 4H)

Melting point: 194-196° C.

Yield: 74%

Example 107

1-Methyl-1H-pyrazole-3-sulfonic acid {3-fluoro-4-[6-methoxy-7-(2-morpholin-4-yl-ethoxy)-quinolin-4-yloxy]-phenyl}-amide

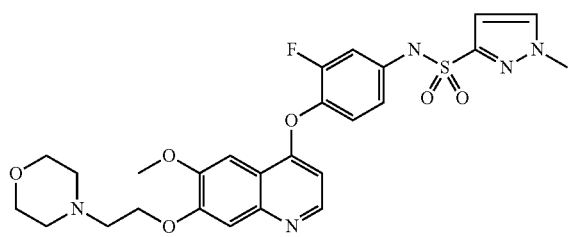 [SMILES: COc1cc2c(Oc3ccc(NS(=O)(=O)c4ccn(C)n4)cc3F)ccnc2cc1OCCN1CCOCC1]

$C_{26}H_{28}FN_5O_6S$ Mw. 557.60

LC/MS purity: 98%, m/z 556 [M−H]⁻, 558 [M+H]⁺ Rt. 2.66 min. (Method B)

¹H NMR (300 MHz, DMSO-d6): 10.74 (s, 1H), 8.45 (s, 1H), 7.88 (s, 1H), 7.49 (s, 1H), 7.43 (s, 1H), 7.36 (t, 1H), 7.20 (d, 1H), 7.07 (d, 1H), 6.68 (s, 1H), 6.38 (s, 1H), 4.27 (bs, 2H), 3.91 (s, 6H), 3.59 (s, 4H), 2.79 (bs, 2H), 2.53 (s, 4H)

Melting point: 213-214° C.

Yield: 69%

Example 108

2-Chloro-N-{3-fluoro-4-[6-methoxy-7-(2-morpholin-4-yl-ethoxy)-quinolin-4-yloxy]-phenyl}-benzenesulfonamide

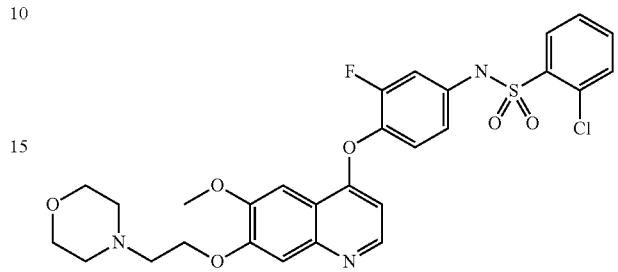

$C_{28}H_{27}ClFN_3O_6S$ Mw. 588.05

LC/MS purity: 96%, m/z 586 [M−H]⁻, 588 [M+H]⁺ Rt. 3.24 min. (Method B)

¹H NMR (300 MHz, DMSO-d6): 11.01 (bs, 1H), 8.43 (s, 1H), 8.01 (d, 1H), 7.67 (s, 2H), 7.56 (s, 1H), 7.46 (s, 1H), 7.42 (s, 1H), 7.34 (t, 1H), 7.13 (d, 1H), 7.02 (d, 1H), 6.32 (s, 1H), 4.26 (bs, 2H), 3.90 (s, 3H), 3.59 (s, 4H), 2.79 (bs, 2H), 2.51 (s, 4H)

Melting point: 180-181° C.

Yield: 76%

Example 109

N-{3-Fluoro-4-[6-methoxy-7-(2-morpholin-4-yl-ethoxy)-quinolin-4-yloxy]-phenyl}-2-nitro-benzenesulfonamide

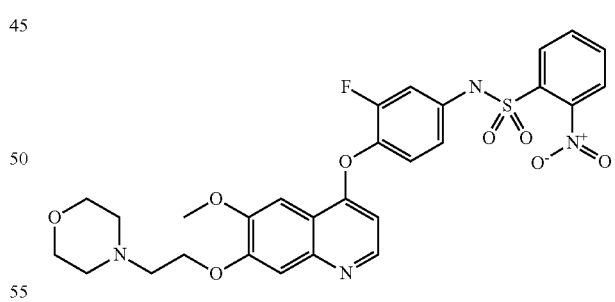

$C_{28}H_{27}FN_4O_8S$ Mw. 598.61

LC/MS purity: 97%, m/z 597 [M−H]⁻, 599 [M+H]⁺ Rt. 2.88 min. (Method B)

¹H NMR (300 MHz, DMSO-d6): 11 (bs, 1H), 8.45 (s, 1H), 8.02 (s, 1H), 7.93 (s, 1H), 7.83 (s, 2H), 7.48 (s, 1H), 7.43 (s, 1H), 7.32 (t, 1H), 7.11 (d, 1H), 6.97 (d, 1H), 6.37 (s, 1H), 4.27 (bs, 2H), 3.92 (s, 3H), 3.59 (s, 4H), 2.81 (bs, 2H), 2.54 (s, 4H)

Melting point: 129-131° C.

Yield: 74%

Example 110

2,6-Difluoro-N-(3-fluoro-4-{6-methoxy-7-[3-(4-methyl-piperazin-1-yl)-propoxy]-quinolin-4-yloxy}-phenyl)-benzenesulfonamide

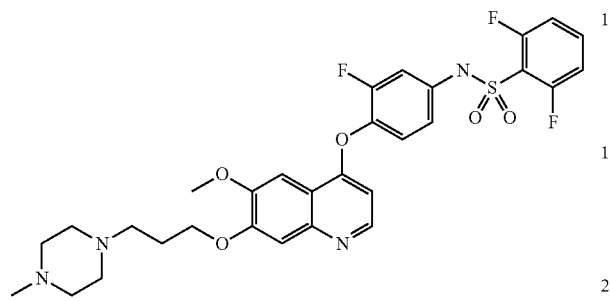

$C_{30}H_{31}F_3N_4O_5S$ Mw. 616.66

LC/MS purity: 97%, m/z 615 [M−H]⁻, 617 [M+H]⁺ Rt. 2.77 min. (Method B)

¹H NMR (300 MHz, DMSO-d6): 10.5 (bs, 1H), 8.44 (d, 1H), 7.6 (t, 1H), 7.48 (s, 1H), 7.37 (s, 1H), 7.19 (m, 3H), 7.05 (d, 1H), 6.90 (d, 1H), 6.34 (d, 1H), 4.18 (bs, 2H), 3.92 (s, 3H), 2.48 (s, 10H), 2.26 (s, 3H), 1.97 (bs, 2H).

Melting point: 199-201° C.

Yield: 41%

Example 111

N-(3-Chloro-4-{6-methoxy-7-[3-(4-methyl-piperazin-1-yl)-propoxy]-quinolin-4-yloxy}-phenyl)-2-fluoro-benzenesulfonamide

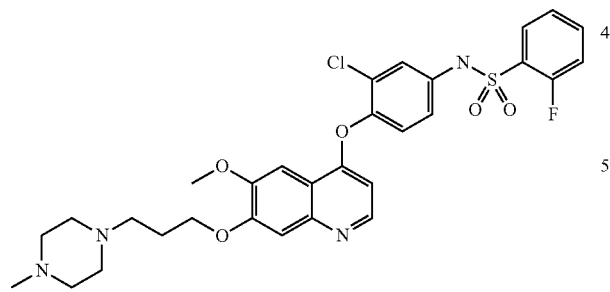

$C_{30}H_{32}ClFN_4O_5S$ Mw. 615.12

LC/MS purity: 95%, m/z 613 [M−H]⁻, 615 [M+H]⁺ Rt. 3.01 min. (Method B)

¹H NMR (300 MHz, DMSO-d6): 11.2 (bs, 1H), 8.43 (dd, 1H), 7.86 (t, 1H), 7.65 (s, 1H), 7.36 (m, 6H), 7.09 (dd, 1H), 6.23 (d, 1H), 4.17 (s, 2H), 3.91 (s, 3H), 2.41 (s, 10H), 2.19 (s, 3H), 1.96 (s, 2H).

Melting point: 170-171° C.

Yield: 52%

Example 112

N-(3-Chloro-4-{6-methoxy-7-[3-(4-methyl-piperazin-1-yl)-propoxy]-quinolin-4-yloxy}-phenyl)-2,5-difluoro-benzenesulfonamide

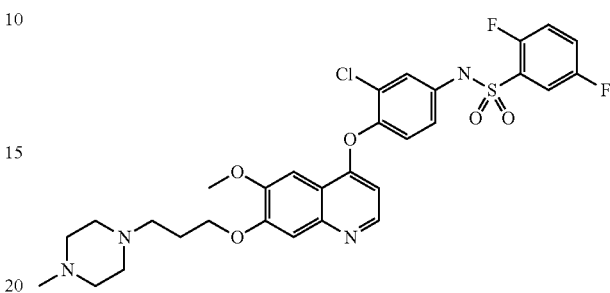

$C_{30}H_{31}ClF_2N_4O_5S$ Mw. 633.11

LC/MS purity: 96%, m/z 631 [M−H]⁻, 633 [M+H]⁺ Rt. 2.94 min. (Method B)

¹H NMR (300 MHz, DMSO-d6): 10.2 (bs, 1H), 8.42 (d, 1H), 7.59 (m, 1H), 7.48 (s, 1H), 7.40 (m, 2H), 7.37 (s, 1H), 7.20 (m, 2H), 7.03 (d, 1H), 6.25 (d, 1H), 4.18 (bs, 2H), 3.92 (s, 3H), 2.49 (s, 10H), 2.28 (s, 3H), 1.97 (bs, 2H).

Melting point: 118-121° C.

Yield: 68%

Example 113

Benzo[b]thiophene-3-sulfonic acid {3-fluoro-4-[6-methoxy-7-(3-piperidin-1-yl-propoxy)-quinolin-4-yloxy]-phenyl}-amide

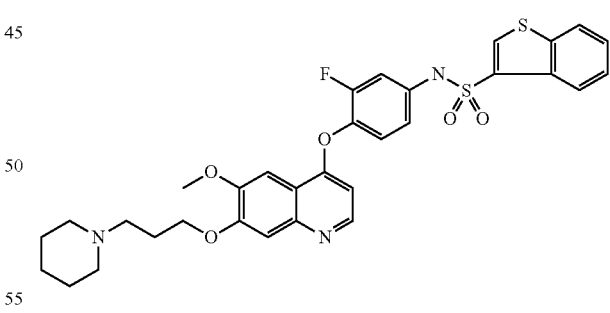

$C_{32}H_{32}FN_3O_5S_2$ Mw. 621.75

LC/MS purity: 98%, m/z 620 [M−H]⁻, 622 [M+H]⁺ Rt. 3.56 min. (Method B)

¹H NMR (300 MHz, DMSO-d6): 10.5 (s, 1H), 8.53 (s, 1H), 8.41 (d, 1H), 8.26 (d, 1H), 8.08 (d, 1H), 7.52 (m, 4H), 7.35 (s, 1H), 7.20 (t, 1H), 7.08 (d, 1H), 6.90 (d, 1H), 4.16 (s, 2H), 3.90 (s, 3H), 2.47 (s, 6H), 1.98 (s, 2H), 1.52 (s, 4H), 1.40 (s, 2H).

Melting point: 128-130° C.

Yield: 65%

Example 114

Benzo[b]thiophene-3-sulfonic acid {3-fluoro-4-[6-methoxy-7-(3-morpholin-4-yl-propoxy)-quinolin-4-yloxy]-phenyl}-amide

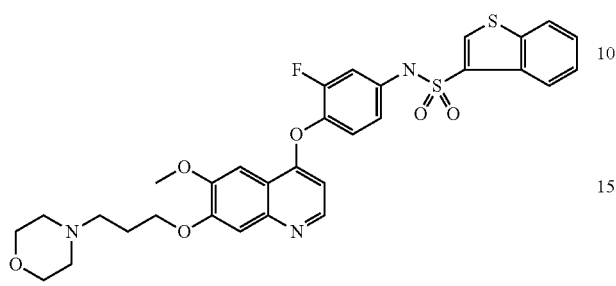

$C_{31}H_{30}FN_3O_6S_2$ Mw. 623.72

LC/MS purity: 99%, m/z 622 [M–H]⁻, 624 [M+H]⁺ Rt. 3.54 min. (Method B)

¹H NMR (300 MHz, DMSO-d6): 11 (bs, 1H), 8.66 (d, 1H), 8.42 (d, 1H), 8.24 (d, 1H), 8.12 (d, 1H), 7.56 (m, 2H), 7.44 (s, 1H), 7.37 (s, 1H), 7.28 (t, 1H), 7.14 (d, 1H), 6.97 (d, 1H), 6.29 (s, 1H), 4.18 (s, 2H), 3.90 (s, 3H), 3.58 (s, 4H), 2.47 (s, 2H), 2.38 (s, 4H), 1.96 (s, 2H).

Melting point: 196-197° C.

Yield: 64%

Example 115

Benzo[b]thiophene-3-sulfonic acid (3-fluoro-4-{6-methoxy-7-[3-(4-methyl-piperidin-1-yl)-propoxy]-quinolin-4-loxy}-phenyl)-amide

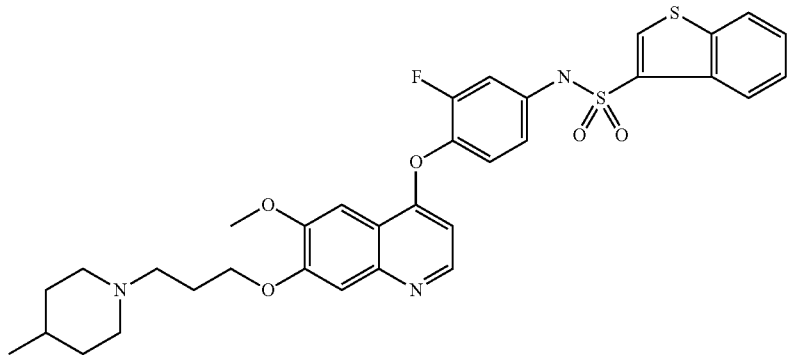 [SMILES: COc1cc2c(Oc3ccc(NS(=O)(=O)c4csc5ccccc45)cc3F)ccnc2cc1OCCCN1CCN(C)CC1]

$C_{33}H_{34}FN_3O_5S_2$ Mw. 635.78

LC/MS purity: 98%, m/z 634 [M–H]⁻, 636 [M+H]⁺ Rt. 3.81 min. (Method B)

¹H NMR (300 MHz, DMSO-d6): 10.9 (bs, 1H), 8.58 (s, 1H), 8.41 (d, 1H), 8.24 (d, 1H), 8.09 (d, 1H), 7.52 (m, 3H), 7.36 (s, 1H), 7.23 (t, 1H), 7.09 (d, 1H), 6.93 (d, 1H), 6.29 (s, 1H), 4.17 (s, 2H), 3.90 (s, 3H), 2.92 (d, 2H), 2.02 (m, 4H), 1.60 (s, 2H), 1.35 (bs, 1H), 1.11 (m, 4H), 0.88 (s, 3H).

Melting point: 132-135° C.

Yield: 61%

Example 116

Benzo[b]thiophene-3-sulfonic acid (3-fluoro-4-{6-methoxy-7-[3-(4-methyl-piperazin-1-yl)-propoxy]-quinolin-4-yloxy}-phenyl)-amide

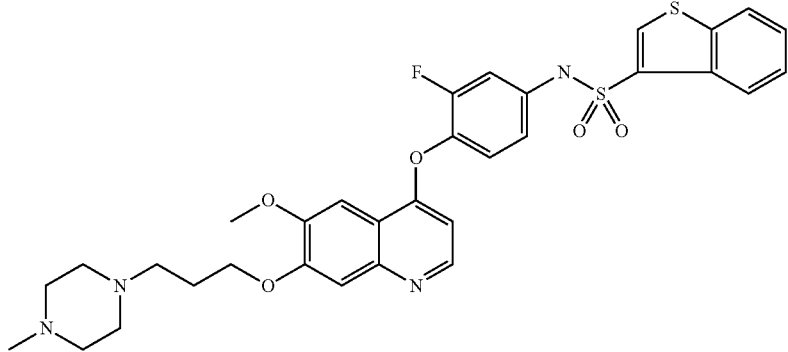

C$_{32}$H$_{33}$FN$_4$O$_5$S$_2$ Mw. 636.77
LC/MS purity: 98%, m/z 635 [M−H]$^-$, 637 [M+H]$^+$ Rt. 3.29 min. (Method B)
$^1$H NMR (300 MHz, DMSO-d6): 10.8 (bs, 1H), 8.58 (s, 1H), 8.42 (d, 1H), 8.24 (d, 1H), 8.09 (d, 1H), 7.52 (m, 3H), 7.45 (s, 1H), 7.35 (s, 1H), 7.09 (d, 1H), 6.93 (d, 1H), 6.29 (s, 1H), 4.16 (s, 2H), 3.90 (s, 3H), 2.43 (m, 10H), 2.18 (s, 3H), 1.95 (s, 2H).
Melting point: 112-114° C.
Yield: 73%

Example 117

Benzo[b]thiophene-3-sulfonic acid (3-chloro-4-{6-methoxy-7-[3-(4-methyl-piperazin-1-yl)-propoxy]-quinolin-4-yloxy}-phenyl)-amide

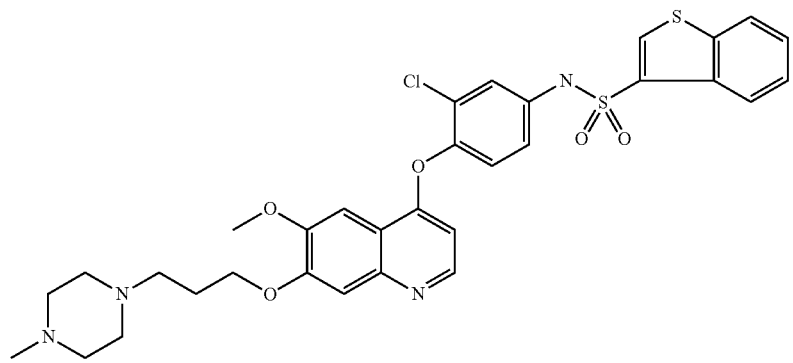 [SMILES: COc1cc2c(Oc3ccc(NS(=O)(=O)c4csc5ccccc45)cc3Cl)ccnc2cc1OCCCN1CCN(C)CC1]

C$_{32}$H$_{33}$ClN$_4$O$_5$S$_2$ Mw. 653.22
LC/MS purity: 99%, m/z 651[M−H]$^-$, 653 [M+H]$^+$ Rt. 3.36 min. (Method B)
$^1$H NMR (300 MHz, DMSO-d6): 11 (bs, 1H), 8.56 (s, 1H), 8.40 (t, 1H), 8.23 (d, 1H), 8.09 (d, 1H), 7.52 (m, 2H), 7.45 (s, 1H), 7.35 (s, 1H), 7.24 (m, 2H), 7.09 (d, 1H), 6.19 (s, 1H), 4.17 (s, 2H), 3.89 (s, 3H), 2.39 (bs, 10H), 2.19 (s, 3H), 1.95 (s, 2H).
Melting point: 98-101° C.
Yield: 75%

Example 118

N-(3-Chloro-4-{6-methoxy-7-[3-(4-methyl-piperazin-1-yl)-propoxy]-quinolin-4-yloxy}-phenyl)-2,6-difluoro-benzenesulfonamide

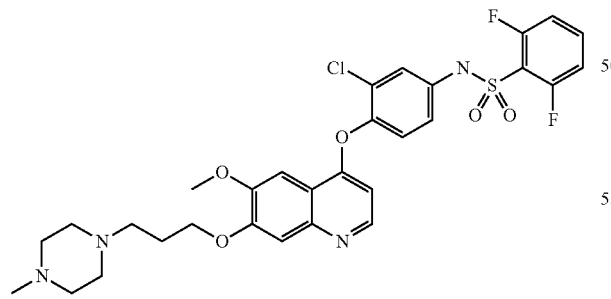

C$_{30}$H$_{31}$ClF$_2$N$_4$O$_5$S Mw. 633.11
LC/MS purity: 99%, m/z 631 [M−H]$^-$, 633 [M+H]$^+$ Rt. 2.84 min. (Method B)
$^1$H NMR (300 MHz, DMSO-d6): 10.8 (bs, 1H), 8.42 (s, 1H), 7.62 (s, 1H), 7.48 (s, 1H), 7.37 (s, 1H), 7.23 (m, 4H), 7.06 (d, 1H), 6.24 (s, 1H), 4.18 (s, 2H), 3.91 (s, 3H), 2.49 (s, 10H), 2.29 (s, 3H), 1.97 (s, 2H).
Melting point: 122-124° C.
Yield: 48%

Example 119

2,6-Dichloro-N-(3-chloro-4-{6-methoxy-7-[3-(4-methyl-piperazin-1-yl)-propoxy]-quinolin-4-yloxy}-phenyl)-benzenesulfonamide

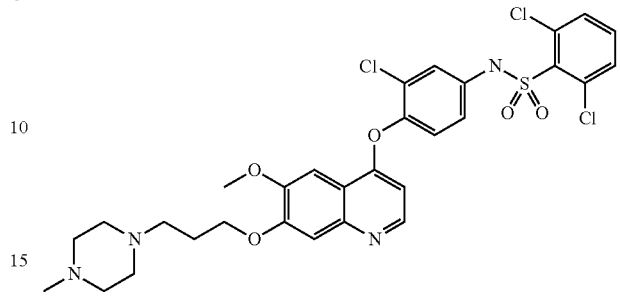

C$_{30}$H$_{31}$Cl$_3$N$_4$O$_5$S Mw. 666.02
LC/MS purity: 98%, m/z 665 [M−H]$^-$, 667 [M+H]$^+$ Rt. 3.12 min. (Method B)
$^1$H NMR (300 MHz, DMSO-d6): 11 (bs, 1H), 8.41 (s, 1H), 7.58 (s, 2H), 7.47 (s, 2H), 7.37 (s, 1H), 7.25 (s, 2H), 7.04 (s, 1H), 6.23 (s, 1H), 4.18 (s, 2H), 3.91 (s, 3H), 2.50 (s, 10H), 2.29 (s, 3H), 1.97 (s, 2H).
Melting point: 171-172° C.
Yield: 34%

Example 120

(3-{4-[2-Fluoro-4-(2-trifluoromethyl-benzenesulfonylamino)-phenoxy]-6-methoxy-quinolin-7-yloxy}-propyl)-carbamic acid tert-butyl ester

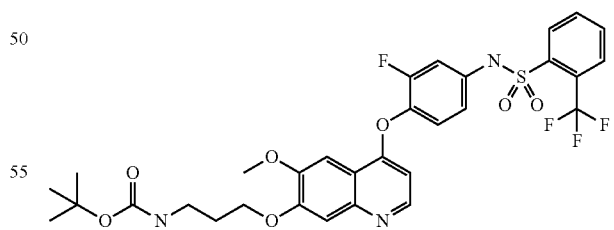

C$_{31}$H$_{31}$F$_4$N$_3$O$_7$S Mw. 665.66
LC/MS purity: 100%, m/z 664 [M−H]$^-$, 666 [M+H]$^+$ Rt. 3.66 min. (Method A)
$^1$H NMR (300 MHz, DMSO-d6): 11 (bs, 1H), 8.45 (s, 1H), 8.15 (d, 1H), 8.02 (d, 1H), 7.90 (bs, 2H), 7.47 (s, 1H), 7.37 (bs, 2H), 7.16 (d, 1H), 7.03 (d, 1H), 6.88 (bs, 1H), 6.36 (d, 1H), 4.16 (bs, 2H), 3.92 (s, 3H), 3.13 (bs, 2H), 1.93 (bs, 2H), 1.38 (s, 9H).
Melting point: 80-82° C.
Yield: 84%

Example 121

(3-{4-[4-(2,5-Difluoro-benzenesulfonylamino)-2-fluoro-phenoxy]-6-methoxy-quinolin-7-yloxy}-propyl)-carbamic acid tert-butyl ester

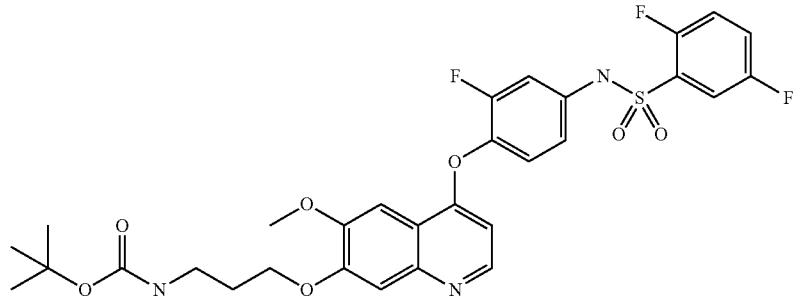 [SMILES: COc1cc2c(Oc3ccc(NS(=O)(=O)c4cc(F)ccc4F)cc3F)ccnc2cc1OCCCNC(=O)OC(C)(C)C]

C$_{30}$H$_{30}$F$_3$N$_3$O$_7$S Mw. 633.64

LC/MS purity: 99%, m/z 632 [M−H]$^−$, 634 [M+H]$^+$ Rt. 3.57 min. (Method A)

$^1$H NMR (300 MHz, DMSO-d6): 11 (bs, 1H), 8.45 (d, 1H), 7.60 (m, 3H), 7.48 (s, 1H), 7.37 (bs, 2H), 7.19 (d, 1H), 7.05 (d, 1H), 6.88 (bs, 1H), 6.35 (d, 1H), 4.16 (bs, 2H), 3.92 (s, 3H), 3.16 (bs, 2H), 1.93 (bs, 2H), 1.38 (s, 9H).

Melting point: 115-118° C.

Yield: 78%

Example 122

N-{4-[7-(3-Amino-propoxy)-6-methoxy-quinolin-4-yloxy]-3-fluoro-phenyl}-2,5-difluoro-benzenesulfonamide hydrochloride

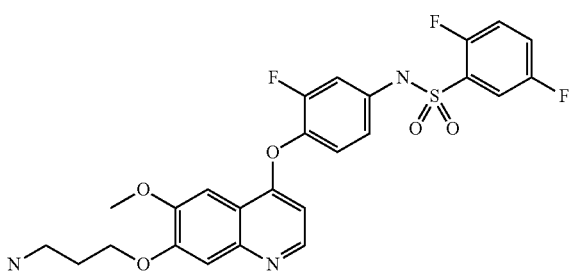 [SMILES: COc1cc2c(Oc3ccc(NS(=O)(=O)c4cc(F)ccc4F)cc3F)ccnc2cc1OCCCN]

C$_{25}$H$_{22}$F$_3$N$_3$O$_5$S.HCl Mw. 533.53

LC/MS purity: 99%, m/z 532 [M−H]$^−$, 534 [M+H]$^+$ Rt. 2.71 min. (Method B)

$^1$H NMR (300 MHz, DMSO-d6): 11.37 (s, 1H), 8.77 (bs, 1H), 8.09 (bs, 2H), 7.61 (m, 4H), 7.28 (d, 1H), 7.15 (d, 1H), 6.85 (bs, 1H), 4.33 (bs, 2H), 4.02 (s, 3H), 3.57 (s, 2H), 3.01 (bs, 2H), 2.19 (bs, 2H).

Melting point: 188-190° C.

Yield: 85%

Example 123

2,5-Difluoro-N-(3-{6-methoxy-7-[3-(4-methyl-piperazin-1-yl)-propoxy]-quinolin-4-yloxy}-phenyl)-benzenesulfonamide

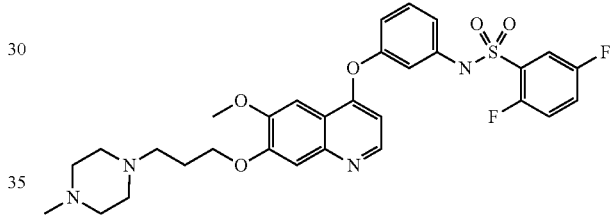

C$_{30}$H$_{32}$F$_2$N$_4$O$_5$S Mw. 598.67

LC/MS purity: 98%, m/z 597 [M−H]$^−$, 599 [M+H]$^+$ Rt. 2.38 min. (Method A)

LC/MS purity: 99%, m/z 631 [M−H]$^−$, 633 [M+H]$^+$ Rt. 2.84 min. (Method B)

$^1$H NMR (300 MHz, DMSO-d6): 11 (bs, 1H), 8.39 (d, 1H), 7.42 (bs, 2H), 7.35 (m, 3H), 7.17 (t, 1H), 6.82 (d, 1H), 6.77 (s, 1H), 6.57 (d, 1H), 6.29 (d, 1H), 4.18 (bs, 2H), 3.90 (s, 3H), 2.40 (s, 10H), 2.16 (s, 3H), 1.96 (s, 2H).

Melting point: 186-188° C.

Yield: 52%

Example 124

2,5-Dichloro-N-(3-chloro-4-{6-methoxy-7-[3-(4-methyl-piperazin-1-yl)-propoxy]-quinolin-4-yloxy}-phenyl)-benzenesulfonamide

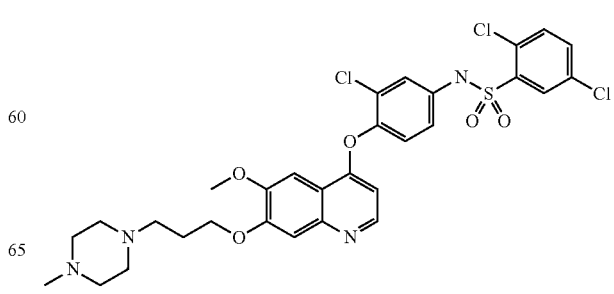

$C_{30}H_{31}Cl_3N_4O_5S$ Mw. 666.02

LC/MS purity: 99%, m/z 664 [M−H]⁻, 666 [M+H]⁺ Rt. 3.39 min. (Method B)

¹H NMR (300 MHz, DMSO-d6): 10.5 (bs, 1H), 8.42 (d, 1H), 7.97 (s, 1H), 7.62 (bs, 2H), 7.48 (s, 1H), 7.37 (s, 1H), 7.19 (m, 2H), 7.00 (d, 1H), 6.25 (d, 1H), 4.17 (t, 2H), 3.91 (s, 3H), 2.49 (s, 10H), 2.32 (s, 3H), 1.97 (s, 2H).

Melting point: 144-145° C.

Yield: 66%

Example 125

2,6-Difluoro-N-(3-{6-methoxy-7-[3-(4-methyl-piperazin-1-yl)-propoxy]-quinolin-4-yloxy}-phenyl)-benzenesulfonamide

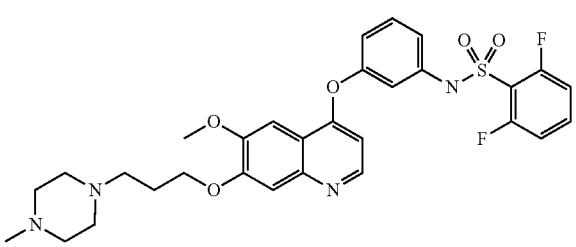 [SMILES: COc1cc2c(Oc3cccc(NS(=O)(=O)c4c(F)cccc4F)c3)ccnc2cc1OCCCN1CCN(C)CC1]

$C_{30}H_{32}F_2N_4O_5S$ Mw. 598.67

LC/MS purity: 98%, m/z 597 [M−H]⁻, 599 [M+H]⁺ Rt. 3.04 min. (Method B)

¹H NMR (300 MHz, DMSO-d6): 10.8 (bs, 1H), 8.43 (d, 1H), 7.64 (m, 1H), 7.40 (s, 1H), 7.37 (s, 1H), 7.31 (t, 1H), 7.18 (t, 2H), 6.97 (d, 1H), 6.88 (s, 1H), 6.80 (s, 1H), 6.20 (d, 1H), 4.18 (t, 2H), 3.89 (s, 3H), 2.46 (t, 2H), 2.41 (s, 8H), 2.20 (s, 3H), 1.96 (t, 2H).

Melting point: 171-172° C.

Yield: 58%

Example 126

N-(3-{6-Methoxy-7-[3-(4-methyl-piperazin-1-yl)-propoxy]-quinolin-4-yloxy}-phenyl)-2-trifluoromethoxy-benzenesulfonamide

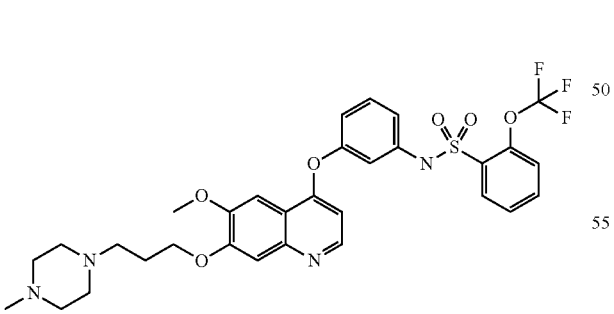

$C_{31}H_{33}F_3N_4O_6S$ Mw. 646.69

LC/MS purity: 99%, m/z 645 [M−H]⁻, 647 [M+H]⁺ Rt. 3.58 min. (Method B)

¹H NMR (300 MHz, DMSO-d6): 11 (bs, 1H), 8.43 (d, 1H), 7.88 (d, 1H), 7.72 (t, 1H), 7.38 (m, 5H), 6.95 (d, 1H), 6.70 (m, 2H), 6.26 (d, 1H), 4.18 (t, 2H), 3.88 (s, 3H), 2.44 (m, 10H), 2.17 (s, 3H), 1.96 (t, 2H).

Melting point: 164-166° C.

Yield: 60%

Example 127

2,5-Dichloro-N-(3-{6-methoxy-7-[3-(4-methyl-piperazin-1-yl)-propoxy]-quinolin-4-yloxy}-phenyl)-benzenesulfonamide

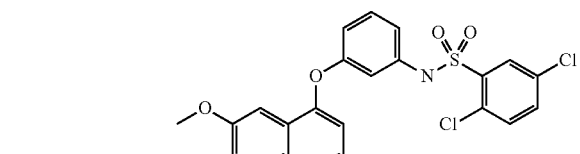

$C_{30}H_{32}Cl_2N_4O_5S$ Mw. 631.58

LC/MS purity: 99%, m/z 629 [M−H]⁻, 631 [M+H]⁺ Rt. 3.45 min. (Method B)

¹H NMR (300 MHz, DMSO-d6): 11.2 (bs, 1H), 8.43 (d, 1H), 7.90 (m, 1H), 7.65 (m, 2H), 7.40 (s, 1H), 7.37 (s, 1H), 7.31 (t, 1H), 6.96 (d, 1H), 6.80 (m, 2H), 6.24 (d, 1H), 4.18 (t, 2H), 3.89 (s, 3H), 2.47 (m, 10H), 2.24 (s, 3H), 1.98 (t, 2H).

Melting point: 111-113° C.

Yield: 55%

Example 128

2,6-Dichloro-N-(3-{6-methoxy-7-[3-(4-methyl-piperazin-1-yl)-propoxy]-quinolin-4-yloxy}-phenyl)-benzenesulfonamide

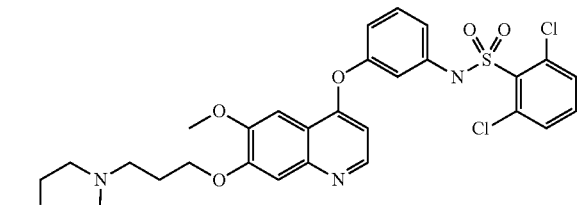

$C_{30}H_{32}CO_2N_4O_5S$ Mw. 631.58

LC/MS purity: 99%, m/z 629 [M−H]⁻, 631 [M+H]⁺ Rt. 3.35 min. (Method B)

¹H NMR (300 MHz, DMSO-d6): 10.2 (bs, 1H), 8.42 (d, 1H), 7.52 (m, 3H), 7.37 (s, 2H), 7.30 (t, 1H), 6.93 (d, 1H), 6.81 (s, 1H), 6.79 (d, 1H), 6.23 (d, 1H), 4.16 (t, 2H), 3.87 (s, 3H), 2.45 (m, 10H), 2.19 (s, 3H), 1.97 (m, 2H).

Melting point: 111-112° C.

Yield: 51%

Example 129

Thiophene-2-sulfonic acid (3-{6-methoxy-7-[3-(4-methyl-piperazin-1-yl)-propoxy]-quinolin-4-yloxy}-phenyl)-amide

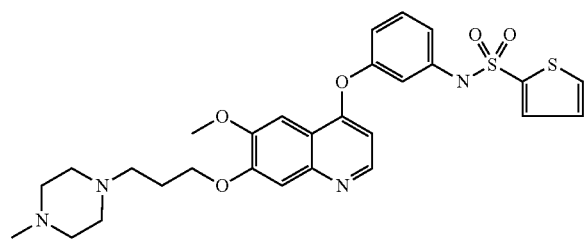 [SMILES: COc1cc2c(Oc3cccc(NS(=O)(=O)c4cccs4)c3)ccnc2cc1OCCCN1CCN(C)CC1]

$C_{28}H_{32}N_4O_5S_2$ Mw. 568.71

LC/MS purity: 97%, m/z 567 [M−H]⁻, 569 [M+H]⁺ Rt. 2.97 min. (Method A)

¹H NMR (300 MHz, DMSO-d6): 10.8 (bs, 1H), 8.47 (d, 1H), 7.88 (d, 1H), 7.41 (m, 4H), 7.10 (d, 1H), 6.98 (d, 1H), 6.90 (s, 2H), 6.32 (d, 1H), 4.18 (bs, 2H), 3.90 (s, 3H), 2.40 (m, 10H), 2.17 (s, 3H), 1.96 (bs, 2H).

Melting point: 188-189° C.

Yield: 31%

Example 130

5-Chloro-thiophene-2-sulfonic acid (3-{6-methoxy-7-[3-(4-methyl-piperazin-1-yl)-propoxy]-quinolin-4-yloxy}-phenyl)-amide

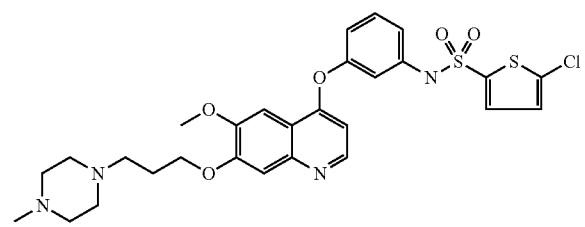 [SMILES: COc1cc2c(Oc3cccc(NS(=O)(=O)c4ccc(Cl)s4)c3)ccnc2cc1OCCCN1CCN(C)CC1]

$C_{28}H_{31}ClN_4O_5S_2$ Mw. 603.16

LC/MS purity: 99%, m/z 601 [M−H]⁻, 603 [M+H]⁺ Rt. 3.05 min. (Method B)

¹H NMR (300 MHz, DMSO-d6): 11 (bs, 1H), 8.47 (s, 1H), 7.36 (m, 4H), 7.14 (d, 1H), 7.00 (s, 1H), 6.86 (s, 2H), 6.36 (d, 1H), 4.18 (bs, 2H), 3.90 (s, 3H), 2.45 (m, 10H), 2.22 (s, 3H), 1.97 (bs, 2H).

Melting point: 162-163° C.

Yield: 52%

Example 131

5-Methyl-thiophene-2-sulfonic acid (3-{6-methoxy-7-[3-(4-methyl-piperazin-1-yl)-propoxy]-quinolin-4-yloxy}-phenyl)-amide

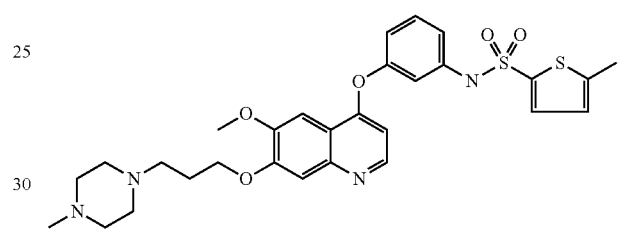

$C_{29}H_{34}N_4O_5S_2$ Mw. 582.74

LC/MS purity: 98%, m/z 581 [M−H]⁻, 583 [M+H]⁺ Rt. 3.21 min. (Method B)

¹H NMR (300 MHz, DMSO-d6): 10.5 (bs, 1H), 8.47 (d, 1H), 7.42 (s, 1H), 7.38 (s, 1H), 7.34 (t, 1H), 7.26 (d, 1H), 7.01 (d, 1H), 6.85 (m, 3H), 6.36 (d, 1H), 4.18 (t, 2H), 3.90 (s, 3H), 2.40 (m, 13H), 2.16 (s, 3H), 1.96 (m, 2H).

Melting point: 147-149° C.

Yield: 33%

Example 132

N-[5-(3-{6-Methoxy-7-[3-(4-methyl-piperazin-1-yl)-propoxy]-quinolin-4-yloxy}-phenylsulfamoyl)-4-methyl-thiazol-2-yl]-acetamide

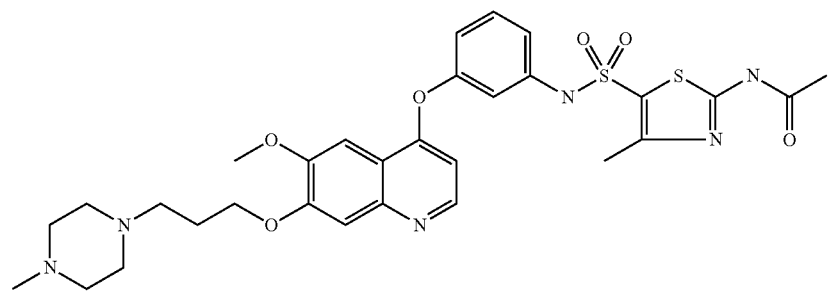 [SMILES: COc1cc2c(Oc3cccc(NS(=O)(=O)c4sc(NC(C)=O)nc4C)c3)ccnc2cc1OCCCN1CCN(C)CC1]

$C_{30}H_{36}N_6O_6S_2$ Mw. 640.78

LC/MS purity: 98%, m/z 639 [M−H]⁻, 641 [M+H]⁺ Rt. 2.68 min. (Method B)

¹H NMR (300 MHz, DMSO-d6): 12.2 (bs, 1H), 8.44 (d, 1H), 7.38 (m, 3H), 7.03 (d, 1H), 6.92 (s, 2H), 6.30 (d, 1H), 4.19 (bs, 2H), 3.90 (s, 3H), 2.40 (m, 16H), 2.16 (s, 3H), 1.96 (m, 2H).

Melting point: 148-150° C.

Yield: 36%

Example 133

Thiophene-3-sulfonic acid (3-{6-methoxy-7-[3-(4-methyl-piperazin-1-yl)-propoxy]-quinolin-4-yloxy}-phenyl)-amide

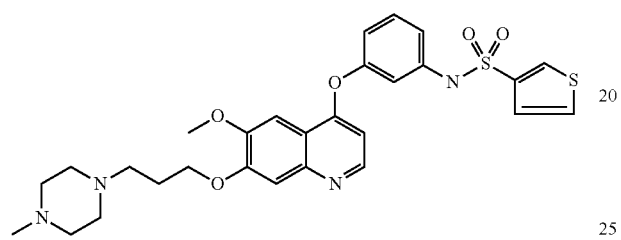

$C_{28}H_{32}N_4O_5S_2$ Mw. 568.71

LC/MS purity: 98%, m/z 567 [M−H]⁻, 569 [M+H]⁺ Rt. 3.11 min. (Method B)

¹H NMR (300 MHz, DMSO-d6): 10.5 (bs, 1H), 8.47 (d, 1H), 8.10 (s, 1H), 7.70 (d, 1H), 7.38 (m, 3H), 7.22 (d, 1H), 7.06 (d, 1H), 6.88 (s, 2H), 6.30 (d, 1H), 4.18 (t, 2H), 3.90 (s, 3H), 2.45 (m, 10H), 2.15 (s, 3H), 1.97 (m, 2H).

Melting point: 176-178° C.

Yield: 41%

Example 134

2,5-Dichloro-thiophene-3-sulfonic acid (3-{6-methoxy-7-[3-(4-methyl-piperazin-1-yl)-propoxy]-quinolin-4-yloxy}-phenyl)-amide

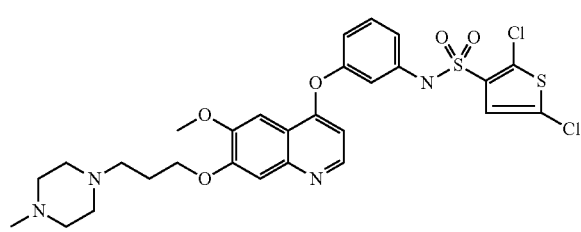 [SMILES: COc1cc2c(Oc3cccc(NS(=O)(=O)c4cc(Cl)sc4Cl)c3)ccnc2cc1OCCCN1CCN(C)CC1]

$C_{28}H_{30}Cl_2N_4O_5S_2$ Mw. 637.60

LC/MS purity: 98%, m/z 635 [M−H]⁻, 637 [M+H]⁺ Rt. 3.19 min. (Method B)

¹H NMR (300 MHz, DMSO-d6): 10.3 (bs, 1H), 8.46 (d, 1H), 7.43 (s, 1H), 7.37 (s, 1H), 7.31 (t, 1H), 7.17 (s, 1H), 6.94 (d, 1H), 6.80 (m, 2H), 6.36 (d, 1H), 4.18 (t, 2H), 3.91 (s, 3H), 2.44 (m, 10H), 2.22 (s, 3H), 1.97 (m, 2H).

Melting point: 177-178° C.

Yield: 35%

Example 135

3-(3-{6-Methoxy-7-[3-(4-methyl-piperazin-1-yl)-propoxy]-quinolin-4-yloxy}-phenylsulfamoyl)-thiophene-2-carboxylic acid methyl ester

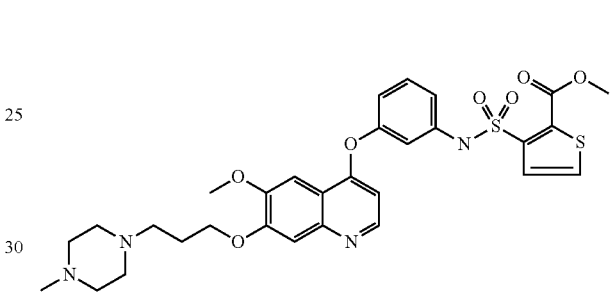

$C_{30}H_{34}N_4O_7S_2$ Mw. 626.75

LC/MS purity: 99%, m/z 625 [M−H]⁻, 627 [M+H]⁺ Rt. 2.37 min. (Method A)

¹H NMR (300 MHz, DMSO-d6): 10.4 (bs, 1H), 8.45 (s, 1H), 7.90 (s, 1H), 7.37 (m, 4H), 6.98 (d, 1H), 6.85 (bs, 2H), 6.00 (s, 1H), 4.18 (bs, 2H), 3.89 (s, 3H), 3.80 (s, 3H), 2.38 (m, 10H), 2.15 (s, 3H), 1.96 (bs, 2H).

Melting point: 84-86° C.

Yield: 33%

Example 136

Benzo[b]thiophene-3-sulfonic acid (3-{6-methoxy-7-[3-(4-methyl-piperazin-1-yl)-propoxy]-quinolin-4-yloxy}-phenyl)-amide

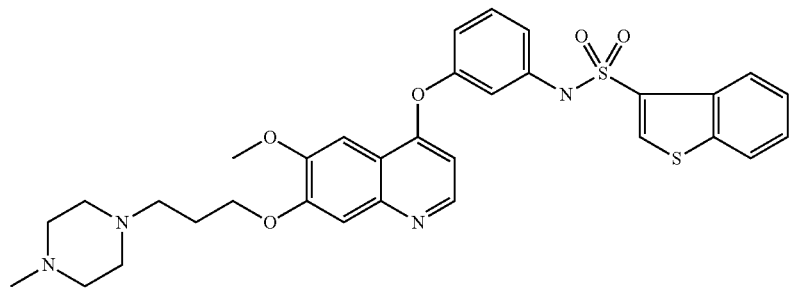 [SMILES: COc1cc2c(Oc3cccc(NS(=O)(=O)c4csc5ccccc45)c3)ccnc2cc1OCCCN1CCN(C)CC1]

$C_{32}H_{34}N_4O_5S_2$ Mw. 618.77

LC/MS purity: 98%, m/z 617 [M−H]⁻, 619 [M+H]⁺ Rt. 3.42 min. (Method B)

¹H NMR (300 MHz, DMSO-d6): 10.7 (bs, 1H), 8.46 (s, 1H), 8.39 (d, 1H), 8.20 (d, 1H), 8.09 (d, 1H), 7.48 (bs, 2H), 7.36 (s, 2H), 7.28 (t, 1H), 7.01 (d, 1H), 6.80 (m, 2H), 6.13 (d, 1H), 4.17 (bs, 2H), 3.87 (s, 3H), 2.40 (m, 10H), 2.16 (s, 3H), 1.95 (bs, 2H).

Melting point: 91-93° C.

Yield: 42%

Example 137

Furan-2-sulfonic acid (3-{6-methoxy-7-[3-(4-methyl-piperazin-1-yl)-propoxy]-quinolin-4-yloxy}-phenyl)-amide

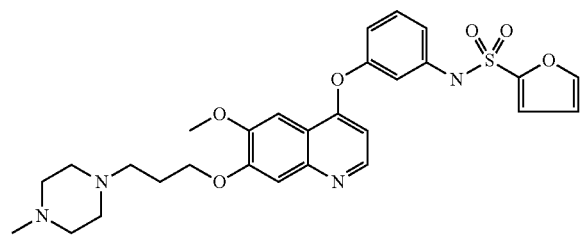 [SMILES: COc1cc2c(Oc3cccc(NS(=O)(=O)c4ccco4)c3)ccnc2cc1OCCCN1CCN(C)CC1]

$C_{28}H_{32}N_4O_6S$ Mw. 552.65

LC/MS purity: 98%, m/z 551 [M−H]⁻, 553 [M+H]⁺ Rt. 2.71 min. (Method B)

¹H NMR (300 MHz, DMSO-d6): 10.5 (bs, 1H), 8.49 (d, 1H), 7.90 (s, 1H), 7.40 (m, 3H), 7.04 (m, 2H), 6.90 (m, 2H), 6.62 (s, 1H), 6.39 (d, 1H), 4.19 (bs, 2H), 3.90 (s, 3H), 2.41 (m, 10H), 2.20 (s, 3H), 1.96 (bs, 2H).

Melting point: 176-177° C.

Yield: 39%

Example 138

3,5-Dimethyl-isoxazole-4-sulfonic acid (3-{6-methoxy-7-[3-(4-methyl-piperazin-1-yl)-propoxy]-quinolin-4-yloxy}-phenyl)-amide

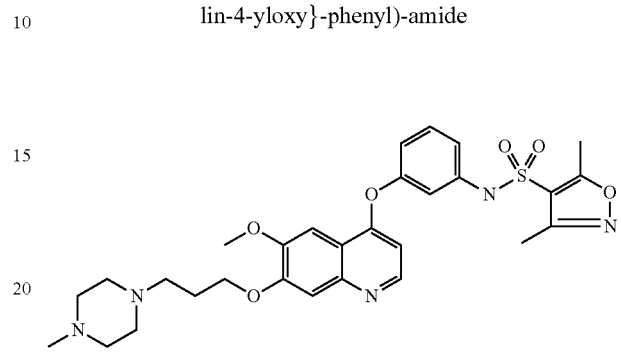

$C_{29}H_{35}N_5O_6S$ Mw. 581.69

LC/MS purity: 99%, m/z 580 [M−H]⁻, 582 [M+H]⁺ Rt. 2.82 min. (Method B)

¹H NMR (300 MHz, DMSO-d6): 11 (bs, 1H), 8.47 (d, 1H), 7.40 (m, 3H), 6.95 (m, 2H), 6.82 (s, 1H), 6.38 (d, 1H), 4.19 (bs, 2H), 3.90 (s, 3H), 2.40 (m, 10H), 2.22 (s, 6H), 2.19 (s, 3H), 1.96 (bs, 2H).

Melting point: 200-202° C.

Yield: 38%

Example 139

1-Methyl-1H-pyrazole-3-sulfonic acid (3-{6-methoxy-7-[3-(4-methyl-piperazin-1-yl)-propoxy]-quinolin-4-yloxy}-phenyl)-amide

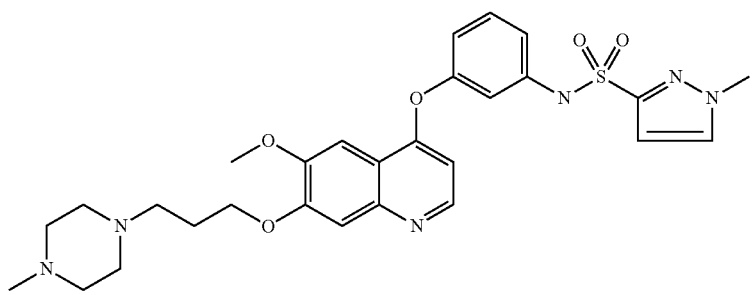

$C_{28}H_{34}N_6O_5S$ Mw. 566.68

LC/MS purity: 98%, m/z 565 [M−H]⁻, 567 [M+H]⁺ Rt. 2.72 min. (Method B)

¹H NMR (300 MHz, DMSO-d6): 10.5 (bs, 1H), 8.48 (d, 1H), 7.82 (s, 1H), 7.43 (s, 1H), 7.38 (s, 1H), 7.33 (t, 1H), 7.02 (s, 1H), 6.96 (s, 1H), 6.84 (d, 1H), 6.55 (d, 1H), 6.38 (d, 1H), 4.18 (bs, 2H), 3.91 (s, 3H), 3.84 (s, 3H), 2.35 (m, 10H), 2.15 (s, 3H), 1.96 (bs, 2H).

Melting point: 87-89° C.

Yield: 26%

Example 140

1-Ethyl-1H-pyrazole-4-sulfonic acid (3-{6-methoxy-7-[3-(4-methyl-piperazin-1-yl)-propoxy]-quinolin-4-yloxy}-phenyl)-amide

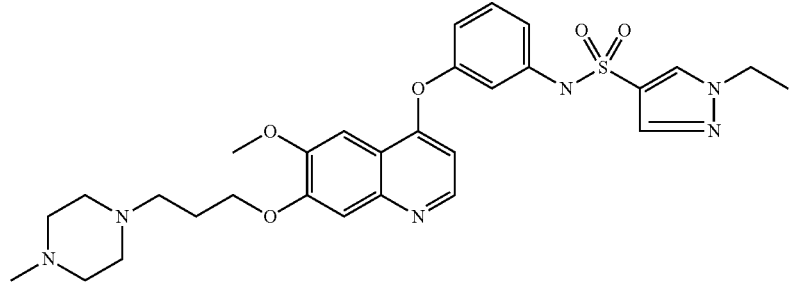 [SMILES: CCn1cc(S(=O)(=O)Nc2cccc(Oc3ccnc4cc(OCCCN5CCN(C)CC5)c(OC)cc34)c2)cn1]

$C_{29}H_{36}N_6O_5S$ Mw. 580.71
LC/MS purity: 98%, m/z 579 [M–H]⁻, 581 [M+H]⁺ Rt. 2.91 min. (Method B)
¹H NMR (300 MHz, DMSO-d6): 10.2 (bs, 1H), 8.46 (d, 1H), 8.25 (s, 1H), 7.66 (s, 1H), 7.44 (s, 1H), 7.38 (m, 2H), 7.06 (d, 1H), 6.91 (m, 2H), 6.38 (d, 1H), 4.15 (bs, 2H), 3.91 (s, 3H), 2.40 (m, 12H), 2.16 (s, 3H), 1.96 (bs, 2H), 1.32 (t, 3H).
Melting point: 87-90° C.
Yield: 38%

Example 141

2-Methyl-1H-imidazole-4-sulfonic acid (3-{6-methoxy-7-[3-(4-methyl-piperazin-1-yl)-propoxy]-quinolin-4-yloxy}-phenyl)-amide

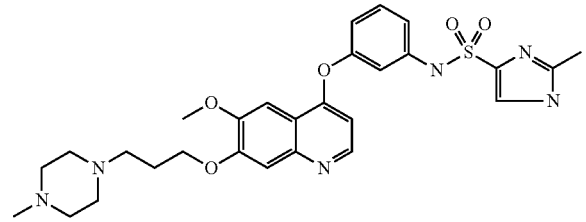

$C_{28}H_{34}N_6O_5S$ Mw. 566.68
LC/MS purity: 96%, m/z 565 [M–H]⁻, 567 [M+H]⁺ Rt. 2.70 min. (Method B)
¹H NMR (300 MHz, DMSO-d6): 12.4 (bs, 1H), 10.2 (bs, 1H), 8.47 (d, 1H), 7.59 (bs, 1H), 7.44 (s, 1H), 7.37 (s, 1H), 7.32 (t, 1H), 7.05 (d, 1H), 6.98 (s, 1H), 6.82 (bs, 1H), 6.35 (d, 1H), 4.18 (bs, 2H), 3.91 (s, 3H), 2.45 (m, 10H), 2.24 (s, 3H), 2.15 (s, 3H), 1.96 (bs, 2H).
Melting point: 118-120° C.
Yield: 33%

Example 142

Cyclopropanesulfonic acid (3-{6-methoxy-7-[3-(4-methyl-piperazin-1-yl)-propoxy]-quinolin-4-yloxy}-phenyl)-amide

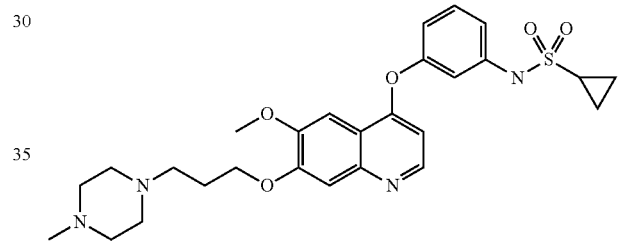

$C_{27}H_{34}N_4O_5S$ Mw. 526.65
LC/MS purity: 99%, m/z 525 [M–H]⁻, 527 [M+H]⁺ Rt. 2.99 min. (Method B)
¹H NMR (300 MHz, DMSO-d6): 10 (bs, 1H), 8.50 (d, 1H), 7.47 (s, 1H), 7.43 (d, 1H), 7.38 (s, 1H), 7.16 (d, 1H), 7.07 (s, 1H), 6.97 (d, 1H), 6.53 (d, 1H), 4.18 (t, 2H), 3.92 (s, 3H), 2.67 (m, 1H), 2.40 (m, 10H), 2.15 (s, 3H), 1.96 (m, 2H), 0.94 (m, 4H).
Melting point: 150-152° C.
Yield: 43%

Example 143

2-Phenyl-ethenesulfonic acid (3-{6-methoxy-7-[3-(4-methyl-piperazin-1-yl)-propoxy]-quinolin-4-yloxy}-phenyl)-amide

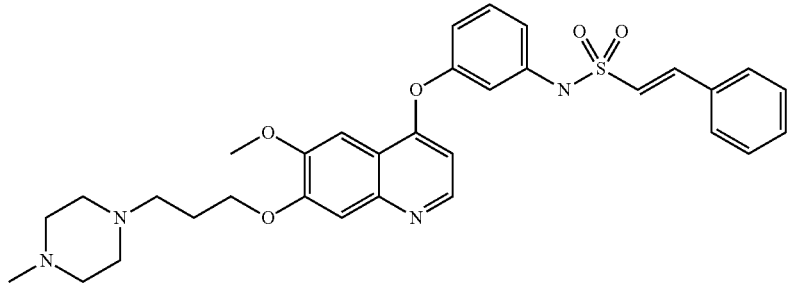 [SMILES: COc1cc2c(Oc3cccc(NS(=O)(=O)/C=C/c4ccccc4)c3)ccnc2cc1OCCCN1CCN(C)CC1]

$C_{32}H_{36}N_4O_5S$ Mw. 588.73

LC/MS purity: 99%, m/z 587 [M–H]⁻, 589 [M+H]⁺ Rt. 3.41 min. (Method B)

¹H NMR (300 MHz, DMSO-d6): 10.2 (bs, 1H), 8.27 (d, 1H), 7.66 (s, 1H), 7.64 (s, 1H), 7.40 (m, 7H), 7.26 (d, 1H), 7.12 (d, 1H), 7.00 (s, 1H), 6.89 (d, 1H), 6.39 (d, 1H), 4.17 (t, 2H), 3.89 (s, 3H), 2.40 (m, 10H), 2.15 (s, 3H), 1.95 (m, 2H).

Melting point: 85-87° C.

Yield: 39%

Example 144

Thiophene-2-sulfonic acid (3-fluoro-4-{6-methoxy-7-[3-(2-methyl-piperidin-1-yl)-propoxy]-quinolin-4-yloxy}-phenyl)-amide

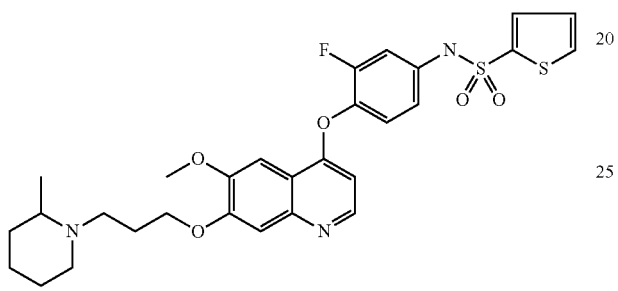

$C_{29}H_{32}FN_3O_5S_2$ Mw. 585.72

LC/MS purity: 98%, m/z 584 [M–H]⁻, 586 [M+H]⁺ Rt. 3.08 min. (Method B)

¹H NMR (300 MHz, DMSO-d6): 10.5 (bs, 1H), 8.45 (d, 1H), 7.78 (d, 1H), 7.49 (s, 2H), 7.38 (s, 1H), 7.24 (t, 1H), 7.07 (m, 2H), 6.92 (d, 1H), 6.36 (d, 1H), 4.18 (t, 2H), 3.92 (s, 3H), 2.94 (m, 2H), 2.50 (m, 2H), 2.30 (m, 1H), 1.96 (m, 2H), 1.50 (m, 4H), 1.27 (m, 2H), 1.05 (d, 3H).

Melting point: 117-119° C.

Yield: 47%

Example 145

5-Chloro-thiophene-2-sulfonic acid (3-fluoro-4-{6-methoxy-7-[3-(2-methyl-piperidin-1-yl)-propoxy]-quinolin-4-yloxy}-phenyl)-amide

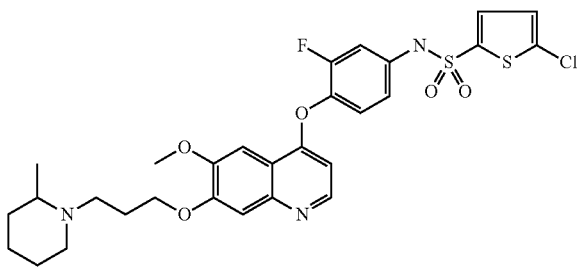 [SMILES: COc1cc2c(Oc3ccc(NS(=O)(=O)c4ccc(Cl)s4)cc3F)ccnc2cc1OCCCN1CCCCC1C]

$C_{29}H_{31}ClFN_3O_5S_2$ Mw. 620.16

LC/MS purity: 99%, 618 m/z [M–H]⁻, 620 [M+H]⁺ Rt. 3.24 min. (Method B)

¹H NMR (300 MHz, DMSO-d6): 10.2 (bs, 1H), 8.44 (d, 1H), 7.50 (s, 1H), 7.38 (s, 1H), 7.18 (d, 1H), 7.09 (t, 1H), 7.03 (d, 1H), 6.83 (d, 1H), 6.77 (d, 1H), 6.37 (d, 1H), 4.19 (t, 2H), 3.93 (s, 3H), 2.97 (m, 2H), 2.70 (m, 2H), 2.36 (m, 1H), 1.99 (m, 2H), 1.56 (m, 4H), 1.29 (m, 2H), 1.08 (d, 3H).

Melting point: 118-120° C.

Yield: 31%

Example 146

2,4-Dichloro-thiophene-3-sulfonic acid (3-fluoro-4-{6-methoxy-7-[3-(2-methyl-piperidin-1-yl)-propoxy]-quinolin-4-yloxy}-phenyl)-amide

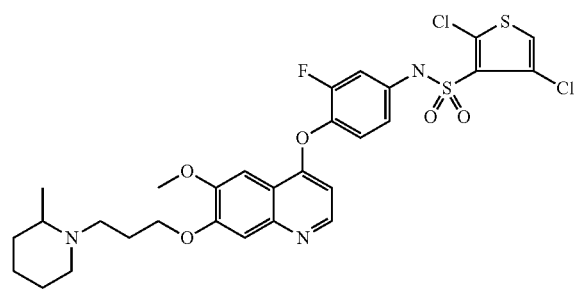 [SMILES: COc1cc2c(Oc3ccc(NS(=O)(=O)c4c(Cl)csc4Cl)cc3F)ccnc2cc1OCCCN1CCCCC1C]

$C_{29}H_{30}Cl_2FN_3O_5S_2$ Mw. 654.61

LC/MS purity: 99%, m/z 652 [M–H]⁻, 654 [M+H]⁺ Rt. 3.39 min. (Method B)

¹H NMR (300 MHz, DMSO-d6): 10 (bs, 1H), 8.45 (d, 1H), 7.51 (s, 1H), 7.39 (s, 1H), 7.15 (s, 1H), 7.10 (d, 1H), 6.93 (d, 1H), 6.78 (d, 1H), 6.39 (d, 1H), 4.21 (t, 2H), 3.93 (s, 3H), 3.04 (m, 2H), 2.71 (m, 2H), 2.49 (m, 1H), 2.03 (m, 2H), 1.60 (m, 4H), 1.34 (m, 2H), 1.11 (d, 3H).

Melting point: 131-132° C.

Yield: 39%

Example 147

Benzo[b]thiophene-3-sulfonic acid (3-fluoro-4-{6-methoxy-7-[3-(2-methyl-piperidin-1-yl)-propoxy]-quinolin-4-yloxy}-phenyl)-amide

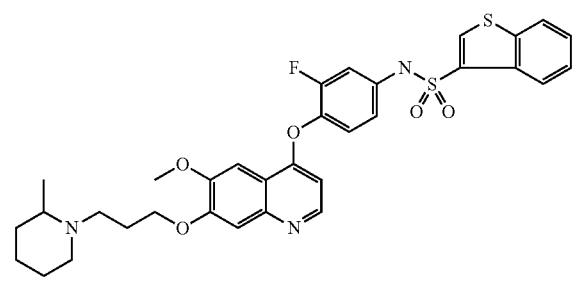

$C_{33}H_{34}FN_3O_5S_2$ Mw. 635.78

LC/MS purity: 99%, m/z 634 [M–H]⁻, 636 [M+H]⁺ Rt. 3.52 min. (Method B)

¹H NMR (300 MHz, DMSO-d6): 10.3 (bs, 1H), 8.53 (s, 1H), 8.41 (d, 1H), 8.25 (d, 1H), 8.09 (d, 1H), 7.50 (m, 2H), 7.45 (s, 1H), 7.37 (s, 1H), 7.20 (t, 1H), 7.07 (d, 1H), 6.90 (d, 1H), 6.29 (d, 1H), 4.17 (t, 2H), 3.90 (s, 3H), 2.90 (m, 2H), 2.49 (m, 2H), 2.28 (m, 1H), 1.94 (m, 2H), 1.53 (m, 4H), 1.26 (m, 2H), 1.04 (d, 3H).

Melting point: 120-122° C.

Yield: 45%

Example 148

Furan-2-sulfonic acid (3-fluoro-4-{6-methoxy-7-[3-(2-methyl-piperidin-1-yl)-propoxy]-quinolin-4-yloxy}-phenyl)-amide C$_{29}$H$_{32}$FN$_3$O$_6$S Mw. 569.65

LC/MS purity: 98%, m/z 568 [M−H]$^-$, 570 [M+H]$^+$ Rt. 2.88 min. (Method B)

$^1$H NMR (300 MHz, DMSO-d6): 10 (bs, 1H), 8.45 (d, 1H), 7.82 (s, 1H), 7.50 (s, 1H), 7.39 (s, 1H), 7.20 (t, 1H), 7.03 (d, 1H), 6.95 (s, 1H), 6.88 (d, 1H), 6.56 (s, 1H), 6.38 (d, 1H), 4.20 (t, 2H), 3.93 (s, 3H), 2.99 (m, 2H), 2.63 (m, 2H), 2.40 (m, 1H), 2.00 (m, 2H), 1.55 (m, 4H), 1.30 (m, 2H), 1.09 (d, 3H).

Melting point: 118-119° C.

Yield: 34%

Example 149

2-Methyl-1H-imidazole-4-sulfonic acid (3-fluoro-4-{6-methoxy-7-[3-(2-methyl-piperidin-1-yl)-propoxy]-quinolin-4-yloxy}-phenyl)-amide C$_{29}$H$_{34}$FN$_5$O$_5$S Mw. 583.68

LC/MS purity: 99%, m/z 582 [M−H]$^-$, 584 [M+H]$^+$ Rt. 2.81 min. (Method B)

$^1$H NMR (300 MHz, DMSO-d6): 12.5 (bs, 1H), 10.6 (bs, 1H), 8.44 (d, 1H), 7.75 (s, 1H), 7.48 (s, 1H), 7.37 (s, 1H), 7.32 (t, 1H), 7.19 (d, 1H), 7.04 (d, 1H), 6.37 (d, 1H), 4.17 (t, 2H), 3.92 (s, 3H), 2.84 (m, 2H), 2.42 (m, 1H), 2.28 (s, 3H), 2.11 (m, 2H), 1.91 (m, 2H), 1.50 (m, 4H), 1.20 (m, 2H), 0.99 (d, 3H).

Melting point: 219-220° C.

Yield: 26%

Example 150

1-Methyl-1H-pyrazole-3-sulfonic acid (3-fluoro-4-{6-methoxy-7-[3-(2-methyl-piperidin-1-yl)-propoxy]-quinolin-4-yloxy}-phenyl)-amide C$_{29}$H$_{34}$FN$_5$O$_5$S Mw. 583.68

LC/MS purity: 98%, m/z 582 [M−H]$^-$, 584 [M+H]$^+$ Rt. 2.56 min. (Method B)

$^1$H NMR (300 MHz, DMSO-d6): 10.7 (bs, 1H), 8.45 (d, 1H), 7.85 (s, 1H), 7.48 (s, 1H), 7.38 (s, 1H), 7.31 (t, 1H), 7.16 (d, 1H), 7.01 (d, 1H), 6.64 (d, 1H), 6.38 (d, 1H), 4.17 (t, 2H), 3.92 (s, 3H), 3.90 (s, 3H), 2.86 (m, 2H), 2.42 (m, 1H), 2.32 (s, 1H), 2.13 (m, 2H), 1.92 (m, 1H), 1.49 (m, 4H), 1.23 (m, 2H), 1.00 (d, 3H).

Melting point: 175-176° C.

Yield: 35%

Example 151

2,5-Difluoro-N-(3-fluoro-4-{6-methoxy-7-[3-(2-methyl-piperidin-1-yl)-propoxy]-quinolin-4-yloxy}-phenyl)-benzenesulfonamide C$_{31}$H$_{32}$F$_3$N$_3$O$_5$S Mw. 615.67

LC/MS purity: 97%, m/z 614 [M−H]$^-$, 616 [M+H]$^+$ Rt. 3.07 min. (Method B)

$^1$H NMR (300 MHz, DMSO-d6): 10 (bs, 1H), 8.44 (d, 1H), 7.56 (t, 1H), 7.49 (s, 1H), 7.38 (m, 3H), 7.14 (t, 1H), 6.97 (d, 1H), 6.82 (d, 1H), 6.36 (s, 1H), 4.20 (t, 2H), 3.92 (s, 3H), 3.05 (m, 2H), 2.72 (m, 2H), 2.50 (m, 1H), 2.03 (m, 2H), 1.60 (m, 4H), 1.34 (m, 2H), 1.11 (d, 3H).

Melting point: 120-122° C.

Yield: 33%

Example 152

2,6-Difluoro-N-(3-fluoro-4-{6-methoxy-7-[3-(2-methyl-piperidin-1-yl)-propoxy]-quinolin-4-yloxy}-phenyl)-benzenesulfonamide

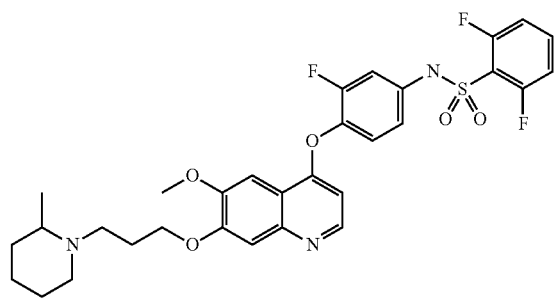 [SMILES: COc1cc2c(Oc3ccc(NS(=O)(=O)c4c(F)cccc4F)cc3F)ccnc2cc1OCCCN1CCCCC1C]

$C_{31}H_{32}F_3N_3O_5S$ Mw. 615.67

LC/MS purity: 100%, m/z 614 [M−H]−, 616 [M+H]+ Rt. 3.03 min. (Method B)

$^1$H NMR (300 MHz, DMSO-d6): 10 (bs, 1H), 8.43 (d, 1H), 7.49 (m, 2H), 7.38 (s, 1H), 7.11 (m, 3H), 6.97 (d, 1H), 6.79 (d, 1H), 6.34 (d, 1H), 4.19 (m, 2H), 3.92 (s, 3H), 2.97 (m, 2H), 2.61 (m, 2H), 2.46 (m, 1H), 2.00 (m, 2H), 1.58 (m, 4H), 1.30 (m, 2H), 1.08 (d, 3H).

Melting point: 132-134° C.

Yield: 26%

Example 153

N-(3-Fluoro-4-{6-methoxy-7-[3-(2-methyl-piperidin-1-yl)-propoxy]-quinolin-4-yloxy}-phenyl)-2-trifluoromethoxy-benzenesulfonamide

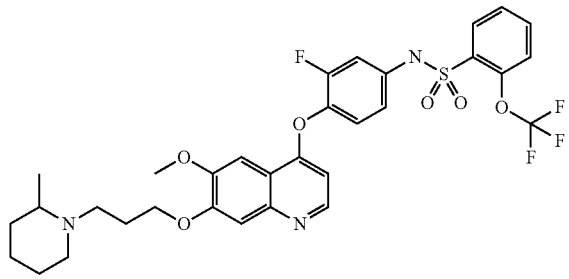 [SMILES: COc1cc2c(Oc3ccc(NS(=O)(=O)c4ccccc4OC(F)(F)F)cc3F)ccnc2cc1OCCCN1CCCCC1C]

$C_{32}H_{33}F_4N_3O_6S$ Mw. 663.69

LC/MS purity: 98%, m/z 662 [M−H]−, 664 [M+H]+ Rt. 3.52 min. (Method B)

$^1$H NMR (300 MHz, DMSO-d6): 10.5 (bs, 1H), 8.43 (d, 1H), 7.99 (d, 1H), 7.68 (t, 1H), 7.48 (m, 3H), 7.38 (s, 1H), 7.19 (t, 1H), 7.02 (d, 1H), 6.85 (d, 1H), 6.33 (d, 1H), 4.19 (t, 2H), 3.92 (s, 3H), 2.96 (m, 2H), 2.55 (m, 2H), 2.36 (m, 1H), 1.98 (t, 2H), 1.55 (m, 4H), 1.29 (m, 2H), 1.07 (d, 3H).

Melting point: 90-92° C.

Yield: 29%

Example 154

2,5-Dichloro-N-(3-fluoro-4-{6-methoxy-7-[3-(2-methyl-piperidin-1-yl)-propoxy]-quinolin-4-yloxy}-phenyl)-benzenesulfonamide

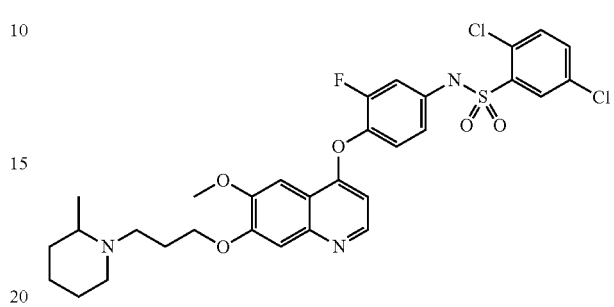

$C_{31}H_{32}Cl_2FN_3O_5S$ Mw. 648.58

LC/MS purity: 98%, m/z 646 [M−H]−, 648 [M+H]+ Rt. 3.39 min. (Method B)

$^1$H NMR (300 MHz, DMSO-d6): 11 (bs, 1H), 8.44 (d, 1H), 7.96 (s, 1H), 7.55 (s, 2H), 7.50 (s, 1H), 7.39 (s, 1H), 7.12 (t, 1H), 6.92 (d, 1H), 6.80 (d, 1H), 6.35 (d, 1H), 4.21 (t, 2H), 3.92 (s, 3H), 3.01 (m, 2H), 2.72 (m, 2H), 2.50 (m, 1H), 2.04 (m, 2H), 1.58 (m, 4H), 1.34 (m, 2H), 1.13 (d, 3H).

Melting point: 128-130° C.

Yield: 37%

Example 155

3-{3-Fluoro-4-[6-methoxy-7-(3-piperidin-1-yl-propoxy)-quinolin-4-yloxy]-phenylsulfamoyl}-thiophene-2-carboxylic acid methyl ester

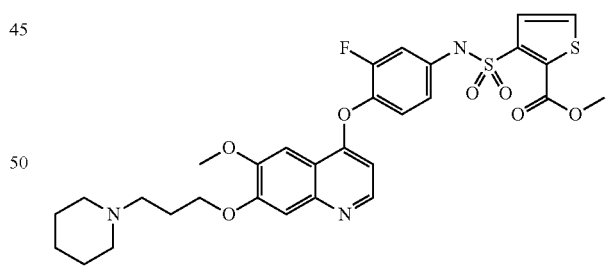

$C_{30}H_{32}FN_3O_7S_2$ Mw. 629.73

LC/MS purity: 97%, m/z 628 [M−H]−, 630 [M+H]+ Rt. 3.38 min. (Method B)

$^1$H NMR (300 MHz, DMSO-d6): 10.2 (bs, 1H), 8.45 (d, 1H), 7.94 (d, 1H), 7.47 (m, 2H), 7.38 (s, 1H), 7.30 (t, 1H), 7.11 (d, 1H), 6.97 (d, 1H), 6.36 (dd, 1H), 4.20 (t, 2H), 3.92 (s, 3H), 3.87 (s, 3H), 2.45 (m, 6H), 1.98 (m, 2H), 1.53 (bs, 4H), 1.40 (m, 2H)

Melting point: 138-139° C.

Yield: 26%

Example 156

3-(3-Fluoro-4-{6-methoxy-7-[3-(4-methyl-piperidin-1-yl)-propoxy]-quinolin-4-yloxy}-phenylsulfamoyl)-thiophene-2-carboxylic acid methyl ester

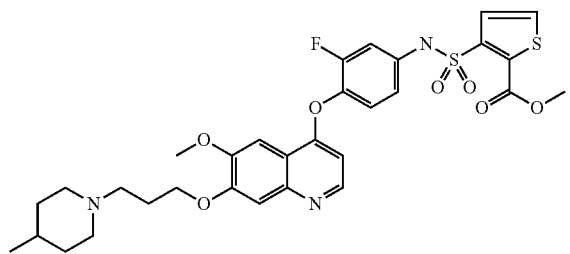

$C_{31}H_{34}FN_3O_7S_2$ Mw. 643.75

LC/MS purity: 99%, m/z 642 [M−H]⁻, 644 [M+H]⁺ Rt. 3.67 min. (Method B)

¹H NMR (300 MHz, DMSO-d6): 10.2 (bs, 1H), 8.45 (d, 1H), 7.95 (d, 1H), 7.47 (bs, 2H), 7.37 (s, 1H), 7.30 (t, 1H), 7.11 (d, 1H), 6.97 (d, 1H), 6.36 (d, 1H), 4.18 (t, 2H), 3.92 (s, 3H), 3.88 (s, 3H), 2.91 (m, 2H), 2.55 (m, 2H), 2.00 (m, 4H), 1.60 (m, 2H), 1.35 (bs, 1H), 1.16 (m, 2H), 0.89 (d, 3H)

Melting point: 139-141° C.

Yield: 29%

Example 157

3-{3-Fluoro-4-[6-methoxy-7-(3-morpholin-4-yl-propoxy)-quinolin-4-yloxy]-phenylsulfamoyl}-thiophene-2-carboxylic acid methyl ester

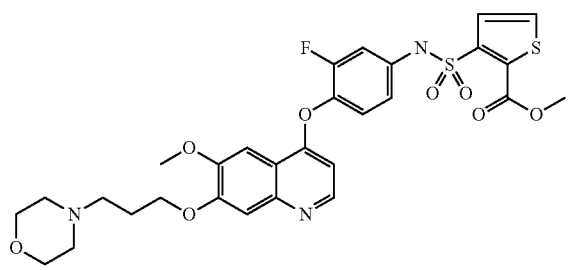 [SMILES: COC(=O)c1sccc1S(=O)(=O)Nc1ccc(Oc2ccnc3cc(OCCCN4CCOCC4)c(OC)cc23)c(F)c1]

$C_{29}H_{30}FN_3O_8S_2$ Mw. 631.70

LC/MS purity: 98%, m/z 630 [M−H]⁻, 632 [M+H]⁺ Rt. 3.33 min. (Method B)

¹H NMR (300 MHz, DMSO-d6): 10.5 (bs, 1H), 8.45 (d, 1H), 7.98 (d, 1H), 7.50 (d, 1H), 7.47 (s, 1H), 7.38 (s, 1H), 7.34 (t, 1H), 7.14 (d, 1H), 7.01 (d, 1H), 6.36 (d, 1H), 4.19 (t, 2H), 3.92 (s, 3H), 3.89 (s, 3H), 3.58 (m, 4H), 2.47 (m, 2H), 2.39 (m, 4H), 1.97 (m, 2H)

Melting point: 167-168° C.

Yield: 31%

Example 158

3-(3-Fluoro-4-{6-methoxy-7-[3-(4-methyl-piperazin-1-yl)-propoxy]-quinolin-4-yloxy}-phenylsulfamoyl)-thiophene-2-carboxylic acid methyl ester

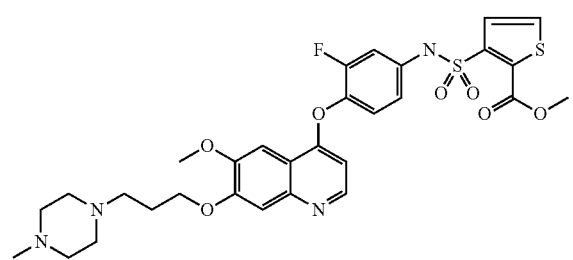

$C_{30}H_{33}FN_4O_7S_2$ Mw. 644.74

LC/MS purity: 98%, m/z 643 [M−H]⁻, 645 [M+H]⁺ Rt. 3.13 min. (Method B)

¹H NMR (300 MHz, DMSO-d6): 10.3 (bs, 1H), 8.45 (d, 1H), 7.95 (d, 1H), 7.47 (s, 2H), 7.37 (s, 1H), 7.31 (t, 1H), 7.12 (d, 1H), 6.98 (d, 1H), 6.36 (d, 1H), 4.17 (t, 2H), 3.92 (s, 3H), 3.88 (s, 3H), 2.42 (m, 10H), 2.18 (s, 3H), 1.95 (m, 2H)

Melting point: 146-148° C.

Yield: 41%

Example 159

1,3,5-Trimethyl-1H-pyrazole-4-sulfonic acid {3-fluoro-4-[6-methoxy-7-(3-piperidin-1-yl-propoxy)-quinolin-4-yloxy]-phenyl}-amide

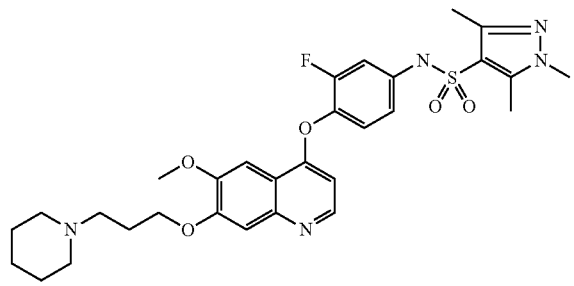 [SMILES: COc1cc2c(Oc3ccc(NS(=O)(=O)c4c(C)nn(C)c4C)cc3F)ccnc2cc1OCCCN1CCCCC1]

$C_{30}H_{36}FN_5O_5S$ Mw. 597.71

LC/MS purity: 97%, m/z 596 [M−H]⁻, 598 [M+H]⁺ Rt. 3.17 min. (Method B)

¹H NMR (300 MHz, DMSO-d6): 10.3 (bs, 1H), 8.46 (d, 1H), 7.48 (s, 1H), 7.37 (s, 1H), 7.36 (t, 1H), 7.08 (d, 1H), 6.97 (d, 1H), 6.37 (d, 1H), 4.18 (t, 2H), 3.92 (s, 3H), 3.66 (s, 3H), 2.85 (d, 2H), 2.43 (m, 2H), 2.38 (m, 5H), 2.21 (s, 3H), 1.95 (m, 2H), 1.50 (bs, 4H), 1.39 (m, 2H)

Melting point: 96-98° C.

Yield: 51%

Example 160

1,3,5-Trimethyl-1H-pyrazole-4-sulfonic acid (3-fluoro-4-{6-methoxy-7-[3-(4-methyl-piperidin-1-yl)-propoxy]-quinolin-4-yloxy}-phenyl)-amide

Example 161

1,3,5-Trimethyl-1H-pyrazole-4-sulfonic acid {3-fluoro-4-[6-methoxy-7-(3-morpholin-4-yl-propoxy)-quinolin-4-yloxy]-phenyl}-amide

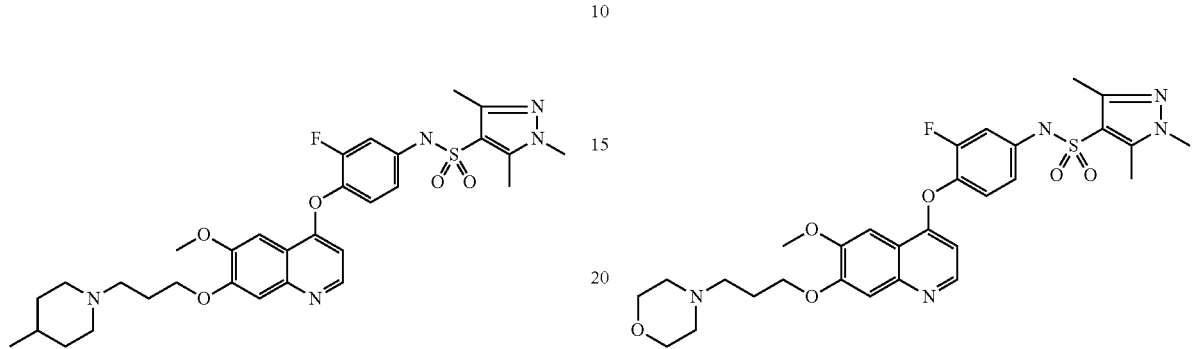

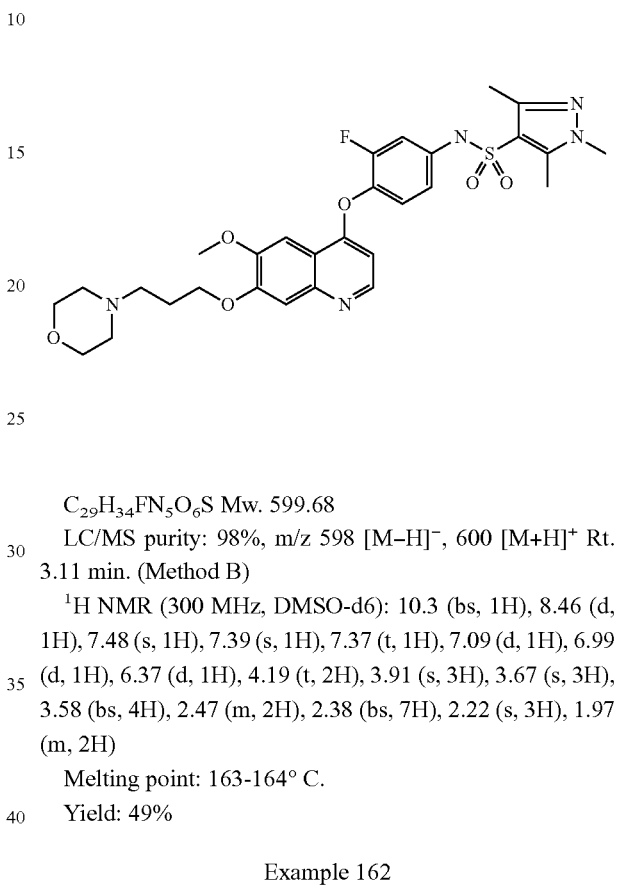

$C_{31}H_{38}FN_5O_5S$ Mw. 611.74

LC/MS purity: 98%, m/z 610 [M−H]⁻, 612 [M+H]⁺ Rt. 3.42 min. (Method B)

¹H NMR (300 MHz, DMSO-d6): 10.3 (bs, 1H), 8.46 (d, 1H), 7.48 (s, 1H), 7.38 (s, 1H), 7.37 (t, 1H), 7.09 (d, 1H), 6.99 (d, 1H), 6.37 (d, 1H), 4.17 (t, 2H), 3.92 (s, 3H), 3.67 (s, 3H), 2.85 (d, 2H), 2.45 (m, 2H), 2.38 (m, 3H), 2.22 (s, 3H), 1.96 (m, 4H), 1.58 (m, 2H), 1.32 (m, 1H), 1.23 (m, 2H), 0.88 (d, 3H)

Melting point: 88-90° C.

Yield: 36%

$C_{29}H_{34}FN_5O_6S$ Mw. 599.68

LC/MS purity: 98%, m/z 598 [M−H]⁻, 600 [M+H]⁺ Rt. 3.11 min. (Method B)

¹H NMR (300 MHz, DMSO-d6): 10.3 (bs, 1H), 8.46 (d, 1H), 7.48 (s, 1H), 7.39 (s, 1H), 7.37 (t, 1H), 7.09 (d, 1H), 6.99 (d, 1H), 6.37 (d, 1H), 4.19 (t, 2H), 3.91 (s, 3H), 3.67 (s, 3H), 3.58 (bs, 4H), 2.47 (m, 2H), 2.38 (bs, 7H), 2.22 (s, 3H), 1.97 (m, 2H)

Melting point: 163-164° C.

Yield: 49%

Example 162

1,3,5-Trimethyl-1H-pyrazole-4-sulfonic acid (3-fluoro-4-{6-methoxy-7-[3-(4-methyl-piperazin-1-yl)-propoxy]-quinolin-4-yloxy}-phenyl)-amide

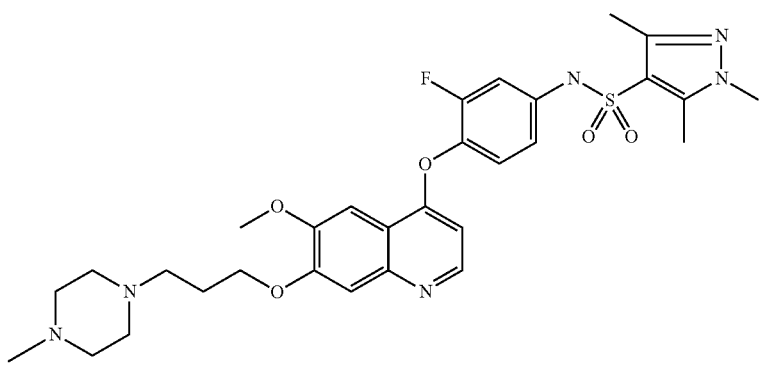

C$_{30}$H$_{37}$FN$_6$O$_5$S Mw. 612.72
LC/MS purity: 98%, m/z 611 [M−H]$^-$, 613 [M+H]$^+$ Rt. 2.89 min. (Method B)
$^1$H NMR (300 MHz, DMSO-d6): 10.3 (bs, 1H), 8.46 (d, 1H), 7.48 (s, 1H), 7.37 (s, 1H), 7.36 (t, 1H), 7.08 (d, 1H), 6.97 (d, 1H), 6.37 (d, 1H), 4.18 (t, 2H), 3.92 (s, 3H), 3.66 (s, 3H), 2.45 (m, 2H), 2.38 (bs, 7H), 2.33 (bs, 4H), 2.21 (s, 3H), 2.15 (s, 3H), 1.95 (m, 2H)
Melting point: 80-81° C.
Yield: 37%

Example 163

1-Methyl-1H-pyrazole-3-sulfonic acid {3-fluoro-4-[6-methoxy-7-(3-piperidin-1-yl-propoxy)-quinolin-4-yloxy]-phenyl}-amide

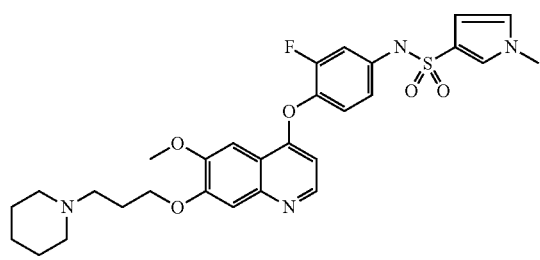 [SMILES: COc1cc2c(Oc3ccc(NS(=O)(=O)c4ccn(C)c4)cc3F)ccnc2cc1OCCCN1CCCCC1]

C$_{28}$H$_{32}$FN$_5$O$_5$S Mw. 569.66
LC/MS purity: 99%, m/z 568 [M−H]$^-$, 570 [M+H]$^+$ Rt. 2.56 min. (Method B)
$^1$H NMR (300 MHz, DMSO-d6): 10.6 (bs, 1H), 8.45 (d, 1H), 7.86 (d, 1H), 7.49 (s, 1H), 7.38 (s, 1H), 7.33 (t, 1H), 7.18 (d, 1H), 7.03 (d, 1H), 6.66 (d, 1H), 6.38 (d, 1H), 4.18 (t, 2H), 3.93 (s, 3H), 3.90 (s, 3H), 2.49 (m, 2H), 2.39 (bs, 4H), 1.96 (m, 2H), 1.50 (bs, 4H), 1.39 (m, 2H)
Melting point: 167-168° C.
Yield: 61%

Example 164

1-Methyl-1H-pyrazole-3-sulfonic acid (3-fluoro-4-{6-methoxy-7-[3-(4-methyl-piperidin-1-yl)-propoxy]-quinolin-4-yloxy}-phenyl)-amide C$_{29}$H$_{34}$FN$_5$O$_5$S Mw. 583.68
LC/MS purity: 98%, m/z 582 [M−H]$^-$, 584 [M+H]$^+$ Rt. 3.02 min. (Method B)
$^1$H NMR (300 MHz, DMSO-d6): 10.6 (bs, 1H), 8.45 (d, 1H), 7.85 (s, 1H), 7.48 (s, 1H), 7.37 (s, 1H), 7.32 (t, 1H), 7.16 (d, 1H), 7.02 (d, 1H), 6.65 (s, 1H), 6.38 (d, 1H), 4.17 (t, 2H), 3.93 (s, 3H), 3.90 (s, 3H), 2.86 (m, 2H), 2.47 (m, 2H), 1.93 (m, 4H), 1.58 (m, 2H), 1.32 (m, 1H), 1.12 (m, 2H), 0.88 (d, 3H)
Melting point: 165-166° C.
Yield: 40%

Example 165

1-Methyl-1H-pyrazole-3-sulfonic acid {3-fluoro-4-[6-methoxy-7-(3-morpholin-4-yl-propoxy)-quinolin-4-yloxy]-phenyl}-amide

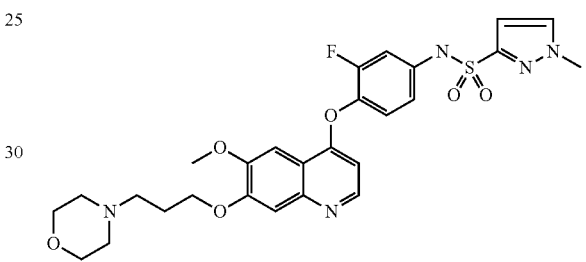

C$_{27}$H$_{30}$FN$_5$O$_6$S Mw. 571.63
LC/MS purity: 98%, m/z 570 [M−H]$^-$, 572 [M+H]$^+$ Rt. 2.74 min. (Method B)
$^1$H NMR (300 MHz, DMSO-d6): 10.8 (bs, 1H), 8.45 (d, 1H), 7.86 (d, 1H), 7.49 (s, 1H), 7.39 (s, 1H), 7.33 (t, 1H), 7.18 (dd, 1H), 7.04 (d, 1H), 6.66 (d, 1H), 6.38 (d, 1H), 4.17 (t, 2H), 3.93 (s, 3H), 3.90 (s, 3H), 3.58 (m, 4H), 2.47 (m, 2H), 2.39 (m, 4H), 1.97 (m, 2H)
Melting point: 198-199° C.
Yield: 53%

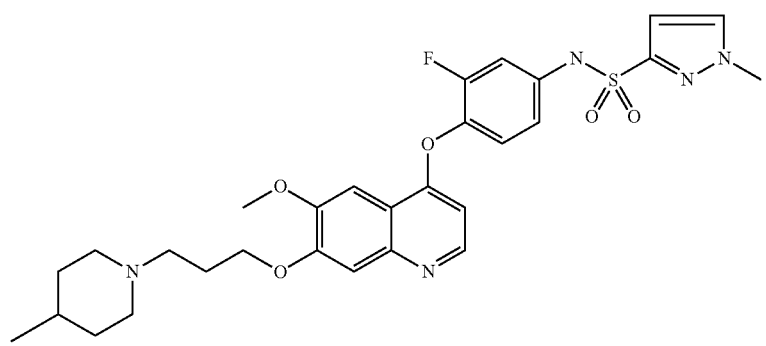

Example 166

1-Methyl-1H-pyrazole-3-sulfonic acid (3-fluoro-4-{6-methoxy-7-[3-(4-methyl-piperazin-1-yl)-propoxy]-quinolin-4-yloxy}-phenyl)-amide

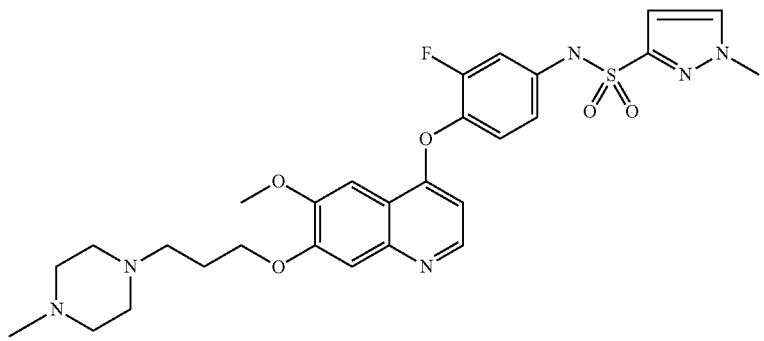

$C_{28}H_{33}FN_6O_5S$ Mw. 584.67
LC/MS purity: 97%, 584 m/z [M−H]⁻, 586 [M+H]⁺ Rt. 2.51 min. (Method B)
¹H NMR (300 MHz, DMSO-d6): 10.4 (bs, 1H), 8.45 (d, 1H), 7.86 (d, 1H), 7.48 (s, 1H), 7.37 (s, 1H), 7.32 (t, 1H), 7.17 (dd, 1H), 7.03 (d, 1H), 6.66 (d, 1H), 6.38 (d, 1H), 4.18 (t, 2H), 3.93 (s, 3H), 3.90 (s, 3H), 2.46 (m, 2H), 2.38 (m, 8H), 2.15 (s, 3H), 1.95 (m, 2H)
Melting point: 157-159° C.
Yield: 74%

Example 167

2-Methyl-3H-imidazole-4-sulfonic acid {3-fluoro-4-[6-methoxy-7-(3-piperidin-1-yl-propoxy)-quinolin-4-yloxy]-phenyl}-amide

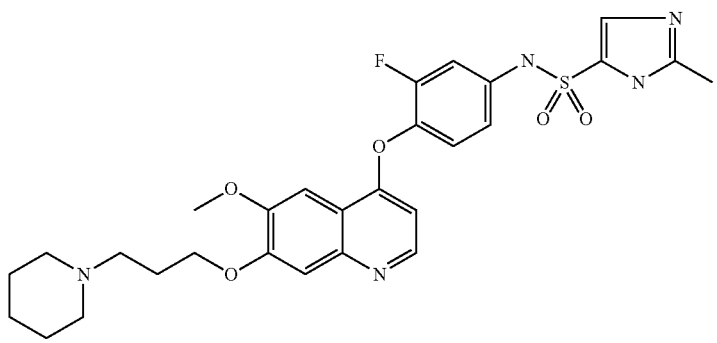 [SMILES: COc1cc2c(Oc3ccc(NS(=O)(=O)c4cnc(C)[nH]4)cc3F)ccnc2cc1OCCCN1CCCCC1]

$C_{28}H_{32}FN_5O_5S$ Mw. 569.66
LC/MS purity: 96%, m/z 568 [M−H]⁻, 570 [M+H]⁺ Rt. 2.79 min. (Method B)
¹H NMR (300 MHz, DMSO-d6): 12.3 (bs, 1H), 10.6 (bs, 1H), 8.44 (d, 1H), 7.72 (bs, 1H), 7.48 (s, 1H), 7.37 (s, 1H), 7.30 (t, 1H), 7.18 (d, 1H), 7.02 (d, 1H), 6.37 (d, 1H), 4.17 (t, 2H), 3.92 (s, 3H), 2.42 (m, 2H), 2.40 (bs, 4H), 2.28 (s, 3H), 1.94 (m, 2H), 1.50 (bs, 4H), 1.39 (m, 2H)
Melting point: 160-163° C.
Yield: 26%

Example 168

2-Methyl-3H-imidazole-4-sulfonic acid (3-fluoro-4-{6-methoxy-7-[3-(4-methyl-piperidin-1-yl)-propoxy]-quinolin-4-yloxy}-phenyl)-amide

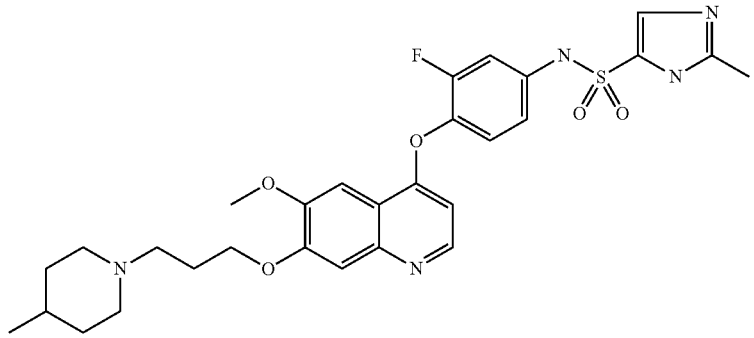

$C_{29}H_{34}FN_5O_5S$ Mw. 583.68

LC/MS purity: 98%, m/z 582 [M−H]⁻, 584 [M+H]⁺ Rt. 3.02 min. (Method B)

¹H NMR (300 MHz, DMSO-d6): 12.4 (bs, 1H), 10.7 (bs, 1H), 8.44 (d, 1H), 7.72 (bs, 1H), 7.48 (s, 1H), 7.37 (s, 1H), 7.30 (t, 1H), 7.19 (d, 1H), 7.03 (d, 1H), 6.37 (d, 1H), 4.17 (t, 2H), 3.92 (s, 3H), 2.84 (m, 2H), 2.44 (m, 2H), 2.38 (s, 3H), 1.95 (m, 2H), 1.88 (m, 2H), 1.57 (m, 2H), 1.33 (m, 1H), 1.15 (m, 2H), 0.88 (d, 3H)

Melting point: 225-226° C.

Yield: 30%

Example 169

2-Methyl-3H-imidazole-4-sulfonic acid {3-fluoro-4-[6-methoxy-7-(3-morpholin-4-yl-propoxy)-quinolin-4-yloxy]-phenyl}-amide

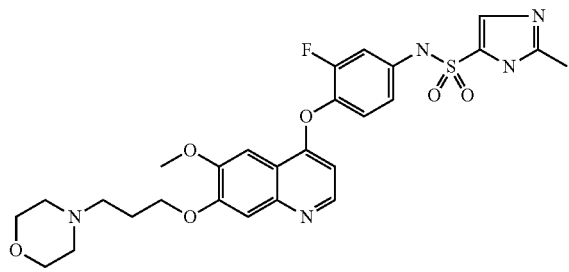 [SMILES: COc1cc2c(Oc3ccc(NS(=O)(=O)c4cnc(C)[nH]4)cc3F)ccnc2cc1OCCCN1CCOCC1]

LC/MS purity: 99%, m/z 570 [M−H]⁻, 572 [M+H]⁺ Rt. 2.73 min. (Method B)

¹H NMR (300 MHz, DMSO-d6): 12.4 (bs, 1H), 10.6 (bs, 1H), 8.45 (d, 1H), 7.72 (bs, 1H), 7.49 (s, 1H), 7.39 (s, 1H), 7.32 (t, 1H), 7.21 (d, 1H), 7.05 (d, 1H), 6.37 (d, 1H), 4.19 (t, 2H), 3.93 (s, 3H), 3.58 (m, 4H), 2.47 (m, 2H), 2.39 (s, 4H), 2.28 (s, 3H), 1.97 (t, 2H)

Yield: 38%

Example 170

2-Methyl-3H-imidazole-4-sulfonic acid (3-fluoro-4-{6-methoxy-7-[3-(4-methyl-piperazin-1-yl)-propoxy]-quinolin-4-yloxy}-phenyl)-amide $C_{28}H_{33}FN_6O_5S$ Mw. 584.67

LC/MS purity: 99%, m/z 583 [M−H]⁻, 585 [M+H]⁺ Rt. 2.52 min. (Method B)

¹H NMR (300 MHz, DMSO-d6): 12.4 (bs, 1H), 10.6 (bs, 1H), 8.44 (d, 1H), 7.73 (bs, 1H), 7.48 (s, 1H), 7.37 (s, 1H), 7.31 (t, 1H), 7.18 (d, 1H), 7.03 (d, 1H), 6.37 (d, 1H), 4.17 (t, 2H), 3.92 (s, 3H), 2.45 (m, 2H), 2.39 (bs, 4H), 2.32 (bs, 4H), 2.28 (s, 3H), 2.14 (s, 3H), 1.85 (m, 2H)

Melting point: 215-217° C.

Yield: 32%

Example 171

2,5-Difluoro-N-(4-{6-methoxy-7-[3-(4-methyl-piperidin-1-yl)-propoxy]-quinolin-4-yloxy}-3-methyl-phenyl)-benzenesulfonamide $C_{32}H_{35}F_2N_3O_5S$ Mw. 611.71

LC/MS purity: 97%, m/z 610 [M−H]⁻, 612 [M+H]⁺ Rt. 3.76 min. (Method B)

¹H NMR (300 MHz, DMSO-d6): 10.7 (bs, 1H), 8.40 (d, 1H), 7.55 (m, 3H), 7.51 (s, 1H), 7.36 (m, 1H), 7.05 (m, 3H), 6.17 (d, 1H), 4.17 (t, 2H), 3.92 (s, 3H), 2.89 (m, 2H), 2.01 (s, 3H), 1.98 (m, 4H), 1.59 (m, 2H), 1.30 (m, 1H), 1.17 (m, 3H), 1.03 (m, 1H), 0.88 (d, 3H)

Melting point: 222-223° C.

Yield: 55%

Example 172

2,6-Difluoro-N-(4-{6-methoxy-7-[3-(4-methyl-piperidin-1-yl)-propoxy]-quinolin-4-yloxy}-3-methyl-phenyl)-benzenesulfonamide

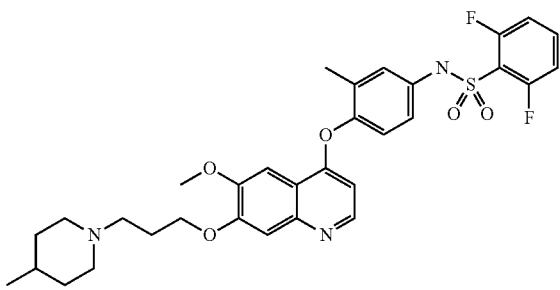 [SMILES: COc1cc2c(Oc3ccc(NS(=O)(=O)c4c(F)cccc4F)cc3C)ccnc2cc1OCCCN1CCC(C)CC1]

$C_{32}H_{35}F_2N_3O_5S$ Mw. 611.71

LC/MS purity: 98%, m/z 610 [M−H]⁻, 612 [M+H]⁺ Rt. 3.64 min. (Method B)

¹H NMR (300 MHz, DMSO-d6): 10.8 (bs, 1H), 8.40 (d, 1H), 7.67 (m, 1H), 7.51 (s, 1H), 7.36 (m, 1H), 7.25 (t, 2H), 7.05 (m, 3H), 6.16 (d, 1H), 4.17 (t, 2H), 3.92 (s, 3H), 2.88 (m, 2H), 2.49 (m, 2H), 1.97 (m, 7H), 1.58 (m, 2H), 1.33 (m, 1H), 1.16 (m, 2H), 0.88 (d, 3H)

Melting point: 191-193° C.

Yield: 44%

Example 173

2,6-Difluoro-N-(3-methoxy-4-{6-methoxy-7-[3-(4-methyl-piperidin-1-yl)-propoxy]-quinolin-4-yloxy}-phenyl)-benzenesulfonamide

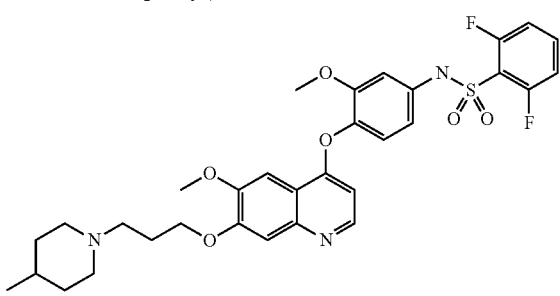

$C_{33}H_{35}F_3N_3O_6S$ Mw. 627.71

LC/MS purity: 99%, m/z 628 [M−H]⁻, 626 [M+H]⁺ Rt. 3.36 min. (Method B)

¹H NMR (300 MHz, DMSO-d6): 11 (bs, 1H), 8.37 (d, 1H), 7.62 (m, 1H), 7.46 (s, 1H), 7.33 (s, 1H), 7.20 (t, 2H), 7.04 (d, 1H), 6.92 (s, 1H), 6.68 (d, 1H), 6.15 (d, 1H), 4.17 (t, 2H), 3.91 (s, 3H), 3.60 (s, 3H), 3.32 (m, 1H), 2.83 (m, 2H), 2.46 (m, 2H), 1.94 (m, 3H), 1.62 (m, 4H), 1.45 (m, 1H), 0.84 (d, 3H)

Melting point: 98-101° C.

Yield: 47%

Example 174

N-(4-{6-Methoxy-7-[3-(4-methyl-piperidin-1-yl)-propoxy]-quinolin-4-yloxy}-3-methyl-phenyl)-2-trifluoromethoxy-benzenesulfonamide

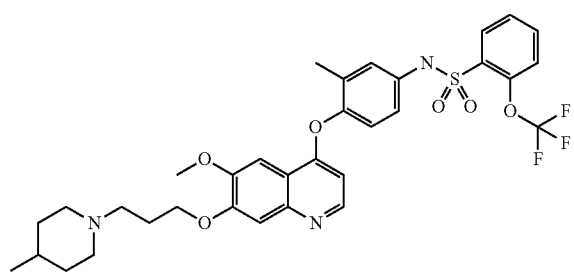 [SMILES: COc1cc2c(Oc3ccc(NS(=O)(=O)c4ccccc4OC(F)(F)F)cc3C)ccnc2cc1OCCCN1CCC(C)CC1]

$C_{33}H_{36}F_3N_3O_6S$ Mw. 659.73

LC/MS purity: 98%, m/z 658 [M−H]⁻, 660 [M+H]⁺ Rt. 4.18 min. (Method B)

¹H NMR (300 MHz, DMSO-d6): 10.6 (bs, 1H), 8.40 (d, 1H), 7.98 (dd, 1H), 7.76 (m, 1H), 7.54 (m, 2H), 7.50 (s, 1H), 7.36 (s, 1H), 7.09 (d, 1H), 7.00 (m, 2H), 6.15 (d, 1H), 4.17 (t, 2H), 3.91 (s, 3H), 2.86 (m, 2H), 2.46 (m, 2H), 2.00 (m, 3H), 1.93 (m, 4H), 1.58 (m, 2H), 1.33 (m, 1H), 1.16 (m, 2H), 0.88 (d, 3H)

Melting point: 168-169° C.

Yield: 51%

Example 175

2,5-Dichloro-N-(4-{6-methoxy-7-[3-(4-methyl-piperidin-1-yl)-propoxy]-quinolin-4-yloxy}-3-methyl-phenyl)-benzenesulfonamide

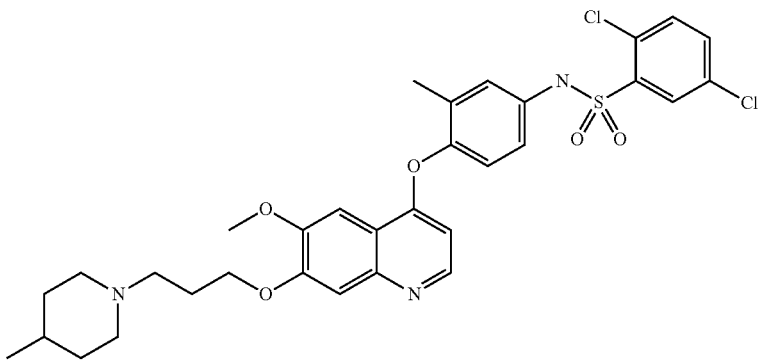 [SMILES: COc1cc2c(Oc3ccc(NS(=O)(=O)c4cc(Cl)ccc4Cl)cc3C)ccnc2cc1OCCCN1CCC(C)CC1]

$C_{32}H_{35}Cl_2N_3O_5S$ Mw. 644.62

LC/MS purity: 100%, m/z 642 [M−H]⁻, 644 [M+H]⁺ Rt. 3.33 min. (Method B)

¹H NMR (300 MHz, DMSO-d6): 10.6 (bs, 1H), 8.40 (d, 1H), 7.97 (d, 1H), 7.69 (m, 2H), 7.50 (s, 1H), 7.36 (s, 1H), 7.07 (d, 1H), 7.01 (m, 2H), 6.16 (d, 1H), 4.17 (t, 2H), 3.91 (s, 3H), 2.91 (m, 2H), 2.51 (m, 2H), 2.01 (m, 7H), 1.60 (m, 2H), 1.35 (m, 1H), 1.15 (m, 2H), 0.88 (d, 3H)

Melting point: 187-188° C.

Yield: 48%

Example 176

2,6-Dichloro-N-(4-{6-methoxy-7-[3-(4-methyl-piperidin-1-yl)-propoxy]-quinolin-4-yloxy}-3-methyl-phenyl)-benzenesulfonamide

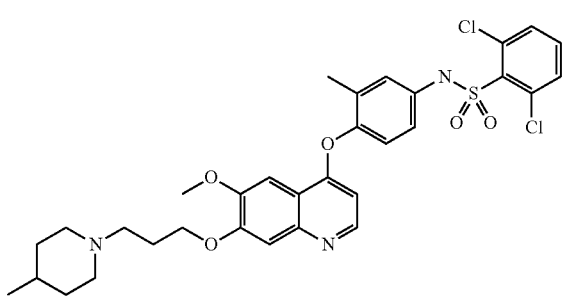

$C_{32}H_{35}Cl_2N_3O_5S$ Mw. 644.62

LC/MS purity: 95%, m/z 642 [M−H]⁻, 644 [M+H]⁺ Rt. 4.00 min. (Method B)

¹H NMR (300 MHz, DMSO-d6): 10.7 (bs, 1H), 8.39 (d, 1H), 7.62 (m, 2H), 7.54 (d, 1H), 7.49 (s, 1H), 7.35 (s, 1H), 7.11 (s, 1H), 7.03 (m, 2H), 6.14 (d, 1H), 4.17 (t, 2H), 3.91 (s, 3H), 2.88 (m, 2H), 2.50 (m, 2H), 1.99 (s, 3H), 1.96 (m, 4H), 1.58 (m, 2H), 1.34 (m, 1H), 1.16 (m, 2H), 0.88 (d, 3H)

Melting point: 209-210° C.

Yield: 35%

Example 177

N-{4-[7-(3-Dimethylamino-propoxy)-6-methoxy-quinolin-4-yloxy]-3-fluoro-phenyl}-2,5-difluoro-benzenesulfonamide

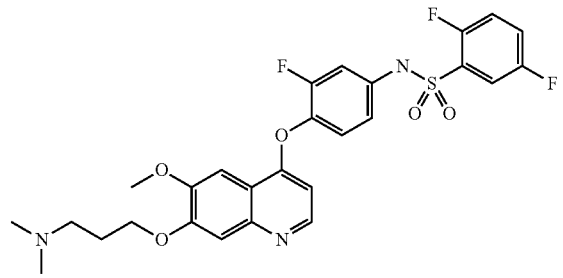 [SMILES: COc1cc2c(Oc3ccc(NS(=O)(=O)c4cc(F)ccc4F)cc3F)ccnc2cc1OCCCN(C)C]

$C_{27}H_{26}F_3N_3O_5S$ Mw. 561.58

LC/MS purity: 99%, m/z 560 [M−H]⁻, 562 [M+H]⁺ Rt. 2.87 min. (Method B)

¹H NMR (300 MHz, DMSO-d6): 11 (bs, 1H), 8.44 (d, 1H), 7.57 (m, 1H), 7.49 (s, 1H), 7.42 (s, 2H), 7.38 (s, 1H), 7.17 (s, 1H), 7.00 (d, 1H), 6.85 (d, 1H), 6.36 (d, 1H), 4.20 (t, 2H), 3.93 (s, 3H), 2.69 (t, 2H), 2.40 (s, 6H), 2.03 (m, 2H)

Melting point: 108-110° C.

Yield: 64%

Example 178

N-{4-[7-(3-Dimethylamino-propoxy)-6-methoxy-quinolin-4-yloxy]-3-fluoro-phenyl}-2,6-difluoro-benzenesulfonamide

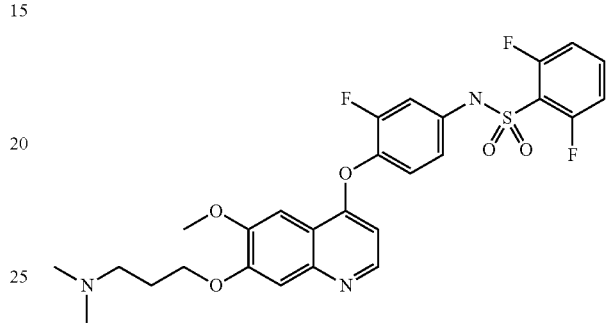

$C_{27}H_{26}F_3N_3O_5S$ Mw. 561.58

LC/MS purity: 99%, m/z 560 [M−H]⁻, 562 [M+H]⁺ Rt. 2.77 min. (Method B)

¹H NMR (300 MHz, DMSO-d6): 10.8 (bs, 1H), 8.44 (d, 1H), 7.56 (m, 1H), 7.49 (s, 1H), 7.37 (s, 1H), 7.18 (m, 3H), 7.01 (dd, 1H), 6.85 (d, 1H), 6.35 (d, 1H), 4.19 (t, 2H), 3.93 (s, 3H), 2.66 (t, 2H), 2.37 (s, 6H), 2.02 (m, 2H)

Melting point: 125-127° C.

Yield: 53%

Example 179

N-{4-[7-(3-Dimethylamino-propoxy)-6-methoxy-quinolin-4-yloxy]-3-fluoro-phenyl}-2-trifluoromethoxy-benzenesulfonamide

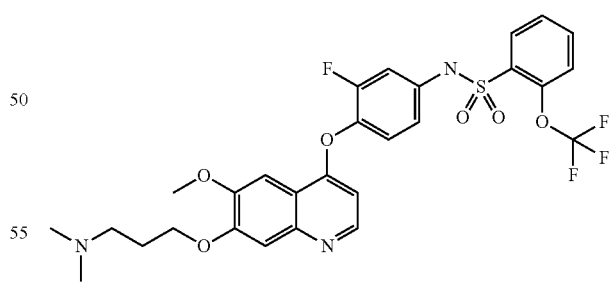

$C_{28}H_{27}F_4N_3O_6S$ Mw. 609.60

LC/MS purity: 99%, m/z 608 [M−H]⁻, 610 [M+H]⁺ Rt. 3.28 min. (Method B)

¹H NMR (300 MHz, DMSO-d6): 10.5 (bs, 1H), 8.44 (d, 1H), 7.99 (d, 1H), 7.69 (t, 1H), 7.51 (m, 3H), 7.37 (s, 1H), 7.21 (t, 1H), 7.04 (dd, 1H), 6.87 (d, 1H), 6.35 (d, 1H), 4.19 (t, 2H), 3.92 (s, 3H), 2.58 (t, 2H), 2.31 (s, 6H), 1.99 (m, 2H)

Melting point: 94-96° C.

Yield: 56%

Example 180

2,5-Dichloro-N-{4-[7-(3-dimethylamino-propoxy)-6-methoxy-quinolin-4-yloxy]-3-fluoro-phenyl}-benzenesulfonamide

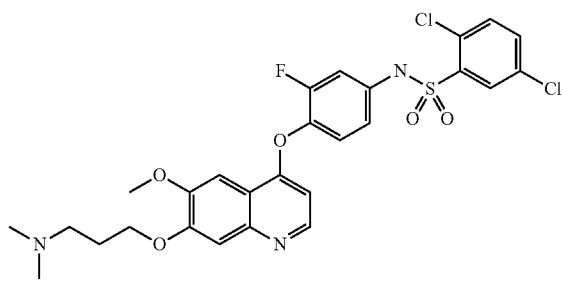

C$_{27}$H$_{26}$CO$_2$FN$_3$O$_5$S Mw. 594.49

LC/MS purity: 99%, m/z 592 [M−H]$^-$, 594 [M+H]$^+$ Rt. 3.15 min. (Method B)

$^1$H NMR (300 MHz, DMSO-d6): 10.5 (bs, 1H), 8.43 (d, 1H), 7.96 (s, 1H), 7.56 (s, 2H), 7.49 (s, 1H), 7.37 (s, 1H), 7.13 (t, 1H), 6.93 (d, 1H), 6.80 (d, 1H), 6.35 (d, 1H), 4.19 (t, 2H), 3.93 (s, 3H), 2.67 (t, 2H), 2.38 (s, 6H), 2.03 (m, 2H)

Melting point: 150-152° C.

Yield: 62%

Example 181

2,6-Dichloro-N-{4-[7-(3-dimethylamino-propoxy)-6-methoxy-quinolin-4-yloxy]-3-fluoro-phenyl}-benzenesulfonamide

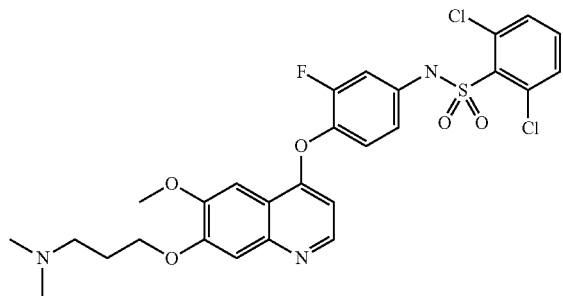 [SMILES: COc1cc2c(Oc3ccc(NS(=O)(=O)c4c(F)cccc4F)cc3F)ccnc2cc1OCCCN(C)C]

C$_{27}$H$_{26}$Cl$_2$FN$_3$O$_5$S Mw. 594.49

LC/MS purity: 100%, m/z 592 [M−H]$^-$, 594 [M+H]$^+$ Rt. 1.23 min. (Method B)

$^1$H NMR (300 MHz, DMSO-d6): 10.4 (bs, 1H), 8.43 (d, 1H), 7.46 (s, 4H), 7.37 (s, 1H), 7.19 (t, 1H), 7.00 (dd, 1H), 6.84 (d, 1H), 6.34 (d, 1H), 4.19 (t, 2H), 3.92 (s, 3H), 2.67 (t, 2H), 2.38 (s, 6H), 2.02 (m, 2H)

Melting point: 197-198° C.

Yield: 44%

Example 182

5-Chloro-thiophene-2-sulfonic acid {4-[7-(3-dimethylamino-propoxy)-6-methoxy-quinolin-4-yloxy]-3-fluoro-phenyl}-amide

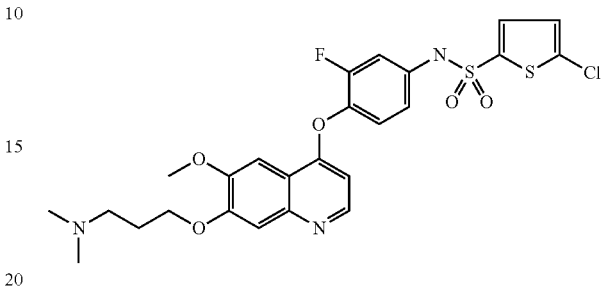

C$_{25}$H$_{25}$ClFN$_3$O$_5$S$_2$ Mw. 566.07

LC/MS purity: 99%, m/z 564 [M−H]$^-$, 566 [M+H]$^+$ Rt. 2.89 min. (Method B)

$^1$H NMR (300 MHz, DMSO-d6): 10.5 (bs, 1H), 8.45 (d, 1H), 7.51 (s, 1H), 7.39 (s, 1H), 7.30 (d, 1H), 7.20 (t, 1H), 7.10 (d, 1H), 7.02 (dd, 1H), 6.88 (d, 1H), 6.39 (d, 1H), 4.21 (t, 2H), 3.94 (s, 3H), 2.76 (t, 2H), 2.45 (s, 6H), 2.05 (m, 2H)

Melting point: 130-132° C.

Yield: 45%

Example 183

N-(5-{4-[7-(3-Dimethylamino-propoxy)-6-methoxy-quinolin-4-yloxy]-3-fluoro-phenylsulfamoyl}-4-methyl-thiazol-2-yl)-acetamide

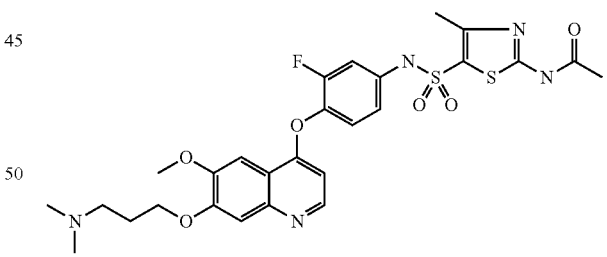

C$_{27}$H$_{30}$FN$_5$O$_6$S$_2$ Mw. 603.69

LC/MS purity: 100%, m/z 602 [M−H]$^-$, 604 [M+H]$^+$ Rt. 2.56 min. (Method B)

$^1$H NMR (300 MHz, DMSO-d6): 12 (bs, 1H), 10.5 (bs, 1H), 8.44 (d, 1H), 7.49 (s, 1H), 7.37 (s, 1H), 7.30 (t, 1H), 7.09 (dd, 1H), 6.96 (d, 1H), 6.36 (d, 1H), 4.18 (t, 2H), 3.93 (s, 3H), 2.54 (t, 2H), 2.39 (s, 3H), 2.26 (s, 6H), 2.15 (s, 3H), 1.98 (m, 2H)

Melting point: 164-166° C.

Yield: 42%

Example 184

3-{4-[7-(3-Dimethylamino-propoxy)-6-methoxy-quinolin-4-yloxy]-3-fluoro-phenylsulfamoyl}-thiophene-2-carboxylic acid methyl ester

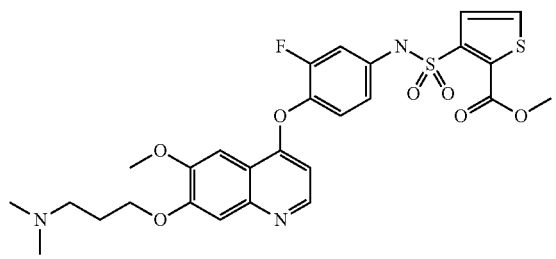

$C_{27}H_{28}FN_3O_7S_2$ Mw. 589.66

LC/MS purity: 96%, m/z 588 [M−H]⁻, 590 [M+H]⁺ Rt. 3.16 min. (Method B)

¹H NMR (300 MHz, DMSO-d6): 10.4 (bs, 1H), 8.45 (d, 1H), 7.94 (d, 1H), 7.48 (s, 1H), 7.46 (s, 1H), 7.37 (s, 1H), 7.29 (t, 1H), 7.11 (dd, 1H), 6.97 (d, 1H), 6.36 (d, 1H), 4.18 (t, 2H), 3.92 (s, 3H), 3.87 (s, 3H), 2.47 (t, 2H), 2.24 (s, 6H), 1.98 (m, 2H)

Melting point: 80-82° C.

Yield: 39%

Example 185

Furan-2-sulfonic acid {4-[7-(3-dimethylamino-propoxy)-6-methoxy-quinolin-4-yloxy]-3-fluoro-phenyl}-amide

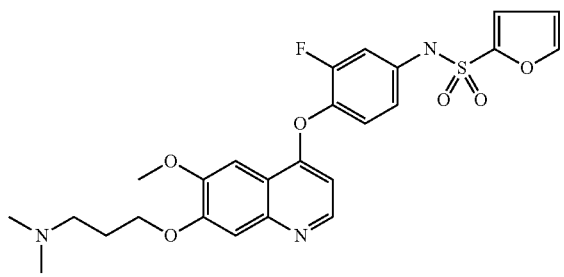 [SMILES: COc1cc2c(Oc3ccc(NS(=O)(=O)c4ccco4)cc3F)ccnc2cc1OCCCN(C)C]

$C_{25}H_{26}FN_3O_6S$ Mw. 515.56

LC/MS purity: 98%, m/z 514 [M−H]⁻, 516 [M+H]⁺ Rt. 2.62 min. (Method B)

¹H NMR (300 MHz, DMSO-d6): 10.4 (bs, 1H), 8.45 (d, 1H), 7.84 (s, 1H), 7.50 (s, 1H), 7.38 (s, 1H), 7.22 (t, 1H), 7.03 (m, 3H), 6.58 (s, 1H), 6.38 (d, 1H), 4.19 (t, 2H), 3.93 (s, 3H), 2.60 (t, 2H), 2.33 (s, 6H), 2.00 (m, 2H)

Melting point: 185-187° C.

Yield: 47%

Example 186

Thiophene-2-sulfonic acid {4-[7-(3-dimethylamino-propoxy)-6-methoxy-quinolin-4-yloxy]-3-fluoro-phenyl}-amide

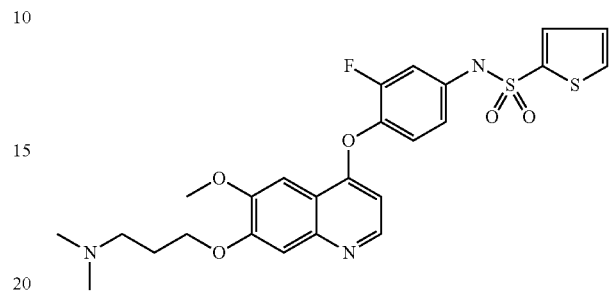

$C_{25}H_{26}FN_3O_5S_2$ Mw. 531.62

LC/MS purity: 99%, m/z 530 [M−H]⁻, 532 [M+H]⁺ Rt. 2.82 min. (Method B)

¹H NMR (300 MHz, DMSO-d6): 10.4 (bs, 1H), 8.46 (d, 1H), 7.85 (s, 1H), 7.54 (s, 1H), 7.49 (s, 1H), 7.38 (s, 1H), 7.30 (t, 1H), 7.11 (m, 2H), 6.98 (d, 1H), 6.37 (d, 1H), 4.19 (t, 2H), 3.93 (s, 3H), 2.57 (t, 2H), 2.30 (s, 6H), 1.99 (m, 2H)

Melting point: 186-188° C.

Yield: 36%

Example 187

2,5-Difluoro-N-(4-fluoro-3-{6-methoxy-7-[3-(4-methyl-piperidin-1-yl)-propoxy]-quinolin-4-yloxy}-phenyl)-benzenesulfonamide

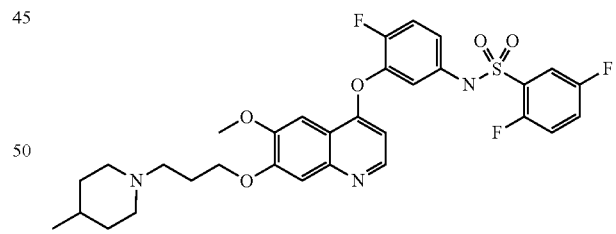

$C_{31}H_{32}F_3N_3O_5S$ Mw. 615.68

LC/MS purity: 97%, m/z 614 [M−H]⁻, 616 [M+H]⁺ Rt. 3.37 min. (Method B)

¹H NMR (300 MHz, DMSO-d6): 10.5 (bs, 1H), 8.44 (d, 1H), 7.46 (m, 5H), 7.27 (t, 1H), 6.95 (m, 2H), 6.27 (d, 1H), 4.20 (t, 2H), 3.93 (s, 3H), 3.03 (m, 2H), 2.67 (t, 2H), 2.18 (m, 2H), 2.04 (m, 2H), 1.64 (m, 2H), 1.40 (m, 1H), 1.20 (m, 2H), 0.90 (d, 3H)

Melting point: 186-188° C.

Yield: 54%

Example 188

2,6-Difluoro-N-(4-fluoro-3-{6-methoxy-7-[3-(4-methyl-piperidin-1-yl)-propoxy]-quinolin-4-yloxy}-phenyl)-benzenesulfonamide

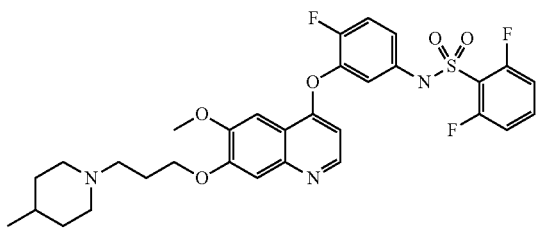 [SMILES: COc1cc2c(Oc3cc(NS(=O)(=O)c4c(F)cccc4F)ccc3F)ccnc2cc1OCCCN1CCC(C)CC1]

$C_{31}H_{32}F_3N_3O_5S$ Mw. 615.68

LC/MS purity: 98%, m/z 614 [M−H]⁻, 616 [M+H]⁺ Rt. 3.26 min. (Method B)

¹H NMR (300 MHz, DMSO-d6): 10.5 (bs, 1H), 8.45 (d, 1H), 7.62 (m, 1H), 7.46 (s, 1H), 7.40 (s, 1H), 7.31 (t, 1H), 7.16 (m, 2H), 6.97 (m, 2H), 6.26 (d, 1H), 4.21 (t, 2H), 3.92 (s, 3H), 3.03 (m, 2H), 2.66 (t, 2H), 2.18 (m, 2H), 2.04 (m, 2H), 1.64 (m, 2H), 1.41 (m, 1H), 1.20 (m, 2H), 0.90 (d, 3H)

Melting point: 185-186° C.

Yield: 38%

Example 189

N-(4-Fluoro-3-{6-methoxy-7-[3-(4-methyl-piperidin-1-yl)-propoxy]-quinolin-4-yloxy}-phenyl)-2-trifluoromethyl-benzenesulfonamide

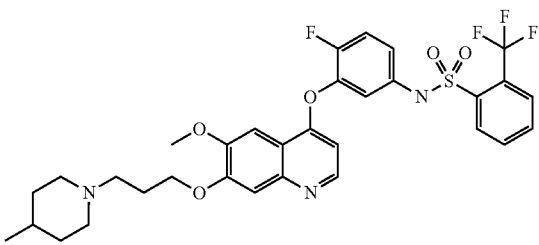 [SMILES: COc1cc2c(Oc3cc(NS(=O)(=O)c4ccccc4C(F)(F)F)ccc3F)ccnc2cc1OCCCN1CCC(C)CC1]

$C_{32}H_{33}F_4N_3O_5S$ Mw. 647.69

LC/MS purity: 97%, m/z 646 [M−H]⁻, 648 [M+H]⁺ Rt. 3.63 min. (Method B)

¹H NMR (300 MHz, DMSO-d6): 10.5 (bs, 1H), 8.45 (d, 1H), 8.04 (m, 1H), 7.91 (m, 1H), 7.77 (m, 2H), 7.42 (s, 1H), 7.39 (s, 1H), 7.30 (t, 1H), 6.94 (m, 2H), 6.28 (d, 1H), 4.20 (t, 2H), 3.91 (s, 3H), 2.98 (m, 2H), 2.60 (t, 2H), 2.05 (m, 4H), 1.62 (m, 2H), 1.40 (m, 1H), 1.20 (m, 2H), 0.89 (d, 3H)

Melting point: 175-177° C.

Yield: 44%

Example 190

N-(4-Fluoro-3-{6-methoxy-7-[3-(4-methyl-piperidin-1-yl)-propoxy]-quinolin-4-yloxy}-phenyl)-2-trifluoromethoxy-benzenesulfonamide

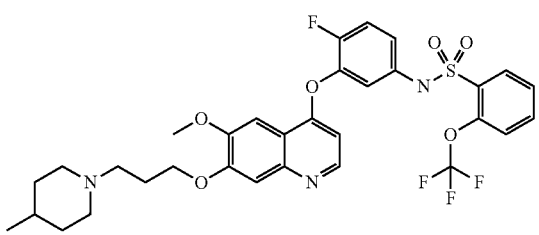 [SMILES: COc1cc2c(Oc3cc(NS(=O)(=O)c4ccccc4OC(F)(F)F)ccc3F)ccnc2cc1OCCCN1CCC(C)CC1]

$C_{32}H_{33}F_4N_3O_6S$ Mw. 663.69

LC/MS purity: 98%, m/z 662 [M−H]⁻, 664 [M+H]⁺ Rt. 3.85 min. (Method B)

¹H NMR (300 MHz, DMSO-d6): 10.5 (bs, 1H), 8.46 (d, 1H), 7.88 (d, 1H), 7.71 (t, 1H), 7.45 (m, 4H), 7.31 (t, 1H), 6.96 (m, 2H), 6.25 (d, 1H), 4.20 (t, 2H), 3.91 (s, 3H), 2.95 (m, 2H), 2.57 (t, 2H), 2.02 (m, 4H), 1.62 (m, 2H), 1.36 (m, 1H), 1.17 (m, 2H), 0.89 (d, 3H)

Melting point: 80-82° C.

Yield: 37%

Example 191

2,5-Dichloro-N-(4-fluoro-3-{6-methoxy-7-[3-(4-methyl-piperidin-1-yl)-propoxy]-quinolin-4-yloxy}-phenyl)-benzenesulfonamide

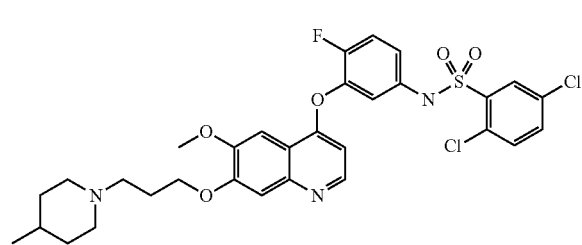 [SMILES: COc1cc2c(Oc3cc(NS(=O)(=O)c4cc(Cl)ccc4Cl)ccc3F)ccnc2cc1OCCCN1CCC(C)CC1]

$C_{31}H_{32}Cl_2FN_3O_5S$ Mw. 648.58

LC/MS purity: 95%, m/z 646 [M−H]⁻, 648 [M+H]⁺ Rt. 3.64 min. (Method B)

¹H NMR (300 MHz, DMSO-d6): 10.5 (bs, 1H), 8.45 (d, 1H), 7.87 (d, 1H), 7.61 (m, 2H), 7.46 (s, 1H), 7.40 (s, 1H), 7.26 (t, 1H), 6.93 (m, 2H), 6.24 (d, 1H), 4.21 (t, 2H), 3.93 (s, 3H), 3.07 (m, 2H), 2.69 (t, 2H), 2.21 (m, 2H), 2.05 (m, 2H), 1.66 (m, 2H), 1.43 (m, 1H), 1.23 (m, 2H), 0.90 (d, 3H)

Melting point: 127-130° C.

Yield: 52%

Example 192

2,6-Dichloro-N-(4-fluoro-3-{6-methoxy-7-[3-(4-methyl-piperidin-1-yl)-propoxy]-quinolin-4-yloxy}-phenyl)-benzenesulfonamide

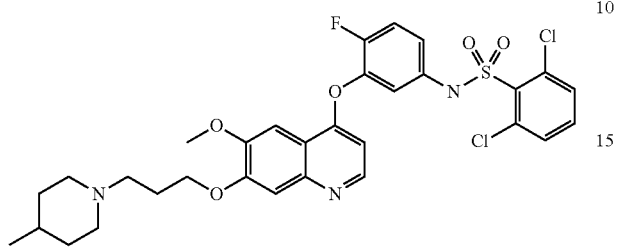

$C_{31}H_{32}Cl_2FN_3O_5S$ Mw. 648.58

LC/MS purity: 97%, m/z 646 [M−H]⁻, 648 [M+H]⁺ Rt. 3.56 min. (Method B)

¹H NMR (300 MHz, DMSO-d6): 10.5 (bs, 1H), 8.43 (d, 1H), 7.45 (m, 5H), 7.30 (t, 1H), 6.93 (m, 2H), 6.22 (d, 1H), 4.21 (t, 2H), 3.93 (s, 3H), 3.00 (m, 2H), 2.64 (m, 2H), 2.10 (m, 4H), 1.64 (m, 2H), 1.39 (m, 1H), 1.19 (m, 2H), 0.90 (d, 3H)

Melting point: 116-118° C.

Yield: 46%

Example 193

N-(2-Chloro-5-{6-methoxy-7-[3-(4-methyl-piperidin-1-yl)-propoxy]-quinolin-4-yloxy}-phenyl)-2,5-difluoro-benzenesulfonamide

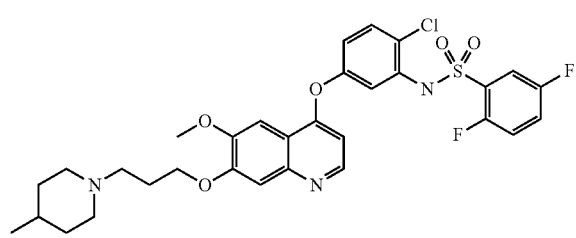 [SMILES: COc1cc2c(Oc3ccc(Cl)c(NS(=O)(=O)c4cc(F)ccc4F)c3)ccnc2cc1OCCCN1CCC(C)CC1]

$C_{31}H_{32}ClF_2N_3O_5S$ Mw. 632.13

LC/MS purity: 97%, m/z 630 [M−H]⁻, 632 [M+H]⁺ Rt. 3.24 min. (Method B)

¹H NMR (300 MHz, DMSO-d6): 9.1 (bs, 1H), 8.36 (d, 1H), 7.44 (s, 1H), 7.38 (t, 1H), 7.25 (m, 4H), 7.05 (d, 1H), 6.43 (dd, 1H), 6.27 (d, 1H), 4.22 (t, 2H), 3.92 (s, 3H), 3.19 (m, 2H), 2.89 (m, 2H), 2.56 (m, 1H), 2.11 (m, 2H), 1.72 (m, 2H), 1.36 (m, 1H), 1.28 (m, 3H), 0.92 (d, 3H)

Melting point: 206-208° C.

Yield: 11%

Example 194

N-(2-Chloro-5-{6-methoxy-7-[3-(4-methyl-piperidin-1-yl)-propoxy]-quinolin-4-yloxy}-phenyl)-2,6-difluoro-benzenesulfonamide

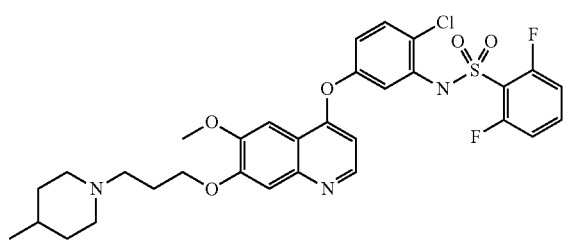 [SMILES: COc1cc2c(Oc3ccc(Cl)c(NS(=O)(=O)c4c(F)cccc4F)c3)ccnc2cc1OCCCN1CCC(C)CC1]

$C_{31}H_{32}ClF_2N_3O_5S$ Mw. 632.13

LC/MS purity: 98%, m/z 630 [M−H]⁻, 632 [M+H]⁺ Rt. 3.23 min. (Method B)

¹H NMR (300 MHz, DMSO-d6): 9.1 (bs, 1H), 8.35 (d, 1H), 7.44 (s, 1H), 7.35 (m, 2H), 7.24 (d, 1H), 7.06 (d, 1H), 6.91 (t, 2H), 6.39 (dd, 1H), 6.23 (d, 1H), 4.23 (t, 2H), 3.92 (s, 3H), 3.17 (m, 2H), 2.97 (m, 2H), 2.57 (m, 1H), 2.14 (m, 2H), 1.75 (m, 2H), 1.53 (m, 1H), 1.26 (m, 3H), 0.93 (d, 3H)

Melting point: 222-226° C.

Yield: 14%

Example 195

N-(2-Chloro-5-{6-methoxy-7-[3-(4-methyl-piperidin-1-yl)-propoxy]-quinolin-4-yloxy}-phenyl)-2-trifluoromethyl-benzenesulfonamide

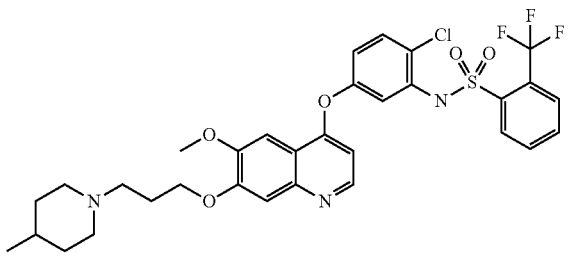 [SMILES: COc1cc2c(Oc3ccc(Cl)c(NS(=O)(=O)c4ccccc4C(F)(F)F)c3)ccnc2cc1OCCCN1CCC(C)CC1]

$C_{32}H_{33}ClF_3N_3O_5S$ Mw. 664.14

LC/MS purity: 98%, m/z 662 [M−H]⁻, 664 [M+H]⁺ Rt. 3.43 min. (Method B)

¹H NMR (300 MHz, DMSO-d6): 9.15 (bs, 1H), 8.31 (d, 1H), 7.95 (d, 1H), 7.72 (d, 1H), 7.57 (m, 2H), 7.38 (s, 1H), 7.36 (s, 1H), 7.27 (d, 1H), 6.89 (d, 1H), 6.40 (d, 1H), 6.19 (d, 1H), 4.22 (t, 2H), 3.89 (s, 3H), 3.31 (m, 2H), 3.01 (m, 2H), 2.61 (m, 1H), 2.15 (m, 2H), 1.75 (m, 2H), 1.54 (m, 1H), 1.29 (m, 3H), 0.93 (d, 3H)

Melting point: 179-181° C.

Yield: 12%

Example 196

N-(2-Chloro-5-{6-methoxy-7-[3-(4-methyl-piperidin-1-yl)-propoxy]-quinolin-4-yloxy}-phenyl)-2-trifluoromethoxy-benzenesulfonamide

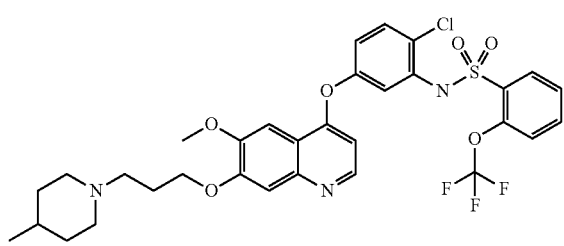 [SMILES: COc1cc2c(Oc3ccc(Cl)c(NS(=O)(=O)c4ccccc4OC(F)(F)F)c3)ccnc2cc1OCCCN1CCC(C)CC1]

$C_{32}H_{33}ClF_3N_3O_6S$ Mw. 680.14

LC/MS purity: 98%, m/z 678 [M−H]−, 680 [M+H]+ Rt. 3.58 min. (Method B)

$^1$H NMR (300 MHz, DMSO-d6): 9.1 (bs, 1H), 8.35 (d, 1H), 7.74 (d, 1H), 7.50 (t, 1H), 7.42 (s, 1H), 7.39 (s, 1H), 7.29 (m, 3H), 7.01 (d, 1H), 6.43 (d, 1H), 6.27 (d, 1H), 4.23 (t, 2H), 3.90 (s, 3H), 3.29 (m, 2H), 3.02 (m, 2H), 2.68 (m, 1H), 2.16 (m, 2H), 1.77 (m, 2H), 1.56 (m, 1H), 1.29 (m, 3H), 0.93 (d, 3H)

Melting point: 123-126° C.

Yield: 9%

Example 197

2,5-Dichloro-N-(2-chloro-5-{6-methoxy-7-[3-(4-methyl-piperidin-1-yl)-propoxy]-quinolin-4-yloxy}-phenyl)-benzenesulfonamide

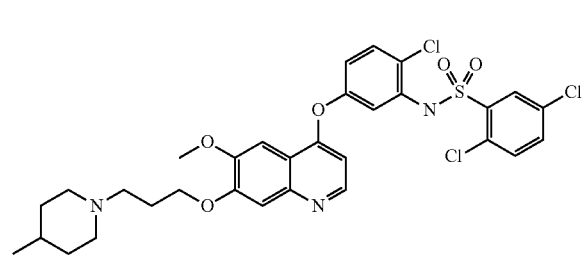 [SMILES: COc1cc2c(Oc3ccc(Cl)c(NS(=O)(=O)c4cc(Cl)ccc4Cl)c3)ccnc2cc1OCCCN1CCC(C)CC1]

$C_{31}H_{32}Cl_3N_3O_5S$ Mw. 665.04

LC/MS purity: 97%, m/z 662 [M−H]−, 664 [M+H]+ Rt. 3.49 min. (Method B)

$^1$H NMR (300 MHz, DMSO-d6): 9.1 (bs, 1H), 8.37 (d, 1H), 7.75 (d, 1H), 7.40 (m, 4H), 7.27 (d, 1H), 6.98 (d, 1H), 6.40 (dd, 1H), 6.24 (d, 1H), 4.22 (t, 2H), 3.92 (s, 3H), 3.31 (m, 2H), 3.17 (m, 2H), 2.98 (m, 1H), 2.11 (m, 2H), 1.73 (m, 2H), 1.55 (m, 1H), 1.26 (m, 3H), 0.92 (d, 3H)

Melting point: 223-224° C.

Yield: 12%

Example 198

2,6-Dichloro-N-(2-chloro-5-{6-methoxy-7-[3-(4-methyl-piperidin-1-yl)-propoxy]-quinolin-4-yloxy}-phenyl)-benzenesulfonamide

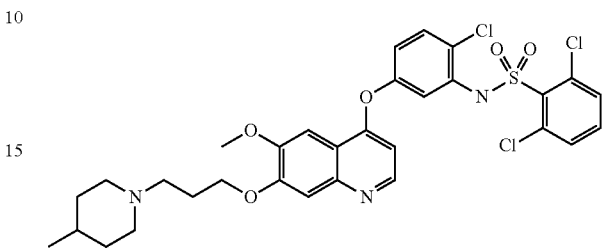

$C_{31}H_{32}Cl_3N_3O_5S$ Mw. 665.04

LC/MS purity: 98%, m/z 662 [M−H]−, 664 [M+H]+ Rt. 3.38 min. (Method B)

$^1$H NMR (300 MHz, DMSO-d6): 9 (bs, 1H), 8.32 (d, 1H), 7.42 (s, 1H), 7.38 (s, 1H), 7.26 (m, 4H), 6.94 (d, 1H), 6.37 (dd, 1H), 6.17 (d, 1H), 4.23 (t, 2H), 3.91 (s, 3H), 3.28 (m, 2H), 2.96 (m, 2H), 2.54 (m, 1H), 2.14 (m, 2H), 1.75 (m, 2H), 1.53 (m, 1H), 1.30 (m, 3H), 0.93 (d, 3H)

Melting point: 206-208° C.

Yield: 9%

Example 199

2,5-Difluoro-N-[3-fluoro-4-(6-methoxy-quinolin-4-yloxy)-phenyl]-benzenesulfonamide

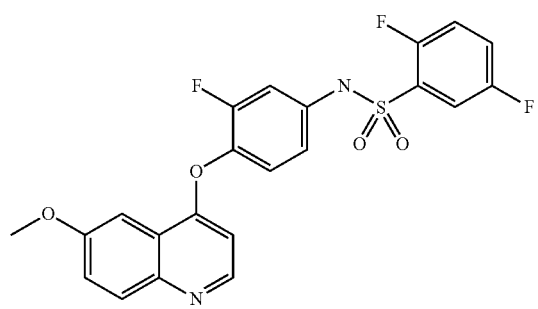 [SMILES: COc1ccc2nccc(Oc3ccc(NS(=O)(=O)c4cc(F)ccc4F)cc3F)c2c1]

$C_{22}H_{15}F_3N_2O_4S$ Mw. 460.43

LC/MS purity: 98%, m/z 459 [M−H]−, 461 [M+H]+ Rt. 3.42 min. (Method B)

$^1$H NMR (300 MHz, DMSO-d6): 11 (bs, 1H), 8.58 (d, 1H), 8.17 (d, 1H), 7.64 (m, 1H), 7.48 (m, 1H), 7.40 (s, 1H), 7.39 (m, 1H), 7.26 (m, 2H), 7.06 (dd, 1H), 6.92 (d, 1H), 6.37 (d, 1H), 3.93 (s, 3H)

Melting point: 249-250° C.

Yield: 81%

Example 200

2,6-Difluoro-N-[3-fluoro-4-(6-methoxy-quinolin-4-yloxy)-phenyl]-benzenesulfonamide

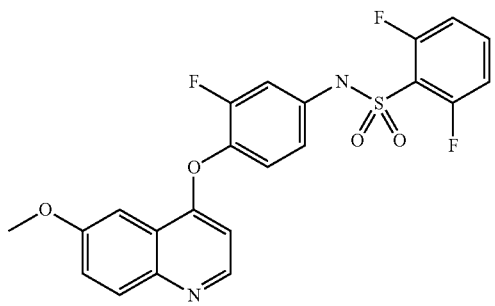

$C_{22}H_{15}F_3N_2O_4S$ Mw. 460.43

LC/MS purity: 98%, m/z 459 [M−H]⁻, 461 [M+H]⁺ Rt. 3.27 min. (Method B)

¹H NMR (300 MHz, DMSO-d6): 11.3 (bs, 1H), 8.59 (d, 1H), 8.17 (d, 1H), 7.70 (m, 1H), 7.4-7.25 (m, 6H), 7.14 (dd, 1H), 7.01 (d, 1H), 3.93 (s, 3H)

Melting point: 227-228° C.

Yield: 69%

Example 201

N-[3-Fluoro-4-(6-methoxy-quinolin-4-yloxy)-phenyl]-2-trifluoromethyl-benzenesulfonamide

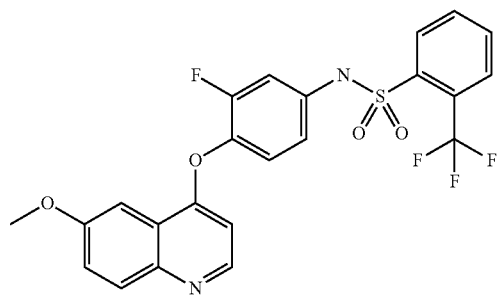 [SMILES: COc1ccc2nccc(Oc3ccc(NS(=O)(=O)c4ccccc4C(F)(F)F)cc3F)c2c1]

$C_{23}H_{16}F_4N_2O_4S$ Mw. 492.45

LC/MS purity: 98%, m/z 491 [M−H]⁻, 493 [M+H]⁺ Rt. 3.75 min. (Method B)

¹H NMR (300 MHz, DMSO-d6): 11 (bs, 1H), 8.59 (d, 1H), 8.18 (s, 1H), 8.15 (s, 1H), 8.02 (d, 1H), 7.89 (m, 2H), 7.40 (s, 1H), 7.36 (d, 1H), 7.29 (dd, 1H), 7.14 (d, 1H), 7.01 (d, 1H), 6.37 (d, 1H), 3.93 (s, 3H)

Melting point: 168-169° C.

Yield: 75%

Example 202

N-[3-Fluoro-4-(6-methoxy-quinolin-4-yloxy)-phenyl]-2-trifluoromethoxy-benzenesulfonamide

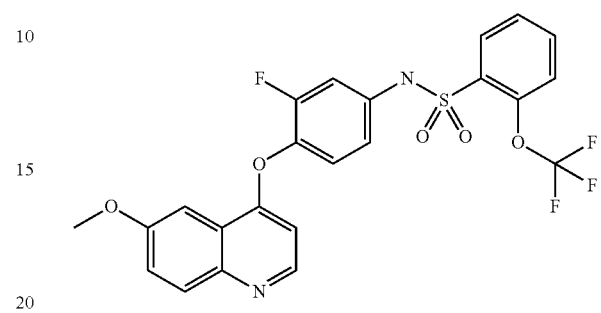

$C_{23}H_{16}F_4N_2O_5S$ Mw. 508.45

LC/MS purity: 99%, m/z 507 [M−H]⁻, 509 [M+H]⁺ Rt. 3.97 min. (Method B)

¹H NMR (300 MHz, DMSO-d6): 11 (bs, 1H), 8.59 (d, 1H), 8.18 (s, 1H), 8.05 (d, 1H), 7.81 (t, 1H), 7.59 (m, 2H), 7.40 (s, 1H), 7.36 (d, 1H), 7.29 (dd, 1H), 7.15 (d, 1H), 7.00 (d, 1H), 6.34 (d, 1H), 3.93 (s, 3H)

Melting point: 175-176° C.

Yield: 69%

Example 203

2,5-Dichloro-N-[3-fluoro-4-(6-methoxy-quinolin-4-yloxy)-phenyl]-benzenesulfonamide

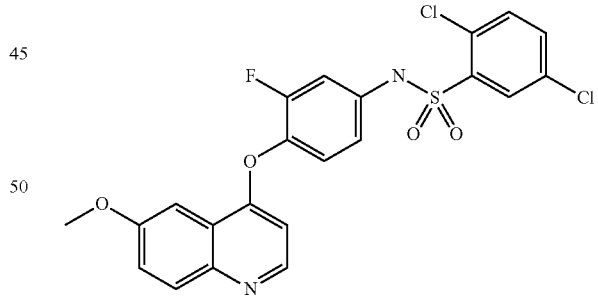

$C_{22}H_{15}Cl_2FN_2O_4S$ Mw. 493.34

LC/MS purity: 98%, m/z 491 [M−H]⁻, 493 [M+H]⁺ Rt. 3.78 min. (Method B)

¹H NMR (300 MHz, DMSO-d6): 11.2 (bs, 1H), 8.58 (d, 1H), 8.17 (d, 1H), 8.05 (d, 1H), 7.74 (m, 2H), 7.39 (d, 1H), 7.35 (t, 1H), 7.28 (dd, 1H), 7.16 (dd, 1H), 7.01 (d, 1H), 6.36 (d, 1H), 3.93 (s, 3H)

Melting point: 253-255° C.

Yield: 70%

Example 204

2,6-Dichloro-N-[3-fluoro-4-(6-methoxy-quinolin-4-yloxy)-phenyl]-benzenesulfonamide

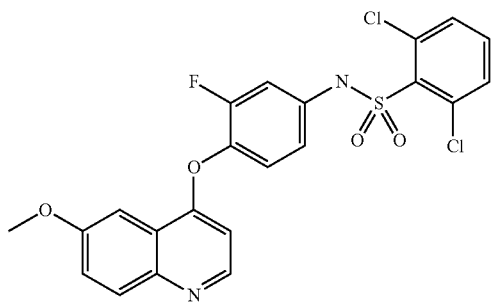 [SMILES: COc1ccc2nccc(Oc3ccc(NS(=O)(=O)c4c(Cl)cccc4Cl)cc3F)c2c1]

$C_{22}H_{15}Cl_2FN_2O_4S$ Mw. 493.34

LC/MS purity: 99%, m/z 491 [M−H]⁻, 493 [M+H]⁺ Rt. 3.69 min. (Method B)

¹H NMR (300 MHz, DMSO-d6): 11.2 (bs, 1H), 8.58 (d, 1H), 8.17 (d, 1H), 7.62 (m, 2H), 7.54 (m, 1H), 7.40 (d, 1H), 7.34 (t, 1H), 7.27 (dd, 1H), 7.00 (dd, 1H), 6.96 (d, 1H), 6.35 (d, 1H), 3.93 (s, 3H)

Melting point: 219-221° C.

Yield: 67%

Example 205

Naphthalene-2-sulfonic acid [3-fluoro-4-(6-methoxy-quinolin-4-yloxy)-phenyl]-amide

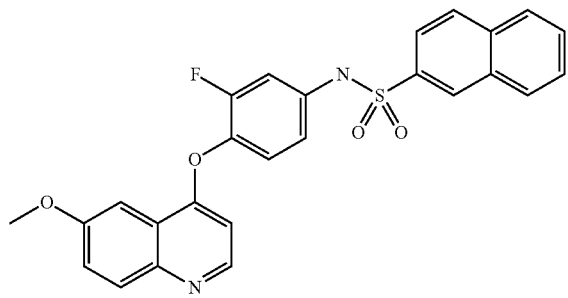 [SMILES: COc1ccc2nccc(Oc3ccc(NS(=O)(=O)c4ccc5ccccc5c4)cc3F)c2c1]

$C_{26}H_{19}FN_2O_4S$ Mw. 474.51

LC/MS purity: 99%, m/z 473 [M−H]⁻, 475 [M+H]⁺ Rt. 4.20 min. (Method B)

¹H NMR (300 MHz, DMSO-d6): 10.8 (bs, 1H), 8.53 (d, 1H), 8.49 (s, 1H), 8.19 (m, 3H), 8.03 (d, 1H), 7.82 (dd, 1H), 7.69 (m, 2H), 7.38 (d, 1H), 7.27 (m, 2H), 7.16 (dd, 1H), 6.99 (t, 1H), 6.28 (d, 1H), 3.92 (s, 3H)

Melting point: 220-222° C.

Yield: 74%

Example 206

Cyclopropanesulfonic acid [3-fluoro-4-(6-methoxy-quinolin-4-yloxy)-phenyl]-amide

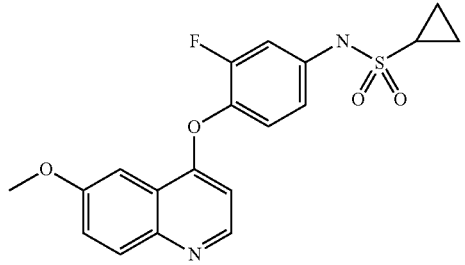 [SMILES: COc1ccc2nccc(Oc3ccc(NS(=O)(=O)C4CC4)cc3F)c2c1]

$C_{19}H_{17}FN_2O_4S$ Mw. 388.42

LC/MS purity: 98%, m/z 387 [M−H]⁻, 389 [M+H]⁺ Rt. 3.64 min. (Method B)

¹H NMR (300 MHz, DMSO-d6): 10.8 (bs, 1H), 8.62 (dd, 1H), 8.22 (d, 1H), 7.48 (d, 1H), 7.43 (s, 1H), 7.29 (m, 2H), 7.18 (d, 1H), 6.48 (d, 1H), 3.94 (s, 3H), 2.76 (m, 1H), 0.99 (m, 4H)

Melting point: 194-196° C.

Yield: 75%

Example 207

2,5-Difluoro-N-(3-methoxy-4-{6-methoxy-7-[3-(4-methyl-piperidin-1-yl)-propoxy]-quinolin-4-yloxy}-phenyl)-benzenesulfonamide

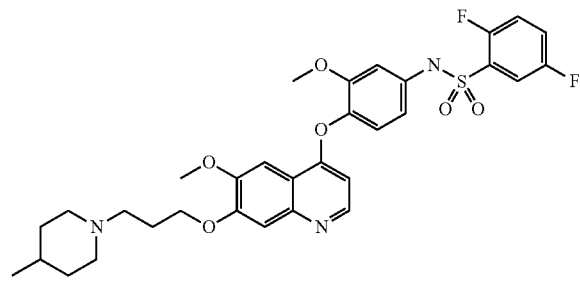 [SMILES: COc1cc2c(Oc3ccc(NS(=O)(=O)c4cc(F)ccc4F)cc3OC)ccnc2cc1OCCCN1CCC(C)CC1]

$C_{32}H_{35}F_2N_3O_6S$ Mw. 627.71

LC/MS purity: 98%, m/z 626 [M−H]⁻, 628 [M+H]⁺ Rt. 3.50 min. (Method B)

¹H NMR (300 MHz, DMSO-d6): 10.5 (bs, 1H), 8.37 (d, 1H), 7.63 (m, 1H), 7.51 (m, 2H), 7.46 (s, 1H), 7.34 (s, 1H), 7.07 (d, 1H), 6.90 (s, 1H), 6.70 (d, 1H), 6.16 (d, 1H), 4.17 (t, 2H), 3.91 (s, 3H), 3.61 (s, 3H), 3.34 (m, 1H), 2.84 (m, 2H), 2.46 (m, 2H), 1.95 (m, 3H), 1.63 (m, 4H), 1.48 (m, 1H), 0.84 (d, 3H)

Melting point: 170-172° C.

Yield: 58%

Example 208

N-(3-Methoxy-4-{6-methoxy-7-[3-(4-methyl-piperidin-1-yl)-propoxy]-quinolin-4-yloxy}-phenyl)-2-trifluoromethyl-benzenesulfonamide

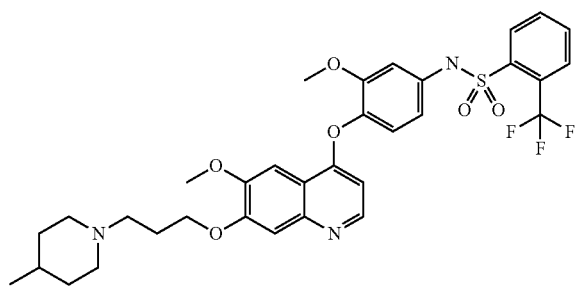 [SMILES: COc1cc2c(Oc3ccc(NS(=O)(=O)c4ccccc4C(F)(F)F)cc3OC)ccnc2cc1OCCCN1CCC(C)CC1]

$C_{33}H_{36}F_3N_3O_6S$ Mw. 659.73

LC/MS purity: 98%, m/z 658 [M−H]⁻, 660 [M+H]⁺ Rt. 3.86 min. (Method B)

¹H NMR (300 MHz, DMSO-d6): 10.6 (bs, 1H), 8.38 (d, 1H), 8.15 (d, 1H), 7.97 (d, 1H), 7.83 (m, 2H), 7.45 (s, 1H), 7.34 (s, 1H), 7.07 (d, 1H), 6.91 (d, 1H), 6.67 (dd, 1H), 6.17 (d, 1H), 4.17 (t, 2H), 3.91 (s, 3H), 3.60 (s, 3H), 3.32 (m, 1H), 2.81 (m, 2H), 2.46 (m, 2H), 1.96 (m, 2H), 1.88 (m, 1H), 1.60 (m, 4H), 1.46 (m, 1H), 0.84 (d, 3H)

Melting point: 216-218° C.

Yield: 53%

Example 209

N-(3,5-Dichloro-4-{6-methoxy-7-[3-(4-methyl-piperidin-1-yl)-propoxy]-quinolin-4-yloxy}-phenyl)-2,6-difluoro-benzenesulfonamide

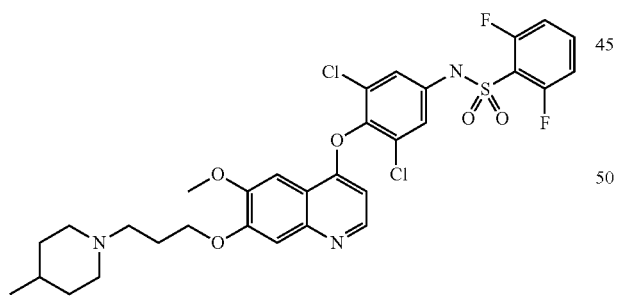

$C_{31}H_{31}Cl_2F_2N_3O_5S$ Mw. 666.58

LC/MS purity: 96%, m/z 664 [M−H]⁻, 666 [M+H]⁺ Rt. 3.34 min. (Method B)

¹H NMR (300 MHz, DMSO-d6): 10.2 (bs, 1H), 8.43 (d, 1H), 7.53 (s, 1H), 7.45 (m, 1H), 7.41 (s, 1H), 7.07 (m, 2H), 7.02 (m, 2H), 6.26 (d, 1H), 4.23 (t, 2H), 3.94 (s, 3H), 3.28 (m, 2H), 2.95 (m, 2H), 2.52 (m, 1H), 2.13 (m, 2H), 1.74 (m, 2H), 1.53 (m, 1H), 1.29 (m, 3H), 0.92 (d, 3H)

Melting point: 146-151° C.

Yield: 7%

Example 210

N-(3,5-Dichloro-4-{6-methoxy-7-[3-(4-methyl-piperidin-1-yl)-propoxy]-quinolin-4-yloxy}-phenyl)-2-trifluoromethyl-benzenesulfonamide

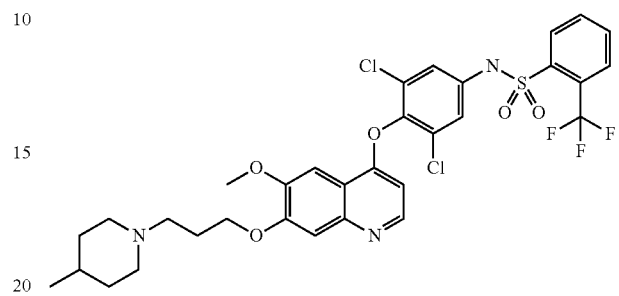

$C_{32}H_{32}Cl_2F_3N_3O_5S$ Mw. 698.59

LC/MS purity: 98%, m/z 696 [M−H]⁻, 698 [M+H]⁺ Rt. 3.59 min. (Method B)

¹H NMR (300 MHz, DMSO-d6): 10.5 (bs, 1H), 8.43 (d, 1H), 8.11 (d, 1H), 7.82 (d, 1H), 7.69 (m, 2H), 7.52 (s, 1H), 7.41 (s, 1H), 6.96 (s, 2H), 6.25 (d, 1H), 4.22 (t, 2H), 3.93 (s, 3H), 3.28 (m, 2H), 2.69 (m, 2H), 2.56 (m, 1H), 2.27 (m, 2H), 1.72 (m, 2H), 1.50 (m, 1H), 1.32 (m, 3H), 0.92 (d, 3H)

Melting point: 148-151° C.

Yield: 22%

Example 211

Acetic acid 4-{4-[4-(2,5-difluoro-benzenesulfonylamino)-2-fluoro-phenoxy]-6-methoxy-quinolin-7-yloxy}-butyl ester

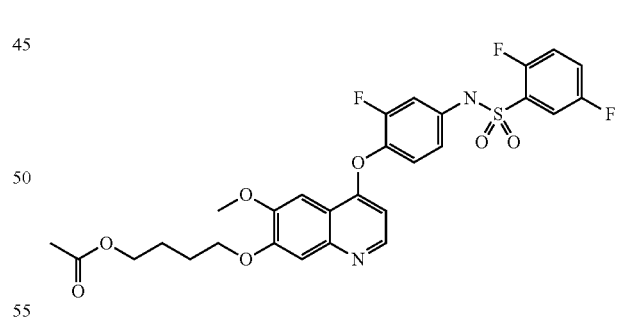

$C_{28}H_{25}F_3N_2O_7S$ Mw. 590.58

LC/MS purity: 98%, m/z 589 [M−H]⁻, 591 [M+H]⁺ Rt. 3.57 min. (Method B)

¹H NMR (300 MHz, DMSO-d6): 11.11 (s, 1H), 8.45 (d, 1H), 7.71-7.35 (m, 6H), 7.18 (d, 1H), 7.05 (d, 1H), 6.36 (d, 1H), 4.17 (bs, 2H), 4.10 (bs, 2H), 3.92 (s, 3H), 2.01 (s, 3H), 1.84 (bs, 2H), 1.80 bs, 2H)

Melting point: 165-167° C.

Yield: 65%

Example 212

Acetic acid 4-{4-[2-fluoro-4-(2-trifluoromethyl-benzenesulfonylamino)-phenoxy]-6-methoxy-quinolin-7-yloxy}-butyl ester

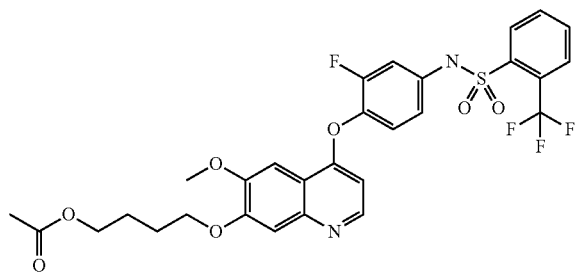 [SMILES: COc1cc2c(Oc3ccc(NS(=O)(=O)c4ccccc4C(F)(F)F)cc3F)ccnc2cc1OCCCCOC(C)=O]

$C_{29}H_{26}F_4N_2O_7S$ Mw. 622.60

LC/MS purity: 98%, m/z 621 [M−H]⁻, 623 [M+H]⁺ Rt. 3.86 min. (Method B)

¹H NMR (300 MHz, DMSO-d6): 11.03 (s, 1H), 8.45 (d, 1H), 8.16 (d, 1H), 8.04 (d, 1H), 7.80 (m, 2H), 7.47 (s, 1H), 7.39 (s, 1H), 7.37 (t, 1H), 7.16 (d, 1H), 7.03 (d, 1H), 6.36 (d, 1H), 4.17 (t, 2H), 4.10 (t, 2H), 3.91 (s, 3H), 2.01 (s, 3H), 1.82 (m, 4H)

Melting point: 143-145° C.

Yield: 74%

Example 213

N-{2-Fluoro-4-[6-methoxy-7-(3-pyrrolidin-1-yl-propoxy)-quinolin-4-yloxy]-phenyl}-2-trifluoromethyl-benzenesulfonamide

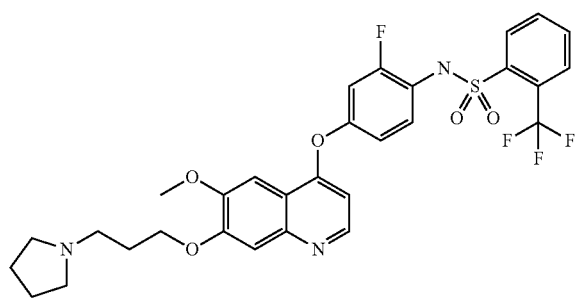 [SMILES: COc1cc2c(Oc3ccc(NS(=O)(=O)c4ccccc4C(F)(F)F)c(F)c3)ccnc2cc1OCCCN1CCCC1]

$C_{30}H_{29}F_4N_3O_5S$ Mw. 619.64

LC/MS purity: 99%, m/z 618 [M−H]⁻, 620 [M+H]⁺ Rt. 2.71 min. (Method A)

¹H NMR (300 MHz, DMSO-d6): 11.03 (s, 1H), 8.45 (d, 1H), 8.16 (d, 1H), 8.04 (d, 1H), 7.80 (m, 2H), 7.47 (s, 1H), 7.39 (s, 1H), 7.37 (t, 1H), 7.16 (d, 1H), 7.03 (d, 1H), 6.36 (d, 1H), 4.17 (t, 2H), 4.10 (t, 2H), 3.91 (s, 3H), 2.01 (s, 3H), 1.82 (m, 4H)

Melting point: 152-156° C.

Yield: 62%

Example 214

N-{3-Fluoro-4-[6-methoxy-7-(4-morpholin-4-yl-butoxy)-quinolin-4-yloxy]-phenyl}-2-trifluoromethyl-benzenesulfonamide

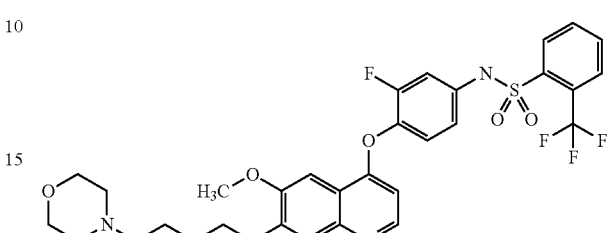

C31H31F4N3O6S Mw. 649.67

LC/MS purity: 97%, m/z 648 [M−H]⁻, 650 [M+H]⁺ Rt. 3.50 min. (Method B)

¹H NMR (300 MHz, DMSO-d6): 11 (bs, 1H), 8.44 (d, 1H), 8.16 (d, 1H), 8.01 (d, 1H), 7.90 (m, 2H), 7.46 (s, 1H), 7.38 (s, 1H), 7.33 (t, 1H), 7.13 (d, 1H), 6.98 (d, 1H), 6.35 (d, 1H), 4.16 (t, 2H), 3.91 (s, 3H), 3.57 (m, 4H), 2.38 (m, 6H), 1.82 (m, 2H), 1.64 (m, 2H)

Melting point: 102-104° C.

Yield: 23%

Example 215

N-(2-Fluoro-4-{6-methoxy-7-[3-(3-methyl-piperidin-1-yl)-propoxy]-quinolin-4-yloxy}-phenyl)-2-trifluoromethyl-benzenesulfonamide

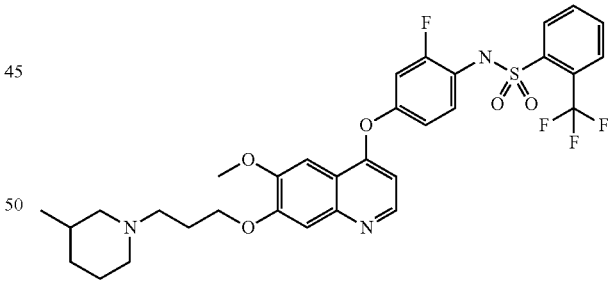

$C_{32}H_{33}F_4N_3O_5S$ Mw. 647.69

LC/MS purity: 95%, m/z 646 [M−H]⁻, m/z 648 [M−H]⁺ Rt. 3.60 min. (Method B)

¹H NMR (300 MHz, DMSO-d6): 10.6 (bs, 1H), 8.44 (d, 1H), 8.07 (d, 1H), 7.81 (d, 1H), 7.65 (m, 2H), 7.43 (s, 1H), 7.35 (s, 1H), 7.14 (t, 1H), 6.96 (d, 1H), 6.76 (d, 1H), 6.43 (d, 1H), 4.17 (t, 2H), 3.90 (s, 3H), 2.85 (m, 2H), 2.42 (m, 2H), 1.98 (m, 2H), 1.82 (m, 1H), 1.61 (m, 4H), 1.51 (m, 1H), 1.03 (m, 1H), 0.84 (d, 3H)

Melting point: 125-126° C.

Yield: 35%

Assay Example A

AXL Cellular Tyrosine Kinase Assay

Establishment of Wild Type AXL (wtAXL) Receptor Tyrosine Kinase-Overexpressing Stable Cell Line NIH-3T3-AXL (Clone 22)

WtAXL cDNA was cloned into vector pLXSN(ESK) and transfected into Phoenix E packaging cells. The viral supernatant was collected and used to infect target cells NIH3T3 N7. Monoclonal NIH3T3-AXL cell lines stably expressing wtAXL were generated by selecting retrovirally infected cells in medium containing puromycin (2 µg/ml) and subsequent clonal separation. NIH-3T3-AXL (clone 22) cells were used for further experiment because AXL was highly expressed and constitutively phosphorylated in these cells. In addition, these cells demonstrated aggressive behaviors on matrigel matrix (Matrigel™ Matrix, BD Biosciences, Bedford, Mass., USA). Moreover, the inhibitory effects of compounds on AXL phosphorylation discovered by using NIH-3T3 AXL (clone 22) system have been confirmed in human breast cancer cells endogenously expressing AXL in our previous study (Zhang Y X, et al. AXL is a potential target for therapeutic intervention in breast cancer progression. Cancer Res. 2008; 68:1905-15).

Determination of the morphology of cells grown on matrigel matrix was carried out as described previously, with some modifications (Thompson E W, et al. Association of increased basement membrane invasiveness with absence of estrogen receptor and expression of vimentin in human breast cancer cell lines. J Cell Physiol 1992; 150:534-44). Briefly, in a 96-well flat-bottomed plate, 10000 cells/100 µl cell suspensions was plated on the surface of precoated matrigel (3 mg/ml). Colony outgrowth was visualized with a Zeiss Axiovert S100 microscope (Carl Zeiss UK, Welwyn Garden City, UK).

NIH-3T3-AXL Cellular Kinase Assay

NIH-3T3-AXL (Clone 22) cells were seeded onto 6-well plates ($1.5 \times 10^5$ cells/well) in 1.5 ml DMEM+10% heat inactivated FBS (GIBCO—Invitrogen GmbH, Karlsruhe, Germany) and cultured overnight, followed by serum depletion in DMEM without FBS for 24 h. Serial dilutions of compounds were added, and the cells were further incubated for 1 h. Cells were washed with PBS and lysed on ice in 500 µl lysis buffer (50 mM HEPES (pH 7.5), 150 mM NaCl, 1 mM EGTA, 10% Glycerol, 1% Triton X-100, 100 mM NaF, 10 mM $Na_4P_2O_7 \cdot 10H_2O$, 1 mM $Na_3VO_4$, 1 mM phenylmethylsulfonyl fluoride, and 10 mg/ml aprotinin) for 15 min. The cell lysate were used for phosphotyrosine AXL enzyme-linked immunosorbant assay (pY-AXL-ELISA). 96-well Nunc MicroWell™ plates (Fischer Scientific GmbH, Schwerte, Germany) were coated over night with homemade anti-Axl capture antibody 2 µg/ml (clone 259/2, IgG1 isotype) in PBS (100 µl/well). Subsequently 96-well plates were blocked with PBS-0.05% Tween®20+10% FBS for 4 h at 37° C. Plates were washed 5 times with PBS-0.05% Tween®20 and 95 µl of lysate was transferred per well for incubation overnight at 4° C. Plates were washed 5 times with PBS-0.05% Tween®20 (Sigma, Steinheim, Germany). For detection of phosphorylated tyrosine we used homemade biotynilated 4G10-antibody (0.5 µg/ml) in PBS-0.05% Tween®20+10% FBS (100 µl/well) and incubated the 96-well plate for 2 h at room temperature. The anti-phosphotyrosine mouse monoclonal antibody 4G10 was biotynilated with Sulfo-NHS®-Biotin according to the suppliers protocol (Pierce, Rockford, Ill., USA) and purified by Mirco Bio-Spin 6 Chromatograpy Columns (BIO RAD Laboratories, Inc., Hercules, Calif., USA) using PBS as diluent. Plates were washed 5 times with PBS-0.05% Tween®20. For biding to biotin Alkaline Phosphatase Conjugated Strepavidin SA110 (Millipore, Billerica, Mass., USA) (1:4000) was used in PBS-0.05% Tween20+10% FBS (100 µl/well) and incubated for 30 min at room temperature. Plates were washed 5 times with PBS-0.05% Tween20. For fluorimetric detection of alkaline phosphatase AttoPhos Substrate Set (Roche diagnostics GmbH, Mannheim, Germany) was used (100 µl/well). The fluorimetric signal was quantified after 90 min at 430/560 nm wavelength using a TECAN Ultra Evolution plate reader (Tecan Deutschland GmbH, Crailsheim, Germany).

Table Ia below shows for the cell line NIH-3T3-Axl in column 2 the half-maximal inhibition concentration ($IC_{50}$) values of representative compounds according to general formula (I) (+=3 µM>$IC_{50}$>500 nM & ++=$IC_{50}$≤500 nM) obtained according to the disclosure above of Assay Example A.

TABLE Ia

Inhibitory effect of the compounds of the present invention on the NIH-3T3-axl cell line

| Example No | pY-Axl-ELISA on NIH-3T3-Axl cells (cellular IC50 [nM]) |
|---|---|
| 4 | ++ |
| 5 | ++ |
| 6 | ++ |
| 7 | ++ |
| 8 | ++ |
| 9 | ++ |
| 10 | ++ |
| 11 | ++ |
| 12 | ++ |
| 34 | ++ |
| 35 | ++ |
| 36 | ++ |
| 37 | ++ |
| 38 | ++ |
| 40 | ++ |
| 43 | ++ |
| 44 | ++ |
| 45 | ++ |
| 46 | ++ |
| 47 | ++ |
| 48 | ++ |
| 49 | ++ |
| 50 | ++ |
| 51 | ++ |
| 52 | ++ |
| 53 | ++ |
| 54 | ++ |
| 55 | ++ |
| 56 | ++ |
| 57 | ++ |
| 58 | ++ |
| 59 | ++ |
| 62 | ++ |
| 63 | ++ |
| 64 | ++ |
| 65 | ++ |
| 66 | ++ |
| 67 | ++ |
| 76 | ++ |
| 77 | ++ |
| 78 | ++ |
| 81 | ++ |
| 82 | ++ |
| 87 | ++ |
| 89 | ++ |
| 99 | ++ |
| 100 | ++ |
| 104 | ++ |
| 106 | ++ |

TABLE Ia-continued

Inhibitory effect of the compounds of the present invention on the NIH-3T3-axl cell line

| Example No | pY-Axl-ELISA on NIH-3T3-Axl cells (cellular IC50 [nM] |
|---|---|
| 108 | ++ |
| 109 | ++ |
| 110 | ++ |
| 111 | ++ |
| 112 | ++ |
| 113 | ++ |
| 114 | ++ |
| 115 | ++ |
| 116 | ++ |
| 117 | ++ |
| 118 | ++ |
| 119 | ++ |
| 120 | ++ |
| 121 | ++ |
| 124 | ++ |
| 127 | + |
| 128 | + |
| 134 | + |
| 136 | + |
| 144 | ++ |
| 145 | ++ |
| 146 | ++ |
| 147 | + |
| 148 | + |
| 151 | ++ |
| 152 | ++ |
| 153 | ++ |
| 154 | ++ |
| 155 | ++ |
| 156 | ++ |
| 157 | ++ |
| 158 | ++ |
| 171 | + |
| 172 | + |
| 173 | + |
| 174 | + |
| 175 | + |
| 176 | + |
| 177 | ++ |
| 178 | ++ |
| 179 | ++ |
| 180 | ++ |
| 181 | ++ |
| 182 | ++ |
| 184 | ++ |
| 185 | + |
| 186 | ++ |
| 191 | + |
| 193 | + |
| 194 | + |
| 197 | + |
| 198 | + |
| 199 | + |
| 201 | + |
| 202 | + |
| 207 | + |
| 208 | ++ |
| 209 | ++ |
| 210 | ++ |
| 211 | ++ |
| 212 | ++ |

Table Ib below shows the inhibitory effect of some compounds of the present invention on the cell line HS578T. In column 2 the experimental data of the "Matrigel outgrowth assay/branching assay" (+=25 µM>IC$_{50}$>10.0 µM & ++=IC$_{50}$≤10.0 µM) as disclosed below under Assay Example E are shown and in column 3 the experimental data of the "Cell vitality assay (ATP assay)" (+=50 µM>IC$_{50}$>12.5 µM & ++=IC$_{50}$≤12.5 µM) as disclosed below in section Assay Example B and in column 4 the experimental data of the "Wound healing migration assay" (+=50 µM>IC$_{50}$>12.5 µM & ++=IC$_{50}$≤12.5 µM) as outlined under Assay Example D are provided.

TABLE Ib

Inhibitory effect of the compounds of the present invention on the HS578T cell line

| Example No | Total branching inhibition in Matrigel HS578T [µM] | IC50 ATP-Assay HS578T after 72 h [µM] | IC50 Wound healing Assay HS578T [µM] |
|---|---|---|---|
| 1 | ++ | ++ | ++ |
| 2 | | | |
| 3 | | | |
| 4 | ++ | ++ | ++ |
| 5 | + | ++ | + |
| 6 | ++ | ++ | ++ |
| 7 | + | ++ | ++ |
| 8 | ++ | + | ++ |
| 9 | + | ++ | + |
| 10 | ++ | + | ++ |
| 11 | + | ++ | ++ |
| 12 | ++ | ++ | ++ |
| 13 | | | |
| 14 | | | |
| 15 | ++ | | |
| 16 | | | |
| 17 | ++ | | |
| 18 | ++ | | |
| 19 | | | |
| 20 | | | |
| 21 | ++ | | |
| 22 | | | |
| 23 | | | |
| 24 | | | |
| 25 | ++ | | |
| 26 | ++ | | |
| 27 | ++ | | |
| 28 | + | | |
| 29 | ++ | | |
| 30 | | | |
| 31 | | | |
| 32 | ++ | | |
| 33 | ++ | | |
| 34 | ++ | ++ | ++ |
| 35 | ++ | ++ | − |
| 36 | + | ++ | + |
| 37 | + | ++ | + |
| 38 | ++ | + | ++ |
| 39 | | | |
| 40 | ++ | ++ | ++ |
| 41 | ++ | | |
| 42 | | | |
| 43 | ++ | ++ | ++ |
| 44 | ++ | ++ | ++ |
| 45 | ++ | ++ | ++ |
| 46 | ++ | ++ | ++ |
| 47 | ++ | ++ | ++ |
| 48 | + | ++ | ++ |
| 49 | + | ++ | ++ |
| 50 | ++ | ++ | ++ |
| 51 | ++ | ++ | ++ |
| 52 | ++ | ++ | ++ |
| 53 | + | ++ | ++ |
| 54 | + | ++ | ++ |
| 55 | ++ | + | ++ |
| 56 | + | + | ++ |
| 57 | ++ | ++ | ++ |
| 58 | ++ | ++ | ++ |
| 59 | ++ | ++ | ++ |
| 60 | | | |
| 61 | | | |
| 62 | + | ++ | + |
| 63 | ++ | ++ | ++ |
| 64 | + | ++ | ++ |
| 65 | + | ++ | ++ |
| 66 | + | ++ | ++ |
| 67 | ++ | ++ | ++ |

TABLE Ib-continued

Inhibitory effect of the compounds of the present invention on the HS578T cell line

| Example No | Total branching inhibition in Matrigel HS578T [μM] | IC50 ATP-Assay HS578T after 72 h [μM] | IC50 Wound healing Assay HS578T [μM] |
|---|---|---|---|
| 68 |  |  |  |
| 69 |  |  |  |
| 70 | ++ |  |  |
| 71 |  |  |  |
| 72 | ++ |  |  |
| 73 |  |  |  |
| 74 |  |  |  |
| 75 | ++ |  |  |
| 76 | + | ++ | + |
| 77 | ++ | ++ | ++ |
| 78 | ++ | ++ | ++ |
| 79 |  |  |  |
| 80 |  |  |  |
| 81 | ++ | ++ | + |
| 82 | ++ | ++ | + |
| 83 | ++ |  |  |
| 84 | ++ |  |  |
| 85 | ++ |  |  |
| 86 | ++ |  |  |
| 87 | ++ | + | ++ |
| 88 | + |  |  |
| 89 | ++ | ++ | ++ |
| 90 |  |  |  |
| 91 |  |  |  |
| 92 | + | ++ | + |
| 93 | ++ |  |  |
| 94 |  |  |  |
| 95 | ++ |  |  |
| 96 |  |  |  |
| 97 |  |  |  |
| 98 |  |  |  |
| 99 | ++ | ++ | ++ |
| 100 | ++ | ++ | ++ |
| 101 | + |  |  |
| 102 | + | ++ | ++ |
| 104 | + | ++ | ++ |
| 106 | + | ++ | + |
| 108 | + | ++ | + |
| 109 | + | ++ | + |
| 110 | ++ | ++ | ++ |
| 111 | ++ | ++ | ++ |
| 112 | ++ | ++ | ++ |
| 113 | ++ | ++ | ++ |
| 114 | + | ++ | + |
| 115 | ++ | ++ | ++ |
| 116 | + | ++ | ++ |
| 117 | + | ++ | ++ |
| 119 | ++ | ++ | ++ |
| 120 | + | + | + |
| 121 | + | + | + |
| 124 | ++ | ++ | ++ |
| 125 | + | ++ | ++ |
| 126 | + | ++ | ++ |
| 127 | ++ | ++ | ++ |
| 128 | ++ | ++ | ++ |
| 129 | ++ | ++ | ++ |
| 130 | ++ | ++ | + |
| 131 | + | ++ | + |
| 132 | + | + | + |
| 133 | ++ | ++ | ++ |
| 134 | ++ | ++ | ++ |
| 135 | + | + | + |
| 136 | ++ | ++ | ++ |
| 137 | + | + | + |
| 138 | + | + | + |
| 139 | + | + | + |
| 140 | + | + | + |
| 141 | + | + | + |
| 142 | + | + | + |
| 143 | ++ | ++ | ++ |
| 144 | + | ++ | ++ |
| 145 | + | ++ | ++ |
| 146 | + | ++ | ++ |
| 147 | ++ | ++ | ++ |
| 148 | + | ++ | + |
| 149 | + | + | + |
| 150 | + | ++ | + |
| 151 | ++ | ++ | ++ |
| 152 | ++ | ++ | ++ |
| 153 | + | ++ | ++ |
| 154 | + | ++ | ++ |
| 155 | + | ++ | ++ |
| 156 | + | ++ | ++ |
| 157 | + | ++ | ++ |
| 158 | + | ++ | ++ |
| 159 | + | ++ | + |
| 160 | + | ++ | ++ |
| 161 | + | ++ | + |
| 162 | + | ++ | + |
| 163 | + | ++ | + |
| 164 | + | ++ | + |
| 165 | + | ++ | + |
| 166 | + | ++ | + |
| 167 | + | + | + |
| 168 | + | + | + |
| 169 | + | + | + |
| 170 | + | + | + |
| 171 | + | + | + |
| 172 | ++ | ++ | ++ |
| 173 | + | ++ | + |
| 174 | ++ | ++ | ++ |
| 175 | ++ | ++ | ++ |
| 176 | ++ | ++ | ++ |
| 177 | ++ | ++ | ++ |
| 178 | ++ | ++ | + |
| 179 | + | ++ | ++ |
| 180 | ++ | ++ | ++ |
| 181 | ++ | ++ | ++ |
| 182 | + | ++ | ++ |
| 183 | + | + | + |
| 184 | + | ++ | ++ |
| 185 | + | ++ | + |
| 186 | + | ++ | ++ |
| 187 | ++ | ++ | ++ |
| 188 | ++ | ++ | ++ |
| 189 | + | + | + |
| 190 | + | + | + |
| 191 | + | ++ | ++ |
| 192 | + | ++ | + |
| 193 | + | + | ++ |
| 194 | + | + | + |
| 195 | + | + | + |
| 196 | + | + | + |
| 197 | + | + | + |
| 198 | + | + | + |
| 199 | + | + | + |
| 200 | + | + | + |
| 201 | + | + | + |
| 202 | + | + | + |
| 203 | + | ++ | ++ |
| 204 | + | + | + |
| 205 | + | + | + |
| 206 | + | + | + |
| 207 | + | ++ | ++ |
| 208 | + | ++ | + |
| 209 | ++ | ++ | ++ |
| 210 | ++ | ++ | ++ |
| 211 | + | ++ | ++ |
| 212 | + | + | + |

Cell Lines Used for Experiments:

| Cell line | Source | Description |
|---|---|---|
| Hs578T | ECACC | Mammary glad, adenocarcinoma |
| MDA-MB231 | ATCC no. HTB-26 | Mammary glad, adenocarcinoma |
| MCF10A | ATCC no. CRL-10317 | Mammary gland; breast |
| MDA-MB435S | ATCC no. HTB-129 | Mammary glad, adenocarcinoma |
| SF126 | M. Rosenblum | Brain, glioblastoma |
| SF763 | SUGEN | Brain, glioblastoma |
| U118 | SUGEN | Brain, glioblastoma |
| U138 | SUGEN | Brain, glioblastoma |
| U373 | SUGEN | Brain, glioblastoma |
| A172 | CRL-1620 | Brain, glioblastoma |
| A549 | ATCC no. CCL-185 | Lung, carcinoma |
| NCI-H460 | ATCC no. HTB-177 | Lung, carcinoma |
| NCI-H1299 | ATCC no. CRL-5803 | Lung, carcinoma |
| C8161 | B. Gillies | Skin, melanoma |
| SK-MEL-28 | ATCC no. HTB-72 | Skin, melanoma |
| MIA PaCa-2 | ATCC no. CRL-1420 | Pancreas, carcinoma |
| ASPC-1 | ATCC no. CRL-1682 | Pancreas, adenocarcinoma |
| Panc-1 | ATCC no. CRL-1469 | Pancreas, epithelioid carcinoma |
| 786-0 | ATCC no. CRL-1932 | Kidney, renal cell adenocarcinoma |
| DU145 | ATCC no. HTB-81 | Prostate, carcinoma |
| PC3 | ATCC no. CRL-1435 | Prostate, adenocarcinoma |
| HT29 | ATCC no. HTB-38 | Colon, colorectal adenocarcinoma |

Assay Example B

Cell Vitality Assay

The CellTiter-Glo® Luminescent Cell Viability Assay (Promega Corporation. Madison, Wis., USA) is method a determining the number of viable cells in culture based on quantification of the ATP being present which is an indicator of metabolically active cells was used according to manufacturers protocol, In detail the assay was performed in a 96 well format were 1000 cells/well were incubated with indicated compound at concentration of 12.5 µM, 6.25 µM, 3.125 µM, 1.56 µM, 0.78 µM, 0.39 µM, 0.195 µM as well as DMSO control for 72 h in 100 µl cell culture medium. IC50 values were calculated as 50% of ATP amount compared to DMSO control.

Protocol for the CellTiter-Glo® Luminescent Cell Viability Assay
1. Prepare opaque-walled multiwell plates with mammalian cells in culture medium, 100 µl per well for 96-well plates
2. Prepare control wells containing medium without cells to obtain a value for background luminescence.
3. Add the compound to be tested to experimental wells, and incubate according to culture protocol.
4. Equilibrate the plate and its contents at room temperature for approximately 30 minutes.
5. Add a volume of CellTiter-Glo® Reagent (Promega Corporation. Madison, Wis.) equal to the volume of cell culture medium present in each well.
6. Mix contents for 2 minutes on an orbital shaker to induce cell lysis.
7. Allow the plate to incubate at room temperature for 10 minutes to stabilize luminescent signal.
8. Record luminescence on Microplate Luminometer LB96V (Berthold Tchnologies, Bad Wildbad, Germany). An integration time of 0.1 and 1 second per well Table IIa below shows the $IC_{50}$ values of representative compounds according to general formula (I) (+=50 µM>$IC_{50}$>12.5 µM & ++=$IC_{50}$≤12.5 µM).

| | IC50 ATP-Assay after 72 h/[µM] | | | | | | | |
|---|---|---|---|---|---|---|---|---|
| Example No | SF763 | A172 | SF126 | U118 | U138 | Hs578T | MDA-MB231 | C8161 |
| 1 | ++ | ++ | ++ | ++ | ++ | + | + | + |
| 4 | | ++ | ++ | ++ | | | | |
| 6 | | ++ | ++ | ++ | | | | |
| 7 | ++ | + | + | + | ++ | ++ | ++ | ++ |
| 8 | ++ | ++ | ++ | ++ | ++ | + | — | ++ |
| 10 | ++ | ++ | ++ | ++ | ++ | + | ++ | ++ |
| 11 | | + | + | + | | | | |
| 12 | | ++ | ++ | ++ | | | | |
| 14 | ++ | | ++ | + | + | — | ++ | ++ |
| 21 | + | | + | + | — | — | + | + |
| 25 | ++ | | ++ | ++ | ++ | ++ | ++ | ++ |
| 29 | + | | ++ | ++ | ++ | + | ++ | ++ |
| 32 | ++ | | ++ | ++ | ++ | ++ | ++ | ++ |
| 33 | ++ | | ++ | ++ | ++ | ++ | ++ | ++ |
| 38 | ++ | ++ | ++ | ++ | ++ | + | ++ | ++ |
| 40 | | ++ | ++ | + | | | | |
| 41 | ++ | | + | ++ | ++ | ++ | ++ | ++ |
| 45 | | ++ | ++ | ++ | | | | |
| 47 | ++ | ++ | ++ | ++ | ++ | ++ | + | + |
| 49 | | ++ | ++ | ++ | | | | |
| 51 | | ++ | ++ | ++ | | | | |
| 54 | | ++ | + | ++ | | | | |
| 55 | + | | ++ | + | + | + | ++ | ++ |
| 56 | ++ | | ++ | + | ++ | + | + | ++ |
| 59 | ++ | | + | + | ++ | ++ | ++ | ++ |
| 63 | ++ | | + | ++ | + | ++ | ++ | ++ |
| 66 | | ++ | ++ | ++ | | | | |
| 70 | + | | ++ | ++ | ++ | + | + | + |
| 72 | + | | + | + | + | + | + | + |
| 77 | ++ | ++ | + | ++ | ++ | ++ | + | ++ |
| 78 | | ++ | ++ | ++ | | | | |
| 87 | ++ | ++ | ++ | ++ | ++ | + | + | ++ |
| 88 | + | | + | ++ | + | ++ | ++ | ++ |
| 93 | + | | ++ | ++ | + | ++ | + | ++ |

-continued

| | IC50 ATP-Assay after 72 h/[μM] | | | | | | | |
|---|---|---|---|---|---|---|---|---|
| Example No | SF763 | A172 | SF126 | U118 | U138 | Hs578T | MDA-MB231 | C8161 |
| 95 | ++ | | ++ | ++ | ++ | + | ++ | + |
| 99 | ++ | ++ | ++ | ++ | ++ | ++ | ++ | + |
| 100 | | ++ | ++ | ++ | | | | |
| 104 | | + | + | + | | | | |
| 110 | | ++ | ++ | ++ | | | | |
| 112 | | ++ | ++ | ++ | | | | |
| 119 | | ++ | ++ | ++ | | | | |
| 151 | | ++ | ++ | ++ | | | | |
| 155 | | ++ | ++ | ++ | | | | |
| 156 | | ++ | ++ | ++ | | | | |
| 157 | | ++ | ++ | ++ | | | | |
| 158 | | ++ | ++ | ++ | | | | |
| 177 | | ++ | ++ | ++ | | | | |
| 178 | | ++ | ++ | ++ | | | | |
| 179 | | ++ | ++ | ++ | | | | |
| 181 | | ++ | ++ | ++ | | | | |
| 184 | | ++ | ++ | ++ | | | | |
| 209 | | ++ | ++ | ++ | | | | |
| 210 | | ++ | ++ | ++ | | | | |

Table IIb below shows the $IC_{50}$ values of representative compounds according to general formula (I) (+=50 μM>$IC_{50}$>12.5 μM & ++=$IC_{50}$≤12.5 μM).

| Example No | MCF10A | MiaPaca-2 | Aspc-1 | Panc-1 | DU145 | PC3 | 786-0 | SF126 |
|---|---|---|---|---|---|---|---|---|
| 24 | ++ | ++ | ++ | + | ++ | + | ++ | ++ |
| 12 | | ++ | ++ | + | ++ | ++ | ++ | ++ |
| 1 | | ++ | ++ | + | ++ | ++ | + | ++ |
| 66 | | ++ | ++ | ++ | ++ | ++ | ++ | ++ |

Table IIc below shows the $IC_{50}$ values of representation compounds according to general formula (I) (+=50 μM>$IC_{50}$>12.5 μM & ++=$IC_{50}$≤12.5 μM).

| Example No | U118 | U373 | A549 | H460 | HT29 | MDA-MB435s | MDA-MB231 |
|---|---|---|---|---|---|---|---|
| 24 | + | ++ | ++ | ++ | ++ | ++ | ++ |
| 12 | ++ | ++ | ++ | ++ | ++ | ++ | ++ |
| 1 | ++ | ++ | ++ | ++ | ++ | ++ | ++ |
| 66 | ++ | ++ | ++ | ++ | ++ | ++ | ++ |

Assay Example C

Apoptosis Assay

The Cellomics BioApplication (Thermo Fischer Cellomics Products, Pittsburgh, Pa.) is an automated image analysis algorithm that provides detailed analysis of phenotypes related to apoptosis. As one of the most prominent characteristics of apoptotics cell a nucleus condensation takes place. This can be measured fluorescence signal intensity using a CCD camera on fully automated microscope system. The Cellomics system is able to quantify the fluorescence intensity per single nucleus and calculates the variation of signal intensity in each cell population. Healthy cell have a low variation of signal intensity in contrast to apoptotic cell with condensed nucleus exhibiting a high variation of signal intensity. Additionally the number of detected cell decreases normally in apoptotic cell populations. In detail 5000 cell per 96 well were labeled with DNA intercalating dye (Hoechst 33342, Sigma, Steinheim, Germany) to visualize the nucleus in a fluorescence microscope under live conditions. The apoptosis assay was performed 24 h and 48 h after addition of compound at concentrations 12.5 μM, 6.25 μM, 3.125 μM, 1.56 μM, 0.78 μM, 0.39 μM as well as DMSO control for 48 h.

Table III below shows the $IC_{50}$ values of representative compounds according to general formula (I) (+=50 μM>$IC_{50}$>12.5 μM & ++=$IC_{50}$≤12.5 μM).

| Example No | Apoptosis induction in C8161 [μM] | Apoptosis induction in Hs578T [μM] | Apoptosis induction in SF126 [μM] | Apoptosis induction in SF763 [μM] | Apoptosis induction in U118 [μM] | Apoptosis induction in U138 [μM] |
|---|---|---|---|---|---|---|
| 1 | ++ | ++ | ++ | + | ++ | ++ |
| 7 | ++ | ++ | — | ++ | + | ++ |
| 8 | ++ | ++ | ++ | ++ | ++ | + |
| 10 | ++ | ++ | + | + | ++ | ++ |

-continued

| Example No | Apoptosis induction in C8161 [μM] | Apoptosis induction in Hs578T [μM] | Apoptosis induction in SF126 [μM] | Apoptosis induction in SF763 [μM] | Apoptosis induction in U118 [μM] | Apoptosis induction in U138 [μM] |
|---|---|---|---|---|---|---|
| 12 | + | | | | | |
| 14 | ++ | ++ | ++ | ++ | + | ++ |
| 15 | ++ | ++ | ++ | ++ | — | ++ |
| 16 | ++ | ++ | ++ | ++ | — | ++ |
| 17 | ++ | ++ | ++ | ++ | + | ++ |
| 18 | ++ | ++ | ++ | ++ | ++ | ++ |
| 21 | ++ | ++ | ++ | ++ | ++ | + |
| 24 | ++ | | | | | |
| 25 | ++ | ++ | ++ | ++ | ++ | ++ |
| 26 | ++ | ++ | + | ++ | + | ++ |
| 27 | ++ | ++ | + | ++ | ++ | ++ |
| 28 | ++ | ++ | ++ | ++ | ++ | ++ |
| 29 | ++ | ++ | ++ | ++ | — | + |
| 32 | ++ | ++ | ++ | ++ | ++ | ++ |
| 33 | ++ | + | ++ | ++ | + | ++ |
| 34 | ++ | + | ++ | ++ | ++ | ++ |
| 35 | ++ | ++ | ++ | ++ | ++ | + |
| 38 | ++ | ++ | ++ | ++ | ++ | ++ |
| 41 | ++ | ++ | ++ | ++ | ++ | ++ |
| 47 | + | ++ | + | ++ | ++ | ++ |
| 55 | ++ | ++ | ++ | ++ | + | ++ |
| 56 | ++ | ++ | ++ | ++ | ++ | ++ |
| 57 | ++ | ++ | ++ | + | ++ | ++ |
| 58 | ++ | + | ++ | ++ | + | ++ |
| 59 | ++ | ++ | ++ | ++ | ++ | ++ |
| 63 | ++ | ++ | ++ | ++ | ++ | ++ |
| 70 | ++ | ++ | ++ | ++ | ++ | ++ |
| 72 | ++ | ++ | + | ++ | ++ | + |
| 75 | ++ | ++ | ++ | ++ | ++ | ++ |
| 77 | ++ | ++ | ++ | ++ | ++ | ++ |
| 80 | + | ++ | + | + | ++ | + |
| 81 | ++ | ++ | ++ | ++ | ++ | ++ |
| 82 | ++ | ++ | ++ | ++ | ++ | ++ |
| 83 | ++ | ++ | ++ | ++ | ++ | ++ |
| 84 | ++ | ++ | ++ | ++ | ++ | ++ |
| 85 | ++ | ++ | ++ | ++ | + | ++ |
| 86 | ++ | ++ | ++ | ++ | ++ | ++ |
| 87 | ++ | ++ | ++ | ++ | ++ | + |
| 88 | ++ | ++ | ++ | ++ | ++ | ++ |
| 93 | ++ | ++ | ++ | ++ | ++ | ++ |
| 95 | ++ | ++ | ++ | ++ | ++ | ++ |
| 99 | ++ | ++ | ++ | ++ | + | ++ |
| 100 | ++ | ++ | ++ | ++ | + | ++ |
| 101 | ++ | ++ | + | ++ | — | ++ |
| 102 | ++ | ++ | ++ | ++ | ++ | ++ |

Assay Example D

Wound Healing Migration Assay

This method mimics cell migration during wound healing in vivo. The basic steps involve creating a "wound" in a cell monolayer, capturing the images at the beginning and at regular intervals during cell migration to close the wound, and comparing the images to quantify the migration rate of the cells. In detail, 150000 cell/24 well have been seeded and allowed to form a monolayer overnight. Subsequently a "wound" or "scratch" has been performed with a 1000 μl pipette tip. The STDV of wound size is normally below 10% at time point t0. The assay was stopped by fixation with 0.05% Crystal violet/20% methanol when control scratches were closed. The assay was terminated between 48 h and 72 h depending on the migration potential of the indicated cell line. The "wounds" were visualized with a Zeiss Axiovert S100 microscope (Carl Zeiss UK, Welwyn Garden City, UK). The tested compounds were used at 12.5 μM, 6.25, 3.125 μM and DMSO control. IC50 values have been calculated as 50% wound size in between t0 and t48 or t72.

Table IV below shows the $IC_{50}$ values of representative compounds according to general formula (I) (+=50 μM>$IC_{50}$>12.5 μM & ++=$IC_{50}$≤12.5 μM).

| Example No | IC50 Wound healing Assay/[μM] | | | | |
|---|---|---|---|---|---|
| | SF763 | C8161 | A172 | SF126 | U118 |
| 1 | ++ | ++ | ++ | ++ | ++ |
| 4 | | ++ | ++ | ++ | ++ |
| 6 | | | ++ | ++ | ++ |
| 7 | ++ | ++ | ++ | ++ | ++ |
| 8 | ++ | + | ++ | ++ | ++ |
| 10 | ++ | ++ | ++ | ++ | ++ |
| 11 | | | + | ++ | + |
| 12 | | ++ | ++ | ++ | ++ |
| 14 | + | + | | | |
| 15 | ++ | + | | | |
| 16 | + | + | | | |
| 17 | + | ++ | | | |
| 18 | + | ++ | | | |
| 21 | + | ++ | | | |
| 24 | | ++ | | | |
| 25 | + | + | | | |
| 26 | ++ | + | | | |
| 27 | ++ | + | | | |
| 28 | ++ | ++ | | | |
| 29 | ++ | ++ | | | |
| 32 | ++ | ++ | | | |

-continued

| Example No | IC50 Wound healing Assay/[μM] | | | | |
|---|---|---|---|---|---|
| | SF763 | C8161 | A172 | SF126 | U118 |
| 33 | + | ++ | | | |
| 34 | + | ++ | | | |
| 35 | ++ | ++ | | | |
| 38 | + | ++ | ++ | ++ | ++ |
| 40 | | ++ | ++ | ++ | |
| 41 | ++ | + | | | |
| 45 | | | ++ | ++ | ++ |
| 47 | ++ | ++ | ++ | ++ | ++ |
| 49 | | | ++ | ++ | ++ |
| 51 | | | ++ | ++ | ++ |
| 54 | | | ++ | ++ | ++ |
| 55 | + | + | | | |
| 56 | + | ++ | | | |
| 57 | + | ++ | | | |
| 58 | ++ | + | | | |
| 59 | ++ | + | | | |
| 63 | ++ | + | | | |
| 66 | | | ++ | ++ | ++ |
| 70 | ++ | + | | | |
| 72 | ++ | ++ | | | |
| 75 | − | + | | | |
| 77 | ++ | ++ | ++ | ++ | ++ |
| 78 | | ++ | ++ | ++ | |
| 80 | ++ | ++ | | | |
| 81 | + | ++ | | | |
| 82 | ++ | ++ | | | |
| 83 | ++ | ++ | | | |
| 84 | + | ++ | | | |
| 85 | + | ++ | | | |
| 86 | + | + | | | |
| 87 | ++ | + | ++ | ++ | ++ |
| 88 | ++ | + | | | |
| 93 | + | ++ | | | |
| 95 | + | + | | | |
| 99 | ++ | + | ++ | ++ | ++ |
| 100 | ++ | + | ++ | ++ | ++ |
| 101 | + | + | | | |
| 102 | ++ | + | | | |
| 104 | | + | ++ | ++ | |
| 110 | | ++ | ++ | ++ | |
| 112 | | ++ | ++ | ++ | |
| 119 | | ++ | ++ | ++ | |
| 151 | | ++ | ++ | ++ | |
| 155 | | ++ | ++ | ++ | |
| 156 | | ++ | ++ | ++ | |
| 157 | | ++ | ++ | ++ | |
| 158 | | ++ | ++ | ++ | |
| 177 | | ++ | ++ | ++ | |
| 178 | | ++ | ++ | ++ | |
| 179 | | ++ | ++ | + | |
| 181 | | ++ | ++ | ++ | |
| 184 | | ++ | ++ | ++ | |
| 209 | | ++ | ++ | ++ | |
| 210 | | ++ | ++ | ++ | |

Assay Example E

Matrigel Outgrowth Assay/Branching Assay

The Matrigel outgrowth assay is based on the ability of tumor cell to penetrate a solid gel of extracellular matrix proteins mimicking the metastasis formation in vivo. While cells with low invasive potential appear as roundish cell or cell cluster, cells with high invasive potential penetrate the Matrigel and form polymorphic structures. In detail 65 μl of Matrigel matrix (Matrigel™ Matrix, BD Biosciences, Bedford, Mass., USA) with a concentration of 3 mg/ml have been polymerized in 96 well plates for 1 h at 37° C. Subsequently 5000 cell/well were seeded into each well containing cell culture medium and indicated compound with concentrations of 3.125 μM, 1.56 μM and 0.78 μM as well as DMSO control. After 48 h, 72 h and 96 h images of cell were taken on an inverted microscope using a 5× objective (Zeiss Axiovert S100 microscope Carl Zeiss UK, Welwyn Garden City, UK). Only compound concentrations were total branching inhibition was evident were accounted as positive. Method was used as previously described, with some modifications (Thompson E W, et al. Association of increased basement membrane invasiveness with absence of estrogen receptor and expression of vimentin in human breast cancer cell lines. J Cell Physiol 1992; 150:534-44).

Table Va below shows the $IC_{50}$ values of representative compounds according to general formula (I) (+=50 μM>$IC_{50}$>5.0 μM & ++=$IC_{50}$≤5.0 μM).

| Example No | Total branching inhibition in Matrigel U118 [μM] | Total branching inhibition in Matrigel U138 [μM] | Total branching inhibition in Matrigel C8161 [μM] | Total branching inhibition in Matrigel Hs578T [μM] |
|---|---|---|---|---|
| 1 | ++ | ++ | ++ | ++ |
| 7 | ++ | + | ++ | + |
| 8 | ++ | ++ | ++ | ++ |
| 10 | ++ | + | ++ | ++ |
| 12 | ++ | + | ++ | ++ |
| 14 | ++ | + | + | + |
| 15 | ++ | ++ | ++ | ++ |
| 16 | + | ++ | ++ | + |
| 17 | ++ | + | ++ | ++ |
| 18 | ++ | ++ | ++ | ++ |
| 21 | + | + | + | ++ |
| 24 | ++ | + | ++ | ++ |
| 25 | ++ | + | ++ | ++ |
| 26 | ++ | + | ++ | ++ |
| 27 | ++ | ++ | ++ | ++ |
| 28 | ++ | ++ | ++ | + |
| 29 | ++ | + | ++ | ++ |
| 32 | ++ | + | ++ | ++ |
| 33 | ++ | + | ++ | ++ |
| 34 | ++ | + | ++ | ++ |
| 35 | ++ | + | ++ | ++ |
| 38 | ++ | + | ++ | ++ |
| 41 | ++ | + | ++ | ++ |
| 47 | ++ | + | ++ | ++ |
| 55 | ++ | + | ++ | ++ |
| 56 | ++ | + | ++ | + |
| 57 | ++ | ++ | + | ++ |
| 58 | ++ | + | ++ | ++ |
| 59 | + | ++ | ++ | ++ |
| 63 | ++ | ++ | + | ++ |
| 66 | ++ | + | ++ | ++ |
| 70 | ++ | ++ | ++ | ++ |
| 72 | ++ | ++ | ++ | ++ |
| 75 | ++ | + | ++ | ++ |
| 77 | ++ | + | + | ++ |
| 80 | ++ | + | ++ | ++ |
| 81 | + | + | ++ | ++ |
| 82 | ++ | + | + | ++ |
| 83 | ++ | ++ | ++ | ++ |
| 84 | ++ | ++ | ++ | ++ |
| 85 | ++ | + | ++ | ++ |
| 86 | ++ | + | ++ | ++ |
| 87 | ++ | + | ++ | ++ |
| 88 | + | + | ++ | + |
| 93 | ++ | + | ++ | ++ |
| 95 | + | + | ++ | ++ |
| 99 | ++ | ++ | + | ++ |
| 100 | ++ | + | ++ | ++ |
| 101 | ++ | + | ++ | + |
| 102 | ++ | + | ++ | ++ |

Table Vb below shows the $IC_{100}$ values of representative compounds according to general formula (I) (+=$IC_{100}$>12.5 μM & ++=$IC_{100}$≤12.5 μM).

| Example No | Total branching inhibition in Matrigel/[μM] | | | | | | | | |
|---|---|---|---|---|---|---|---|---|---|
| | A172 | SF126 | U118 | PC3 | U373 | U138 | SK-MEL28 | U87MG | NCI-H1299 |
| 1 | ++ | ++ | ++ | ++ | ++ | ++ | ++ | + | ++ |
| 4 | + | ++ | ++ | | | | | | |
| 6 | + | ++ | ++ | | | | | | |
| 7 | + | ++ | ++ | | | | | | |
| 8 | ++ | ++ | ++ | | | | | | |
| 10 | ++ | ++ | ++ | | | | | | |
| 11 | + | + | + | | | | | | |
| 12 | ++ | ++ | ++ | ++ | ++ | ++ | ++ | + | ++ |
| 14 | | ++ | | | | ++ | | | |
| 24 | ++ | ++ | ++ | ++ | ++ | ++ | ++ | + | ++ |
| 38 | ++ | ++ | + | | | | | | |
| 40 | + | ++ | + | | | | | | |
| 45 | + | ++ | ++ | | | | | | |
| 47 | + | ++ | ++ | | | | | | |
| 49 | + | + | + | | | | | | |
| 51 | + | ++ | ++ | | | | | | |
| 54 | + | ++ | + | | | | | | |
| 66 | + | ++ | ++ | ++ | ++ | ++ | ++ | ++ | ++ |
| 77 | + | ++ | ++ | | | | | | |
| 78 | + | ++ | + | | | | | | |
| 87 | ++ | ++ | ++ | | | | | | |
| 99 | + | ++ | ++ | | | | | | |
| 100 | + | ++ | ++ | | | | | | |
| 104 | + | + | + | | | | | | |
| 110 | + | ++ | ++ | | | | | | |
| 112 | ++ | ++ | ++ | | | | | | |
| 119 | ++ | ++ | ++ | | | | | | |
| 151 | ++ | ++ | ++ | | | | | | |
| 155 | ++ | ++ | ++ | | | | | | |
| 156 | + | ++ | ++ | | | | | | |
| 157 | + | ++ | + | | | | | | |
| 158 | + | ++ | ++ | | | | | | |
| 177 | ++ | ++ | ++ | | | | | | |
| 178 | + | ++ | ++ | | | | | | |
| 179 | + | ++ | ++ | | | | | | |
| 181 | + | ++ | ++ | | | | | | |
| 184 | + | ++ | ++ | | | | | | |
| 209 | ++ | ++ | ++ | | | | | | |
| 210 | + | ++ | ++ | | | | | | |

Assay Example F

Boyden Chamber Migration Assay

The Boyden chamber assay is based on a chamber of two medium-filled compartments separated by a microporous membrane of 8 μM (Cell culture insert 8.0 μM pore size, BD Biosciences, Bedford, Mass.). The boyden chamber migration assays were carried out according to the supplier's instructions. In general, 20000 cells are placed in the upper compartment with medium containing 0% FCS plus 0.1% BSA and are allowed to migrate 16 h through the pores of the membrane into the lower compartment, which is filled with cell culture medium containing 10% FCS as chemotactic agents. The cells remaining in the insert were removed with a cotton swab, and the cells on the bottom of the filter were fixed and counted. (Zhang Y X, et al. AXL is a potential target for therapeutic intervention in breast cancer progression. Cancer Res. 2008; 68:1905-15).

Table VI below shows the $IC_{50}$ values of representative compounds according to general formula (I) (+=50 μM>$IC_{50}$>5.0 μM & ++=$IC_{50}$≤5.0 μM).

| Example No | IC50 Boyden chamber migration assay Hs578T [μM] | Example No | IC50 Boyden chamber migration assay Hs578T [μM] | Example No | IC50 Boyden chamber migration assay Hs578T [μM] |
|---|---|---|---|---|---|
| 1 | ++ | 38 | + | 86 | ++ |
| 7 | ++ | 41 | ++ | 87 | ++ |
| 8 | ++ | 47 | ++ | 88 | ++ |
| 10 | ++ | 55 | ++ | 93 | + |
| 14 | ++ | 56 | ++ | 95 | ++ |
| 15 | ++ | 57 | + | 99 | ++ |
| 16 | ++ | 58 | ++ | 100 | ++ |
| 17 | ++ | 59 | ++ | 101 | ++ |
| 18 | ++ | 63 | ++ | 102 | ++ |
| 21 | ++ | 70 | ++ | 86 | ++ |
| 25 | ++ | 72 | ++ | 87 | + |
| 26 | ++ | 75 | ++ | 88 | ++ |
| 27 | ++ | 77 | ++ | 93 | ++ |
| 28 | ++ | 80 | ++ | 95 | ++ |
| 29 | ++ | 81 | ++ | 99 | ++ |
| 32 | ++ | 82 | + | 100 | ++ |
| 33 | ++ | 83 | ++ | 101 | ++ |
| 34 | ++ | 84 | ++ | 102 | ++ |
| 35 | ++ | 85 | ++ | 12 | ++ |
| 24 | ++ | 25 | ++ | 32 | ++ |

Assay Example G

Cell Viability Assay

| Cell line | ATCC no. | Description |
|---|---|---|
| HCT116 wt | CCL-247 ™ | Colorectal carcinoma; Aurora A amplification, Src expression |
| HCT116 def | | Colorectal carcinoma, p53 mutant |
| SW480 | CCL-228 ™ | Colorectal adenocarcinoma; Aurora A amplification, p53 and ras mutation, is positive for expression of c-myc, K-ras, H-ras, N-ras, myb, sis and fos oncogene |
| HT29 | HTB-28 ™ | Colorectal adenocarcinoma; is positive for expression of c-myc, K-ras, H-ras, N-ras, Myb, sis and fos oncogenes, p53 mutation, Aurora A amplification |
| H1993 | CRL-5909 ™ | adenocarcinoma, KEAP1 mutation, MET amplification, CDK6 (copy number >=4 and <7) and CDK4 (copy number >=4 and <7) amplification |
| H1975 | CRL-5908 ™ | adenocarcinoma, EGFR mutant |
| H1650 | CRL-5883 ™ | adenocarcinoma, EGFR del mutant |
| RKO | CRL-2577 ™ | Colon carcinoma, wild type p53+ |
| HCC827 | CRL-2868 ™ | adenocarcinoma, EGFR mutant, MYC and CDK4 (copy number >7) amplification |
| H358 | CRL-5807 ™ | bronchioalveolar carcinoma, RAS mutant |
| H1666 | CRL-5885 ™ | adenocarcinoma; bronchoalveolar carcinoma RAF mutant |
| A549 | CCL-185 ™ | lung carcinoma, EGFR and PLK mutant, wild type p53 |

Conditions of Cell Viability Assay

| Conditions | |
|---|---|
| reference compound: | staurosporine conc 20 nM |
| compound | 10 μM |
| cell number: | 1000 cell/well |
| volume: | 100 μl/well |
| incubation time: | 72 h |
| detection: | CellTiter-Glo Luminescent Cell Viability Assay |

The CellTiter-Glo® Luminescent Cell Viability Assay (Promega Corporation. Madison, Wis., USA) is method a determining the number of viable cells in culture based on quantification of the ATP being present which is an indicator of metabolically active cells was used according to manufacturers protocol. In detail the assay was performed in a 96 well format were 1000 cells/well were incubated with compound at concentration 10 μM as well as DMSO control for 72 h in 100 μl cell culture medium. Percentage of inhibition was calculated compared to ATP amount of DMSO control.

Table VII below shows the percentage (%) of viable cells in the culture treated with representative compounds according to general formula (I) (a=0%-20% viable cells; b=21%-40% viable cells; c=41%-60% viable cells; d>60% viable cells).

| Example | HCT 116wt | HCT 116def | SW480 | HT29 | H1993 | H1975 | H1650 | RKO | HCC827 | H358 | H1666 | A549 |
|---|---|---|---|---|---|---|---|---|---|---|---|---|
| 1 | a | a | a | b | b | b | c | a | b | a | c | d |
| 3 | a | a | a | a | b | b | c | a | d | a | c | b |
| 7 | a | b | a | a | b | b | a | a | a | a | b | c |
| 8 | a | a | a | b | a | a | a | b | a | a | b | c |
| 10 | a | a | a | b | a | b | b | a | a | a | b | b |
| 12 | b | b | b | b | c | c | b | a | b | a | c | d |
| 13 | a | a | a | a | a | a | b | a | a | a | a | b |
| 14 | a | b | a | a | b | b | a | b | b | c | c | c |
| 15 | d | d | b | c | b | c | c | c | d | c | c | d |
| 16 | c | c | a | b | b | a | b | b | c | a | c | c |
| 18 | a | a | a | a | a | a | b | a | b | a | b | b |
| 19 | a | b | a | a | a | b | b | a | b | a | b | b |
| 20 | a | b | a | a | b | b | b | a | c | a | b | d |
| 21 | d | c | b | b | b | c | c | c | d | b | c | d |
| 22 | b | b | a | a | a | a | b | b | b | a | b | d |
| 23 | a | a | a | a | a | a | b | a | b | a | b | c |
| 27 | a | a | a | b | a | b | c | a | d | a | c | d |
| 28 | b | b | a | b | b | b | b | a | b | a | c | b |
| 29 | a | a | a | a | a | a | b | a | b | b | c | c |
| 32 | a | b | a | a | a | b | b | b | c | a | c | c |
| 33 | a | b | a | a | a | b | d | a | b | b | b | c |
| 34 | a | b | a | b | a | a | b | a | d | a | b | d |
| 35 | a | b | a | a | b | a | b | c | c | a | b | d |
| 38 | b | b | a | b | b | d | a | c | c | a | b | d |
| 41 | c | a | a | b | b | a | c | a | c | a | b | b |
| 47 | a | b | b | c | a | a | c | a | c | a | b | c |
| 55 | a | b | b | b | a | d | a | c | c | a | a | b |
| 56 | b | b | a | a | c | a | c | b | b | a | b | d |
| 57 | d | b | a | a | b | a | c | a | d | b | c | d |

-continued

| Example | HCT 116wt | HCT 116def | SW480 | HT29 | H1993 | H1975 | H1650 | RKO | HCC827 | H358 | H1666 | A549 |
|---|---|---|---|---|---|---|---|---|---|---|---|---|
| 58 | a | b | a | a | c | a | d | a | d | b | b | c |
| 59 | a | a | a | a | a | b | d | a | b | b | c | b |
| 63 | a | b | a | b | a | a | c | d | b | a | c | b |
| 70 | c | b | b | b | a | a | c | a | b | b | b | b |
| 72 | b | c | a | a | a | c | c | a | c | b | b | d |
| 75 | b | b | a | a | b | a | b | a | d | a | c | d |
| 77 | a | b | a | c | b | a | b | b | d | a | c | c |
| 80 | b | b | a | c | a | a | d | a | b | a | b | d |
| 81 | b | b | a | b | b | a | b | c | a | a | b | c |
| 82 | a | b | b | a | a | b | b | c | b | b | c | d |
| 83 | a | b | b | a | a | c | b | d | a | a | b | b |
| 84 | a | a | a | a | a | b | a | a | d | a | c | d |
| 85 | a | b | a | b | a | b | b | a | a | b | c | c |
| 86 | b | b | b | a | a | b | b | b | c | a | c | d |
| 87 | c | a | a | a | c | a | b | c | c | a | c | d |
| 88 | c | a | b | b | a | a | c | c | a | a | b | c |
| 93 | d | b | a | a | b | a | b | a | b | a | b | d |
| 95 | b | b | a | a | a | a | b | a | b | a | b | d |
| 99 | a | d | a | b | b | b | b | b | c | a | c | b |
| 100 | a | a | a | b | c | c | b | a | b | a | b | d |
| 101 | b | b | a | a | b | c | c | a | b | a | c | c |
| 102 | a | a | a | a | b | b | c | b | b | a | c | c |

Assay Example H

Cancer Cell Line Based Cellular Kinase Assay

Indicated cancer cell lines were seeded onto 6-well plates ($1.5 \times 10^5$ cells/well) in 1.5 ml DMEM+10% heat inactivated FBS (GIBCO—Invitrogen GmbH, Karlsruhe, Germany) and cultured overnight, followed by serum depletion in DMEM without FBS for 24 h. Serial dilutions of compounds were added, and the cells were incubated for 1 h followed by Gas6 mediated Axl activation with 250 ng/ml recombinant human Gas6 (Catalog Number: 885GS, R&D Systems, Inc., Minneapolis, USA) for 30 minutes. Cells were washed with PBS and lysed on ice in 500 µl lysis buffer (50 mM HEPES (pH 7.5), 150 mM NaCl, 1 mM EGTA, 10% Glycerol, 1% Triton X-100, 100 mM NaF, 10 mM $Na_4P_2O_7 \cdot 10H_2O$, 1 mM $Na_3VO_4$, 1 mM phenylmethylsulfonyl fluoride, and 10 mg/ml aprotinin) for 15 min. The cell lysate were used for phosphotyrosine AXL enzyme-linked immunosorbant assay (pY-AXL-ELISA). 96-well Nunc MicroWell™ plates (Fischer Scientific GmbH, Schwerte, Germany) were coated over night with homemade anti-Axl capture antibody 2 µg/ml (clone 259/2, IgG1 isotype) in PBS (100 µl/well). Subsequently 96-well plates were blocked with PBS-0.05% Tween®20+10% FBS for 4 h at 37° C.

Plates were washed 5 times with PBS-0.05% Tween®20 and 95 µl of lysate was transferred per well for incubation overnight at 4° C. Plates were washed 5 times with PBS-0.05% Tween®20 (Sigma, Steinheim, Germany). For detection of phosphorylated tyrosine we used homemade biotynilated 4G10-antibody (0.5 µg/ml) in PBS-0.05% Tween®20+10% FBS (100 µl/well) and incubated the 96-well plate for 2 h at room temperature. The anti-phosphotyrosine mouse monoclonal antibody 4G10 was biotynilated with Sulfo-NHS®-Biotin according to the suppliers protocol (Pierce, Rockford, Ill., USA) and purified by Mirco Bio-Spin 6 Chromatograpy Columns (BIO RAD Laboratories, Inc., Hercules, Calif., USA) using PBS as diluent. Plates were washed 5 times with PBS-0.05% Tween®20. For biding to biotin Alkaline Phosphatase Conjugated Strepavidin SA110 (Millipore, Billerica, Mass., USA) (1:4000) was used in PBS-0.05% Tween®20+10% FBS (100 µl/well) and incubated for 30 min at room temperature. Plates were washed 5 times with PBS-0.05% Tween®20. For fluorimetric detection of alkaline phosphatase AttoPhos Substrate Set (Roche diagnostics GmbH, Mannheim, Germany) was used (100 µl/well). The fluorimetric signal was quantified after 90 min at 430/560 nm wavelength using a TECAN Ultra Evolution plate reader (Tecan Deutschland GmbH, Crailsheim, Germany).

Table VIII below shows the $IC_{50}$ values of representative compounds according to general formula (I) (+=50 µM>$IC_{50}$>12.5 µM & ++=$IC_{50}$≤12.5 µM).

| Origin | Cell line | AXL | TC | AXL | TC | AXL | TC | AXL | TC |
|---|---|---|---|---|---|---|---|---|---|
| Breast | Hs578T |  | 24 | ++ | 12 |  | 1 |  | 66 |
| Breast | MDA-MB231 | ++ | 24 | ++ | 12 | ++ | 1 | ++ | 66 |
| Brain | SF126 | ++ | 24 | ++ | 12 | ++ | 1 | ++ | 66 |
| Brain | U118 | + | 24 | ++ | 12 | ++ | 1 | ++ | 66 |
| Brain | U138 | ++ | 24 | ++ | 12 | ++ | 1 | ++ | 66 |
| Brain | U373 | ++ | 24 | ++ | 12 | ++ | 1 | ++ | 66 |
| Brain | U87MG | — | 24 | + | 12 | + | 1 | — | 66 |
| Brain | A172 | ++ | 24 | ++ | 12 | ++ | 1 | ++ | 66 |
| Skin | C8161 | + | 24 | + | 12 | + | 1 | + | 66 |
| Skin | SK-MEL-28 | — | 24 | + | 12 | + | 1 | — | 66 |
| Pancreas | ASPC-1 | ++ | 24 | ++ | 12 | ++ | 1 | ++ | 66 |
| Prostate | PC3 | + | 24 | ++ | 12 | ++ | 1 | ++ | 66 |
| Prostate | DU145 | ++ | 24 | ++ | 12 | ++ | 1 | ++ | 66 |
| Lung | H460 | ++ | 24 | ++ | 12 | ++ | 1 | ++ | 66 |
| Lung | A549 | ++ | 24 | ++ | 12 | ++ | 1 | ++ | 66 |
| Lung | H1299 | ++ | 24 | ++ | 12 | ++ | 1 | ++ | 66 |

TC: tested compound (3 µM-0.1 µM)
AXL: Inhibition of AXL-pY

The invention claimed is:

1. A method of treating a subject having AXL receptor tyrosine kinase induced cancer, tumors or cancer metastases comprising administering to the subject who would benefit from such treatment a therapeutically effective amount a compound of the general formula (I) or a pharmaceutical composition containing at least one compound of the general formula (I)

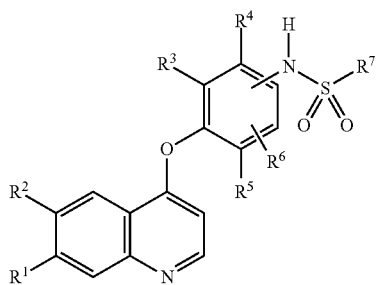

(I)

wherein
—$R^1$ or —$R^2$ represents —O—X—$R^8$;
if —$R^1$ represents —O—X—$R^8$ than —$R^2$ represents —H, —OH, —OCH$_3$, —OCF$_3$, —OC$_2$H$_5$, —OC$_3$H$_7$, —OCH$_2$CH$_2$—OCH$_3$, —OCH$_2$CH$_2$OC$_2$H$_5$;
if —$R^2$ represents —O—X—$R^8$ than —$R^1$ represents —H, —OH, —OCH$_3$, —OCF$_3$, —OC$_2$H$_5$, —OC$_3$H$_7$, —OCH$_2$CH$_2$—OCH$_3$, —OCH$_2$CH$_2$OC$_2$H$_5$;
—X— represents —CR$^{11}$R$^{12}$—CR$^{13}$R$^{14}$—, —CR$^{11}$R$^{12}$—CR$^{13}$R$^{14}$—CR$^{15}$R$^{16}$—, —CR$^{11}$R$^{12}$—CR$^{13}$R$^{14}$—CR$^{15}$R$^{16}$—CR$^{17}$R$^{18}$—, —CR$^{11}$R$^{12}$—CR$^{13}$R$^{14}$—CR$^{15}$R$^{16}$—CR$^{17}$R$^{18}$—CR$^{19}$R$^{20}$—, —CR$^{11}$R$^{12}$—CR$^{13}$R$^{14}$—CR$^{15}$R$^{16}$—CR$^{17}$R$^{18}$—CR$^{19}$R$^{20}$—CR$^{21}$R$^{22}$, —(CH$_2$)$_n$—NH—, —CO—, —(CH$_2$)$_n$—CO—, —(CH$_2$)$_n$—NH—CO—NH—, —(CH$_2$)$_n$—CO—NH—, —(CH$_2$)$_n$—O—CO—NH—, —(CH$_2$)$_n$—O—CO—, —(CH$_2$)$_n$—O—, —(CH$_2$)$_n$—;
n is an integer selected from 1, 2, 3, 4, 5 and 6;
—$R^3$, —$R^4$, —$R^5$, —$R^6$ are independently of each other selected from hydrogen, halogen, nitro, C$_{1-6}$ alkyl, C$_3$-C$_{10}$-cycloalkyl, C$_{1-6}$ alkoxy, wherein the C$_{1-6}$ alkyl, C$_3$-C$_{10}$-cycloalkyl or C$_{1-6}$ alkoxy groups are optionally mono- or polysubstituted by hydroxyl, halogen, C$_{1-4}$ alkyl and/or C$_{1-4}$ alkoxy, wherein the C$_{1-4}$ alkyl and/or C$_{1-4}$ alkoxy groups are optionally mono- or polysubstituted by hydroxyl and/or halogen;
—$R^7$ represents
(i) a saturated or unsaturated three- to twelve-membered carbocyclic or heterocyclic ring system which is optionally mono- or polysubstituted by hydroxy, C$_{1-6}$ alkyl, C$_3$-C$_{10}$-cycloalkyl, C$_{2-6}$ alkenyl, C$_{2-6}$ alkynyl, C$_{1-6}$ alkoxy, a halogen atom, or a saturated or unsaturated three- to eight-membered carbocyclic or heterocyclic group, and the C$_{1-6}$ alkyl, C$_3$-C$_{10}$-cycloalkyl, C$_{2-6}$ alkenyl, C$_{2-6}$ alkynyl, and C$_{1-6}$ alkoxy groups are optionally substituted by a halogen atom or a saturated or unsaturated three- to eight-membered carbocyclic or heterocyclic group,
(ii) C$_{1-6}$ alkyl or C$_{1-6}$ alkoxy which is unsubstituted or substituted by a saturated or unsaturated three- to twelve-membered carbocyclic or heterocyclic ring system which is optionally mono- or polysubstituted by hydroxy, C$_{1-6}$ alkyl, C$_{2-6}$ alkenyl, C$_{2-6}$ alkynyl, C$_{1-6}$ alkoxy, a halogen atom, or a saturated or unsaturated three- to eight-membered carbocyclic or heterocyclic group, and the C$_{1-6}$ alkyl, C$_{2-6}$ alkenyl, C$_{2-6}$ alkynyl, and C$_{1-6}$ alkoxy groups are optionally substituted by a halogen atom or a saturated or unsaturated three- to eight-membered carbocyclic or heterocyclic group,
(iii) a nitrogen atom substituted with a saturated or unsaturated three- to twelve-membered or heterocyclic ring system which is optionally mono- or polysubstituted by hydroxy, C$_{1-6}$ alkyl, C$_{2-6}$ alkenyl, C$_{2-6}$ alkynyl, C$_{1-6}$ alkoxy, a halogen atom, or a saturated or unsaturated three- to eight-membered carbocyclic or heterocyclic group, and the C$_{1-6}$ alkyl, C$_{2-6}$ alkenyl, C$_{2-6}$ alkynyl, and C$_{1-6}$ alkoxy groups are optionally substituted by a halogen atom or a saturated or unsaturated three- to eight-membered carbocyclic or heterocyclic group,
—$R^8$ represents hydroxyl, halogen, C$_{1-6}$-alkoxy, C$_{1-6}$ alkylcarbonyl, C$_3$-C$_{10}$-cycloalkyl, —NH—CO—NR$^9$R$^{10}$, —CO—NR$^9$R$^{10}$,
—NR$^9$R$^{10}$;
wherein —NR$^9$R$^{10}$ represents

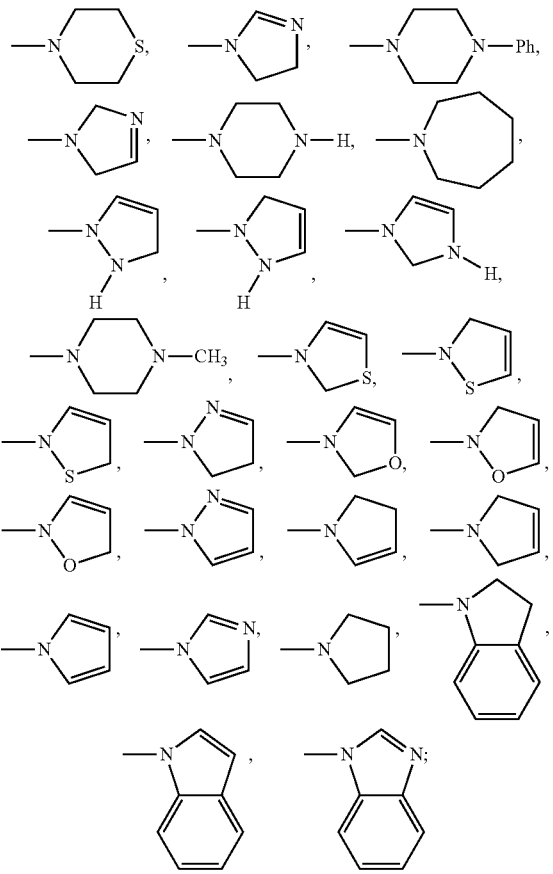

$R^{11}$-$R^{22}$ represent independently of each other linear or branched, substituted or unsubstituted C$_1$-C$_{20}$-alkyl, —H, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OPh, —OCH$_2$-Ph, —OCPh$_3$, —SH, —SCH$_3$, —SC$_2$H$_5$, —SC$_3$H$_7$, —S-cyclo-C$_3$H$_5$, —SCH(CH$_3$)$_2$, —SC(CH$_3$)$_3$, —NO$_2$, —F, —Cl, —Br, —I, —N$_3$, —CN, —OCN, —NCO, —SCN, —NCS, —CHO, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, —COCN, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —OOC—CH$_3$, —OOC—C$_2$H$_5$, —OOC—C$_3$H$_7$, —OOC-cyclo-C$_3$H$_5$, —OOC—CH(CH$_3$)$_2$, —OOC—C(CH$_3$)$_3$, —CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON(cyclo-C$_3$H$_5$)$_2$, —CON[CH(CH$_3$)$_2$]$_2$, —CON[C(CH$_3$)$_3$]$_2$, —NH$_2$, —NHCH$_3$, —NHC$_2$H$_5$, —NHC$_3$H$_7$, —NH-cyclo- $C_3H_5$, —$NHCH(CH_3)_2$, —$NHC(CH_3)_3$, —$N(CH_3)_2$, —$N(C_2H_5)_2$, —$N(C_3H_7)_2$, —$N(cyclo-C_3H_5)_2$, —$N[CH(CH_3)_2]_2$, —$N[C(CH_3)_3]_2$, —$SOCH_3$, —$SOC_2H_5$, —$SOC_3H_7$, —$SO$-cyclo-$C_3H_5$, —$SOCH(CH_3)_2$, —$SOC(CH_3)_3$, —$SO_2CH_3$, —$SO_2C_2H_5$, —$SO_2C_3H_7$, —$SO_2$-cyclo-$C_3H_5$, —$SO_2CH(CH_3)_2$, —$SO_2C(CH_3)_3$, —$SO_3H$, —$SO_3CH_3$, —$SO_3C_2H_5$, —$SO_3C_3H_7$, —$SO_3$-cyclo-$C_3H_5$, —$SO_3CH(CH_3)_2$, —$SO_3C(CH_3)_3$, —$OCHF_2$, —$OCF_3$, —$OC_2F_5$, —O—$COOCH_3$, —O—$COOC_2H_5$, —O—$COOC_3H_7$, —O—COO-cyclo-$C_3H_5$, —O—$COOCH(CH_3)_2$, —O—$COOC(CH_3)_3$, —NH—CO—$NH_2$, —NH—CO—$NHCH_3$, —NH—CO—$NHC_2H_5$, —NH—CO—$NHC_3H_7$, —NH—CO—NH-cyclo-$C_3H_5$, —NH—CO—$NH[CH(CH_3)_2]$, —NH—CO—$NH[C(CH_3)_3]$, —NH—CO—$N(CH_3)_2$, —NH—CO—$N(C_2H_5)_2$, —NH—CO—$N(C_3H_7)_2$, —NH—CO—$N(cyclo-C_3H_5)_2$, —NH—CO—$N[CH(CH_3)_2]_2$, —NH—CO—$N[C(CH_3)_3]_2$, —NH—CS—$NH_2$, —NH—CS—NH-cyclo-$C_3H_5$, —NH—CS—$NHC_3H_7$, —NH—CS—$NH[CH(CH_3)_2]$, —NH—CS—$NH[C(CH_3)_3]$, —NH—CS—$N(CH_3)_2$, —NH—CS—$N(C_2H_5)_2$, —NH—CS—$N(C_3H_7)_2$, —NH—CS—$N(cyclo-C_3H_5)_2$, —NH—CS—$N[CH(CH_3)_2]_2$, —NH—CS—$N[C(CH_3)_3]_2$, —NH—C(=NH)—$NH_2$, —NH—C(=NH)—$NHCH_3$, —NH—C(=NH)—$NHC_2H_5$, —NH—CS—$NHC_2H_5$, —NH—C(=NH)—$NHC_3H_7$, —NH—C(=NH)—NH-cyclo-$C_3H_5$, —NH—C(=NH)—$NH[CH(CH_3)_2]$, —NH—C(=NH)—$NH[C(CH_3)_3]$, —NH—CS—$NHCH_3$, —NH—C(=NH)—$N(CH_3)_2$, —NH—C(=NH)—$N(C_2H_5)_2$, —NH—C(=NH)—$N(C_3H_7)_2$, —NH—C(=NH)—$N(cyclo-C_3H_5)_2$, —$Si(CH_3)_3$, —NH—C(=NH)—$N[CH(CH_3)_2]_2$, —NH—C(=NH)—$N[C(CH_3)_3]_2$, —O—CO—$NH_2$, —O—CO—$NHCH_3$, —O—CO—$NHC_2H_5$, —O—CO—$NHC_3H_7$, —O—CO—NH-cyclo-$C_3H_5$, —O—CO—$NH[CH(CH_3)_2]$, —O—CO—$NH[C(CH_3)_3]$, —O—CO—$N(CH_3)_2$, —O—CO—$N(C_2H_5)_2$, —O—CO—$N(C_3H_7)_2$, —O—CO—$N(cyclo-C_3H_5)_2$, —O—CO—$N[CH(CH_3)_2]_2$, —O—CO—$N[C(CH_3)_3]_2$, —O—CO—$OCH_3$, —O—CO—$OC_2H_5$, —O—CO—$OC_3H_7$, —O—CO—O-cyclo-$C_3H_5$, —O—CO—$OCH(CH_3)_2$, —O—CO—$OC(CH_3)_3$, —$CH_2F$—$CHF_2$, —$CF_3$, —$CH_2Cl$, —$CHCl_2$, —$CCl_3$, —$CH_2Br$—$CHBr_2$, —$CBr_3$, —$CH_2I$—$CHI_2$, —$CI_3$, —$CPh_3$, —$CH_2$—$CH_2F$—$CH_2$—$CHF_2$, —$CH_2$—$CF_3$, —$CH_2$—$CH_2Cl$, —$CH_2$—$CHCl_2$, —$CH_2$—$CCl_3$, —$CH_2$—$CH_2Br$—$CH_2$—$CHBr_2$, —$CH_2$—$CBr_3$, —$CH_2$—$CH_2I$—$CH_2$—$CHI_2$, —$CH_2$—$CI_3$, —$CH_3$, —$C_2H_5$, —$C_3H_7$, -cyclo-$C_3H_5$, —$CH(CH_3)_2$, —$C(CH_3)_3$, —$C_4H_9$, —$CH_2$—$CH(CH_3)_2$, —$CH(CH_3)$—$C_2H_5$, —$C(CH_3)_3$, -Ph, —$CH_2$-Ph, —CH=$CH_2$, —$CH_2$—CH=$CH_2$, —$C(CH_3)$=$CH_2$, —CH=CH—$CH_3$, —$C_2H_4$—CH=$CH_2$, —CH=$C(CH_3)_2$, —C≡CH, —C≡C—$CH_3$, —$CH_2$—C≡CH;

and stereoisomeric forms, solvates, hydrates and/or pharmaceutically acceptable salts thereof.

2. The method according to claim 1, wherein the group $R^8$—X—O— is selected from:

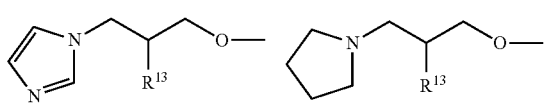

wherein
the substituent —$R^{13}$ has the meanings as defined in claim 1.

3. The method according to claim 1, wherein —$R^1$ or —$R^2$ represents —O—X—$R^8$;
if —$R^1$ represents —O—X—$R^8$ than —$R^2$ represents —H, —OH, —$OCH_3$, —$OCF_3$, —$OC_2H_5$, —$OC_3H_7$, —$OCH_2CH_2$—$OCH_3$, —$OCH_2CH_2$—$OC_2H_5$;
if —$R^2$ represents —O—X—$R^8$ than —$R^1$ represents —H, —OH, —$OCH_3$, —$OCF_3$, —$OC_2H_5$, —$OC_3H_7$, —$OCH_2CH_2$—$OCH_3$, —$OCH_2CH_2$—$OC_2H_5$;
—X— represents —$CR^{11}R^{12}$—$CR^{13}R^{14}$—, —$CR^{11}R^{12}$—$CR^{13}R^{14}$—$CR^{15}R^{16}$, —$CR^{11}R^{12}$—$CR^{13}R^{14}$—$CR^{15}R^{16}$—$CR^{17}R^{18}$—, —$CR^{11}R^{12}$—$CR^{13}R^{14}$—$CR^{15}R^{16}$—$CR^{17}R^{18}$—$CR^{19}R^{20}$—, —$CR^{11}R^{12}$—$CR^{13}R^{14}$—$CR^{15}R^{16}$—$CR^{17}R^{18}$—$CR^{19}R^{20}$—$CR^{21}R^{22}$—, —$(CH_2)_n$—NH—, —CO—, —$(CH_2)_n$—CO—, —$(CH_2)_n$—NH—CO—NH—, —$(CH_2)_n$—CO—NH—, —$(CH_2)_n$—O—CO—NH—, —$(CH_2)_n$—O—CO—, —$(CH_2)_n$—O—, —$(CH_2)_n$—;
n is an integer selected from 1, 2, 3, 4, 5 and 6;
—$R^3$, —$R^4$, —$R^5$, —$R^6$ are independently of each other selected from hydrogen, halogen, nitro, $C_{1-6}$ alkyl, $C_3$-$C_{10}$-cycloalkyl, $C_{1-6}$ alkoxy, wherein the $C_{1-6}$ alkyl, $C_3$-$C_{10}$-cycloalkyl or $C_{1-6}$ alkoxy groups are optionally mono- or polysubstituted by hydroxyl, halogen, $C_{1-4}$ alkyl and/or $C_{1-4}$ alkoxy, wherein the $C_{1-4}$ alkyl and/or $C_{1-4}$ alkoxy groups are optionally mono- or polysubstituted by hydroxyl and/or halogen;
—$R^7$ represents
(i) a saturated or unsaturated three- to twelve-membered carbocyclic or heterocyclic ring system which is optionally mono- or polysubstituted by hydroxy, $C_{1-6}$ alkyl, $C_3$-$C_{10}$, cycloalkyl, $C_{2-6}$ alkenyl, $C_{2-6}$ alkynyl, $C_{1-6}$ alkoxy, a halogen atom, or a saturated or unsaturated three- to eight-membered carbocyclic or heterocyclic group, and the $C_{1-6}$ alkyl, $C_3$-$C_{10}$-cycloalkyl, $C_{2-6}$ alkenyl, $C_{2-6}$ alkynyl, and $C_{1-6}$ alkoxy groups are optionally substituted by a halogen atom or a saturated or unsaturated three- to eight-membered carbocyclic or heterocyclic group,
(ii) $C_{1-6}$ alkyl or $C_{1-6}$ alkoxy which is unsubstituted or substituted by a saturated or unsaturated three- to twelve-membered carbocyclic or heterocyclic ring system which is optionally mono- or polysubstituted by hydroxy, $C_{1-6}$ alkyl, $C_{2-6}$ alkenyl, $C_{2-6}$ alkynyl, $C_{1-6}$ alkoxy, a halogen atom, or a saturated or unsaturated three- to eight-membered carbocyclic or heterocyclic group, and the $C_{1-6}$ alkyl, $C_{2-6}$ alkenyl, $C_{2-6}$ alkynyl, and $C_{1-6}$ alkoxy groups are optionally substituted by a halogen atom or a saturated or unsaturated three- to eight-membered carbocyclic or heterocyclic group,
(iii) a nitrogen atom substituted with a saturated or unsaturated three- to twelve-membered or heterocyclic ring system which is optionally mono- or polysubstituted by hydroxy, $C_{1-6}$ alkyl, $C_{2-6}$ alkenyl, $C_{2-6}$ alkynyl, $C_{1-6}$ alkoxy, a halogen atom, or a saturated or unsaturated three- to eight-membered carbocyclic or heterocyclic group, and the $C_{1-6}$ alkyl, $C_{2-6}$ alkenyl, $C_{2-6}$ alkynyl, and $C_{1-6}$ alkoxy groups are optionally substituted by a halogen atom or a saturated or unsaturated three- to eight-membered carbocyclic or heterocyclic group,
—$R^8$ represents

$R^{11}$-$R^{22}$ represent independently of each other linear or branched, substituted or unsubstituted $C_1$-$C_{20}$-alkyl, —H, —OH, —OCH₃, —OC₂H₅, —OC₃H₇, —O-cyclo-C₃H₅, —OCH(CH₃)₂, —OC(CH₃)₃, —OC₄H₉, —OPh, —OCH₂-Ph, —OCPh₃, —SH, —SCH₃, —SC₂H₅, —SC₃H₇, —S-cyclo-C₃H₅, —SCH(CH₃)₂, —SC(CH₃)₃, —NO₂, —F, —Cl, —Br, —I, —N₃, —CN, —OCN, —NCO, —SCN, —NCS, —CHO, —COCH₃, —COC₂H₅, —COC₃H₇, —CO-cyclo-C₃H₅, —COCH(CH₃)₂, —COC(CH₃)₃, —COOH, —COCN, —COOCH₃, —COOC₂H₅, —COOC₃H₇, —COO-cyclo-C₃H₅, —COOCH(CH₃)₂, —COOC(CH₃)₃, —OOC—CH₃, —OOC—C₂H₅, —OOC—C₃H₇, —OOC-cyclo-C₃H₅, —OOC—CH(CH₃)₂, —OOC—C(CH₃)₃, —CONH₂, —CONHCH₃, —CONHC₂H₅, —CONHC₃H₇, —CONH-cyclo-C₃H₅, —CONH[CH(CH₃)₂], —CONH[C(CH₃)₃], —CON(CH₃)₂, —CON(C₂H₅)₂, —CON(C₃H₇)₂, —CON(cyclo-C₃H₅)₂, —CON[CH(CH₃)₂]₂, —CON[C(CH₃)₃]₂, —NH₂, —NHCH₃, —NHC₂H₅, —NHC₃H₇, —NH-cyclo-C₃H₅, —NHCH(CH₃)₂, —NHC(CH₃)₃, —N(CH₃)₂, —N(C₂H₅)₂, —N(C₃H₇)₂, —N(cyclo-C₃H₅)₂, —N[CH(CH₃)₂]₂, —N[C(CH₃)₃]₂, —SOCH₃, —SOC₂H₅, —SOC₃H₇, —SO-cyclo-C₃H₅, —SOCH(CH₃)₂, —SOC(CH₃)₃, —SO₂CH₃, —SO₂C₂H₅, —SO₂C₃H₇, —SO₂-cyclo-C₃H₅, —SO₂CH(CH₃)₂, —SO₂C(CH₃)₃, —SO₃H, —SO₃CH₃, —SO₃C₂H₅, —SO₃C₃H₇, —SO₃-cyclo-C₃H₅, —SO₃CH(CH₃)₂, —SO₃C(CH₃)₃, —OCHF₂, —OCF₃, —OC₂F₅, —O—COOCH₃, —O—COOC₂H₅, —O—COOC₃H₇, —O—COO-cyclo-C₃H₅, —O—COOCH(CH₃)₂, —O—COOC(CH₃)₃, —NH—CO—NH₂, —NH—CO—NHCH₃, —NH—CO—NHC₂H₅, —NH—CO—NHC₃H₇, —NH—CO—NH-cyclo-C₃H₅, —NH—CO—NH[CH(CH₃)₂], —NH—CO—NH[C(CH₃)₃], —NH—CO—N(CH₃)₂, —NH—CO—N(C₂H₅)₂, —NH—CO—N(C₃H₇)₂, —NH—CO—N(cyclo-C₃H₅)₂, —NH—CO—N[CH(CH₃)₂]₂, —NH—CO—N[C(CH₃)₃]₂, —NH—CS—NH₂, —NH—CS—NH-cyclo-C₃H₅, —NH—CS—NHC₃H₇, —NH—CS—NH[CH(CH₃)₂], —NH—CS—NH[C(CH₃)₃], —NH—CS—N(CH₃)₂, —NH—CS—N(C₂H₅)₂, —NH—CS—N(C₃H₇)₂, —NH—CS—N(cyclo-C₃H₅)₂, —NH—CS—N[CH(CH₃)₂]₂, —NH—CS—N[C(CH₃)₃]₂, —NH—C(=NH)—NH₂, —NH—C(=NH)—NHCH₃, —NH—C(=NH)—NHC₂H₅, —NH—CS—NHC₂H₅, —NH—C(=NH)—NHC₃H₇, —NH—C(=NH)—NH-cyclo-C₃H₅, —NH—C(=NH)—NH[CH(CH₃)₂], —NH—C(=NH)—NH[C(CH₃)₃], —NH—CS—NHCH₃, —NH—C(=NH)—N(CH₃)₂, —NH—C(=NH)—N(C₂H₅)₂, —NH—C(=NH)—N(C₃H₇)₂, —NH—C(=NH)—N(cyclo-C₃H₅)₂, —Si(CH₃)₃, —NH—C(=NH)—N[CH(CH₃)₂]₂, —NH—C(=NH)—N[C(CH₃)₃]₂, —O—CO—NH₂, —O—CO—NHCH₃, —O—CO—NHC₂H₅, —O—CO—NHC₃H₇, —O—CO—NH-cyclo-C₃H₅, —O—CO—NH[CH(CH₃)₂], —O—CO—NH[C(CH₃)₃], —O—CO—N(CH₃)₂, —O—CO—N(C₂H₅)₂, —O—CO—N(C₃H₇)₂, —O—CO—N(cyclo-C₃H₅)₂, —O—CO—N[CH(CH₃)₂]₂, —O—CO—N[C(CH₃)₃]₂, —O—CO—OCH₃, —O—CO—OC₂H₅, —O—CO—OC₃H₇, —O—CO—O-cyclo-C₃H₅, —O—CO—OCH(CH₃)₂, —O—CO—OC(CH₃)₃, —CH₂F—CHF₂, —CF₃, —CH₂Cl, —CHCl₂, —CCl₃, —CH₂Br—CHBr₂, —CBr₃, —CH₂I—CHI₂, —O₃, —CPh₃, —CH₂—CH₂F—CH₂—CHF₂, —CH₂—CF₃, —CH₂—CH₂Cl, —CH₂—CHCl₂, —CH₂—CCl₃, —CH₂—CH₂Br—CH₂—CHBr₂, —CH₂—CBr₃, —CH₂—CH₂I—CH₂—CHI₂, —CH₂—CI₃, —CH₃, —C₂H₅, —C₃H₇, -cyclo-C₃H₅, —CH(CH₃)₂, —C(CH₃)₃, —C₄H₉, —CH₂—CH(CH₃)₂, —CH(CH₃)—C₂H₅, —C(CH₃)₃, -Ph, —CH₂-Ph, —CH=CH₂, —CH₂—CH=CH₂, —C(CH₃)=CH₂, —CH=CH—CH₃, —C₂H₄—CH=CH₂, —CH=C(CH₃)₂, —C≡CH, —C≡C—CH₃, —CH₂—C≡CH.

4. The method according to claim 1, wherein the group R⁸—X—O— is

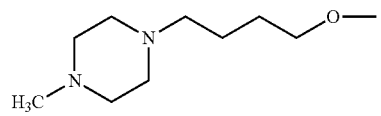

wherein
the substituent —R²² refers to phenyl, benzyl, C₁-C₆-alkyl, pyrrolidin-1-yl, piperidin-1-yl, piperazin-1-yl, —OH, —CH₂—OH, —C₂H₄—OH, —OCH₃, —CH₂—OCH₃, —C₂H₄—OCH₃;
C₁-C₆-alkyl refers to —CH₃, —C₂H₅, —C₃H₇, —CH(CH₃)₂, —C₄H₉, —CH₂—CH(CH₃)₂, —CH(CH₃)—C₂H₅, —C(CH₃)₃, —CH(CH₃)—C₃H₇, —CH₂—CH(CH₃)—C₂H₅, —CH(CH₃)—CH(CH₃)₂, —C₅H₁₁, —C(CH₃)₂—C₂H₅, —CH₂—C(CH₃)₃, —CH(C₂H₅)₂, —C₂H₄—CH(CH₃)₂, —C₆H₁₃, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, and —CH(CH₃)—C(CH₃)₃,
wherein in the afore-mentioned groups one or more hydrogen atom(s) can be replaced by —OH, —OCH₃, —OC₂H₅, —SH, —SCH₃, —SC₂H₅, —NO₂, —F, —Cl, —Br, —I, —N₃, —COCH₃, —COC₂H₅, —COOCH₃, —COOC₂H₅, —OOC—CH₃, —OOC—C₂H₅, —COOH, —CONH₂, —CON(CH₃)₂, —CON(C₂H₅)₂, —NH₂, —NHCH₃, —NHC₂H₅, —N(CH₃)₂, —N(C₂H₅)₂, —SOCH₃, —SOC₂H₅, —SO₃H, —OCF₃, —CF₃, —C≡CH.

5. The method according to claim 1, wherein the compound is selected from the group consist of:
2,5-Difluoro-N-(3-fluoro-4-{6-methoxy-7-[3-(4-methyl-piperazin-1-yl)-propoxy]-quinolin-4-yloxy}-phenyl)-benzenesulfonamide,
Biphenyl-3-sulfonic acid (3-fluoro-4-{6-methoxy-7-[3-(4-methyl-piperazin-1-yl)-propoxy]-quinolin-4-yloxy}-phenyl)-amide,
N-(3-Fluoro-4-{6-methoxy-7-[3-(4-methyl-piperazin-1-yl)-propoxy]-quinolin-4-yloxy}-phenyl)-3-phenoxy-benzenesulfonamide,
2-Cyano-N-(3-fluoro-4-{6-methoxy-7-[3-(4-methyl-piperazin-1-yl)-propoxy]-quinolin-4-yloxy}-phenyl)-benzenesulfonamide,
2,4-Difluoro-N-(3-fluoro-4-{6-methoxy-7-[3-(4-methyl-piperazin-1-yl)-propoxy]-quinolin-4-yloxy}-phenyl)-benzenesulfonamide,
2,3,4-Trifluoro-N-(3-fluoro-4-{6-methoxy-7-[3-(4-methyl-piperazin-1-yl)-propoxy]-quinolin-4-yloxy}-phenyl)-benzenesulfonamide,
4-Fluoro-N-(3-fluoro-4-{6-methoxy-7-[3-(4-methyl-piperazin-1-yl)-propoxy]-quinolin-4-yloxy}-phenyl)-3-methoxy-benzene sulfonamide, 2-Bromo-N-(3-fluoro-4-{6-methoxy-7-[3-(4-methyl-piperazin-1-yl)-propoxy]-quinolin-4-yloxy}-phenyl)-benzenesulfonamide,
2,5-Dichloro-N-(3-fluoro-4-{6-methoxy-7-[3-(4-methyl-piperazin-1-yl)-propoxy]-quinolin-4-yloxy}-phenyl)-benzenesulfonamide,
N-(3-Fluoro-4-{6-methoxy-7-[3-(4-methyl-piperazin-1-yl)-propoxy]-quinolin-4-yloxy}-phenyl)-2-nitro-benzenesulfonamide,
3-Fluoro-(3-fluoro-4-{6-methoxy-7-[3-(4-methyl-piperazin-1-yl)-propoxy]-quinolin-4-yloxy}-phenyl)-benzenesulfonamide,
3-Chloro-4-fluoro-N-(3-fluoro-4-{6-methoxy-7-[3-(4-methyl-piperazin-1-yl)-propoxy]-quinolin-4-yloxy}-phenyl)-benzenesulfonamide,
N-(3-Fluoro-4-{6-methoxy-7-[3-(4-methyl-piperazin-1-yl)-propoxy]-quinolin-4-yloxy}-phenyl)-2-trifluoromethyl-benzenesulfonamide,
N-(3-Fluoro-4-{6-methoxy-7-[3-(4-methyl-piperazin-1-yl)-propoxy]-quinolin-4-yloxy}-phenyl)-2-trifluoromethoxy-benzenesulfonamide,
2-Fluoro-N-(3-fluoro-4-{6-methoxy-7-[3-(4-methyl-piperazin-1-yl)-propoxy]-quinolin-4-yloxy}-phenyl)-benzenesulfonamide,
4-Chloro-2-fluoro-N-(3-fluoro-4-{6-methoxy-7-[3-(4-methyl-piperazin-1-yl)-propoxy]-quinolin-4-yloxy}-phenyl)-benzenesulfonamide,
N-(3-Fluoro-4-{6-methoxy-7-[3-(4-methyl-piperazin-1-yl)-propoxy]-quinolin-4-yloxy}-phenyl)-2-methyl-benzenesulfonamide,
2-Chloro-N-(3-fluoro-4-{6-methoxy-7-[3-(4-methyl-piperazin-1-yl)-propoxy]-quinolin-4-yloxy}-phenyl)-benzenesulfonamide,
3-Difluoromethoxy-N-(3-fluoro-4-{6-methoxy-7-[3-(4-methyl-piperazin-1-yl)-propoxy]-quinolin-4-yloxy}-phenyl)-benzenesulfonamide,
Thiophene-2-sulfonic acid (3-fluoro-4-{6-methoxy-7-[3-(4-methyl-piperazin-1-yl)-propoxy]-quinolin-4-yloxy}-phenyl)-amide,
2,6-Dichloro-N-(3-fluoro-4-{6-methoxy-7-[3-(4-methyl-piperazin-1-yl)-propoxy]-quinolin-4-yloxy}-phenyl)-benzenesulfonamide,
N-(3-Fluoro-4-{6-methoxy-7-[3-(4-methyl-piperazin-1-yl)-propoxy]-quinolin-4-yloxy}-phenyl)-2-methoxy-benzenesulfonamide,
3,5-Dichloro-N-(3-fluoro-4-{6-methoxy-7-[3-(4-methyl-piperazin-1-yl)-propoxy]-quinolin-4-yloxy}-phenyl)-2-methoxy-benzenesulfonamide,
3,5-Dichloro-N-{3-fluoro-4-[6-methoxy-7-(3-morpholin-4-yl-propoxy)-quinolin-4-yloxy]-phenyl}-2-methoxy-benzenesulfonamide,
2,6-Difluoro-N-{3-fluoro-4-[6-methoxy-7-(3-morpholin-4-yl-propoxy)-quinolin-4-yloxy]-phenyl}-benzenesulfonamide,
2-Fluoro-N-{3-fluoro-4-[6-methoxy-7-(2-morpholin-4-yl-ethoxy)-quinolin-4-yloxy]-phenyl}-benzenesulfonamide,
2,6-Difluoro-N-{3-fluoro-4-[6-methoxy-7-(2-morpholin-4-yl-ethoxy)-quinolin-4-yloxy]-phenyl}-benzenesulfonamide,
2,5-Difluoro-N-{3-fluoro-4-[6-methoxy-7-(4-morpholin-4-yl-butoxy)-quinolin-4-yloxy]-phenyl}-benzenesulfonamide,
2,5-Difluoro-N-{3-fluoro-4-[7-(4-morpholin-4-yl-butoxy)-quinolin-4-yloxy]-phenyl}-benzenesulfonamide,
N-(3-Fluoro-4-{6-[3-(4-methyl-piperazin-1-yl)-propoxy]-quinolin-4-yloxy}-phenyl)-2-trifluoromethyl-benzenesulfonamide,
N-(3-Fluoro-4-{7-methoxy-6-[3-(4-methyl-piperazin-1-yl)-propoxy]-quinolin-4-yloxy}-phenyl)-2-trifluoromethyl-benzenesulfonamide,
N-(3-Chloro-4-{6-methoxy-7-[3-(4-methyl-piperazin-1-yl)-propoxy]-quinolin-4-yloxy}-phenyl)-2-trifluoromethyl-benzenesulfonamide,
N-(3,5-Dichloro-4-{6-methoxy-7-[3-(4-methyl-piperazin-1-yl)-propoxy]-quinolin-4-yloxy}-phenyl)-2,6-difluoro-benzene sulfonamide,
N-{4-[6,7-Bis-(2-methoxy-ethoxy)-quinolin-4-yloxy]-3-fluoro-phenyl}-2,6-difluoro-benzenesulfonamide,
{4-[2-Fluoro-4-(2-fluoro-benzenesulfonylamino)-phenoxy]-6-methoxy-quinolin-7-yloxy}-acetic acid ethyl ester,
2-{4-[2-Fluoro-4-(2-trifluoromethyl-benzenesulfonylamino)-phenoxy]-6-methoxy-quinolin-7-yloxy}-N,N-dimethyl-acetamide,
Cyclohexanecarboxylic acid 4-[4-(2,5-difluoro-benzenesulfonylamino)-2-fluoro-phenoxy]-6-methoxy-quinolin-7-yl ester,
N-(3-Fluoro-4-{6-methoxy-7-[3-(tetrahydro-pyran-4-ylamino)-propoxy]-quinolin-4-yloxy}-phenyl)-2-trifluoromethyl-benzenesulfonamide,
N-{4-[7-(3-Cyclopropylamino-propoxy)-6-methoxy-quinolin-4-yloxy]-3-fluoro-phenyl}-2-trifluoromethyl-benzenesulfonamide,
N-{4-[7-(3-Cyclobutylamino-propoxy)-6-methoxy-quinolin-4-yloxy]-3-fluoro-phenyl}-2-trifluoromethyl-benzenesulfonamide,
N-(4-{7-[3-(3-tert-Butyl-ureido)-propoxy]-6-methoxy-quinolin-4-yloxy}-3-fluoro-phenyl)-2-trifluoromethyl-benzenesulfonamide,
N-(3-{6-Methoxy-7-[3-(4-methyl-piperazin-1-yl)-propoxy]-quinolin-4-yloxy}-phenyl)-2-trifluoromethyl-benzenesulfonamide,
N-{3-Fluoro-4-[6-methoxy-7-(2-morpholin-4-yl-ethoxy)-quinolin-4-yloxy]-phenyl}-2-methoxy-benzenesulfonamide,
2,6-Dichloro-N-{3-fluoro-4-[6-methoxy-7-(2-morpholin-4-yl-ethoxy)-quinolin-4-yloxy]-phenyl}-benzenesulfonamide,
Thiophene-2-sulfonic acid {3-fluoro-4-[6-methoxy-7-(2-morpholin-4-yl-ethoxy)-quinolin-4-yloxy]-phenyl}-amide,
2,5-Dichloro-N-{3-fluoro-4-[6-methoxy-7-(2-morpholin-4-yl-ethoxy)-quinolin-4-yloxy]-phenyl}-benzenesulfonamide,
1-Methyl-1H-pyrazole-3-sulfonic acid {3-fluoro-4-[6-methoxy-7-(2-morpholin-4-yl-ethoxy)-quinolin-4-yloxy]-phenyl}-amide,
2-Chloro-N-{3-fluoro-4-[6-methoxy-7-(2-morpholin-4-yl-ethoxy)-quinolin-4-yloxy]-phenyl}-benzenesulfonamide,
N-{3-Fluoro-4-[6-methoxy-7-(2-morpholin-4-yl-ethoxy)-quinolin-4-yloxy]-phenyl}-2-nitro-benzenesulfonamide,
2,6-Difluoro-N-(3-fluoro-4-{6-methoxy-7-[3-(4-methyl-piperazin-1-yl)-propoxy]-quinolin-4-yloxy}-phenyl)-benzenesulfonamide,
N-(3-Chloro-4-{6-methoxy-7-[3-(4-methyl-piperazin-1-yl)-propoxy]-quinolin-4-yloxy}-phenyl)-2-fluoro-benzenesulfonamide, N-(3-Chloro-4-{6-methoxy-7-[3-(4-methyl-piperazin-1-yl)-propoxy]-quinolin-4-yloxy}-phenyl)-2,5-difluoro-benzenesulfonamide, Benzo[b]thiophene-3-sulfonic acid {3-fluoro-4-[6-methoxy-7-(3-morpholin-4-yl-propoxy)-quinolin-4-yloxy]-phenyl}-amide, Benzo[b]thiophene-3-sulfonic acid (3-fluoro-4-{6-methoxy-7-[3-(4-methyl-piperazin-1-yl)-propoxy]-quinolin-4-yloxy}-phenyl)-amide, Benzo[b]thiophene-3-sulfonic acid (3-chloro-4-{6-methoxy-7-[3-(4-methyl-piperazin-1-yl)-propoxy]-quinolin-4-yloxy}-phenyl)-amide, N-(3-Chloro-4-{6-methoxy-7-[3-(4-methyl-piperazin-1-yl)-propoxy]-quinolin-4-yloxy}-phenyl)-2,6-difluoro-benzenesulfonamide, 2,6-Dichloro-N-(3-chloro-4-{6-methoxy-7-[3-(4-methyl-piperazin-1-yl)-propoxy]-quinolin-4-yloxy}-phenyl)-benzenesulfonamide, 2,5-Difluoro-N-(3-{6-methoxy-7-[3-(4-methyl-piperazin-1-yl)-propoxy]-quinolin-4-yloxy}-phenyl)-benzenesulfonamide, 2,5-Dichloro-N-(3-chloro-4-{6-methoxy-7-[3-(4-methyl-piperazin-1-yl)-propoxy]-quinolin-4-yloxy}-phenyl)-benzenesulfonamide, 2,6-Difluoro-N-(3-{6-methoxy-7-[3-(4-methyl-piperazin-1-yl)-propoxy]-quinolin-4-yloxy}-phenyl)-benzenesulfonamide, N-(3-{6-Methoxy-7-[3-(4-methyl-piperazin-1-yl)-propoxy]-quinolin-4-yloxy}-phenyl)-2-trifluoromethoxy-benzenesulfonamide, 2,5-Dichloro-N-(3-{6-methoxy-7-[3-(4-methyl-piperazin-1-yl)-propoxy]-quinolin-4-yloxy}-phenyl)-benzenesulfonamide, 2,6-Dichloro-N-(3-{6-methoxy-7-[3-(4-methyl-piperazin-1-yl)-propoxy]-quinolin-4-yloxy}-phenyl)-benzenesulfonamide, Thiophene-2-sulfonic acid (3-{6-methoxy-7-[3-(4-methyl-piperazin-1-yl)-propoxy]-quinolin-4-yloxy}-phenyl)-amide, 5-Chloro-thiophene-2-sulfonic acid (3-{6-methoxy-7-[3-(4-methyl-piperazin-1-yl)-propoxy]-quinolin-4-yloxy}-phenyl)-amide, 5-Methyl-thiophene-2-sulfonic acid (3-{6-methoxy-7-[3-(4-methyl-piperazin-1-yl)-propoxy]-quinolin-4-yloxy}-phenyl)-amide, N-[5-(3-{6-Methoxy-7-[3-(4-methyl-piperazin-1-yl)-propoxy]-quinolin-4-yloxy}-phenylsulfamoyl)-4-methyl-thiazol-2-yl]-acetamide, Thiophene-3-sulfonic acid (3-{6-methoxy-7-[3-(4-methyl-piperazin-1-yl)-propoxy]-quinolin-4-yloxy}-phenyl)-amide, 2,5-Dichloro-thiophene-3-sulfonic acid (3-{6-methoxy-7-[3-(4-methyl-piperazin-1-yl)-propoxy]-quinolin-4-yloxy}-phenyl)-amide, 3-(3-{6-Methoxy-7-[3-(4-methyl-piperazin-1-yl)-propoxy]-quinolin-4-yloxy}-phenylsulfamoyl)-thiophene-2-carboxylic acid methyl ester, Benzo[b]thiophene-3-sulfonic acid (3-{6-methoxy-7-[3-(4-methyl-piperazin-1-yl)-propoxy]-quinolin-4-yloxy}-phenyl)-amide, Furan-2-sulfonic acid (3-{6-methoxy-7-[3-(4-methyl-piperazin-1-yl)-propoxy]-quinolin-4-yloxy}-phenyl)-amide, 3,5-Dimethyl-isoxazole-4-sulfonic acid (3-{6-methoxy-7-[3-(4-methyl-piperazin-1-yl)-propoxy]-quinolin-4-yloxy}-phenyl)-amide, 1-Methyl-1H-pyrazole-3-sulfonic acid (3-{6-methoxy-7-[3-(4-methyl-piperazin-1-yl)-propoxy]-quinolin-4-yloxy}-phenyl)-amide, 1-Ethyl-1H-pyrazole-4-sulfonic acid (3-{6-methoxy-7-[3-(4-methyl-piperazin-1-yl)-propoxy]-quinolin-4-yloxy}-phenyl)-amide, 2-Methyl-1H-imidazole-4-sulfonic acid (3-{6-methoxy-7-[3-(4-methyl-piperazin-1-yl)-propoxy]-quinolin-4-yloxy}-phenyl)-amide, Cyclopropanesulfonic acid (3-{6-methoxy-7-[3-(4-methyl-piperazin-1-yl)-propoxy]-quinolin-4-yloxy}-phenyl)-amide, 2-Phenyl-ethenesulfonic acid (3-{6-methoxy-7-[3-(4-methyl-piperazin-1-yl)-propoxy]-quinolin-4-yloxy}-phenyl)-amide, 3-{3-Fluoro-4-[6-methoxy-7-(3-morpholin-4-yl-propoxy)-quinolin-4-yloxy]-phenylsulfamoyl}-thiophene-2-carboxylic acid methyl ester, 3-(3-Fluoro-4-{6-methoxy-7-[3-(4-methyl-piperazin-1-yl)-propoxy]-quinolin-4-yloxy}-phenylsulfamoyl)-thiophene-2-carboxylic acid methyl ester, 1,3,5-Trimethyl-1H-pyrazole-4-sulfonic acid {3-fluoro-4-[6-methoxy-7-(3-morpholin-4-yl-propoxy)-quinolin-4-yloxy]-phenyl}-amide, 1,3,5-Trimethyl-1H-pyrazole-4-sulfonic acid (3-fluoro-4-{6-methoxy-7-[3-(4-methyl-piperazin-1-yl)-propoxy]-quinolin-4-yloxy}-phenyl)-amide, 1-Methyl-1H-pyrazole-3-sulfonic acid {3-fluoro-4-[6-methoxy-7-(3-morpholin-4-yl-propoxy)-quinolin-4-yloxy]-phenyl}-amide, 1-Methyl-1H-pyrazole-3-sulfonic acid (3-fluoro-4-{6-methoxy-7-[3-(4-methyl-piperazin-1-yl)-propoxy]-quinolin-4-yloxy}-phenyl)-amide, 2-Methyl-3H-imidazole-4-sulfonic acid {3-fluoro-4-[6-methoxy-7-(3-morpholin-4-yl-propoxy)-quinolin-4-yloxy]-phenyl}-amide, 2-Methyl-3H-imidazole-4-sulfonic acid (3-fluoro-4-{6-methoxy-7-[3-(4-methyl-piperazin-1-yl)-propoxy]-quinolin-4-yloxy}-phenyl)-amide, Acetic acid 4-{4-[4-(2,5-difluoro-benzenesulfonylamino)-2-fluoro-phenoxy]-6-methoxy-quinolin-7-yloxy}-butyl ester, Acetic acid 4-{4-[2-fluoro-4-(2-trifluoromethyl-benzenesulfonylamino)-phenoxy]-6-methoxy-quinolin-7-yloxy}-butyl ester, N-{2-Fluoro-4-[6-methoxy-7-(3-pyrrolidin-1-yl-propoxy)-quinolin-4-yloxy]-phenyl}-2-trifluoromethyl-benzenesulfonamide, and N-{3-Fluoro-4-[6-methoxy-7-(4-morpholin-4-yl-butoxy)-quinolin-4-yloxy]-phenyl}-2-trifluoromethyl-benzenesulfonamide.

6. The method according to claim 1, wherein the AXL receptor tyrosine kinase induced cancer, tumor or cancer metastase is selected from the group consisting of: adenocarcinoma, choroidal melanoma, acute leukemia, acoustic neurinoma, ampullary carcinoma, anal carcinoma, astrocytoma, basal cell carcinoma, pancreatic cancer, desmoid tumor, bladder cancer, bronchial carcinoma, breast cancer, Burkitt's lymphoma, corpus cancer, CUP-syndrome (carcinoma of unknown primary), colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, glioblastomas, gynecologic tumors, ear, nose and throat tumors, hematologic neoplasias, hairy cell leukemia, urethral cancer, skin cancer, skin testis cancer, brain tumors (gliomas), brain metastases, testicle cancer, hypophysis tumor, carcinoids, Kaposi's sarcoma, laryngeal cancer, germ cell tumor, bone cancer, colorectal carcinoma, head and neck tumors (tumors of the ear, nose and throat area), colon carcinoma, craniopharyngiomas, oral cancer (cancer in the mouth area and on lips), cancer of the central nervous system, liver cancer, liver metastases, leukemia, eyelid tumor, lung cancer, lymph node cancer (Hodgkin's/Non-Hodgkin's), lymphomas, stomach cancer, malignant melanoma, malignant neoplasia, malignant tumors gastrointestinal tract, breast carcinoma, rectal cancer, medulloblastomas, melanoma, meningiomas, Hodgkin's disease, mycosis fungoides, nasal cancer, neurinoma, neuroblastoma, kidney cancer, renal cell carcinomas, non-Hodgkin's lymphomas, oligodendroglioma, esophageal carcinoma, osteolytic carcinomas and osteoplastic carcinomas, osteosarcomas, ovarial carcinoma, pancreatic carcinoma, penile cancer, plasmocytoma, prostate cancer, pharyngeal cancer, rectal carcinoma, retinoblastoma, vaginal cancer, thyroid carcinoma, Schneeberger disease, esophageal cancer, spinalioms, T-cell lymphoma (mycosis fungoides), thymoma, tube carcinoma, eye tumors, urethral cancer, urologic tumors, urothelial carcinoma, vulva cancer, wart appearance, soft tissue tumors, soft tissue sarcoma, Wilm's tumor, cervical carcinoma and tongue cancer.

7. The method according to claim 1, wherein the administration of the compound of general formula (I) or the pharmaceutical composition containing at least one compound of general formula (I) is selected from dermal, intradermal, intragastral, intracutan, intravasal, intravenous, intramuscular, intraperitoneal, intranasal, intravaginal, intrabuccal, percutan, rectal, subcutaneous, sublingual, topical, or transdermal administration.

8. The method according to claim 1, wherein the pharmaceutical composition containing at least one compound of the general formula (I) further contains at least one pharmaceutically acceptable carrier, excipient and/or diluents.

* * * * *

UNITED STATES PATENT AND TRADEMARK OFFICE
CERTIFICATE OF CORRECTION

PATENT NO. : 9,169,241 B2  Page 1 of 1
APPLICATION NO. : 14/202951
DATED : October 27, 2015
INVENTOR(S) : Ullrich et al.

It is certified that error appears in the above-identified patent and that said Letters Patent is hereby corrected as shown below:

In the Claims:

Claim 1, col. 190, line 7, please delete "represents hydroxyl, halogen," and substitute therefor --represents halogen,--.

Claim 3, col. 193, line 63, please delete "–O$_3$" and substitute therefor --CI$_3$,--.

Signed and Sealed this
Seventeenth Day of May, 2016

Michelle K. Lee
*Director of the United States Patent and Trademark Office*